US006982263B2

(12) United States Patent
Hickey et al.

(10) Patent No.: US 6,982,263 B2
(45) Date of Patent: Jan. 3, 2006

(54) NITRILES USEFUL AS REVERSIBLE INHIBITORS OF CYSTEINE PROTEASES

(75) Inventors: Eugene R. Hickey, Danbury, CT (US); Younes Bekkali, Danbury, CT (US); Usha R. Patel, Brookfield, CT (US); Denice Mary Spero, West Redding, CT (US); David S. Thomson, Ridgefield, CT (US); Erick Richard Roush Young, Danbury, CT (US)

(73) Assignee: Boehringer Ingelheim Pharmaceuticals, Inc., Ridgefield, CT (US)

(*) Notice: Subject to any disclaimer, the term of this patent is extended or adjusted under 35 U.S.C. 154(b) by 231 days.

(21) Appl. No.: 10/163,015

(22) Filed: Jun. 4, 2002

(65) Prior Publication Data

US 2003/0119827 A1 Jun. 26, 2003

Related U.S. Application Data

(60) Provisional application No. 60/296,863, filed on Jun. 8, 2001.

(51) Int. Cl.
C07D 207/16 (2006.01)
C07D 211/66 (2006.01)
C07D 217/56 (2006.01)
C07D 223/12 (2006.01)
C07D 413/12 (2006.01)

(52) U.S. Cl. .............................. 514/235.2; 514/237.2; 514/237.5; 514/329; 514/426; 514/482; 544/130; 544/141; 544/144; 544/163; 546/215; 548/557; 558/393

(58) Field of Classification Search .............. 514/235.2, 514/237.2, 237.5, 329, 426, 482; 544/130, 544/141, 144, 163; 546/215; 548/557; 558/393

See application file for complete search history.

(56) References Cited

U.S. PATENT DOCUMENTS

| 4,021,224 | A | | 5/1977 | Pallos et al. |
|---|---|---|---|---|
| 4,137,070 | A | * | 1/1979 | Pallos et al. ................ 504/112 |
| 4,267,174 | A | | 5/1981 | Berger et al. |
| 4,282,212 | A | | 8/1981 | Berger et al. |
| 4,321,194 | A | | 3/1982 | Bosies et al. |
| 4,409,236 | A | | 10/1983 | Bosies et al. |
| 4,410,532 | A | | 10/1983 | Bosies et al. |
| 5,714,471 | A | | 2/1998 | Rowe et al. |
| 5,776,718 | A | | 7/1998 | Palmer et al. |
| 6,143,774 | A | | 11/2000 | Heckmann et al. |
| 6,395,897 | B1 | | 5/2002 | Cywin et al. |
| 6,420,364 | B1 | | 7/2002 | Emmanuel |
| 6,492,362 | B1 | | 12/2002 | Graupe et al. |
| 2003/0105099 | A1 | | 6/2003 | Graupe et al. |
| 2004/0014796 | A1 | | 1/2004 | Graupe et al. |

FOREIGN PATENT DOCUMENTS

| WO | WO 92/22570 A1 | 12/1992 |
|---|---|---|
| WO | WO 94/10155 A1 | 5/1994 |
| WO | WO 96/40737 A1 | 12/1996 |
| WO | WO 97/17339 A1 | 5/1997 |
| WO | WO 99/24460 A2 | 5/1999 |
| WO | WO 00/38687 A1 | 7/2000 |
| WO | WO 00/39115 A1 | 7/2000 |
| WO | WO 00/48993 A1 | 8/2000 |
| WO | WO 00/49007 A1 | 8/2000 |
| WO | WO 00/55124 A2 | 9/2000 |
| WO | WO 00/59881 A1 | 10/2000 |
| WO | WO 01/09110 A1 | 2/2001 |
| WO | WO 01/17562 A1 | 3/2001 |
| WO | WO 01/17959 A2 | 3/2001 |
| WO | WO 01/18216 A2 | 3/2001 |
| WO | WO 01/77073 A1 | 10/2001 |
| WO | WO 01/87828 A1 | 11/2001 |
| WO | WO 02/098850 A2 | 12/2002 |

OTHER PUBLICATIONS

Wolff, Manfred E. "Burger's Medicinal Chemistry, 5ed, Part I", John Wiley & Sons, 1995, pp. 975–977.*

Banker, G.S. et al, "Modern Pharmaceutics, 3ed.", Marcel Dekker, New York, 1996, pp. 451–596.*

Marquis, Robert W., Ann. Reports Med. Chem., vol. 35, pp. 309–320, 2000.*

Riese R.J. et al, J. Clin. Invest., 101(11), pp. 2351–2363, 1998.*

Saegusa K., et al, J Clin Invest. Aug. 2002;110(3):361–9.*

Thurmond RL et al, J Pharmacol Exp Ther. Oct. 17, 2003, abstract cited in PMID: 14566006.*

Mary J. Bossard, et al. "Proteolytic Activity of Human Osteoclast Cathepsin K" J. Biol. Chem., vol. 271, No. 21, May 24, 1996, pp. 12517–12524.

(Continued)

Primary Examiner—Thomas C. McKenzie
(74) Attorney, Agent, or Firm—Michael P. Morris; Philip I. Datlow; Anthony P. Bottino

(57) ABSTRACT

Disclosed are novel nitrile compounds of formula (I) further defined herein, which compounds are useful as reversible inhibitors of cysteine proteases such as cathepsin K, S, F, L and B. These compounds are useful for treating diseases and pathological conditions exacerbated by these proteases such as, but not limited to, osteoporosis, rheumatoid arthritis, multiple sclerosis, asthma and other autoimmune diseases, Alzheimer's disease, atherosclerosis. Also disclosed are processes for making such novel compounds.

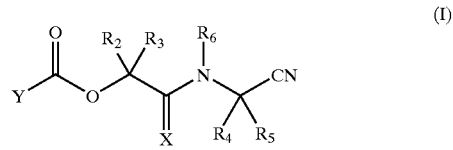

(I)

22 Claims, No Drawings

OTHER PUBLICATIONS

Harold A. Chapman, et al. "Emerging Roles for Cysteine Proteases in Human Biology", Ann. Rev. Physiol. 1997, 59:63–88.

Harold A. Chapman, et al. "Endosomal Proteolysis and MHC Class II Function" Curr. Opinion in Immunol. 1998, 10:93–102.

Fred H. Drake, et al, "Cathepsin K, but Not Cathepsins B, L, or S, Is Abundantly Expressed in Human Osteoclasts" J. Biol. Chem. 1996, vol. 271, No. 21, pp. 12511–12516.

Juan C. Engel, et al. "Cysteine Protease Inhibitors Cure an Experimental Trypanosoma cruzi Infection" J. Exp. Med. vol. 188, No. 4, 1998, pp 725–734.

Bruce D. Gelb, et al. "Pycnodysostosis, a Lysosomal Disease Caused by Cathepsin K Deficiency" Science, vol. 273, No. 5279, pp 1236–1238 1996.

Maxine Gowen "Inhibition of cathepsin K—a novel approach to antiresorptive therapy" Exp. Opin. Invest. Drugs (1997) 6(9):1199–1202.

Maxine Gowen "Cathepsin K Knockout Mice Develop Osteopetrosis Due to a Deficit in Matrix Degradation but Not Demineralization" J. Bone and Mineral Research vol. 14, No. 10, 1999 pp 1654–1663.

Wu–Shiun Hou "Characterization of novel cathepsin K mutations in the pro and mature polypeptide regions causing pycnodysostosis" J. Clin. Invest. vol. 103, No. 5:731–738 1999.

Klaus M. Hummel, et al. "Cysteine Proteinase Cathepsin k mRNA Is Expressed in Synovium of Patients with Rheumatoid Arthritis and is Detected at Sites of Synovial Bone Destruction" J. Rheumatology 1998: 25:10 pp 1887–1894.

Woomi Kim, et al. "Recent developments of cathepsin inhibtors and their selectivity" Exp. Opin. Ther. Patents (2002) 12(3):419–432.

Cynthia A. Lemere, et al. "The Lysosomal Cysteine Protease, Cathepsin S, Is Increased in Alzheimer's Disease and Down Syndrome Brain" Am. J. Pathology vol. 146, No. 4, 1995, pp 848–860.

Amanda J. Littlewood–Evans, et al. "The Osteoclast–associated Protease Cathepsin K Is Expressed in Human Breast Carcinoma" Cancer Research vol. 57, pp 5386–5390, 1997.

Robert W. Marquis, et al. "Inhibition of Cysteine Protease" Annual Reports in Medicinal Chemistry, vol. 35, pp 309–320.

Mary Teresa Moran, et al. "Pathologic gene expression in Gaucher disease: up–regulation of cysteine proteinases including osteoclastic cathepsin K" Blood, vol. 96, No. 5 pp 1969–1978 2000.

Ulf Muller–Ladner, et al. "Cysteine proteinases in arthritis and inflammation" Perspectives in Drug Discovery and Design, vol. 6, pp 87–98 1996.

Terry Y. Nakagawa, et al. "Impaired Invariant Chain Degradation and Antigen Presentation and Diminished Collagen–Induced Arthritis in Cathepsin S Null Mice" Immunity, vol. 10, 207–217, 1999.

Jan Potempa, et al. "Host and Porphyromonas gingivalls proteinases in periodonitis: A biochemical model of infection and tissue destruction" Perspectives in Drug Discovery and Design, 2 (1994) 445–458.

Richard J. Riese, et al. "Essential Role for Cathepsin S in MHC Class II–Associated Invariant Chain Processing and Peptide Loading" Immunity, vol. 4, pp 357–366, 1996.

Richard J. Riese, et al. "Cathepsin S Activity Regulates Antigen Presentation and Immunity" J. Clin. Invest. vol. 101, No. 11, 1998, pp 2351–2363.

Gideon A. Rodan, et al. "Therapeutic Approaches to Bone Diseases" Science vol. 289, pp 1508–1514, 2000.

Kaoru Saegusa, et al. "Cathepsin S inhibitor prevents autoantigen presentation and autoimmunity" J. Clin. Invest. 2002, vol. 110, No. 3 pp 361–369.

Paul Saftig, et al. "Impaired osteoclastic bone resorption leads to osteopetrosis in cathepsin–K–deficient mice" Proc. Natl. Acad. Sci. USA, 1998, vol. 95, pp 13453–13458.

Andrey Semenov, et al. "Antimalarial Synergy of Cysteine and Aspartic Protease Inhibitors" Antimicrobial Agents and Chemotherapy 1998, vol. 42, No. 9, pp 2254–2258.

Guo–Ping Shi, et al. "Cathepsin S Required for Normal MHC Class II Peptide Loading and Germinal Center Development" Immunity, vol. 10, pp 197–206, 1999.

Guo–Ping Shi, et al. "Role for Cathepsin F in Invariant Chain Processing and Major Histocompatibility Complex Class II Peptide Loading by Macrophages" J. Exp. Med. vol. 191, No. 7, 2000, pp 1177–1185.

Ward W. Smith, et al. "Cathepsin K as a target for the treatment of osteoporosis" Expert Opinion on Therapeutic Patents 1999, 9(6):683–694.

Galina K. Sukhova, et al. "Expression of the Elastolytic Cathepsins S and K in human Atheroma and Regulation of their Production in Smooth Muscle Cells" J. Clin. Invest. vol. 102, No. 3, 1998, pp 576–583.

Nobuhiro Suzumori, et al. "Increased concentrations of cathepsin D in peritoneal fluid from women with endometriosis" Mol. Human Reprod. vol. 7, No. 5 pp 459–462, 2001.

Dennis S. Yamashita, et al. "Cathepsin K and the Design of Inhibitors of Cathepsin K" Curr. Pharm. Design, 2000, vol. 6, 1–24.

Tao Zheng, et al. "Inducible targeting of IL–13 to the adult lung causes matrix metalloproteinase—and cathepsin–dependent emphysema" J. Clin. Invest. 2000, vol. 106, No. 9, pp 1081–1093.

Howard C. Ansel, et al. "Pharmaceutical Dosage Forms and Drug Delivery Systems" Fifth Edition, Lea & Febiger 1990, pp 51–133.

Atkinson, et al; "Desilylative elimination of the quinazolinone ring from 1–(4–oxoquinazolin–3–yl)–2–silylaziridines; preparation of an N–H aziridine in high enantiomeric excess by in situ nucleophilic addition to the derived azirine"; J Chem Soc Perkin Trans 1, 1997, pp. 897–900.

Atkinson, et al, "Preparation of N–H aziridines in high enantiomeric excess by in situ azirdine–azirine–aziridine interconversion"; Chem Commun 1996, pp 789–790.

Bergemann, et al; "Studies on the Reactivity of alpha–Cyano–alpha–isocyanoalkanoates–Versatile Synthons for the Assembly of Imidazoles"; Helvetica Chimica Acta, vol. 82(1999), pp 909–916.

Bossard, et al; "Mechanism of Inhibition of Cathepsin K by Potent, Selective 1,5–Diacylcarbohydrazides: A New Class of Mechanism–Based Inhibitors of Thiol Proteases"; Biochemistry 1999, 38, pp 15893–15902.

DesJarlais, et al; "Use of X–ray Co–crystal Structures and Molecular Modeling To Design Potent and Selective Non–peptide Inhibitors of Cathepsin K"; J Am Chem Soc 1998. 120. pp. 9114–9115.

Falgueyret, et al; "Novel, Nonpeptidic Cyanamides as Potent and Reversible Inhibitors of Human Cathepsins K and L"; J Med Chem 2001, 44, pp 94–104.

Gour–Salin, et al; "Inhibition of papain by peptide nitriles: conversion of the nitrile group into other functionalities via the papain:nitrile thioimidate ester adduct1"; Can J Chem vol. 69, 1991, pp. 1288–1297.

Hanzlik, et al; "Reversible binding of peptide aldehydes to papain. Structure–activity relationships"; Biochimica et Biophysica Acta, 1073, 1991, pp. 33–42.

Hanzlik, et al; "Reversible covalent binding of peptide nitriles to papain"; Biochimica et Biophysica Acta, 1035, 1990, pp. 62–70.

Koos, et al; "alpha–Amino–alpha–Trifluoromethyl–Phenylacetonitrile: A Potential Reagent For 19F NMR Determination of Enantiometric Purity of Acids"; Tetrahedron, vol. 49, No. 8, 1993, pp. 1541–1546.

Liang, et al; "Inhibition of Papain by Nitriles: Mechanistic Studies Using NMR and Kinetic Measurements1"; Archives of Biochemistry and Biophysics, vol. 252, No. 2, 1987, pp. 626–634.

Liu, et al; "The contribution of intermolecular hydrogen bonding to the kinetic specificity of papain"; Biochimica et Biophysica Acta. 1158, 1993, pp. 264–272.

Liu, et al; "Structure–Activity Relationships for Inhibition of Papain by Peptide Michael Acceptors"; J Med Chem 1992, 35, pp. 1967–1075.

Marquis, et al; "Azepanone–Based Inhibitors of Human and Rat Cathepsin K"; J Med Chem, 2001, 44, pp. 1380–1395.

Marquis, et al; "Cyclic Ketone Inhibitors of the Cysteine Protease Cathepsin K"; J Med Chem 2001, 44, pp. 725–736.

Marquis, et al; "Potent Dipeptidylketone Inhibitors of the Cysteine Protease Cathepsin K"; Bioorganic & Medicinal Chemistry, 7, 1999, pp. 581–588.

Palmer, et al; "Vinyl Sulfones as Mechanism–Based Cysteine Protease Inhibitors"; J Med Chem, 1995, 38 pp. 3193–3196.

Rasnick, et al; "Small sythetic inhibitors of cysteine proteases"; Perspectives in Drug Discovery and Design, vol. 6, pp. 47–63.

Thompson et al; "Design of potent and selective human cathepsin K inhibitors that span the active site"; Proc Natl Acad Sci USA, vol. 94, 1997, pp. 14249–14254.

Thompson, et al; "Structure–Based Design of Cathepsin K Inhibitors Containing a Benzyloxy–Substituted Benzoyl peptidomimetic"; J Med Chem 1998, 41, pp. 3923–3927.

Votta, et al; "Peptide Aldehyde Inhibitors of Cathepsin K Inhibit Bone Resorption both In Vitro and In Vivo"; J Bone and Mineral Research; vol. 12, 1997, pp. 1396–1406.

Xia, et al; "Localization of Rat Cathepsin K in Osteoclasis and Resorption Plts: Inhibition of Bone Resorption and Cathepsin K–Activity by Peptidyl Vinyl Sulfones"; Biol. Chem., vol. 380, 1999, pp. 679–687.

Yamashita, et al; "Solid–Phase Synthesis of a Combinatorial Array of 1,3–Bis(acylamino)–2–butanones, Inhibitors of the Cysteine Proteases Cathepsins K and L"; J Comb Chem 1999, 1, pp. 207–215.

Marquis, et al; "Conformationally Constrained 1,3–Diamino Ketones: A Series of Potent Inhibitors of the Cysteine Protease Cathepsin K"; J Med Chem; 1998; 41, pp. 3563–3567.

* cited by examiner

NITRILES USEFUL AS REVERSIBLE INHIBITORS OF CYSTEINE PROTEASES

This application claims the benefit of U.S. Provisional Application No. 60/296,863, filed on Jun. 8, 2001, which application is herein incorporated by reference in its entirety.

FIELD OF THE INVENTION

This invention relates to peptidyl carbamates and related compounds. The compounds are reversible inhibitors of the cysteine proteases cathepsins S, K, F, L and B and certain embodiments described are preferable for inhibition of cathepsin K. The compounds are therefore useful in the treatment of cysteine protease mediated diseases including osteoporosis, autoimmune diseases and other related diseases. The invention also relates to processes for preparing such compounds and pharmaceutical compositions comprising them.

BACKGROUND OF THE INVENTION

Cathepsin K and cathepsin S are members of the papain family, within the papain superfamily of cysteine proteases. The papain family is the largest group of cysteine proteases and includes proteases such as cathepsins B, H, K, L, O and S. (A. J. Barrett et al., 1996, Perspectives in Drug Discovery and Design, 6, 1). The cysteine proteases have important roles in human biology and diseases including osteoporosis, chronic inflammation and immune disorders, atherosclerosis, and emphysema (H. A. Chapman et al., 1997, Ann. Rev. Physiol., 59, 63). Cysteine proteases are also involved in the pathogenesis of some infectious diseases, including malaria (A. Semenov et al., Antimicrobial Agents and Chemotherapy, 1998, 42, 2254) and Chagas' disease, (J. C. Engel et al., J. Exp. Med., 1998, 188, 725). Bacterial cysteine proteases contribute to the pathogenesis of gingivitis (J. Potempa et al., Perspectives in Drug Discovery and Design, 1994, 2, 445).

Cathepsin K has been found to be highly expressed in osteoclasts, cells involved in bone resorption (F. H. Drake et al., J. Biol. Chem., 1996, 271, 12511). Collagen and osteonectin, two protein components of bone matrix have been found to be substrates of activated cathepsin K (M. J. Bossard et al., J. Biol. Chem., 1996, 271, 12517). Inhibitors of cathepsin K have been shown to have anti-resorptive activity in vitro and in vivo (S. K. Thompson et al., Proc. Natl. Acad. Sci. USA, 1997, 94, 14249). The essential role of cathepsin K in bone resorption has also been confirmed in cells and organisms lacking this protease. At the cellular level, cathepsin K deficient osteoclasts, when tested for functional activity on dentine, produced fewer resorption pits as compared to wild-type osteoclasts (P. Saftig et al., Proc Natl Acad Sci USA 1998, 95,13453). Cathepsin K knockout mice develop osteopetrosis, a disease characterized by an increase in bone mass, due to a deficit in matrix degradation but not demineralization of hydroxyapatite. These knockout mice displayed osteopetrosis of the long bones and vertebrae as well as abnormal joint morphology (M. Gowen et al., J. Bone Miner Res. 1999, 14, 1654). The phenotype of the cathepsin K knockout mice resembles the human genetic disorder pycnodysostosis which is due to a mutation in the cathepsin K gene (W-S Hu et al., Journal of Clinical Investigation, 1999, 103, 731; B. D. Gelb et al, Science, 1996, 273, 1236). Patients with this disease have short, dense bones. These and other findings suggest that cathepsin K may play an important role in diseases involving bone resorption, excessive bone loss or cartilage or bone matrix degradation including osteoporosis (D. S Yamashita et al, Current Pharmaceutical Design, 2000, 6, 1), Gaucher disease (M. T. Moran et al, Blood, 2000, 96, 1969), Paget's disease, gingivitis, and periodontitis (G. A. Rodan et al, Science, 2000, 289, 1508), and rheumatoid arthritis (K. M. Hummel et al, J. Rheumatol., 1998, 25, 1887) (also see for example H. A. Chapman et al, Annu. Rev. Physiol., 1997, 59, 63; M. Gowen, Exp. Opin. Invest. Drugs, 1997, 6, 1199; and W. W. Smith et al., Exp. Opin. Ther. Patents, 1999, 9, 683).

The inhibition of cathepsin K has been described by B. D. Gelb et al (U.S. Pat. No. 5,830,850) as a method to ameliorate symptoms caused by bone resorption disorders, including osteoporosis, arthritides and periodontal disease, and damage caused by macrophage-medicated inflammatory processes. Studies in breast cancer research have shown that invading breast cancer cells have expressed low levels of Cathepsin K suggesting that these tumor cells may be able to directly resorb bone by the release of Cathepsin K. Inhibition of Cathepsin K may play a role in the metastatic potential and course of the disease (A. J. Littlewood-Evans et al, Cancer Research, 1997, 57, 5386). Increases in bone resorption and demineralization of bone are skeletal complications associated with many cancers and with bone metastases of breast and prostate tumors (G. A. Rodan et al, Science, 2000, 289, 1508). Cathepsin K has also been observed in giant cell aortitis suggesting that disorders associated with excessive elastin degradation such as lymphangiomyomatosis, vascular inflammation, and cardiovascular disease such as atherosclerosis may be attenuated with Cathepsin K inhibitors (H. A. Chapman et al, Annu. Rev. Physiol., 1997, 59, 63; D. S Yamashita et al, Current Pharmaceutical Design, 2000, 6, 1; and G. K. Sukhova et al, J. Clin. Invest., 1998, 102, 576).

Cathepsin S plays a key role in regulating antigen presentation and immunity (H. A. Chapman, 1998, Current Opinion in Immunology, 10, 93; R. J. Riese et al., 1998, J. Clin. Invest., 101, 2351; R. J. Riese et al., 1996, Immunity, 4, 357). Cathepsin S deficient mice have impaired invariant chain degradation resulting in decreased antigen presentation and germinal center formation, and diminished susceptibility to collagen-induced arthritis indicating the therapeutic potential for a cathepsin S inhibitor (G. Shi et al., 1999, Immunity, 10, 197; T. Y. Nakagawa et al, 1999, Immunity, 10, 207).

Control of antigen-specific immune responses has long been desirable as a useful therapy for autoimmune diseases. Such diseases include Crohn's disease, rheumatoid arthritis, and Multiple Sclerosis, as well as other T-cell-mediated immune responses (C. Janeway and P. Travers, 1996, Immunobiology, The Immune System in Health and Disease, Chapter 12). Furthermore, cathepsin S, which has broad pH specificity, has been implicated in a variety of other diseases involving extracellular proteolysis, such as Alzheimer's disease (U. Muller-Ladner et al., 1996, Perspectives in Drug Discovery and Design, 6, 87), atherosclerosis (G. K. Sukhova et al., 1998, J. Clin. Invest., 102, 576) and endometriosis (WO 9963115, 1999). A cathepsin S inhibitor has been found to block the rise in IgE titers and eosinophil infiltration in the lung in a mouse model of pulmonary hypersensitivity, suggesting that cathepsin S may be involved in asthma (R. J. Riese et al., J. Clin. Investigation, 1998, 101, 2351). Cathepsin inhibitors such as Leupeptin and E-64 were shown to have positive effects in a murine model of emphysema (J. A. Elias et al., J. Clin. Investigation, 2000, 106, 1081).

Another cysteine protease, cathepsin F has been found in macrophages and is also involved in antigen processing. It has been postulated that cathepsin F in stimulated lung macrophages and possibly other antigen presenting cells could play a role in airway inflammation (G.-P. Shi et al., J. Exp. Med., 2000, 191, 1177).

Cysteine proteases are characterized by having a cysteine residue at the active site which serves as a nucleophile. The active site also contains a histidine residue. The imidazole ring on the histidine serves as a base to generate a thiolate anion on the active site cysteine, increasing its nucleophilicity. When a substrate is recognized by the protease, the amide bond to be cleaved is directed to the active site, where the thiolate attacks the carbonyl carbon forming an acyl-enzyme intermediate and cleaving the amide bond, liberating an amine. Subsequently, water cleaves the acyl-enzyme species regenerating the enzyme and liberating the other cleavage product of the substrate, a carboxylic acid.

Inhibitors of cysteine proteases contain a functionality that can react reversibly or irreversibly with the active site cysteine. Examples of reactive functionalities that have been described (D. Rasnick, 1996, Perspectives in Drug Discovery and Design, 6, 47) on cysteine protease inhibitors include peptidyl diazomethanes, epoxides, monofluoroalkanes and acyloxymethanes, which irreversibly alkylate the cysteine thiol. Other irreversible inhibitors include Michael acceptors such as peptidyl vinyl esters and other carboxylic acid derivatives (S. Liu et al., J. Med Chem., 1992, 35, 1067) and vinyl sulfones (J. T. Palmer et al., 1995, J. Med Chem., 38, 3193).

Reactive functionalities that form reversible complexes with the active site cysteine include peptidyl aldehydes (R. P. Hanzlik et al., 1991, Biochim. Biophys. Acta., 1073, 33), which are non-selective, inhibiting both cysteine and serine proteases as well as other nucleophiles. Peptidyl nitrites (R. P. Hanzlik et al., 1990, Biochim. Biophys. Acta., 1035, 62) are less reactive than aldehydes and therefore more selective for the more nucleophilic cysteine proteases. Various reactive ketones have also been reported to be reversible inhibitors of cysteine proteases (D. Rasnick, 1996, ibid). In addition to reacting with the nucleophilic cysteine of the active site, reactive ketones may react with water, forming a hemiketal which may act as a transition state inhibitor.

Inhibitors of cathepsin K have been reported in the literature. D. S. Yamashita et al., (J. Am. Chem. Soc., 1997, 119, 11351) described 1,3-diamino-2-propanone inhibitors. S. K. Thompson et al. (Proc. Natl. Acad. Sci. USA, 1997, 94, 14249) described bis-aza analogs of these propanones as well as an aza-thiazole derivative. Introduction of a conformational constraint to the 1,3-diamino-2-propanones has led to 3-amido-pyrrolidin-4-one derivatives, 4-amido-piperidin-3-one derivatives, and eventually to azapanone-based inhibitors of Cathepsin K, as reported by R. W. Marquis et al. (J. Med. Chem. 1998, 41, 3563; J. Med. Chem. 2001, 44, 725; J. Med. Chem. 2001, 44, 1380). R. W. Marquis et al. (Bioorg. and Med. Chem. Letters, 1999, 7, 581) described peptidic alkoxymethylketones and thiomethylketones as cathepsin K inhibitors. Peptidyl vinyl sulfone cathepsin K inhibitors were described by L. Xia et al. (Biological Chem., 1999, 380, 679). Peptide aldehyde inhibitors of cathepsin K were reported by B. J. Votta et al. (J. Bone & Mineral Res., 1997, 12, 1396). J.-P. Falgueyret et al. (J. Med. Chem. 2001, 44, 94–104) described non-peptidic cyanamides as potent Cathepsin K inhibitors. T. Gamble et al. (49$^{th}$ Annual American Society for Mass Spectrometry Conference, May 27–31, 2001, Chicago, Ill.) described in vitro metabolism studies on cyanamide-containing Cathepsin K inhibitors. D. F. Veber has discussed numerous inhibitors of Cathepsin K including the following: 1,5-diacylcarbohydrazides (Biochemistry, 1999, 38, 15893; J. Med. Chem. 1998, 41, 3923), conformationally constrained 1,3-diamino ketones (J. Med. Chem. 1998; 41, 3563), and 1,3-bis(acylamino)-2-butanones, (J. Combinatorial Chem. 1999, 1, 207; J. Am. Chem. Soc. 1998, 120, 9114; J. Am. Chem. Soc. 1997, 119, 11351).

Examples of cathepsin S inhibitors have been reported. J. L. Klaus et al. (WO 9640737) described reversible inhibitors of cysteine proteases including cathepsin S, containing an ethylene diamine. In U.S. Pat. No. 5,776,718 to Palmer et al. there is disclosed in it's broadest generic aspect a protease inhibitor comprising a targeting group linked through a two carbon atom chain to an electron withdrawing group (EWG). The compounds of the present application are structurally distinct and are thus excluded from the disclosure in the U.S. Pat. No. 5,776,718. Other examples of cathepsin S inhibitors have been reported by E. T. Altmann et al, (WO 9924460, 1999) which describes dipeptide nitrites asserted to have activity as inhibitors of Cathepsins B, K, L and S. The WO publication does not disclose any compounds possessing a carboxylate linkage, Y—C(O)—O—, and fails to provide any description, methods or examples for particular spiroheterocylic moieties at the P1 position.

Certain acetamido acetonitrile derivatives have been disclosed by Tucker et al. (WO 00/49007) as inhibitors of cathepsin S and L. This WO publication likewise does not disclose or suggest any compounds possessing the carboxylate linkage, Y—C(O)—O—, as in the novel compounds according to the present invention.

Certain other cathepsin inhibitors have recently been disclosed by Marquis et al., WO 00/38687 and WO 00/39115; Altmann et al, WO 00/48993; Buysse et al., WO 00/55124; Singh et al, WO 00/59881 and Cowen et al. (WO 01/87828). Cathepsin inhibitors containing a cyclic cyanamide functionality were described by P. Prasit et al. (WO 01/77073). The compounds of the present invention are structurally distinct from the compounds disclosed in the aforementioned references.

Additional peptidyl nitrites have been reported as protease inhibitors. For example, both nitrites and ketoheterocycles are described by B. A. Rowe et al. (U.S. Pat. No. 5,714,471) as protease inhibitors useful in the treatment of neurodegenerative diseases. Peptidyl nitrites are reported by B. Malcolm et al. (WO 9222570) as inhibitors of picornavirus protease. B. J. Gour-Salin (Can. J. Chem., 1991, 69, 1288) and T. C. Liang (Arch. Biochim. Biophys., 1987, 252, 626) described peptidyl nitrites as inhibitors of papain.

A reversible inhibitor presents a more attractive therapy than irreversible inhibitors. Even compounds with high specificity for a particular protease can bind non-target enzymes. An irreversible compound could therefore permanently inactivate a non-target enzyme, increasing the likelihood of toxicity. Furthermore, any toxic effects resulting from inactivation of the target enzyme would be mitigated by reversible inhibitors, and could be easily remedied by modified or lower dosing. Finally, covalent modification of an enzyme by an irreversible inhibitor could potentially generate an antibody response by acting as a hapten.

In light of the above, there is a clear need for compounds which reversibly and selectively inhibit cysteine proteases such as cathepsin K and cathepsin S for indications in which these proteases exacerbate disease.

BRIEF DESCRIPTION OF THE INVENTION

It is therefore an object of this invention to provide novel compounds according to the formula (I) as described herein which reversibly inhibit the cysteine proteases, such as cathepsins K, S, F, L and B. It is a further object of the invention to provide methods for treating diseases and pathological conditions exacerbated by these cysteine proteases such as, but not limited to, rheumatoid arthritis, multiple sclerosis, and other autoimmune diseases, osteoporosis, asthma, Alzheimer's disease, atherosclerosis and endometriosis. It is yet a further object of the invention to provide novel processes for preparation of the above-mentioned novel compounds.

DETAILED DESCRIPTION OF THE INVENTION

A proposed mechanism of action of the cysteine protease inhibitors of this invention is that the inhibitors contain a functionality that can react (reversibly or irreversibly) with the active site cysteine. The reactive functionality is attached to a peptide or peptide mimic that can be recognized and accommodated by the region of the protease surrounding the active site. The nature of both the reactive functionality and the remaining portion of the inhibitor determine the degree of selectivity and potency toward a particular protease.

Given the similarity of the active sites in cysteine proteases, it may be anticipated that a given class of inhibitors might have activity against more that one cysteine protease. It may also be expected that due to structural differences between individual cysteine proteases, different compounds of the invention may have different inhibitory potencies against different cysteine proteases. Thus some of the compounds of the invention may also be expected to be most effective in treating diseases mediated by cysteine proteases that they inhibit most potently. The activity of particular compounds disclosed herein against cysteine proteases cathepsin K, S, F, L and B may be determined by the screens described in the section entitled "Assessment of Biological Properties."

As used herein, each of the following terms, used alone or in conjunction with other terms, are defined as follows (except where noted to the contrary):

The term "alkyl" refers to a saturated aliphatic hydrocarbon radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups, each optionally partially or fully halogenated. Examples of "alkyl" include alkyl groups which are straight chain alkyl groups containing from one to eight carbon atoms and branched alkyl groups containing from three to eight carbon atoms. Other examples include alkyl groups which are straight chain alkyl groups containing from one to six carbon atoms and branched alkyl groups containing from three to six carbon atoms. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O).

The term "cycloalkyl" refers to the mono- or polycyclic analogs of an alkyl group, as defined above, including fully saturated and mono- or polyunsaturated groups. Examples of cycloalkyl groups are saturated cycloalkyl groups containing from three to eight carbon atoms, for example, three to six carbon atoms. Examples of polycyclic cycloalkyl groups include, for example, tetrahydronaphthalene and indane.

The term "aryl" refers to 6–10 membered mono- or polycyclic aromatic carbocycles, for example, phenyl and naphthyl. The term "aryl" includes aryl groups that are optionally partially or fully halogenated.

The term "halo" refers to a halogen radical selected from fluoro, chloro, bromo or iodo. Representative halo groups of the invention are fluoro, chloro and bromo.

The term "heterocycle" or "heterocyclyl" refers to a stable 4–8 membered (but preferably, 5 or 6 membered) monocyclic or 8–11 membered bicyclic heterocycle radical which may be either saturated or unsaturated, and is non-aromatic, and may be optionally partially or fully halogenated. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heterocycle" include radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, tetrahydroquinoline, tetrahydroisoquinoline, azetidinyl, oxetanyl, dihydrobenzofuranyl, dihydrobenzothienyl, tetrahydropyranyl, tetrahydrothiopyranyl, tetrahydrofuranyl, hexahydropyrimidinyl, hexahydropyridazinyl, 1,4,5,6-tetrahydropyrimidin-2-ylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione.

The term "heteroaryl" refers to a stable 5–8 membered (but preferably, 5 or 6 membered) monocyclic or 8–11 membered bicyclic aromatic heterocycle radical, each optionally partially or fully halogenated. Each heterocycle consists of carbon atoms and from 1 to 4 heteroatoms chosen from nitrogen, oxygen and sulfur. The heterocycle may be attached by any atom of the cycle, which results in the creation of a stable structure. Examples of "heteroaryl" include radicals such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzothiazolyl, benzoxazolyl, benzisoxazolyl, benzisothiazolyl, purinyl, quinolizinyl, quinolinyl, isoquinolinyl, cinnolinyl, phthalazinyl, quinazolinyl, quinoxalinyl, naphthyridinyl, pteridinyl, carbazolyl, acridinyl, phenazinyl, phenothiazinyl and phenoxazinyl, Each aryl or heteroaryl unless otherwise specified includes its partially or fully hydrogenated derivative. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

The terms "heterocycle", "heteroaryl" or "aryl", when associated with another moiety, unless otherwise specified shall have the same meaning as given above. For example, "aroyl" refers to aryl linked to a carbonyl group (C=O).

The phrase "C6–C10 bridged bicyclic ring group" means any bicyclic ring group having from 6 to 10 carbon atoms and containing a chemical bridging group, which bicyclic group may also contain one or more double bonds in the rings. Examples of such bicyclic ring groups for this definition of $R_4+R_5$ include: aza-bicyclo[3.2.1]octane, aza-bicyclo[2.2.1]heptane, aza-bicyclo[2.2.2]octane, aza-bicyclo[3.2.2]nonane, aza-bicyclo[2.1.1]hexane, aza-bicyclo[3.1.1]heptane, aza-bicyclo[3.3.2]decane and 2-oxa and 2-thia-5-aza-bicyclo[2.2.1]heptane.

As used herein above and throughout this application, "nitrogen" and "sulfur" include any oxidized form of nitrogen and sulfur and the quaternized form of any basic nitrogen, including protonated species and quaternary ammonium salt forms.

In the broadest generic aspect, the invention provides novel compounds of the formula (I):

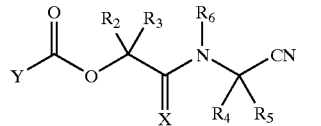

(I)

wherein:
Y is $R_1$, $R_1O$—, $R_1S$—, $(R_1)_2N$—, $(R_1)_3C$—;
Each $R_1$ is independently hydrogen, C1–10 alkyl, C3–8 cycloalkyl, aryl, benzyl, tetrahydronaphthyl, indenyl, indanyl, C1–10alkylsulfonylC1–10alkyl, C3–8cycloalkylsulfonylC1–10alkyl, arylsulfonylC1–10alkyl, a heterocyclyl or heteroaryl selected from pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, dihydrobenzofuranyl, dihydrobenzothienyl, benzimidazolyl, benzothiazolyl, benzisoxazolyl, benzisothiazolyl, quinolinyl, tetrahydroquinolinyl, isoquinolinyl, tetrahydroisoquinolinyl, quinazolinyl, tetrahydroquinazolinyl, benzoxazolyl, 2H-benzo[e][1,3]oxazine and quinoxalinyl,
wherein each $R_1$ is optionally substituted by one or more $R_a$;
or $R_1$ is $R_a$ or $R_b$;
Each $R_a$ is independently hydrogen, C1–10 alkyl, C3–8 cycloalkyl, aryl, tetrahydronaphthyl, indenyl, indanyl, a heterocycle or heteroaryl selected from the group consisting of pyrrolidinyl, piperidinyl, morpholinyl, thiomorpholinyl, piperazinyl, indolinyl, furanyl, thienyl, pyrrolyl, oxazolyl, dihydro-oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, benzoxazolyl, benzisoxazolyl, quinolinyl, isoquinolinyl, quinazolinyl, and quinoxalinyl, C1–10 alkoxy, C1–10alkanoyl, C1–10alkanoyloxy, aryloxy, benzyloxy, aroyl, C1–10 alkoxycarbonyl, aryloxycarbonyl, aroyloxy, heterocyclyloxy, heterocyclyl-C1–6alkoxy, heteroaryloxy or heteroaryl-C1–6alkoxy, wherein the heterocyclyl or heteroaryloxy moiety is selected from those described in this paragraph, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl,
or $R_a$ is C1–10 mono- or dialkyl amino, C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by one or more C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_a$ is C1–10 alkoxycarbonylamino, aryloxycarbonylamino, heterocyclylcarbonylamino, heteroarylcarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl,
or $R_a$ is halogen, hydroxy, oxo, carboxy, cyano, nitro, carboxamide, amidino or guanidino,
wherein $R_a$ may be further optionally substituted by one or more $R_b$;
$R_b$ is a C1–6 saturated or unsaturated alkyl group wherein one or more carbon atoms are optionally replaced by O, N, S(O), S(O)$_2$ or S and wherein said alkyl group is optionally independently substituted with one or two oxo groups, and/or one or more: —NH$_2$, C1–4 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl;
or $R_b$ is C3–6 cycloalkyl, C1–6 alkoxy, aryl, aryloxy, benzyloxy, halogen, hydroxy, oxo, carboxy, cyano, nitro, mono-C1–5alkylamino, di-C1–5alkylamino, carboxamide, amidino or guanidino;
$R_2$ and $R_3$ are each independently a hydrogen, C3–8 cycloalkyl, arylC1–5alkyl, aryl, or a C1–10 saturated or unsaturated alkyl group wherein one or more C atoms are optionally replaced by O, NH, S(O), S(O)$_2$ or S and wherein said alkyl group is optionally independently substituted with one or two oxo groups, and/or one or more: —NH$_2$, C$_{1-4}$ alkyl, aryl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl, benzoxazolyl or quinoxalinyl; wherein each $R_2$ and $R_3$ is independently optionally substituted by one or more $R_c$; or $R_2$ and $R_3$ are each independently $R_c$;

$R_c$ is C1–10 alkyl, C3–8 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiro[2.5]octanyl, cubanyl, tetrahydronaphthyl, decahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, dihydrobenzofuranyl, octohydrobenzofuranyl, benzofuranyl, benzothienyl, dihydrobenzofuranyl, dihydrobenzothienyl, benzimidazolyl, benzothiazolyl, tetrahydroquinolinyl, quinolinyl, tetrahydroisoquinolinyl, isoquinolinyl, quinazolinyl, quinoxalinyl, C1–10 alkoxy, aryloxy, C1–10 alkanoyl, aroyl, C1–10 alkoxycarbonyl, aryloxycarbonyl, C1–10 alkanoyloxy, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_c$ is C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_c$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_c$ is halogen, hydroxy, oxo, carboxy, cyano, nitro, amidino or guanidino;

Each $R_c$ may be further optionally substituted by one or more $R_d$;

$R_d$ is C1–5 alkyl, C3–6 cycloalkyl, aryl, arylC1–5alkyl, C1–5 alkoxy, aryloxy, arylC1–5alkoxy, aroyl, amino, halogen, hydroxy, oxo, carboxy, cyano, nitro, amidino or guanidino; or $R_2$ and $R_3$ together with the carbon they are attached optionally form a nonaromatic 3–10 membered mono- or bicyclic optionally partially unsaturated cycloalkyl or a 3–10 membered mono- or bicyclic heterocycle each in turn optionally substituted by one or more $R_c$ as described hereinabove;

$R_4$ and $R_5$ are each independently a hydrogen, or a C1–10 saturated or unsaturated alkyl group wherein one or more C atoms are optionally replaced by O, NH, S(O), S(O)$_2$ or S and wherein said alkyl group is optionally independently substituted with one or two oxo groups, and/or one or more: —NH$_2$, C$_{1-4}$ alkyl, aryl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl, benzoxazolyl or quinoxalinyl;

or $R_4$ and $R_5$ are each independently C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, C3–7cycloalkylsulfonylC1–5alkyl, arylsulfonylC1–5alkyl, heterocyclyl selected from pyrrolidinyl, piperidinyl, morpholinyl, thiomorpholinyl, piperazinyl, indolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridizinyl, tetrazolyl, triazolyl, pyrazolyl, indolyl, benzofuranyl, benzothienyl, dihydrobenzofuranyl, dihydrobenzothienyl, benzimidazolyl, benzothiazolyl, quinolinyl, tetrahydroquinolinyl, isoquinolinyl, tetrahydroisoquinolinyl, quinazolinyl, tetrahydroquinazolinyl, benzoxazolyl and quinoxalinyl, C1–10alkanoyl, aroyl, C1–10alkoxycarbonyl, arylC1–5alkoxycarbonyl, aryloxycarbonyl, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_4$ and $R_5$ are each independently C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_4$ and $R_5$ are each independently C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_4$ and $R_5$ are each independently halogen, hydroxy, carboxy, cyano, nitro, carboxamide, amidino or guanidino;

wherein each $R_4$ and $R_5$ may be further optionally independently substituted by one or more $R_e$;

or $R_4$ and $R_5$ together with the carbon they are attached to optionally form a heterocyclic ring said heterocyclic ring being selected from:

azepanyl, piperidinyl, pyrrolidinyl, azetidinyl, oxepanyl, tetrahydropyranyl, tetrahydrothiopyranyl, tetrahydrofuranyl, oxetanyl, azocanyl, oxocanyl, 1,3-diazocanyl, 1,4-diazocanyl, 1,5-diazocanyl, 1,3-dioxocanyl, 1,4-dioxocanyl, 1,5-dioxocanyl, 1,3-oxazocanyl, 1,4-oxazocanyl, 1,5-oxazocanyl, 1,3-diazepanyl, 1,4-diazepanyl, 1,3-dioxepanyl, 1,4-dioxepanyl, 1,3-oxazepanyl, 1,4-oxazepanyl, 1,2-thiazocanyl-1,1-dioxide, 1,2,8-thiadiazocanyl-1,1-dioxide, 1,2-thiazepanyl-1,1-dioxide, 1,2,7-thiadiazepanyl-1,1-dioxide, tetrahydrothiophenyl, hexahydropyrimidinyl, hexahydropyridazinyl, piperazinyl, 1,4,5,6-tetrahydropyrimidinyl, pyrazolidinyl, dihydrooxazolyl, dihydrothiazolyl, dihydroimidazolyl, isoxazolinyl, oxazolidinyl, 1,2-thiazinanyl-1,1-dioxide, 1,2,6-thiadiazinanyl-1,1-dioxide, isothiazolidinyl-1,1-dioxide, imidazolidinyl-2,4-dione, imidazolidinyl, morpholinyl, dioxanyl, tetrahydropyridinyl, thiomorpholinyl, thiazolidinyl, dihydropyranyl, dithianyl, decahydro-quinolinyl, decahydro-isoquinolinyl, 1,2,3,4-tetrahydro-quinolinyl, indolinyl, octahydro-quinolizinyl, dihydro-indolizinyl, octahydro-indolizinyl, octahydro-indolyl, decahydroquinazolinyl, decahydroquinoxalinyl, 1,2,3,4-tetrahydroquinazolinyl or 1,2,3,4-tetrahydroquinoxalinyl;

or $R_4$ and $R_5$ together with the carbon they are attached to optionally form a C6–C10 bridged bicyclic ring group wherein one or more carbon atoms are optionally replaced by a heteroatom chosen from N, O, S, S(O) or S(O)$_2$;

or $R_4$ and $R_5$ together with the carbon they are attached to optionally form a carbocyclic ring group, said carbocyclic ring group being selected from:

cyclopropanyl, cyclobutanyl, cyclopentanyl, cyclohexanyl, cycloheptanyl, cyclooctanyl, cyclononanyl, cyclodecanyl, cubanyl, bicyclo[1.1.0]propanyl, bicyclo[2.1.0]butanyl, bicyclo[3.1.0]hexanyl, bicyclo[4.1.0]heptanyl, bicyclo[5.1.0]octanyl, bicyclo[2.2.0]hexanyl, bicyclo[3.2.0]heptanyl, bicyclo[4.2.0]octanyl, bicyclo[5.2.0]nonanyl, bicyclo[3.3.0]octanyl, bicyclo[4.3.0]nonanyl, bicyclo[5.3.0]decanyl, bicyclo[4.4.0]decanyl, bicyclo[5.4.0]undecanyl, bicyclo[1.1.1]pentanyl, bicyclo[2.1.1]hexanyl, bicyclo[3.1.1]heptanyl, bicyclo[4.1.1]octanyl, bicyclo[5.1.1]nonanyl, bicyclo[2.2.1]heptanyl, bicyclo[3.2.1] octanyl, bicyclo[4.2.1]nonanyl, bicyclo[5.2.1] decanyl, bicyclo[2.2.2]octanyl, bicyclo[3.2.2]nonanyl, bicyclo[4.2.2]decanyl, bicyclo[5.2.2]undecanyl, bicyclo[3.3.2]decanyl, bicyclo[4.3.2]undecanyl, bicyclo[5.3.2] dodecanyl, bicyclo[3.3.3]undecanyl, bicyclo[4.3.3] dodecanyl, bicyclo[5.3.3]tridecanyl;

each of the above ring groups formed by the combination of $R_4$ and $R_5$ being optionally substituted with one or more $R_e$; or $R_4$ and $R_5$ are each independently $R_e$;

$R_e$ is a C1–10 saturated or unsaturated alkyl group wherein one or more C atoms are optionally replaced by O, NH, S(O), S(O)$_2$ or S and wherein said alkyl group is optionally independently substituted with one or two oxo groups, and/or one or more: —NH$_2$, C$_{1-4}$ alkyl, aryl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl, benzoxazolyl or quinoxalinyl;

or $R_e$ is a C1–10alkoxy, C1–10alkoxyC1–10alkyl, C1–10alkylaminoC1–10alkyl C1–10alkylthioC1–10alkyl wherein the sulfur atom may be oxidized to a sulfoxide or sulfone, C3–8 cycloalkyl, C3–8 cycloalkyloxy, aryl, tetrahydronaphthyl, indenyl, indanyl, pyrrolidinyl, piperidinyl, morpholinyl, thiomorpholinyl, piperazinyl, indolinyl, thiopyranyl, tetrahydrothiopyranyl, pyranyl, tetrahydropyranyl, tetrahydrofuranyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, benzoxazolyl, benzisoxazolyl, quinolinyl, isoquinolinyl, quinazolinyl, quinoxalinyl, C1–10alkanoyl, aroyl, C1–10alkanoyloxy, aryloxy, benzyloxy, C1–10 alkoxycarbonyl, arylC1–3alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_e$ is ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_e$ is amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_e$ is halogen, hydroxy, oxo, carboxy, cyano, nitro, carboxamide, amidino or guanidino, wherein $R_e$ may be further optionally substituted by one or more $R_f$;

$R_f$ is C1–5 alkyl, C3–6 cycloalkyl, tolylsulfonyl, C1–5 alkoxy, aryl, aryloxy, benzyloxy, halogen, hydroxy, oxo, carboxy, cyano, nitro, carboxamide, amidino or guanidino;

or $R_f$ is aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_f$ is amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl;

or $R_f$ is a C1–10 saturated or unsaturated alkyl group wherein one or more C atoms are optionally replaced by O, NH, S(O), S(O)$_2$ or S and wherein said alkyl group is optionally independently substituted with one or two oxo groups, and/or one or more: —NH$_2$, C$_{1-4}$ alkyl, aryl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl, benzoxazolyl or quinoxalinyl;

$R_6$ is hydrogen, hydroxy, C1–3 alkyl, or C3–6 cycloalkyl;

X is O or S; or the pharmaceutically acceptable derivatives thereof;

with the provisos that:

(1) when $R_2$ is hydrogen; and $R_3$ is hydrogen, propyl or phenyl; and $R_4$ is hydrogen, methyl, ethyl or benzyl; and $R_5$ is alkoxycarbonyl; and $R_6$ is hydrogen; then Y is not methyl or chloromethyl;

(2) when $R_2$ is hydrogen; and $R_3$ is phenyl; and $R_4$ is phenyl; and $R_5$ is trifluoromethyl; and $R_6$ is hydrogen; then Y is not methyl;

(3) when $R_2$ is hydrogen or alkyl; and $R_3$ is hydrogen, alkyl or benzyl; and $R_4$ is hydrogen, alkyl or cycloalkyl; and $R_5$ is hydrogen, alkyl or cycloalkyl; or $R_4$ and $R_5$ together with the carbon atom they are attached to form cylopentanyl, cyclohexanyl or cycloheptanyl; and $R_6$ is hydrogen; then Y is not methyl or phenyl substituted by optionally substituted pyrimidinyl.

In another embodiment of the invention, there are provided novel compounds of the formula (I) as described immediately above, and wherein:

Y is $R_1$, $R_1O$—, $(R_1)_2N$— or $(R_1)_3C$—;

Each $R_1$ is independently hydrogen, C1–7 alkyl, C3–7 cycloalkyl, phenyl, naphthyl, benzyl, tetrahydronaphthyl, C1–7alkylsulfonylC1–7alkyl, C3–7cycloalkylsulfonylC1–7alkyl, arylsulfonylC1–7alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, thiazolyl, imidazolyl, pyridinyl, isoxazolyl, pyrimidinyl, pyrazinyl, pyridazinyl, indolyl, quinolinyl, isoquinolyl, tetrahydroisoquinolyl, benzofuranyl, benzothienyl, benzimidazolyl, benzothiazolyl, benzoisoxazolyl, benzisothiazolyl, benzoxazolyl, or 2H-benzo[e][1,3] oxazine; wherein each $R_1$ is optionally substituted by one or more $R_a$; or $R_1$ is $R_a$ or $R_b$;

Each $R_a$ is independently hydrogen, C1–7 alkyl, C3–6 cycloalkyl, phenyl, naphthyl, pyrrolidinyl, piperidinyl, morpholinyl, thiomorpholinyl, piperazinyl, furanyl, thienyl, oxazolyl, dihydro-oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothiazolyl, benzoxazolyl, quinolinyl, isoquinolinyl, quinazolinyl, quinoxalinyl, C1–7 alkoxy, C1–7alkanoyl, C1–7alkanoyloxy, aryloxy, benzyloxy, aroyl, C1–7 alkoxycarbonyl, aryloxycarbonyl, aroyloxy, carbamoyl wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_a$ is C1–7 alkanoylamino, aroylamino, C1–7 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_a$ is C1–7 alkoxycarbonylamino, aryloxycarbonylamino, heterocyclylcarbonylamino, heteroarylcarbonylamino, C1–7 alkylcarbamoyloxy, arylcarbamoyloxy, C1–7 alkylsulfonylamino, arylsulfonylamino, C1–7 alkylaminosulfonyl, arylaminosulfonyl, amino wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_a$ is halogen, hydroxy, oxo, carboxy, cyano, nitro, carboxamide, amidino or guanidino, wherein $R_a$ may be further optionally substituted by one or more $R_b$;

$R_b$ is a C1–6 saturated alkyl group wherein one or two carbon atoms are optionally replaced by O or S and wherein said alkyl group is optionally independently substituted with one or two oxo groups and/or one or more: C1–4 alkyl, aryl, piperidinyl, morpholinyl, thiomorpholinyl or piperazine;

or $R_b$ is C3–6 cycloalkyl, aryl, C1–6 alkoxy, aryloxy, benzyloxy, halogen, hydroxy, oxo, carboxy, cyano, nitro, carboxamide, amidino or guanidino;

$R_2$ is hydrogen or methyl or ethyl;

$R_3$ is a hydrogen, C2–5alkylene, C3–7 cycloalkyl, arylC1–3alkyl, aryl or a C1–6 saturated alkyl group wherein one or two of the C atoms are optionally replaced by O, NH or S;

wherein $R_3$ is optionally substituted by one or more $R_c$; or $R_3$ is $R_c$;

$R_c$ is C1–5 alkyl, C3–7 cycloalkyl, aryl, indanyl, indenyl, bicyclo[2.2.1]heptanyl, bicyclo[2.2.2]octanyl, bicyclo

[4.1.0]heptanyl, bicyclo[3.1.0]hexanyl, bicyclo[1.1.1]pentanyl, spiro[2.5]octanyl, cubanyl, 1,2,3,4-tetrahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl, quinoxalinyl, C1–5 alkoxy, aryloxy, C 1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_c$ is C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_c$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_c$ is halogen, hydroxy, oxo, carboxy, cyano, nitro, amidino or guanidino;

Each $R_c$ may be further optionally substituted by one or more $R_d$;

$R_d$ is C1–5 alkyl, C3–6 cycloalkyl, aryl, arylC1–4-alkyl, C1–5 alkoxy, aryloxy, arylC1–5alkoxy, aroyl, halogen, hydroxy, oxo or cyano;

or $R_2$ and $R_3$ together with the carbon they are attached optionally form a nonaromatic 5–7 membered cycloalkyl or a 5–7 membered heterocycle, each optionally substituted by $R_c$ as described hereinabove;

$R_4$ and $R_5$ are each independently hydrogen, or a C1–8 saturated alkyl group wherein one or two C atoms are optionally replaced by O, S(O), S(O)$_2$ or S and wherein said alkyl group is optionally substituted with one or two oxo groups and/or one or more: aryl, indolyl or indolinyl;

or $R_4$ and $R_5$ are each independently C1–8alkoxyC1–8alkyl, C1–8alkylaminoC1–8alkyl, C1–8alkylthioC1–8alkyl wherein the sulfur atom may be oxidized to a sulfoxide or sulfone, C3–7 cycloalkyl, aryl, tetrahydronaphthyl, indanyl, heterocyclyl selected from pyrrolidinyl, piperidinyl, morpholinyl, thiomorpholinyl, piperazinyl, indolinyl, pyranyl, tetrahydropyranyl, thiopyranyl, tetrahydrothiopyranyl, furanyl, tetrahydrofuranyl, thienyl, oxazolyl, thiazolyl, imidazolyl, pyridinyl, pyrimidinyl, pyrazinyl, tetrazolyl, triazolyl, pyrazolyl, indolyl, benzofuranyl, benzothienyl, benzimidazolyl, benzothiazolyl, quinolinyl, isoquinolinyl, quinazolinyl, benzoxazolyl and quinoxalinyl, C1–7alkanoyl, aroyl, C1–7 alkoxycarbonyl, arylC1–4alkoxycarbonyl, aryloxycarbonyl, carbamoyl wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_4$ and $R_5$ are each independently C1–7 alkanoylamino, aroylamino, C1–7 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–7alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_4$ and $R_5$ are each independently C1–7 alkoxycarbonylamino, aryloxycarbonylamino, C1–7 alkylcarbamoyloxy, arylcarbamoyloxy, C1–7 alkylsulfonylamino, arylsulfonylamino, C1–7 alkylaminosulfonyl, arylaminosulfonyl, amino wherein the nitrogen atom may be independently mono or di-substituted by C1–7 alkyl, aryl, pyrrolidinyl, piperidinyl, morpholinyl, thiomorpholinyl, piperazinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_4$ and $R_5$ are each independently halogen, hydroxy, carboxy, cyano, nitro or carboxamide, wherein each $R_4$ and $R_5$ may be further optionally independently substituted by one or more $R_e$;

or $R_4$ and $R_5$ together with the carbon they are attached optionally form a heterocyclic ring said heterocyclic ring being selected from:

piperidinyl, pyrrolidinyl, tetrahydropyranyl, tetrahydrothiopyranyl, azetidinyl, azepanyl, oxepanyl, tetrahydrofuranyl, oxetanyl, hexahydropyrimidinyl, hexahydropryidazinyl, piperazinyl, 1,4,5,6-tetrahydropyrimidinyl, octahydro-indolizinyl, octahydro-quinolizinyl, decahydro-quinolinyl, 1,2,3,4-tetrahydro-quinolinyl, dihydro-oxazolyl, 1,2-thiazinanyl-1,1-dioxide, 1,2,6-thiadiazinanyl-1,1-dioxide, isothiazolidinyl-1,1-dioxide, imidazolidinyl, pyrazolidinyl or $R_4$ and $R_5$ together with the carbon atom they are attached to form a cyclopropanyl, cyclobutanyl, cyclopentanyl, cyclohexanyl, cycloheptanyl, or a bridged bicyclo group chosen from aza-bicyclo[3.2.1]octane, aza-bicyclo[2.2.1]heptane, aza-bicyclo[2.2.2]octane, aza-bicyclo[3.2.2]nonane, aza-bicyclo[2.1.1]hexane, aza-bicyclo[3.1.1]heptane, aza-bicyclo[3.3.2]decane and 2-oxa or 2-thia-5-aza-bicyclo[2.2.1]heptane;

each ring being substituted with one or more $R_e$;

$R_e$ is C1–8 saturated alkyl group wherein one or two of the C atoms are optionally replaced by O, S(O), S(O)$_2$ or S, and wherein said alkl group is optionally independently substituted with one or two oxo groups and/or one or more: $C_{1-4}$alkyl or aryl;

or $R_e$ is C1–7alkoxy, C1–7alkoxyC1–7alkyl, C1–7alkylaminoC1–7alkyl, C1–7alkylthioC1–7alkyl wherein the sulfur atom may be oxidized to a sulfoxide or sulfone, C3–7 cycloalkyl, aryl, tetrahydronaphthyl, indanyl, pyrrolidinyl, piperidinyl, morpholinyl, thiomorpholinyl, piperazinyl, thiopyranyl, tetrahydrothiopyranyl, tetrahydropyranyl, tetrahydrofuranyl, furanyl, thienyl, oxazolyl, thiazolyl, imidazolyl, pyridinyl, pyrimidinyl, pyrazinyl, indolyl, benzofuranyl, benzothienyl, benzimidazolyl, benzothiazolyl, benzoxazolyl, quinolinyl, isoquinolinyl, quinazolinyl, quinoxalinyl, C1–5 alkanoyl, aroyl, C1–5alkanoyloxy, aryloxy, benzyloxy, C1–5 alkoxycarbonyl, aryloxycarbonyl, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_e$ is ureido wherein either nitrogen atom may be independently substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_e$ is amino wherein the nitrogen atom may be independently mono or di-substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_e$ is halogen, hydroxy, oxo, carboxy, cyano, nitro, carboxamide, amidino or guanidino, wherein $R_e$ may be further optionally substituted by one or more $R_f$;

$R_f$ is methyl, ethyl, t-butyl, tolylsulfonyl, C1–3 alkoxy, cyclopropyl, cyclobutyl, cyclopentyl, cyclohexyl, phenyl, naphthyl, phenoxy, benzyloxy, fluoro, chloro, bromo, hydroxy, oxo, carboxy, cyano, nitro amino or carboxamide;

$R_6$ is hydrogen or methyl; and

X is O.

In yet another embodiment of the invention, there are provided novel compounds of the formula (I) as described immediately above, and wherein:

wherein:

Each $R_1$ is independently hydrogen, C1–5 alkyl, C3–6 cycloalkyl, phenyl, benzyl, naphthyl, C1–3alkylsulfonylC1–3alkyl, C3–6cycloalkylsulfonylC1–3alkyl, arylsulfonylC1–3alkyl, pyrrolidinyl, piperidinyl, morpholinyl, thiomorpholinyl, piperazinyl, furanyl, thienyl, oxazolyl, thiazolyl, imidazolyl, pyridinyl, isoxazolyl, pyrimidinyl, pyrazinyl, pyridazinyl, indolyl, quinolinyl, tetrahydroisoquinolyl, benzofuranyl, benzthienyl, benzimidazolyl, benzothiazolyl, benzoxazolyl, 2H-benzo[e][1,3]oxazine; wherein each $R_1$ is optionally substituted by one or more $R_a$; or $R_1$ is $R_a$ or $R_b$;

Each $R_a$ is independently hydrogen, C1–3 alkyl, cyclopropyl, cyclopentyl, cyclohexyl, phenyl, naphthyl, pyrrolidinyl, piperidinyl, morpholinyl, thiomorpholinyl, piperazinyl, furanyl, thienyl, oxazolyl, dihydro-oxazolyl, thiazolyl, imidazolyl, pyridinyl, pyrimidinyl, benzimidazolyl, benzothiazolyl, benzoxazolyl, C1–3 alkoxy, C1–3alkanoyl, C1–3alkanoyloxy, aryloxy, benzyloxy, aroyl, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl, piperazinyl, thienyl, oxazolyl, thiazolyl, imidazolyl, pyridinyl, pyrimidinyl, benzimidazolyl or benzothiazolyl, or $R_a$ is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or $R_a$ is C1–5 alkoxycarbonylamino, aryloxycarbonylamino, heterocyclylcarbonylamino, heteroarylcarbonylamino, C1–5 alkylcarbamoyloxy, arylcarbamoyloxy, C1–5alkylsulfonylamino, arylsulfonylamino, C1–5 alkylaminosulfonyl, arylaminosulfonyl, amino wherein the nitrogen atom may be independently mono or di-substituted by C1–6 alkyl, aryl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, wherein $R_a$ may be further optionally substituted by one or more $R_b$;

$R_b$ is a C1–6 saturated alkyl group wherein one or two carbon atoms are optionally replaced by O or S and wherein said alkyl group is optionally independently substituted with an oxo group and/or one or more: C1–4 alkyl, aryl, piperidinyl, morpholinyl, thiomorpholinyl or piperazine;

or $R_b$ is C3–6 cycloalkyl, aryl, C1–3 alkoxy, aryloxy, benzyloxy, halogen, hydroxy, oxo, carboxy, cyano, nitro, carboxamide, amidino or guanidino;

$R_2$ is hydrogen or methyl;

$R_3$ is hydrogen, C2–5alkylene, C3–6 cycloalkyl or arylC1–2alkyl, phenyl, naphthyl, or a C1–6 saturated alkyl group wherein one or two of the C atoms are optionally replaced by O, NH or S; wherein $R_3$ is optionally substituted by one or more $R_c$; or $R_3$ is $R_c$;

$R_c$ is C1–4 alkyl, C5–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiro[2.5]octanyl, cubanyl, 1,2,3,4-tetrahydronaphthyl, pyrrolidinyl, piperidinyl, morpholinyl, thiomorpholinyl, indolinyl, furanyl, tetrahydrofuranyl, pyranyl, tetrahydropyranyl, thienyl, pyrrolyl, oxazolyl, thiazolyl, imidazolyl, pyrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl, quinoxalinyl, C1–4 alkoxy, phenoxy, naphthyloxy, C1–3 alkanoyl, benzoyl, C1–3 alkoxycarbonyl, phenoxycarbonyl, C1–3 alkanoyloxy, benzoyloxy, carbamoyl wherein the nitrogen atom may be independently mono or di-substituted by C1–5 alkyl or aryl, or $R_c$ is C1–3 alkanoylamino, benzoylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–5 alkyl or aryl, or $R_c$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–5 alkyl or aryl, or $R_c$ is halogen, hydroxy, oxo, carboxy, cyano, nitro, amidino or guanidino, wherein each $R_c$ may be further optionally substituted by one or more $R_d$;

$R_d$ is C1–3 alkyl, C3–6 cycloalkyl, phenyl, benzyl, C1–3 alkoxy, phenoxy, phenylC1–3alkoxy, benzoyl, halogen, hydroxy, oxo or cyano;

$R_2$ and $R_3$ together with the carbon they are attached optionally form a nonaromatic 5–6 membered cycloalkyl or a 5–6 membered heterocycle, each optionally substituted by $R_c$ as described hereinabove;

$R_4$ and $R_5$ are each independently hydrogen, or a C1–5 saturated alkyl group wherein one or two C atoms are optionally replaced by O, S(O), S(O)$_2$ or S and wherein said alkyl group is optionally substituted with one oxo group and/or one or more: phenyl, naphthyl or indolyl;

or $R_4$ and $R_5$ are each independently C1–6alkoxyC1–6alkyl, C1–6alkylaminoC1–6alkyl, C1–6alkylthioC1–6alkyl wherein the sulfur atom may be oxidized to a sulfoxide or sulfone, C3–6 cycloalkyl, phenyl, naphthyl, indanyl, heterocyclyl selected from pyrrolidinyl, piperidinyl, morpholinyl, thiomorpholinyl, piperazinyl, tetrahydropyranyl, tetrahydrothiopyranyl, furanyl, tetrahydrofuranyl, thienyl, oxazolyl, thiazolyl, imidazolyl, pyridinyl, pyrimidinyl, pyrazolyl, benzofuranyl, benzothienyl, benzimidazolyl, benzothiazolyl, quinolinyl, isoquinolinyl and benzoxazolyl, C1–3alkanoyl, benzoyl, naphthoyl, C1–4 alkoxycarbonyl, arylC1–2alkoxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl or pyrimidinyl, or $R_4$ and $R_5$ are each independently C1–4 alkanoylamino, aroylamino, C1–4 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, phenyl, naphthyl, pyrrolidinyl, piperidinyl, morpholinyl, piperazinyl, oxazolyl, thiazolyl, imidazolyl, pyridinyl, pyrimidinyl, pyrazinyl, indolyl, benzofuranyl, benzothienyl, benzimidazolyl or benzothiazolyl, or $R_4$ and $R_5$ are each independently C1–4 alkoxycarbonylamino, phenoxycarbonylamino, C1–4 alkylcarbamoyloxy, phenylcarbamoyloxy, C1–4 alkylsulfonylamino, phenylsulfonylamino, C1–3 alkylaminosulfonyl, phenylaminosulfonyl, amino wherein the nitrogen atom may be independently mono or di-substituted by C1–4 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzothiazolyl, or $R_4$ and $R_5$ are each independently halogen, hydroxy, carboxy, cyano, nitro or carboxamide, wherein each $R_4$ and $R_5$ may be further optionally indenpendtly substituted by one or more $R_e$;

or $R_4$ and $R_5$ together with the carbon they are attached optionally form cyclopropanyl, cyclopentanyl, cyclohexanyl, or a heterocyclic ring said heterocyclic ring being selected from: piperidinyl, pyrrolidinyl, azetidinyl, tetrahydropyranyl, tetrahydrothiopyranyl, tetrahydrofuranyl, each ring being optionally substituted with one or more $R_e$;

$R_e$ is C1–5 saturated alkyl group wherein one or two of the C atoms are optionally replaced by O, S(O), S(O)$_2$ or S, and wherein said alkyl group is optionally independently substituted with one oxo group and/or one or more: $C_{1-4}$alkyl, phenyl or naphthyl;

or $R_e$ is C1–4 alkoxy, C3–7 cycloalkyl, phenyl, naphthyl, indanyl, pyrrolidinyl, piperidinyl, morpholinyl, thiomorpholinyl, piperazinyl, tetrahydrothiopyranyl, tetrahydropyranyl, tetrahydrofuranyl, thienyl, oxazolyl, thiazolyl, imidazolyl, pyridinyl, pyrimidinyl, pyrazinyl, indolyl, benzimidazolyl, benzothiazolyl, benzoxazolyl, quinolinyl, isoquinolinyl, quinazolinyl, quinoxalinyl, C1–4 alkanoyl, aroyl, C1–4alkanoyloxy, phenoxy, naphthyloxy, benzyloxy, C1–4 alkoxycarbonyl, phenoxycarbonyl, benzoyloxy, carbamoyl wherein the nitrogen atom may be independently mono or di-substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl, or benzothiazolyl, or $R_e$ is ureido wherein either nitrogen atom may be independently substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzothiazolyl, or $R_e$ is amino wherein the nitrogen atom may be independently mono or di-substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzothiazolyl, or $R_e$ is halogen, hydroxy, oxo, carboxy, cyano, nitro or carboxamide, wherein $R_e$ may be further optionally substituted by one or more $R_f$;

$R_f$ is methyl, ethyl, t-butyl, tolylsulfonyl, methoxy, cyclopropyl, cyclopentyl, cyclohexyl, phenyl, phenoxy, benzyloxy, fluoro, chloro, bromo, hydroxy, oxo, carboxy or carboxamide;

and $R_6$ is hydrogen.

In yet still another embodiment of the invention, there are provided novel compounds of the formula (I) as described immediately above, and wherein:

Each $R_1$ is independently hydrogen, C1–5 alkyl, C3–6 cycloalkyl, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, tetrahydroisoquinolyl; benzofuranyl, benzthienyl, benzimidazolyl, benzothiazolyl, benzoxazolyl, 2-H-benzo[e][1,3]oxazine; wherein each $R_1$ is optionally substituted by one or more $R_a$; or $R_1$ is $R_a$ or $R_b$;

Each $R_a$ is independently C1–3 alkyl, cyclopropyl, cyclohexyl, phenyl, pyrrolidinyl, piperidinyl, morpholinyl, thiomorpholinyl, piperazinyl, thienyl, oxazolyl, dihydro-oxazolyl, imidazolyl, pyridinyl, C1–3 alkoxy, C1–3alkanoyl, C1–3alkanoyloxy, aryloxy, benzyloxy, benzoyl, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl or piperazinyl, or $R_a$ is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or $R_a$ is C1–3 alkoxycarbonylamino, aryloxycarbonylamino, heterocyclylcarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl, aryl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, wherein $R_a$ may be further optionally substituted by one or more $R_b$;

$R_b$ is C1–4 saturated alkyl wherein one carbon atom is optionally replaced by O and wherein said alkyl group is optionally independently substituted with an oxo group and/or one or two: C1–4 alkyl, phenyl, morpholinyl or thiomorpholinyl;

or $R_b$ is cyclopropyl, cyclopentyl, cyclohexyl, phenyl, methoxy, ethoxy, n-propoxy, i-propoxy, phenoxy, benzyloxy, fluoro, chloro, bromo, iodo, hydroxy, oxo, carboxy, cyano, nitro or carboxamide;

$R_2$ is hydrogen;

$R_3$ is a hydrogen, C2–4alkylene, C5–6 cycloalkyl, benzyl or naphthylmethyl, phenyl, or a C1–4 saturated alkyl group wherein one of the C atoms is optionally replaced by O, NH or S; wherein $R_3$ is optionally substituted by one or more $R_c$; or $R_3$ is $R_c$;

$R_c$ is C1–3 alkyl, C3–6 cycloalkyl, phenyl, naphthyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiro[2.5]octanyl, cubanyl, 1,2,3,4-tetrahydronaphthyl, furanyl, tetrahydropyranyl, thienyl, oxazolyl, thiazolyl, imidazolyl, pyridinyl, pyrimidinyl, indolyl, benzofuranyl, benzothienyl, benzothiazolyl, C1–3 alkoxy, phenoxy, naphthyloxy, C1–2 alkanoyl, benzoyl, C1–2 alkoxycarbonyl, phenoxycarbonyl, C1–2alkanoyloxy, benzoyloxy, carbamoyl wherein the nitrogen atom may be independently mono or di-substituted by C1–3 alkyl or aryl, or $R_c$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl or aryl, or $R_c$ is C1–2 alkoxycarbonylamino, phenoxycarbonylamino, C1–2 alkylcarbamoyloxy, arylcarbamoyloxy, C1–2 alkylsulfonylamino, phenylsulfonylamino, C1–2alkylaminosulfonyl, phenylaminosulfonyl, amino wherein the nitrogen atom may be independently mono or di-substituted by C1–3 alkyl or phenyl, or $R_c$ is halogen, hydroxy, oxo, carboxy or cyano, wherein each $R_c$ may be further optionally substituted by one or more $R_d$;

$R_d$ is methyl, cyclopropyl, cyclohexyl, phenyl, benzyl, methoxy, phenoxy, benzyloxy, benzoyl, fluoro, chloro, oxo or cyano;

$R_2$ and $R_3$ together with the carbon they are attached optionally form cyclohexyl optionally substituted by $R_c$ as described hereinabove;

$R_4$ and $R_5$ are each independently hydrogen, or a C1–5 saturated alkyl group wherein one C atom is optionally replaced by O, S or $S(O)_2$ and wherein said alkyl group is optionally substituted with phenyl or indolyl;

or $R_4$ and $R_5$ are each independently C1–5alkoxyC1–5alkyl, C1–5alkylaminoC1–5alkyl, C1–5alkylthioC1–5alkyl wherein the sulfur atom may be oxidized to a sulfoxide or sulfone, C3–6 cycloalkyl, phenyl, naphthyl, indanyl, heterocyclyl selected from pyrrolidinyl, piperidinyl, morpholinyl, thiomorpholinyl, piperazinyl, tetrahydropyranyl, oxazolyl, thiazolyl, imidazolyl, pyridinyl, pyrimidinyl, benzimidazolyl and benzothiazolyl, C1–3alkanoyl, benzoyl, naphthoyl, C1–3 alkoxycarbonyl, benzyloxycarbonyl, phenoxycarbonyl, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl or pyrimidinyl, or $R_4$ and $R_5$ are each independently C1–3 alkanoylamino, aroylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzofuranyl, benzothienyl, benzimidazolyl or benzothiazolyl, or $R_4$ and $R_5$ are each independently is C1–3 alkoxycarbonylamino, phenoxycarbonylamino, C1–3 alkylcarbamoyloxy, phenylcarbamoyloxy, C1–3 alkylsulfonylamino, phenylsulfonylamino, C1–3 alkylaminosulfonyl, phenylaminosulfonyl, amino wherein the nitrogen atom may be independently mono or di-substituted by C1–3 alkyl, phenyl, pyrrolidinyl, piperidinyl, morpholinyl, thiomorpholinyl, piperazinyl, oxazolyl, thiazolyl, imidazolyl, pyridinyl, pyrimidinyl, benzimidazolyl or benzothiazolyl, or $R_4$ and $R_5$ are each independently halogen, hydroxy, oxo, carboxy, cyano or carboxamide, each $R_4$ and $R_5$ may be further optionally independently substituted by one or more $R_e$;

or $R_4$ and $R_5$ together with the carbon they are attached optionally form a cyclopropanyl or a heterocyclic ring said heterocyclic ring being selected from:

piperidinyl, pyrrolidinyl and tetrahydropyranyl, each ring being optionally substituted with one or more $R_e$;

$R_e$ is C1–5 saturated alkyl group wherein one of the C atoms is optionally replaced by O, S(O), $S(O)_2$ or S, and wherein said alkyl group is optionally independently substituted with one oxo group and/or a $C_{1-4}$alkyl or phenyl;

or $R_e$ is C1–3 alkoxy, C3–7 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzothiazolyl, benzoxazolyl, C1–3 alkanoyl, aroyl, C1–3alkanoyloxy, phenoxy, benzyloxy, C1–3 alkoxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzothiazolyl, or $R_e$ is ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzothiazolyl, or $R_e$ is amino wherein the nitrogen atom may be independently mono or di-substituted by C1–3 alkyl, phenyl, naphthyl, pyrrolidinyl, piperidinyl, morpholinyl, piperazinyl, oxazolyl, thiazolyl, imidazolyl, pyridinyl, pyrimidinyl, benzimidazolyl or benzothiazolyl, or $R_e$ is halogen, hydroxy, oxo, carboxy, cyano or carboxamide, wherein $R_e$ may be further optionally substituted by one or more $R_f$;

and $R_f$ is methyl, cyclopentyl, cyclohexyl, phenyl, tolylsulfonyl, methoxy, phenoxy, benzyloxy, fluoro, chloro, bromo, hydroxy, oxo, carboxy or carboxamide.

In yet still another embodiment of the invention, there are provided novel compounds of the formula (I) as described immediately above, and wherein:

Each $R_1$ is independently a hydrogen, methyl, ethyl, i-propyl, cyclopropyl, cyclopentyl, cyclohexyl, phenyl, benzyl, naphthyl, pyrrolidinyl, piperidinyl, morpholinyl, thiomorpholinyl, piperazinyl, furanyl, thienyl, thiazolyl, quinolyl, tetrahydroisoquinolyl, imidazolyl, pyridinyl, pyrazinyl, or 2H-benzo[e][1,3]oxazine; wherein each $R_1$ is optionally substituted by one or more $R_a$; or $R_1$ is $R_a$ or $R_b$;

Each $R_a$ is independently methyl, ethyl, cyclopropyl, phenyl, pyrrolidinyl, piperidinyl, morpholinyl, thiomorpholinyl, piperazinyl, thienyl, dihyrdooxazolyl, imidazolyl, pyridinyl, methoxy, acetyl, acetoxy, phenoxy, benzyloxy, benzoyl, methoxycarbonyl, phenoxycarbonyl, benzoyloxy, carbamoyl wherein the nitrogen atom may be independently mono or di-substituted by methyl, ethyl or phenyl, or $R_a$ is acetylamino, benzoylamino, methylthio, phenylthio wherein the sulfur atom may be oxidized to a sulfoxide or sulfone, ureido wherein either nitrogen atom may be independently substituted by methyl, ethyl or phenyl, or $R_a$ is C1–3alkoxycarbonylamino, phenoxycarbonylamino, piperazinylcarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, phenyl, or piperidinyl, or $R_a$ is fluoro, chloro, bromo, iodo, hydroxy, oxo, carboxy, cyano, nitro or carboxamide, wherein $R_a$ may be further optionally substituted by one or more $R_b$;

$R_b$ is C1–4 saturated alkyl group, wherein one carbon atom is optionally replaced by O and wherein said alkyl group is optionally independently substituted with an oxo group and/or a C1–4 alkyl, phenyl or morpholinyl;

or $R_b$ is cyclopropyl, phenyl, methoxy, phenoxy, benzyloxy, fluoro, chloro, hydroxy, oxo, carboxy or carboxamide;

$R_3$ is a hydrogen, C2–4alkylene, C5–6 cycloalkyl, phenyl, benzyl or naphthylmethyl or a C1–4 saturated alkyl group wherein one of the C atoms is optionally replaced by O or S;

wherein $R_3$ is optionally substituted by one or more $R_c$; or $R_3$ is $R_c$;

$R_c$ is methyl, ethyl, n-propyl, i-propyl, C3–6 cycloalkyl, phenyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiro[2.5]octanyl, cubanyl, 1,2,3,4-tetrahydronaphthyl, thienyl, oxazolyl, thiazolyl, pyridinyl, indolyl, benzofuranyl, benzothienyl, benzothiazolyl, methoxy, ethoxy, phenoxy, acetyl, benzoyl, methoxycarbonyl, phenoxycarbonyl, acetoxy, benzoyloxy, carbamoyl wherein the nitrogen atom may be independently mono or di-substituted by methyl, ethyl or aryl, or $R_c$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or aryl, or $R_c$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_c$ is fluoro, chloro or oxo, wherein each $R_c$ may be further optionally substituted by one or more $R_d$;

$R_d$ is methyl, cyclopropyl, phenyl, methoxy, fluoro, chloro or oxo;

$R_4$ and $R_5$ are each independently hydrogen, C1–4 saturated alkyl, C1–4alkoxyC1–4alkyl, C1–4alkylaminoC1–4alkyl, C1–4alkylthioC1–4alkyl wherein the sulfur atom may be oxidized to a sulfoxide or sulfone, cyclopropyl, cyclopentyl, cyclohexyl, phenyl, naphthyl, benzyl, indanyl, heterocyclyl selected from pyrrolidinyl, piperidinyl, morpholinyl, piperazinyl, tetrahydropyranyl, oxazolyl, thiazolyl, imidazolyl, pyridinyl, pyrimidinyl, benzimidazolyl and benzothiazolyl, C1–2alkanoyl, benzoyl, naphthoyl, C1–2 alkoxycarbonyl, benzyloxycarbonyl, phenoxycarbonyl, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_4$ and $R_5$ are each independently C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzothiazolyl, or $R_4$ and $R_5$ are each independently C1–2 alkoxycarbonylamino, phenoxycarbonylamino, C1–2 alkylcarbamoyloxy, phenylcarbamoyloxy, C1–2 alkylsulfonylamino, phenylsulfonylamino, C1–2 alkylaminosulfonyl, phenylaminosulfonyl, amino wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_4$ and $R_5$ are each independently fluoro, chloro, bromo, hydroxy, oxo, carboxy or carboxamide, wherein each $R_4$ and $R_5$ may be further optionally indenpendtly substituted by one or more $R_e$;

$R_e$ is C1–3 saturated alkyl, C1–3 alkoxy, C3–6 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzothiazolyl, benzoxazolyl, C1–2 alkanoyl, aroyl, C1–2alkanoyloxy, phenoxy, benzyloxy, C1–2 alkoxycarbonyl, phenoxycarbonyl, benzoyloxy, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is amino wherein the nitrogen atom may be independently mono or di-substituted by C1–2 alkyl, phenyl, naphthyl, pyrrolidinyl, piperidinyl, morpholinyl, piperazinyl, oxazolyl, thiazolyl, imidazolyl, pyridinyl or pyrimidinyl, or $R_e$ is fluoro, chloro, bromo, hydroxy, oxo, carboxy or carboxamide, wherein $R_e$ may be further optionally substituted by one or more $R_f$; and $R_f$ is methyl, cyclopentyl, cyclohexyl, phenyl, tolylsulfonyl, methoxy, phenoxy, benzyloxy, fluoro, chloro, hydroxy, oxo, carboxy or carboxamide.

In yet a further embodiment of the invention, there are provided novel compounds of the formula (I) as described immediately above, and wherein:

Each $R_1$ is independently hydrogen, methyl, ethyl, i-propyl, cyclopropyl, cyclohexyl, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl, quinolyl, tetrahydroisoquinolyl, or 2H-benzo[e][1,3]oxazine; wherein each $R_1$ is optionally substituted by one or more $R_a$; or $R_1$ is $R_a$ or $R_b$;

Each $R_a$ is independently methyl, phenyl, thienyl, dihydro-oxazolyl, pyridinyl, methoxy, acetyl, acetoxy, phenoxy, benzyloxy, benzoyl, methoxycarbonyl, benzoyloxy, carbamoyl wherein the nitrogen atom may be independently mono or di-substituted by methyl or phenyl, or $R_a$ is acetylamino, methylthio, phenylthio wherein the sulfur atom may be oxidized to a sulfoxide or sulfone, ureido wherein either nitrogen atom may be independently substituted by methyl or phenyl, or $R_a$ is methoxycarbonylamino, piperazinylcarbonylamino, methylcarbamoyloxy, phenylcarbamoyloxy, methylsulfonylamino, phenylsulfonylamino, amino wherein the nitrogen atom may be independently mono or di-substituted by methyl or phenyl, or $R_a$ is fluoro, chloro, hydroxy, oxo, carboxy, cyano or carboxamide;

wherein $R_a$ may be further optionally substituted by one or more $R_b$;

$R_b$ is an alkyl group selected from methyl, ethyl, n-propyl or i-propyl, wherein one carbon atom is optionally replaced by O and wherein said alkyl group is optionally independently substituted with an oxo group and/or phenyl or morpholinyl;

or $R_b$ is phenyl, methoxy, phenoxy, fluoro, chloro or oxo;

$R_3$ is a hydrogen, methyl, ethyl, n-propyl, n-butyl, i-butyl, methoxymethyl, methylthiomethyl, propenyl, butenyl, i-butenyl, cyclohexyl, phenyl, benzyl or naphthylmethyl wherein $R_3$ is optionally substituted by one or more $R_c$;

$R_c$ is methyl, ethyl, n-propyl, i-propyl, cyclopropyl, cyclopentyl, cyclohexyl, phenyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, pyridinyl, methoxy, phenoxy, acetyl, benzoyl, methoxycarbonyl, phenoxycarbonyl, acetoxy, benzoyloxy, methylthio wherein the sulfur atom may be oxidized to a sulfoxide or sulfone, phenylthio wherein the sulfur atom may be oxidized to a sulfoxide or sulfone, dimethylamino, diethylamino, fluoro, chloro or oxo;

$R_4$ and $R_5$ are each independently hydrogen, C1–4 saturated alkyl, C1–2alkoxyC1–2alkyl, C1–2alkylaminoC1–2alkyl, C1–2alkylthioC1–2alkyl wherein the sulfur atom may be oxidized to a sulfoxide or sulfone, cyclopropyl, cyclopentyl, cyclohexyl, phenyl, benzyl, heterocyclyl selected from pyrrolidinyl, piperidinyl, morpholinyl, tetrahydropyranyl, pyridinyl, and pyrimidinyl, acetyl, benzoyl, methoxycarbonyl, ethoxycarbonyl, benzyloxycarbonyl, carbamoyl wherein the nitrogen atom may be independently mono or di-substituted by methyl, ethyl or phenyl, or $R_4$ and $R_5$ are each independently acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or phenyl, or $R_4$ and $R_5$ are each independently methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_4$ and $R_5$ are each independently fluoro, chloro, hydroxy, oxo, carboxy or carboxamide, wherein each $R_4$ and $R_5$ may be further optionally indenpendtly substituted by one or more $R_e$;

$R_e$ is methyl, methoxy, ethoxy, cyclopropyl, cyclopentyl, cyclohexyl, phenyl, naphthyl, indanyl, piperidinyl, morpholinyl, indolyl, thienyl, pyridinyl, acetyl, benzoyl, acetyloxy, phenoxy, benzyloxy, methoxycarbonyl, ethoxycarbonyl, carbamoyl wherein the nitrogen atom may be independently mono or di-substituted by methyl, ethyl or phenyl, or R_e is ureido wherein either nitrogen atom may be independently substituted by methyl, ethyl or phenyl, or R_e is amino wherein the nitrogen atom may be independently mono or di-substituted by methyl, ethyl or phenyl, or R_e is fluoro, chloro, hydroxy, oxo, carboxy or carboxamide, wherein R_e may be further optionally substituted by one or more R_f; and R_f is methyl, cyclopentyl, cyclohexyl, phenyl, tolylsulfonyl, methoxy, phenoxy, benzyloxy, carboxy, fluoro, chloro or oxo.

In yet still a further embodiment of the invention, there are provided novel compounds of the formula (I) as described immediately above, and wherein:

Each $R_1$ is independently hydrogen, i-propyl, benzyloxy, cyclohexyl, benzyl, phenyl, carboxyphenyl, naphthyl, 4-(acetylamino)-phenyl, 4-(methanesulfonylamino)-phenyl, 4-methoxyphenyl, 3-phenoxyphenyl, 4-chlorophenyl, 3,4-dichlorophenyl, 4-fluorophenyl, 2-fluorophenyl, 2-fluoro-4-chlorophenyl, naphthyl, thienylmethyl, piperidinyl, morpholinyl, pyrrolidinyl, piperazinyl, furanyl, thienyl, thiazolyl, quinolyl, tetrathydroisoquinolyl, 5-chlorothienyl, pyridin-4-yl, pyrazinyl, 2H-benzo[e][1,3]oxazine, methylamino, ethylamino, dimethylamino or diethylamino;

$R_3$ is methyl, ethyl, n-propyl, i-propyl, n-butyl, i-butyl, methoxymethyl, methylthiomethyl, vinyl, propenyl, butenyl, i-butenyl, cyclohexyl, phenyl, benzyl or naphthylmethyl wherein $R_3$ is optionally substituted by one or more $R_c$;

$R_c$ is methyl, cyclopropyl, cyclohexyl, cyclopentyl, phenyl, indanyl, 1,2,3,4-tetrahydronaphthyl, methoxy, methylthio wherein the sulfur atom may be oxidized to a sulfoxide or sulfone, dimethylamino, fluoro or chloro;

$R_4$ and $R_5$ are each independently hydrogen, methyl, ethyl, n-propyl, n-butyl, t-butyl, i-propyl, i-butyl, methoxymethyl, methylthiomethyl or methylthioethyl wherein the sulfur atom may be oxidized to a sulfoxide or sulfone, cyclopropyl, cyclopentyl, cyclohexyl, phenyl, benzyl, piperidinyl, tetrahydropyranyl, pyrimidinyl, acetyl, benzoyl, ethoxycarbonyl, benzyloxycarbonyl, methylsulfonylamino, phenylsulfonylamino, methylamino, dimethylamino, fluoro, oxo or carboxy, wherein each $R_4$ and $R_5$ may each be further optionally independently substituted by one or more $R_e$;

$R_e$ is methyl, cyclopropyl, cyclopentyl, cyclohexyl, phenyl, carboxyphenyl, naphthyl, indanyl, thienyl, methylthienyl, methoxy, phenoxy, benzyloxy, piperidinyl, pyridinyl, indolyl, 1-(tolyl-sulfonyl)-indolyl, carbamoyl wherein the nitrogen atom may be independently mono or di-substituted by methyl, phenyl or benzyl, or $R_e$ is hydroxy, fluoro, chloro, oxo, dimethylamino or trifluoromethyl.

In yet another embodiment of the invention, there are provided novel compounds of the formula (I) as described immediately above, and wherein:

Y is $R_1$, $R_1O—$ or $R_1NH—$;

Each $R_1$ is independently hydrogen, phenyl, benzyl, naphthyl, 4-(acetylamino)-phenyl, 4-(methanesulfonylamino)-phenyl, 3-phenoxyphenyl, 4-chlorophenyl, 3,4-dichlorophenyl, 4-fluorophenyl, thienylmethyl, morpholinyl, pyrrolidinyl, piperidinyl, piperazinyl, furanyl, thienyl, thiazolyl, quinolyl, tetrahydroisoquinolyl, 5-chlorothienyl, pyridin-4-yl, 2H-benzo[e][1,3]oxazine or pyrazinyl;

$R_3$ is ethyl, n-propyl, n-butyl, i-butyl, 2,2-dimethylpropyl, 3-methylbutyl, 3,3-dimethylbutyl, 2,2,3-trimethylbutyl, 2,2,3,3,-tetramethylbutyl, cyclopropylmethyl, cyclohexylmethyl, methoxymethyl, methylthiomethyl, methylsulfonylmethyl, dimethylaminomethyl, propenyl, i-butenyl, cyclohexyl, phenyl, benzyl, 4-methoxybenzyl, 4-chlorobenzyl, 3,4-dichlorobenzyl, 3-chlorobenzyl, 2,4-dichlorobenzyl, 4-methylbenzyl, 3-methylbenzyl or naphth-2-ylmethyl;

and $R_4$ and $R_5$ are each independently hydrogen, methyl, ethyl, n-propyl, n-butyl, n-pentyl, 2-pentyl, 3-pentyl, phenylethyl, phenylpropyl, 2,2-dimethylpropyl, t-butyl, i-propyl, i-butyl, cyclopropyl, cyclopentyl, cyclohexyl, cyclopropylmethyl, cyclopentylmethyl, cyclohexylmethyl, phenyl, benzyl, naphthylmethyl, indanylmethyl, pyridinylmethyl, indolylmethyl, thienylmethyl, 5-methylthienylmethyl, piperidinyl, piperidinylcarbonyl, pyridinylcarbonyl, tetrahydropyranyl, pyrimidinyl, acetyl, benzoyl, ethoxycarbonyl, benzyloxycarbonyl, t-butoxycarbonyl, methylcarbamoyl, phenylcarbamoyl, benzylcarbamoyl, methylsulfonylamino, phenylsulfonylamino, methylamino, dimethylamino, methylcyclohexyl, methylbenzyl, trifluoromethylbenzyl, methoxybenzyl, 3-carboxyphenylmethoxymethyl, phenoxybenzyl, benzyloxybenzyl, benzyloxymethyl, N-[(4-methylphenyl)-sulfonyl]-indolylmethyl, fluorobenzyl, difluorobenzyl, chlorobenzyl, N,N-dimethylaminoacetyl, trifluoromethylbenzyl, fluoro, oxo or carboxy.

In yet even still another embodiment of the invention, there are provided novel compounds of the formula (I) as described immediately above, and wherein:

Each $R_1$ is independently hydrogen, phenyl, benzyl, naphthyl, tetrahydroisoquinolin-2-yl or morpholin-4-yl, $R_3$ is ethyl, n-propyl, n-butyl, i-butyl, 2,2-dimethylpropyl, cyclopropylmethyl, cyclohexylmethyl, dimethylaminomethyl, phenyl or benzyl;

and $R_4$ is hydrogen;

and $R_5$ is methyl, ethyl, n-propyl, n-butyl, n-pentyl, 2-pentyl, 3-pentyl, phenylethyl, phenylpropyl, 2,2-dimethylpropyl, t-butyl, i-propyl, i-butyl, cyclopropyl, cyclopentyl, cyclohexyl, cyclopropylmethyl, cyclopentylmethyl, cyclohexylmethyl, phenyl, benzyl, naphthylmethyl, indanylmethyl, pyridinylmethyl, indolylmethyl, thienylmethyl, methylthienylmethyl, methylbenzyl, methoxybenzyl, methoxybenzyl-m-carboxylic acid, phenoxybenzyl, benzyloxybenzyl, benzyloxymethyl, N-[(4-methylphenyl)-sulfonyl]-indolylmethyl, fluorobenzyl, difluorobenzyl, chlorobenzyl, N,N-dimethylaminoacetyl or trifluoromethylbenzyl.

In still another embodiment of the invention, there are provided novel compounds of the formula (I) as described immediately above, and wherein:

$R_5$ phenylethyl, phenylpropyl, 2,2-dimethylpropyl, cyclopropylmethyl, cyclopentylmethyl, cyclohexylmethyl, benzyl, naphthylmethyl, indanylmethyl, pyridinylmethyl, indolylmethyl, thienylmethyl, methylthienylmethyl, methylbenzyl, methoxybenzyl, phenoxybenzyl, benzyloxybenzyl, benzyloxymethyl.

An additional subgeneric aspect of the invention is directed to a compound of formula (I):

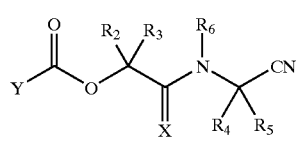

wherein:
Y is C1–6alkoxy, C1–6alkylamino, naphthyl, morpholinyl, tetrahydroisoquinolinyl, phenylamino, benzylamino, naphthylamino, benzyloxy, benzofuranyl, benzothienyl, phenylpiperazinyl, pyridinylthienyl, C1–3alkoxyphenylpiperidinylamino, C1–3alkoxycarbonylpiperidinylamino-thiazolyl, benzylpiperazinyl-carbonylaminophenyl, morpholin-4-yl-C1–3alkoxybenzofuranyl, C1–3alkoxycarbonylaminophenyl, quinolinylamino, wherein each is optionally substituted by one or more C1–3alkyl or halogen;
$R_2$ is hydrogen or methyl;
$R_3$ is hydrogen;
C1–10 saturated alkyl group optionally substituted by one or more: halogen;
  C3–6cycloalkyl optionally substituted by one or more C1–3alkyl;
  phenyl or naphthyl optionally substituted by one or more halogen, C1–3alkyl or C1–3alkoxy;
  decahydronaphthyl;
  spiro[2.5]octyl optionally substituted by one or more C1–3alkyl;
  indanyl;
  C1–3alkylthio wherein the sulfur atom may oxidized to a sulfoxide or a sulfone;
  or biphenylyl;
C2–6alkenyl;
C3–6cycloalkyl optionally substituted by one or more C1–3alkyl;
dialkylaminomethyl;
phenyl
or pyridyl;
or $R_2$ and $R_3$ together with the carbon atom they are attached to form cyclopentyl, cyclohexyl, tetrahydropyranyl, pyrrolidinyl optionally substituted with C1–3alkyl, C3–6cycloalkyl, C3–6cycloalkyl-C1–3-alkyl or phenyl-C1–3alkyl, or piperidnyl optionally substituted with C1–3alkyl, C3–6cycloalkyl, C3–6cycloalkyl-C1–3-alkyl or phenyl-C1–3alkyl;
$R_4$ is hydrogen or C1–6 saturated alkyl group;
$R_5$ is hydrogen, C1–6 saturated alkyl group, C1–3alkylsulfonyl-C1–3alkyl, phenyl-C1–3alkyl, trifluoromethylbenzyl, phenylethylindolyl-C1–3-alkyl or benzyloxy-C1–3-alkyl,
wherein each is optionally substituted by halo, carboxy, or C1–3alkoxy;
or $R_4$ and $R_5$ together with the carbon atom they are attached to form a cyclopropanyl, cyclobutanyl, cyclopentanyl, cyclohexanyl, cycloheptanyl, tetrahydropyranyl; or pyrrolidinyl, piperidinyl or azepanyl, each being optionally substituted with one or more: oxo, C1–3alkyl, hydroxyC1–3alkyl, benzyloxyC1–3alkyl, C3–6cycloalkyl, C3–6cycloalkyl-C1–3-alkyl, phenyl-C1–3alkyl, tosyl-indolylC1–3alkyl, C1–3alkanoyl, phenylC1–3alkanoyl, pyridinylC1–3alkanoyl, morpholinylC1–3alkanoyl, C1–3alkylcarbamoyl, C1–3alkoxy-C1–3alkylcarbamoyl, C1–3alkoxycarbamoyl, C1–3alkoxy-C1–3alkoxycarbamoyl, phenylcarbamoyl, phenylC1–3alkylcarbamoyl, benzyloxycarbamoyl, cyclohexanylcarbonyl, cyclohexylC1–3alkoxycarbonyl, phenylcarbonyl, phenylC1–3alkoxycarbonyl, piperidinylcarbonyl, piperazinylcarbonyl, or tetrahydropyranylcarbonyl, wherein each of the foregoing substituents on the pyrrolidinyl, piperidinyl or azepanyl can be further optionally substituted by one or more C1–3alkyl or halogen;
and
$R_6$ is hydrogen or methyl.

In another embodiment of the invention, there are provided compounds within the subgeneric aspect described immediately above wherein:
Y is naphthyl, morpholinyl, tetrahydroisoquinolinyl, benzylamino, naphthylamino, benzyloxy, 4-phenylpiperazin-1-yl, 5-(pyridin-4-yl)-2-thienyl, 1-(4-alkoxyphenyl)-piperidin-4-yl amino, 2-[1-(alkoxycarbonyl)-piperidin-4-yl amino] thiazol-4-yl, 4-[4-(benzyl)-piperazin-1-yl carbonylamino]phenyl or 4-(alkoxycarbonylamino)phenyl, quinolin-2-yl amino, wherein each is optionally substituted by one or more halogen;
$R_2$ is hydrogen or methyl;
$R_3$ is ethyl, n-propyl, n-butyl, i-butyl, 2,2-dimethylpropyl, cyclopropyl, cyclopropylmethyl, cyclobutanylmethyl, cyclopentanylmethyl, gcyclohexylmethyl, cyclohexylethyl, dialkylaminomethyl, phenyl, benzyl, phenylethyl or pyridyl;
or $R_2$ and $R_3$ together with the carbon atom they are attached to form cyclopentyl or cyclohexyl;
$R_4$ is hydrogen, methyl or ethyl;
$R_5$ is hydrogen, methyl, ethyl, n-propyl, i-propyl, n-butyl, i-butyl, methylsulfonylethyl, benzyl, trifluoromethylbenzyl, phenylethyl, indolylmethyl, benzyloxymethyl, methoxy-benzyloxymethyl or halo-benzyloxymethyl;
or $R_4$ and $R_5$ together with the carbon atom they are attached to form a cyclohexanyl;
and
$R_6$ is hydrogen.

Some preferred examples of possible $R_1$ groups are shown below:

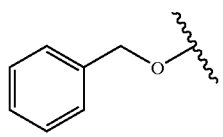
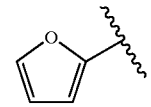
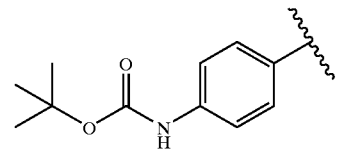
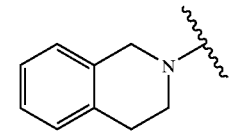
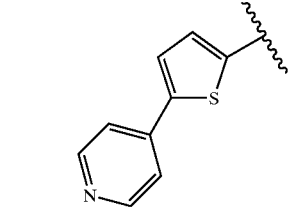
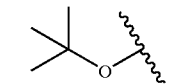

-continued
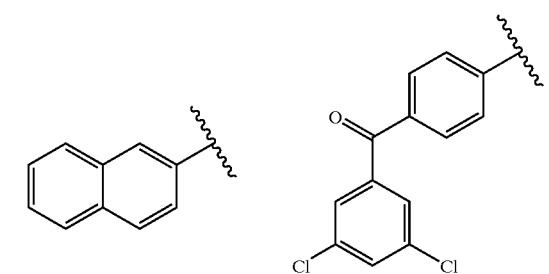
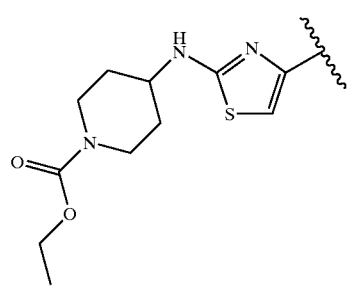
Some preferred examples of possible $R_3$ group are as shown below:
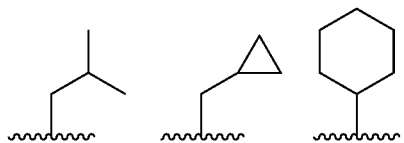
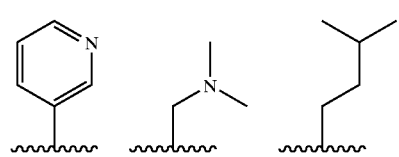
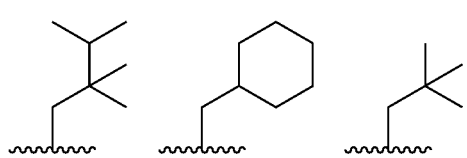
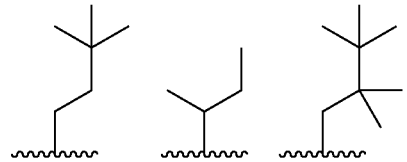
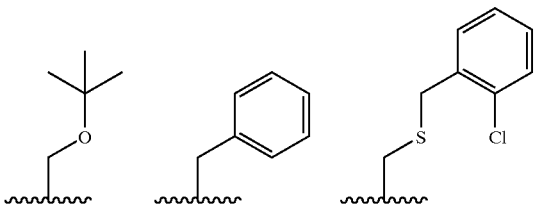
Some preferred examples of possible spirocyclic groups when $R_2$ and $R_3$ combine to form a ring are shown below:
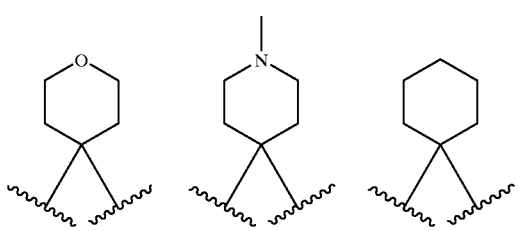

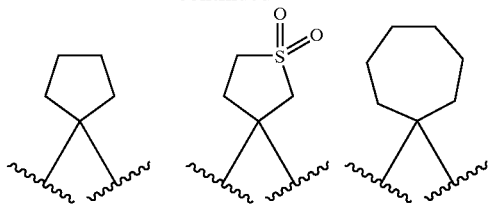

Some preferred examples of possible R$_5$ groups are shown below:

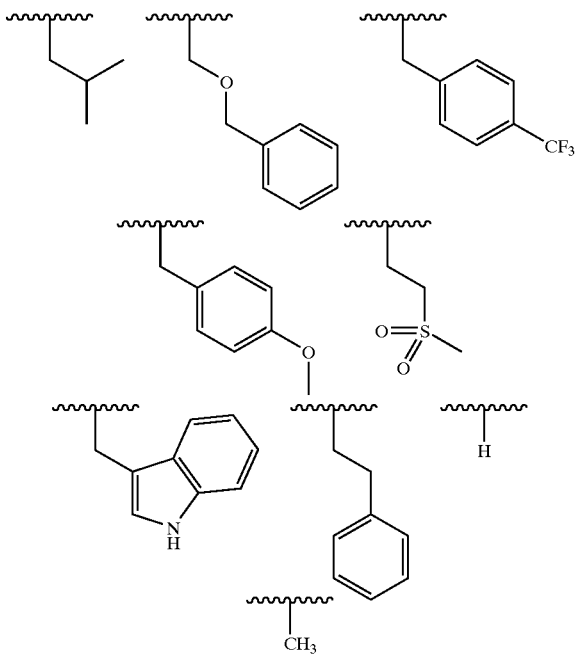

Some preferred examples of possible spirocyclic groups when R$_4$ and R$_5$ combine to form a ring are shown below:

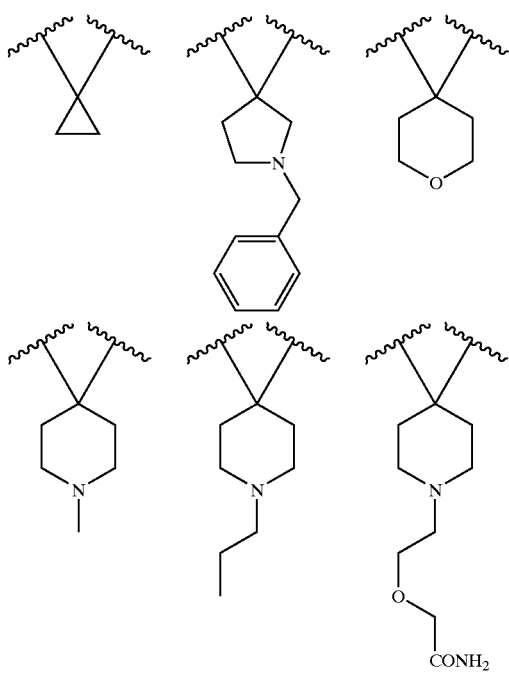

Any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic carbon may be in the R or S configuration unless otherwise specified, or a combination of configurations. In one preferred embodiment, in the compounds of the invention where R$_2$ is hydrogen and R$_3$ is other than hydrogen, the stereoconfiguration about the carbon atom to which R$_2$ and R$_3$ are attached is as shown below:

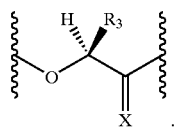

In further preferred embodiment, when R$_4$ is hydrogen and R$_5$ is other than hydrogen, the stereoconfiguration about the carbon atom to which R$_4$ and R$_5$ are attached is as shown below:

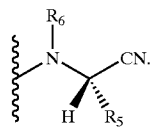

Of course, both these preferred stereoconfigurations may occur in the same compound.

Some of the compounds of formula (I) can exist in more than one tautomeric form. The invention includes all such tautomers.

It shall be understood by one of ordinary skill in the art that all compounds of the invention are those which are chemically stable.

The invention includes pharmaceutically acceptable derivatives of compounds of formula (I). A "pharmaceutically acceptable derivative" refers to any pharmaceutically acceptable acid, salt or ester of a compound of this invention, or any other compound such as a prodrug which, upon administration to a patient, is capable of providing (directly or indirectly) a compound of this invention, a pharmacologically active metabolite thereof or pharmacologically active residue thereof.

In addition, the compounds of this invention include prodrugs of compounds of the formula (I). Prodrugs include those compounds that, upon simple transformation, are modified to produce the compounds of the invention. Simple chemical transformations include hydrolysis, oxidation and reduction which occur enzymatically, metabolically or otherwise. Specifically, when a prodrug of this invention is administered to a patient, the prodrug may be transformed into a compound of formula (I), thereby imparting the desired pharmacological effect.

In order that the invention herein described may be more fully understood, the following detailed description is set forth. As used herein, the following abbreviations are used:

BOC or t-BOC is tertiary-butoxycarbonyl;
t-Bu is tertiary-butyl;
DMF is dimethylformamide;
EtOAc is ethyl acetate;
THF is tetrahydrofuran;
Ar is argon;
EDC is 1-(3-dimethylaminopropyl)-3-ethylcarbodiimide hydrochloride and
HOBT is 1-hydroxybenzotriazole.

General Synthetic Methods

The invention also provides processes of making the present novel compounds. Compounds of the invention may be prepared by methods described below. Standard peptide coupling, protection and deprotection reactions (see for example M. Bodanszky, 1984, The Practice of Peptide Synthesis, Springer-Verlag) are employed in these syntheses and are incorporated herein by reference in their entirety. Methods of preparing the carbamate functionality are also well known in the chemical literature (see for example R. Warras et al., Tetrahedron Letters, 1998, 39, 2715 and G. Papageorgiou and J. E. T. Corrie, Tetrahedron, 1997, 53, 3917). Intermediates used in the preparation of the compounds of the invention are either commercially available or readily prepared by methods known to those skilled in the art. The synthesis of a number of intermediates useful in the preparation of compounds of the invention are described and exemplified in U.S. patent application Ser. No. 09/655,351, filed Sep. 8, 2000 (Emmanuel et al.) which is incorporated by reference.

Compounds of the invention having formula (I) may be prepared by Method A as illustrated in Scheme I:

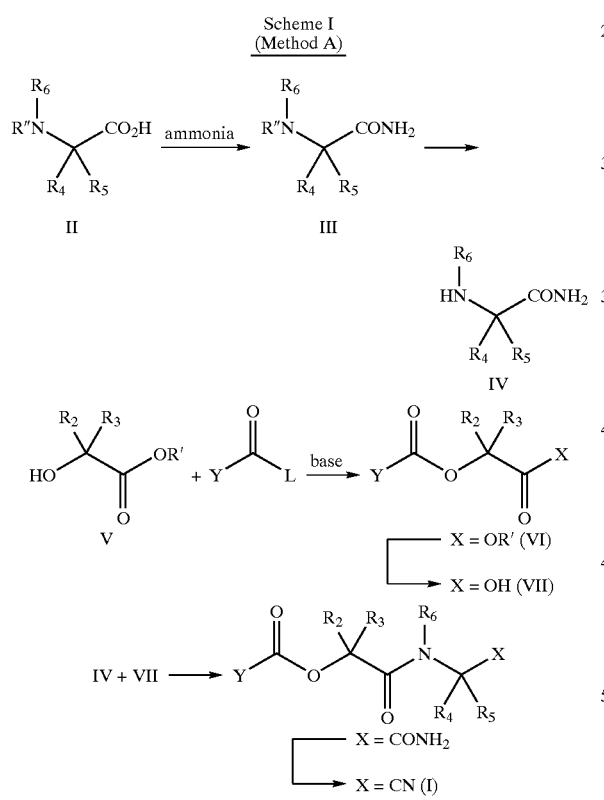

According to Method A a suitably protected amino acid bearing $R_4$ and $R_5$ (II) is allowed to react with ammonia under standard coupling conditions to provide amide (III). An example of a suitable protecting group R" is the t-butoxycarbonyl (BOC) group. An example of standard coupling conditions would be combining the starting materials in the presence of a coupling reagent such as 1-(3-dimethylaminopropyl)-3-ethylcarbodiimide (EDC) with 1-hydroxybenzotriazole (HOBT), in a suitable solvent such as DMF or methylene chloride. A base such as N-methylmorpholine may be added. This is followed by deprotection to give amino acid amide IV. A protected hydroxy ester (V) bearing $R_2$ and $R_3$, where R' is a suitable protecting group, is then reacted with an appropriate activated acid [YC(O)L] such as an acid chloride (Y=$(R_1)_3$C—, L=Cl), or a chloroformate derivative (Y=$R_1$O, L=Cl) in the presence of a suitable base such as N,N-diisopropylethylamine to provide VI. Alternately, if one desires a compound of formula (I) where Y=$(R_1)_2$N, one may prepare a mixed anhydride from the hydroxy group of formula (V) by reacting formula (V) with a suitable chloroformate such as p-nitrophenyl chloroformate, followed by reaction with the desired amine to provide the necessary intermediate (VI) where Y=$(R_1)_2$N (see Synthetic Example 2, part c). Conversion to the carboxylic acid provides VII. Standard peptide coupling of IV and VII, followed by dehydration of the amide provides the desired nitrile I. An example of suitable dehydration conditions is cyanuric chloride in DMF.

In a variation (Method B) illustrated in Scheme II, an amino acid amide bearing $R_4$ and $R_5$ (IV) is coupled with a hydroxy acid (VIII) bearing $R_2$ and $R_3$. Coupling conditions would be as described above. This is then followed by reaction with YC(O)L or coupling via the mixed anhydride (as described in Method A). Conversion of the resulting amide to the nitrile by dehydration as above provides I.

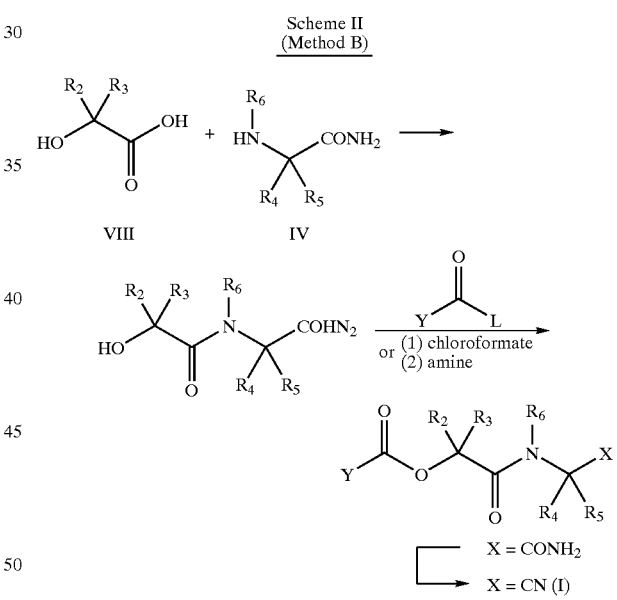

Compounds of the invention having formula (I) may also be prepared by Method C as illustrated in Scheme III.

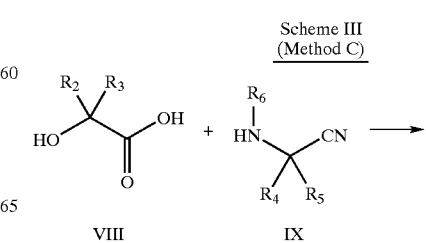

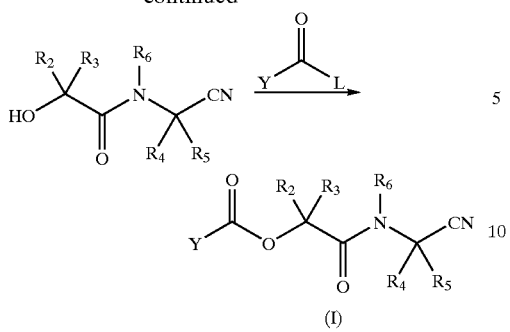

In this variation (Method C) an amino nitrile bearing $R_4$ and $R_5$ (IX) is coupled with a hydroxy acid bearing $R_2$ and $R_3$ (VIII) under the coupling conditions described above. This is followed by reaction with YC(O)L or coupling via the mixed anhydride as described above to furnish the nitrile (I).

Compounds of the invention having formula (I) may also be prepared by as outlined below in Scheme IV (Method D).

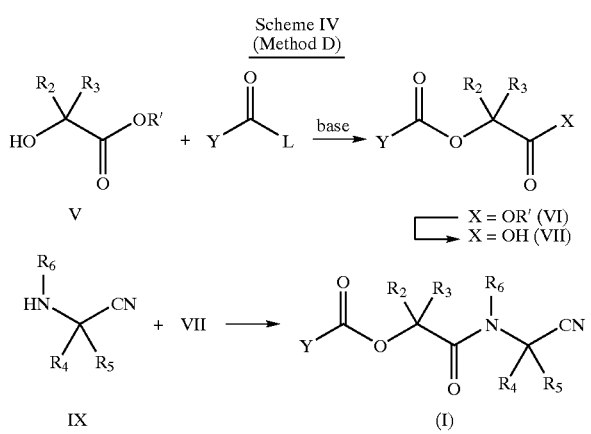

In this variation, a hydroxy ester (V) bearing $R_2$ and $R_3$ is reacted with YC(O)L, or coupling via the mixed anhydride, to provide the compound of formula (VI) as described in Method A. Conversion to the carboxylic acid provides VII is as described in Method A. Standard peptide coupling of an amino nitrile bearing $R_4$ and $R_5$ (IX) with (VII) yields the desired nitrile (I).

In cases where $R_4$ and $R_5$ form a heterocycle in the intermediate aminonitrile (IX) used in Methods C and D above, the required intermediate may be prepared from the corresponding ketone, as outlined in Scheme V

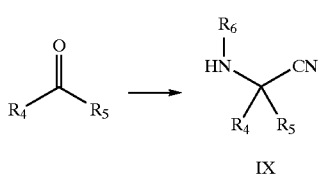

In this method, the corresponding ketone is reacted with a primary amine or an ammonium salt, such as ammonium chloride, and a cyanide salt, such as potassium cyanide or sodium cyanide, in a suitable solvent, such as water or a solution of ammonia in methanol, at about room temperature to reflux temperature.

The amide functionality at P2 of the compounds of formula (I) (i.e., —C(O)—N($R_6$)—) may be converted to the thioamide to provide compounds of formula (I) with X=S by methods known in the art, for example by the use of Lawesson's reagent (K. Klausen et al., Tetrahedron, 1981, 37, 3635).

In each of the methods described above, required starting materials are either commercially available or easily prepared by those skilled in the art, for example see:

Leung, M.-k.; Lai, J.-L.; Lau, K.-H.-; Yu, H.-h.; Hsiao, J.-J. *J. Org. Chem.* 1996, 61, 4175–4179;

Mee, J. D. *J. Org. Chem.* 1975, 40, 2135–2136;

Micovic, I. V.; Roglic, G. M.; Ivanovic, M. D.; Dosen-Micovic, L.; Kiricojevic, V. D.; Popovic, J. B. *J. Chem. Soc, Perkin Trans. 1*, 1996, 2041–2050;

Tornus, I.; Schaumann, E. *Tetrahedron* 1996, 52, 725–732;

Jadhav, P. K.; Woerner, F. J. *Tetrahedron Letters* 1995, 36, 6383–6386;

Kochhar, K. S.; et al. *Tetrahedron Letters* 1984, 25, 1871–1874; and

Fordon, K. J.; Crane, C. G.; Burrows, C. J. *Tetrahedron Letters* 1994, 35, 6215–6216.

These references are incorporated herein by reference in their entirety,

In order that this invention be more fully understood, the following examples are set forth. These examples are for the purpose of illustrating embodiments of this invention, and are not to be construed as limiting the scope of the invention in any way.

The examples which follow are illustrative and, as recognized by one skilled in the art, particular reagents or conditions could be modified as needed for individual compounds. Starting materials used in the scheme below are either commercially available or easily prepared from commercially available materials by those skilled in the art.

SYNTHETIC EXAMPLES

Example 1

Morpholine-4-carboxylic acid 1-[(benzyloxymethyl-cyano-methyl)-carbamoyl]-3-methyl-butyl ester

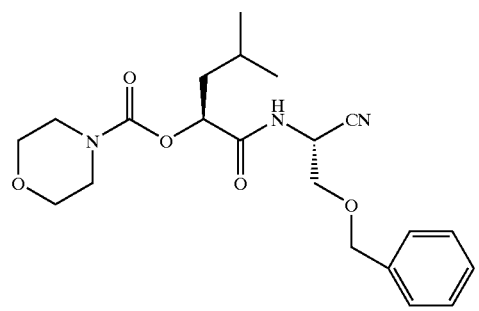

(a) N-(t-butoxycarbonyl)-L-(O-benzyl)serinamide

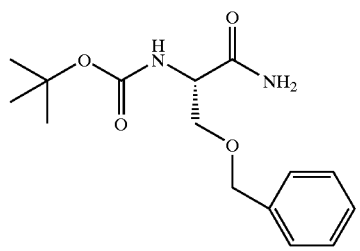

NH$_4$OH (10 mL) was added to a premixed (15 min) solution of N-(t-butoxycarbonyl)-L-(O-benzyl)serine (10.0 g, 33.9 mmol), EDC (7.80 g, 40.7 mmol), and 1-hydroxybenzotriazole (HOBT) (5.50 g, 40.7 mmol) in DMF (120 mL) at room temperature. After 16 h the reaction mixture was diluted with CH$_2$Cl$_2$ and filtered, washed sequentially with 10% aq. HCl, satd. NaHCO$_3$, H$_2$O (×3), brine, then dried over Na$_2$SO$_4$, and concentrated giving N-(t-butoxycarbonyl)-L-(O-benzyl)serinamide (11.5 g) as a white solid.

(b) 2-Amino-3-benzyloxy-propionamide hydrochloride

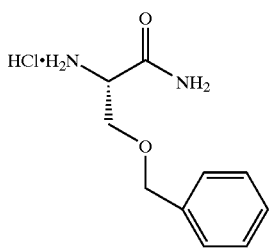

N-(t-butoxycarbonyl)-L-(O-benzyl)serinamide (1.00 g) was dissolved in anhydrous THF (5 mL) and cooled in an ice/water bath. A 4 M solution of HCl in dioxane (5 mL) was added and the reaction stirred for two h and then concentrated under reduced pressure to provide a glass which was triturated with diethyl ether to obtain 2-amino-3-benzyloxy-propionamide hydrochloride as a white solid (0.9 g). This material was used without further purification.

(c) 2-Hydroxy-4-methyl-pentanoic acid (2-benzyloxy-1-carbamoyl-ethyl)-amide

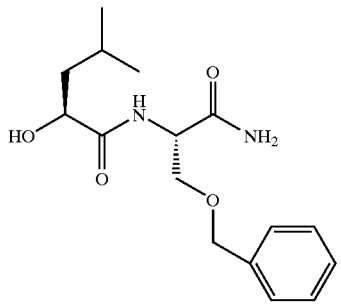

2-Hydroxyisocaproic acid (0.143 g, 1.0 mmol) was dissolved in 4 mL of DMF and cooled to 0° C. with an ice-water bath. EDC (0.278 g, 1.4 mmol) and HOBT (0.190 g, 1.4 mmol) were added and stirring, under argon, continued for 25 min. To the cold solution was added 2-amino-3-benzyloxy-propionamide hydrochloride (0.250 g, 1.0 mmol), followed by addition of N-methylmorpholine (0.35 mL, 3.2 mmol) and stirring was continued overnight (16 h).

The solution was diluted with 100 mL of EtOAc and washed sequentially with a 1.0 M solution of HCl (3×10 mL), a saturated solution of NaHCO$_3$ (3×10 mL), water (100 mL) and brine (100 mL). The organic layer was dried over MgSO$_4$, filtered and concentrated by rotary evaporation to give (0.17 g, 55%) of the crude product which was chromatographed (SiO$_2$, 3% MeOH in EtOAc) to give the desired product (0.11 g, 35%).

(d) Morpholine-4-carboxylic acid 1-(2-benzyloxy-1-carbamoyl-ethylcarbamoyl)-3-methyl-butyl Ester

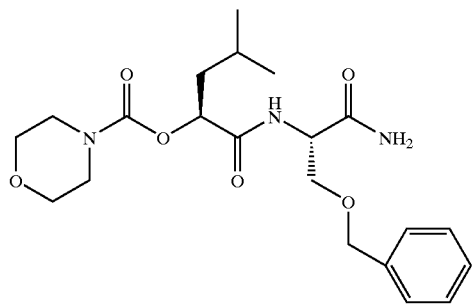

To a solution of 2-hydroxy-4-methyl-pentanoic acid (2-benzyloxy-1-carbamoyl-ethyl)-amide (0.169 g, 0.55 mmol) in CH$_2$Cl$_2$ (5 mL) was added 4-morpholinecarbonyl chloride (0.082 g, 0.55 mmol), Et$_3$N (0.15 mL, 1.1 mmol) and DMAP (0.034 g, 0.27 mmol). The resulting mixture was allowed to stir overnight (20 h) under argon at room temperature. When the reaction was complete the mixture was diluted with CH$_2$Cl$_2$ (10 mL), then washed with HCl (1.0 N, 10 mL), water and brine, dried over Na$_2$SO$_4$, and concentrated to give the desired product as an off-white oil in 0.20 g 86% yield of the crude product which was chromatographed (SiO$_2$, 5% hexanes in EtOAc) to give desired product in (0.12 g, 52%).

(e) Morpholine-4-carboxylic acid 1-[(benzyloxymethyl-cyano-methyl)-carbamoyl]-3-methyl-butyl Ester

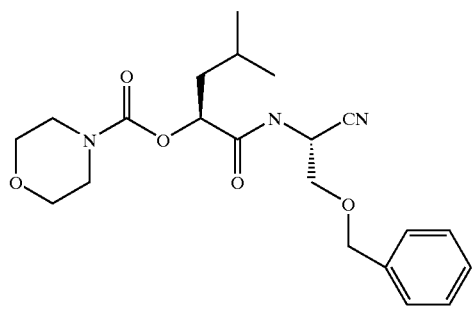

Morpholine-4-carboxylic acid 1-(2-benzyloxy-1-carbamoyl-ethylcarbamoyl)-3-methyl-butyl ester (0.100 g, 0.23 mmol) was dissolved in 3 mL of DMF and cooled to 0° C. with an ice-water bath. To this solution was added cyanuric chloride (0.044 g, 0.23 mmol) and the reaction mixture was stirred for 1 h. The reaction was quenched with cold water (2 mL), extracted with EtOAc (3×100 mL), and the organic layers were combined and washed with 100 mL brine. The organic layer was dried over MgSO$_4$, filtered and concentrated to give the crude residue. The residue was purified by chromatography (SiO$_2$, 50% hexane in EtOAc) to give the title compound as a clear oil (0.055 g, 60%); $^1$H NMR (CDCl$_3$) 7.35 (5H, m), 6.76 (1H, d), 5.1 (2H, m), 4.65 (2H, m), 3.82–3.35 (10H, m), 1.7 (3H, m), 0.95 (6H, m). MS: m/z=404 M+1.

Example 2

Benzyl-carbamic acid 1-(4-cyano-1-propyl-piperidin-4-ylcarbamoyl)-3-methyl-butyl ester

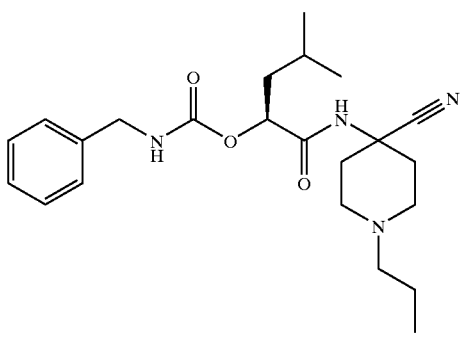

(a) 4-Amino-1-propyl-piperidine-4-carbonitrile

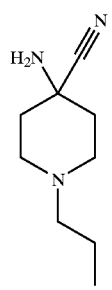

To a suspension of ammonium chloride (5.02 g, 93.8 mmol), sodium cyanide (8.51 g, 173.6 mmol) and MgSO$_4$ (7.0 g) in 200 mL of NH$_3$/MeOH (2.0 M) was added 1-propyl-4-piperidone (23.4 g, 165 mmol). Stirring was continued for 3.5 h at 60° C. The solution was cooled to room temperature and filtered. The filtrate was concentrated and the residue was taken up in Et$_2$O (200 mL) treated with MgSO$_4$ and stirred under argon for 3 h. The mixture was then filtered and concentrated to provide the product as a light brown oil (20 g crude).

(b) 2-Hydroxy-4-methyl-pentanoic acid (4-cyano-1-propyl-piperidin-4-yl)-amide

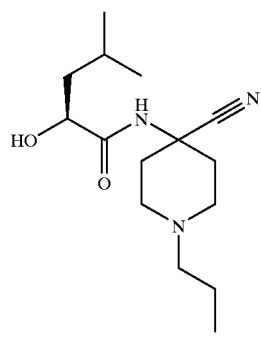

2-Hydroxy-4-methyl-pentanoic acid (4-cyano-1-propyl-piperidin-4-yl)-amide was prepared by a method analogous to that of Example 1, part (c). The product was used in the next step without purification.

(c) Benzyl-carbamic acid 1-(4-cyano-1-propyl-piperidin-4-ylcarbamoyl)-3-methyl-butyl ester

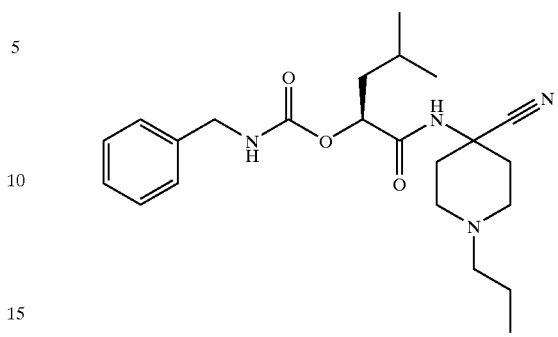

To a solution of 2-hydroxy-4-methyl-pentanoic acid (4-cyano-1-propyl-piperidin-4-yl)-amide (0.316 g, 1.1 mmol) in CH$_2$Cl$_2$ (30 mL) was added DMAP (0.192 g, 1.6 mmol), p-nitrophenyl chloroformate (0.249 g, 1.2 mmol), and N-methylmorpholine (0.136 mL, 1.2 mmol). The resulting mixture was allowed to stir overnight (20 h) under argon at room temperature, then treated with benzylamine (1.68 g, 16 mmol) and allowed to stir overnight (20 h). When the reaction was complete the mixture was diluted with CH$_2$Cl$_2$ (50 mL), then washed with saturated aq. NaHCO$_3$ (50 mL), water and brine, dried over Na$_2$SO$_4$, filtered and evaporated in vacuo to give 0.200 g (50% yield) of the desired product after purification by prep-HPLC;

$^1$H NMR (CDCl$_3$) 7.3 (5H, m), 6.3 (1H, s), 5.2 (1H, m), 5.0 (1H, m), 4.42 (2H, m), 2.75 (1H, m), 2.35 (5H, m), 1.98–1.35 (9H, m), 1.0–0.8 (9H, m). MS: m/z=415 M+1.

Example 3

Benzyl-carbamic acid 1-(1-benzyl-3-cyano-pyrrolidin-3-ylcarbamoyl)-3-methyl-butyl ester

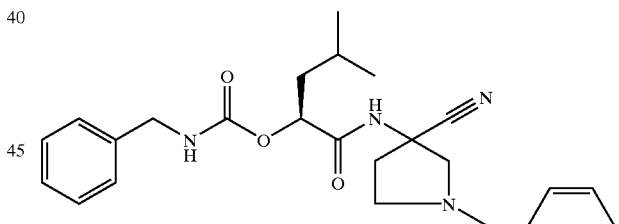

(a) 3-Amino-1-benzyl-pyrrolidine-3-carbonitrile

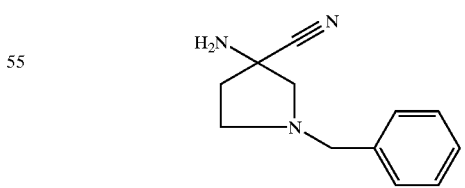

3-Amino-3-cyano-1-benzylpyrrolidine was prepared by a method analogous to that of Example 2-part (a) with the exception that no sodium carbonate was added to the reaction mixture. The product was extracted from the crude reaction with EtOAc (3×100 mL) and was used without further purification.

(b) 2-Hydroxy-4-methyl-pentanoic acid (1-benzyl-3-cyano-pyrrolidin-3-yl)-amide

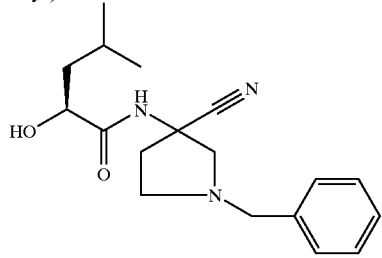

2-Hydroxy-4-methyl-pentanoic acid (1-benzyl-3-cyano-pyrrolidin-3-yl)-amide was prepared by a method analogous to that of Example 1, part (c). The product was used in the next step without purification.

(c) Benzyl-carbamic acid 1-(1-benzyl-3-cyano-pyrrolidin-3-ylcarbamoyl)-3-methyl-butyl ester

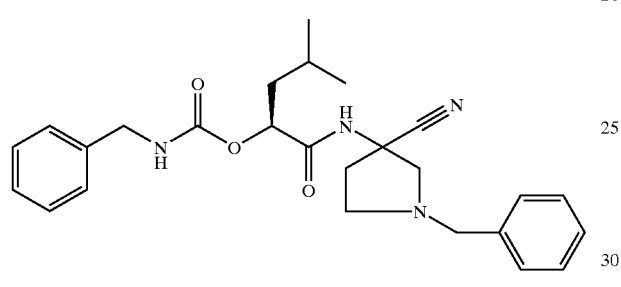

To a solution of 2-hydroxy-4-methyl-pentanoic acid (1-benzyl-3-cyano-pyrrolidin-3-yl)-amide (0.315 g, 1.0 mmol) in dry THF (27 mL) was added DMAP (0.171 g, 1.4 mmol), p-nitrophenyl chloroformate (0.221 g, 1.1 mmol), and N-methylmorpholine (0. 121 mL, 1.1 mmol). The resulting mixture was allowed to stir overnight (20 h) under argon at room temperature, then treated with benzylamine (0.150 g, 1.4 mmol) and allowed to stir overnight (24 h). When the reaction was complete, the mixture was diluted with EtOAc (50 mL), then washed sequentially with saturated aq. NaHCO$_3$ (50 mL), water and brine, dried over Na$_2$SO$_4$, filtered and concentrated to give 0.180 g (40% yield ) of the desired product after purification by prep-HPLC; $^1$H NMR (CDCl$_3$) 7.25 (10H, m), 6.25 (1H, s), 5.4–5.1 (2H, m), 4.45 (2H, m), 3.65 (2H, m), 3.1–3.0 (1H, m), 2.98–2.57 (5H, m), 2.16 (1H, m), 1.73 (2H, m), 0.9 (6H, m). MS, m/z 449=M+1.

Using the procedures described in the General Synthetic Methods section and in the synthetic examples above, the following compounds may be prepared:

Morpholine-4-carboxylic acid 1-(4-cyano-1-methyl-piperidin-4-ylcarbamoyl)-3-methyl-butyl ester

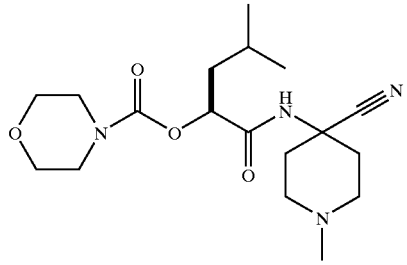

Morpholine-4-carboxylic acid 1-(4-cyano-1-propyl-piperidin-4-ylcarbamoyl)-3-methyl-butyl ester

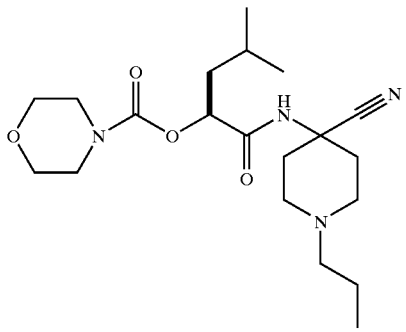

Morpholine-4-carboxylic acid 1-(1-benzyl-4-cyano-piperidin-4-ylcarbamoyl)-3-methyl-butyl ester Morpholine-4-carboxylic acid 1-(1-benzyl-3-cyano-pyrrolidin-3-ylcarbamoyl)-3-methyl-butyl ester

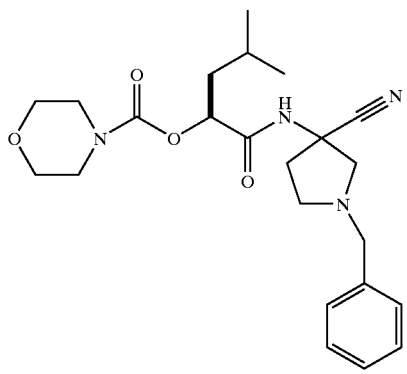

Morpholine-4-carboxylic acid 1-(3-cyano-1-cyclohexylmethyl-pyrrolidin-3-ylcarbamoyl)-3-methyl-butyl ester

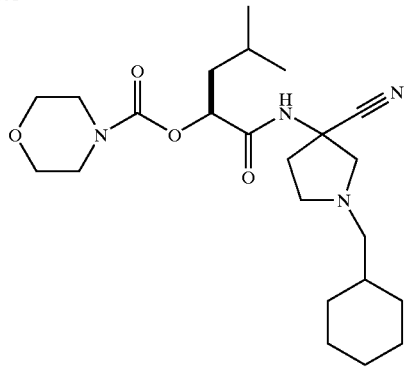

Morpholine-4-carboxylic acid 1-(3-cyano-1-cyclohexyl-pyrrolidin-3-ylcarbamoyl)-3-methyl-butyl ester

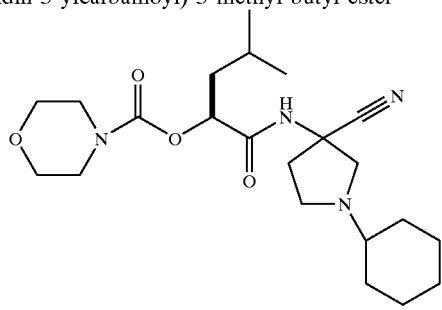

Morpholine-4-carboxylic acid 1-(3-cyano-1-cyclohexyl-pyrrolidin-3-ylcarbamoyl)-cyclohexyl ester

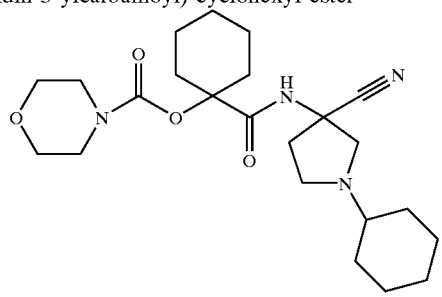

Morpholine-4-carboxylic acid 1-(3-cyano-1-cyclohexylmethyl-pyrrolidin-3-ylcarbamoyl)-cyclohexyl ester

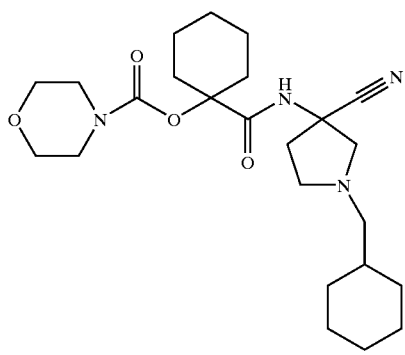

Morpholine-4-carboxylic acid 1-(1-benzyl-3-cyano-pyrrolidin-3-ylcarbamoyl)-cyclohexyl ester

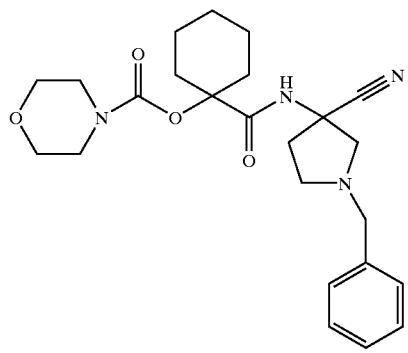

Morpholine-4-carboxylic acid 1-(1-benzyl-4-cyano-piperidin-4-ylcarbamoyl)-cyclohexyl ester

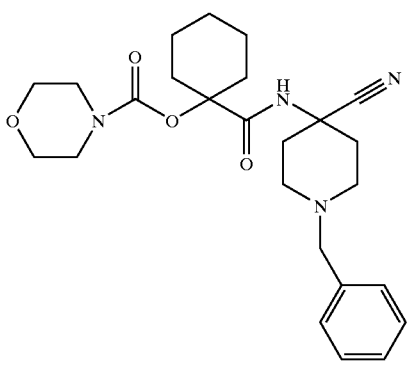

Morpholine-4-carboxylic acid 1-(4-cyano-1-propyl-piperidin-4-ylcarbamoyl)-cyclohexyl ester

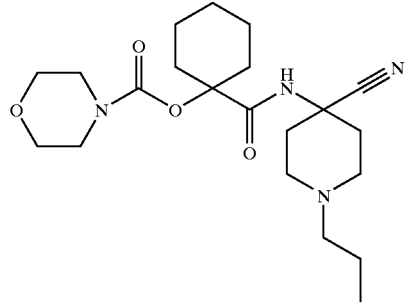

Morpholine-4-carboxylic acid 1-(4-cyano-1-methyl-piperidin-4-ylcarbamoyl)-cyclohexyl ester

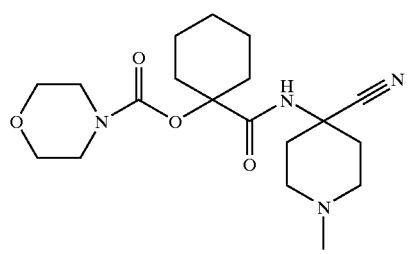

47

Benzyl-carbamic acid 1-(4-cyano-1-methyl-piperidin-4-ylcarbamoyl)-3-methyl-butyl ester

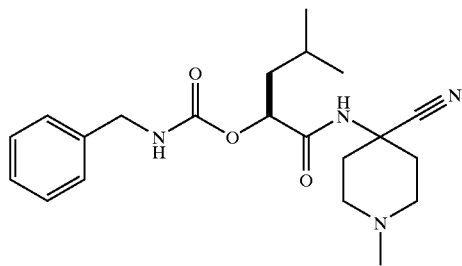

Benzyl-carbamic acid 1-(4-cyano-1-propyl-piperidin-4-ylcarbamoyl)-3-methyl-butyl ester

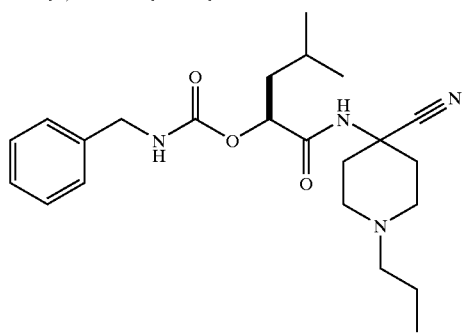

Benzyl-carbamic acid 1-(1-benzyl-4-cyano-piperidin-4-ylcarbamoyl)-3-methyl-butyl ester

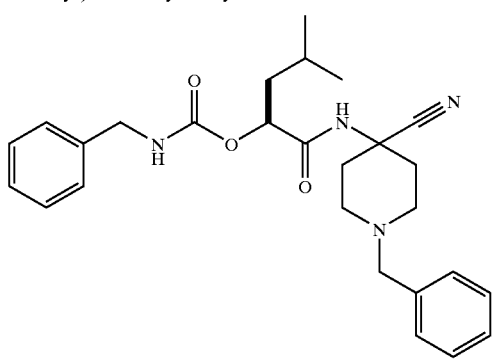

Benzyl-carbamic acid 1-(1-benzyl-3-cyano-pyrrolidin-3-ylcarbamoyl)-3-methyl-butyl ester

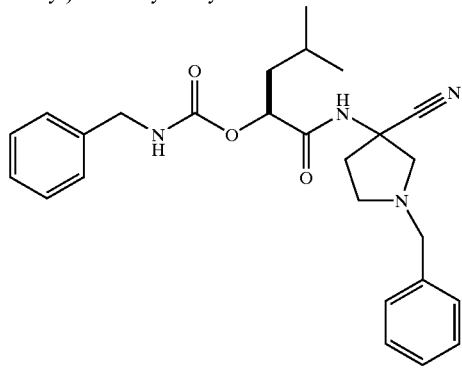

48

Benzyl-carbamic acid 1-(3-cyano-1-cyclohexylmethyl-pyrrolidin-3-ylcarbamoyl)-3-methyl-butyl ester

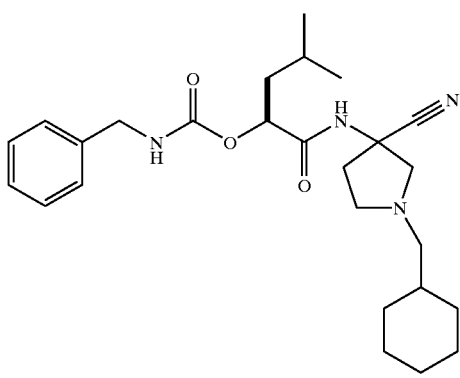

Benzyl-carbamic acid 1-(3-cyano-1-cyclohexyl-pyrrolidin-3-ylcarbamoyl)-3-methyl-butyl ester

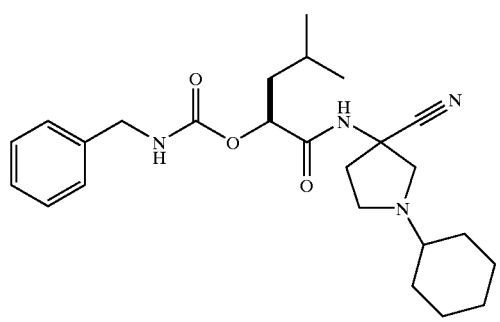

Benzyl-carbamic acid 1-(4-cyano-1-methyl-piperidin-4-ylcarbamoyl)-cyclohexyl ester

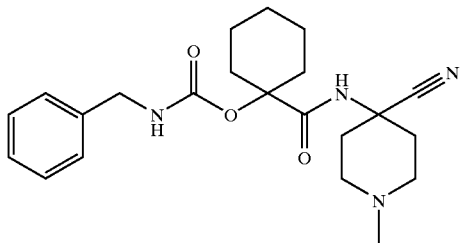

Benzyl-carbamic acid 1-(4-cyano-1-propyl-piperidin-4-ylcarbamoyl)-cyclohexyl ester

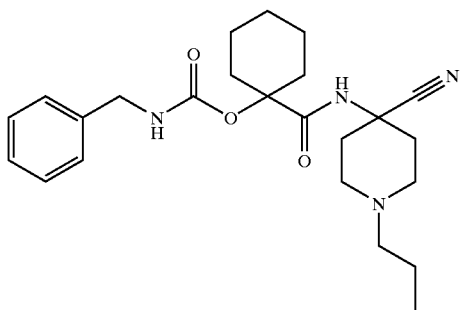

Benzyl-carbamic acid 1-(1-benzyl-4-cyano-piperidin-4-ylcarbamoyl)-cyclohexyl ester

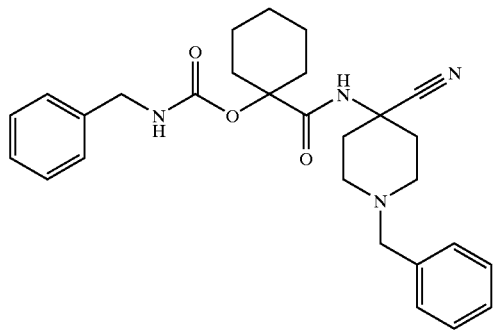

Benzyl-carbamic acid 1-(1-benzyl-3-cyano-pyrrolidin-3-ylcarbamoyl)-cyclohexyl ester

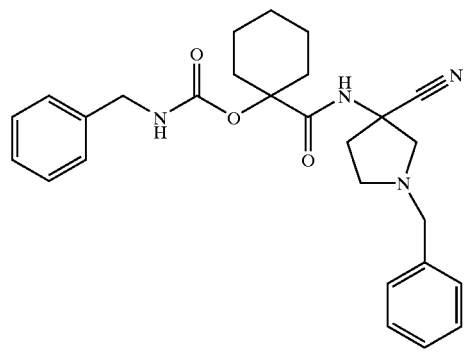

Benzyl-carbamic acid 1-(3-cyano-1-cyclohexylmethyl-pyrrolidin-3-ylcarbamoyl)-cyclohexyl ester

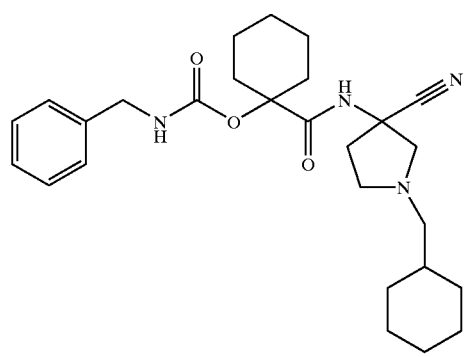

Benzyl-carbamic acid 1-(3-cyano-1-cyclohexyl-pyrrolidin-3-ylcarbamoyl)-cyclohexyl ester

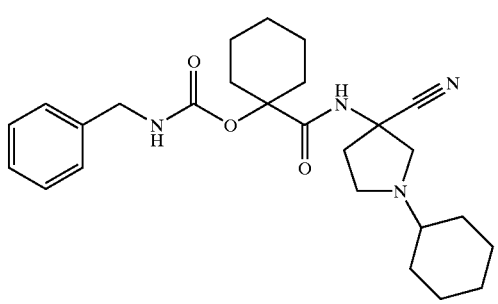

Naphthalen-2-yl-carbamic acid 1-(4-cyano-1-methyl-piperidin-4-ylcarbamoyl)-3-methyl-butyl ester

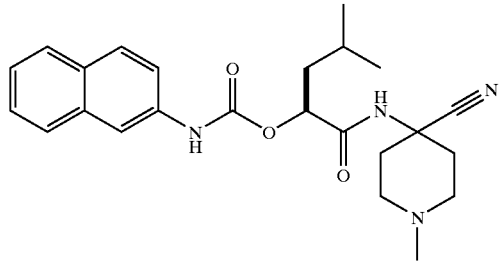

Naphthalen-2-yl-carbamic acid 1-(4-cyano-1-propyl-piperidin-4-ylcarbamoyl)-3-methyl-butyl ester

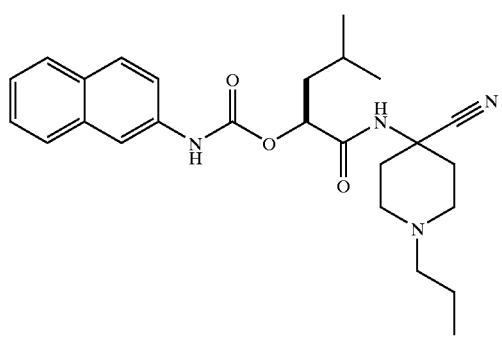

Naphthalen-2-yl-carbamic acid 1-(1-benzyl-4-cyano-piperidin-4-ylcarbamoyl)-3-methyl-butyl ester

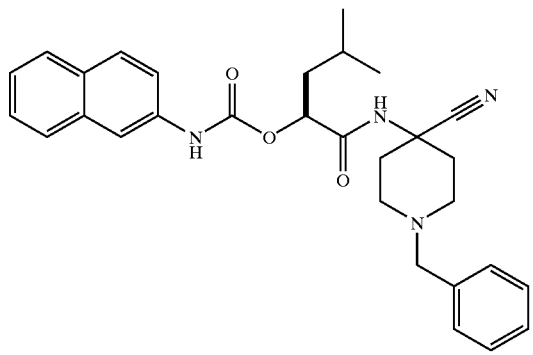

Naphthalen-2-yl-carbamic acid 1-(1-benzyl-3-cyano-pyrrolidin-3-ylcarbamoyl)-3-methyl-butyl ester

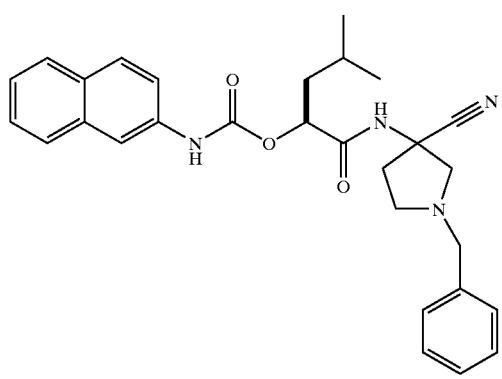

Naphthalen-2-yl-carbamic acid 1-(3-cyano-1-cyclohexylmethyl-pyrrolidin-3-ylcarbamoyl)-3-methyl-butyl ester

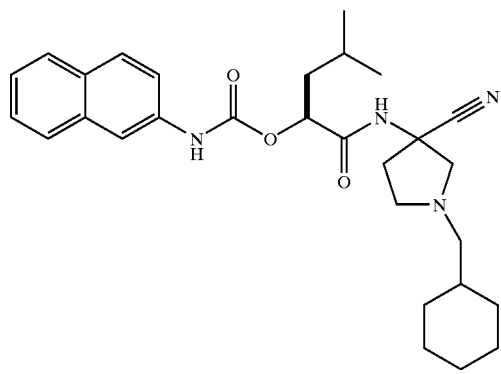

Naphthalen-2-yl-carbamic acid 1-(3-cyano-1-cyclohexyl-pyrrolidin-3-ylcarbamoyl)-3-methyl-butyl ester

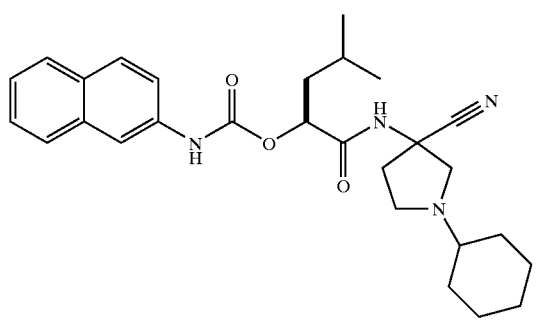

Naphthalen-2-yl-carbamic acid 1-(4-cyano-1-methyl-piperidin-4-ylcarbamoyl)-cyclohexyl ester

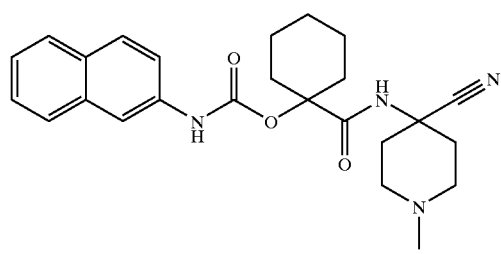

Naphthalen-2-yl-carbamic acid 1-(4-cyano-1-propyl-piperidin-4-ylcarbamoyl)-cyclohexyl ester

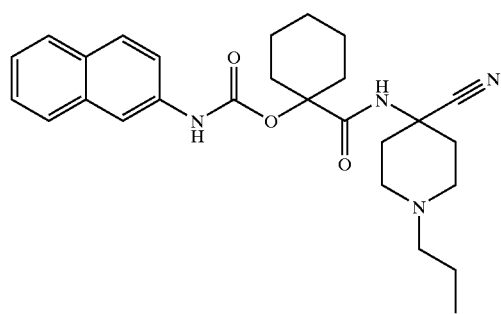

Naphthalen-2-yl-carbamic acid 1-(1-benzyl-4-cyano-piperidin-4-ylcarbamoyl)-cyclohexyl ester

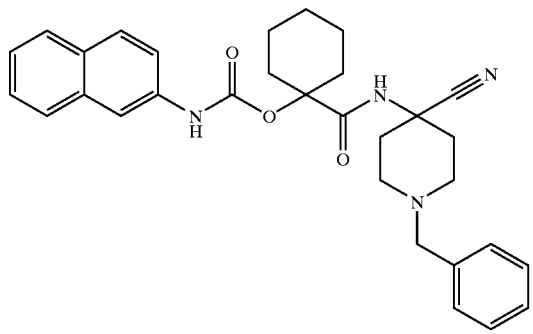

Naphthalen-2-yl-carbamic acid 1-(1-benzyl-3-cyano-pyrrolidin-3-ylcarbamoyl)-cyclohexyl ester

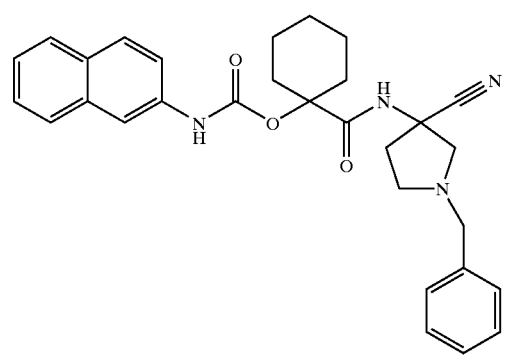

Naphthalen-2-yl-carbamic acid 1-(3-cyano-1-cyclohexylmethyl-pyrrolidin-3-ylcarbamoyl)-cyclohexyl ester

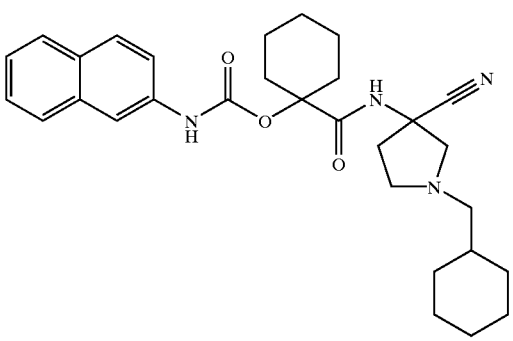

Naphthalen-2-yl-carbamic acid 1-(3-cyano-1-cyclohexyl-pyrrolidin-3-ylcarbamoyl)-cyclohexyl ester

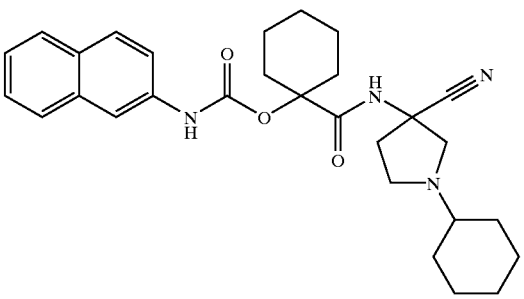

Morpholine-4-carboxylic acid 1-[3-cyano-1-(4-fluoro benzyl)-pyrrolidin-3-ylcarbamoyl]-cyclohexyl ester

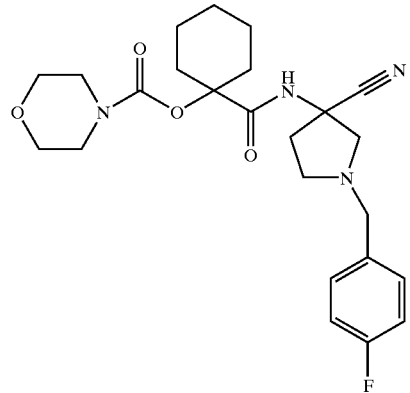

Morpholine-4-carboxylic acid 1-[3-cyano-1-(2,4-difluoro benzyl)-pyrrolidin-3-ylcarbamoyl]-cyclohexyl ester

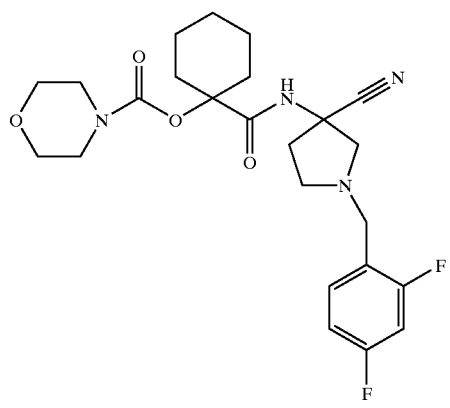

Morpholine-4-carboxylic acid 1-[3-cyano-1-(2,4,6-trifluoro-benzyl)-pyrrolidin-3-ylcarbamoyl]-3-methyl-butyl ester

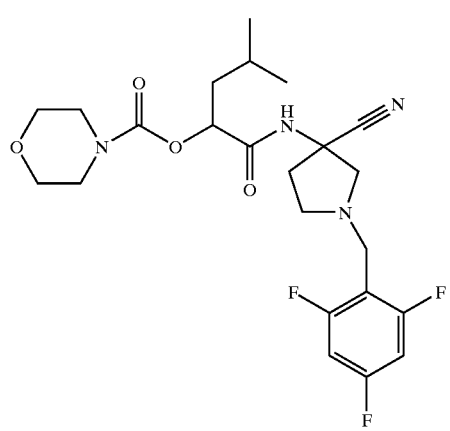

Benzyl-carbamic acid 1-[3-cyano-1-(2,3,4,5,6-pentafluoro-benzyl)-pyrrolidin-3-ylcarbamoyl]-cyclohexyl ester

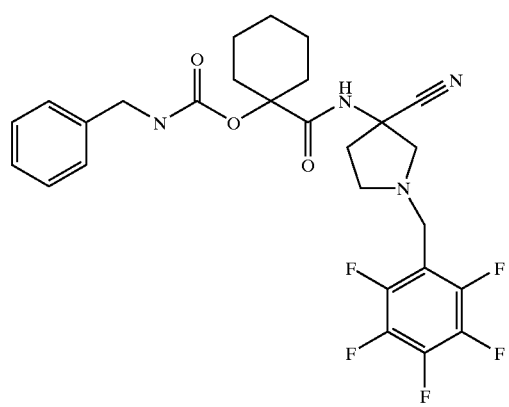

Morpholine-4-carboxylic acid 1-[4-cyano-1-(2,4-difluoro benzyl)-piperidin-4-ylcarbamoyl]-3-methyl-butyl ester

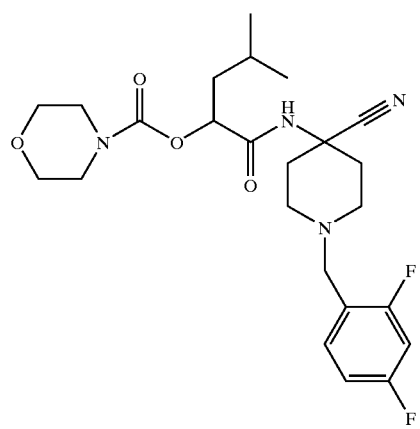

Morpholine-4-carboxylic acid 1-[4-cyano-1-(2,6-difluoro benzyl)-piperidin-4-ylcarbamoyl]-3-methyl-butyl ester

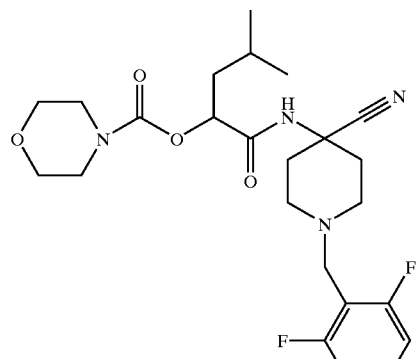

55
Morpholine-4-carboxylic acid 1-[4-cyano-1-(3,5-difluoro benzyl)-piperidin-4-ylcarbamoyl]-3-methyl-butyl ester

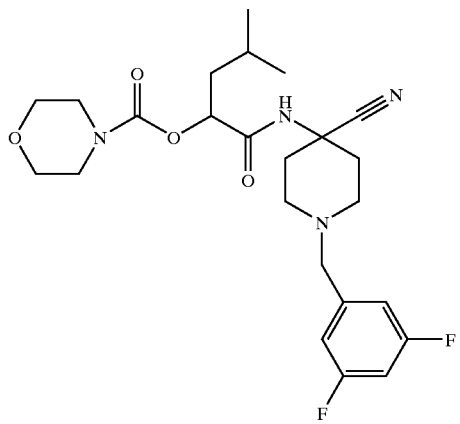

56
Morpholine-4-carboxylic acid 1-{3-cyano-1-[1-(toluene-4-sulfonyl)-1H-indol-3-ylmethyl]-pyrrolidin-3-ylcarbamoyl}-3-methyl-butyl ester

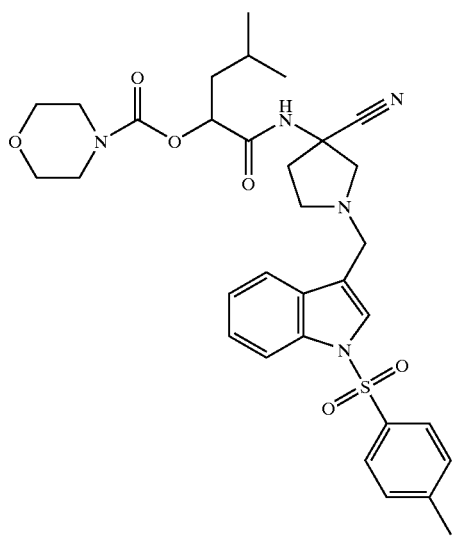

Benzyl-carbamic acid 1-[4-cyano-1-(2,4,6-trifluoro benzyl)-piperidin-4-ylcarbamoyl]-3-methyl-butyl ester

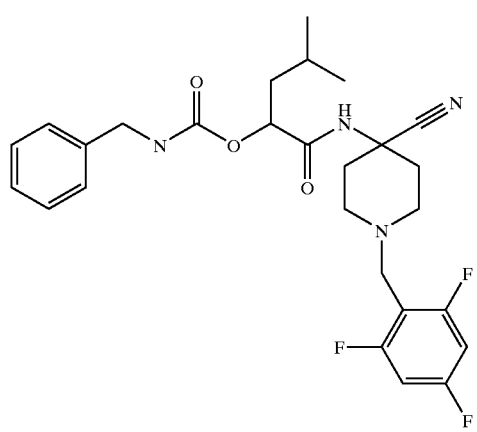

Benzyl-carbamic acid 1-{4-cyano-1-[1-(toluene-4-sulfonyl)-1H-indol-3-ylmethyl]-piperidin-4-ylcarbamoyl}-3-methyl-butyl ester

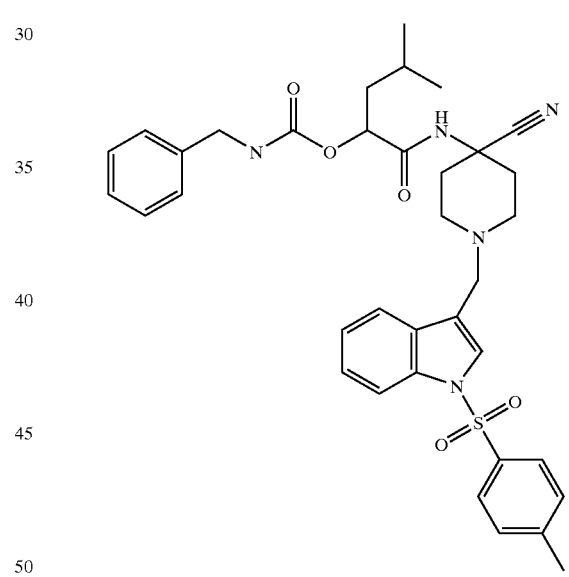

Additional compounds that may be prepared using the procedures described above are shown in the Tables below:

| Structure | Chemical Name* |
|---|---|
| ![structure] | Benzyl-carbamic acid 1-(cyanomethyl-carbamoyl)-3-methyl-butyl ester |

| Structure | Chemical Name* |
|---|---|
| 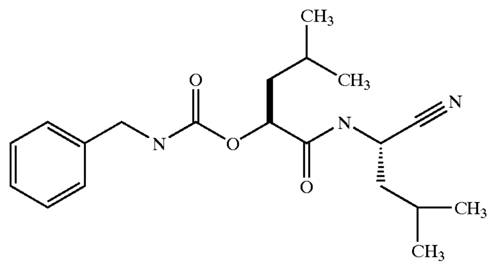 | Benzyl-carbamic acid 1-(1-cyano-3-methyl-butylcarbamoyl)-3-methyl-butyl ester |
| 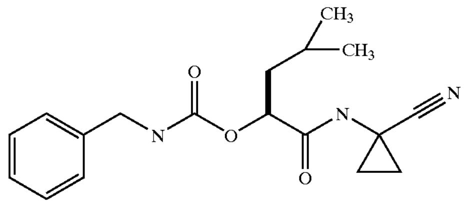 | Benzyl-carbamic acid 1-(1-cyano-cyclopropylcarbamoyl)-3-methyl-butyl ester |
| 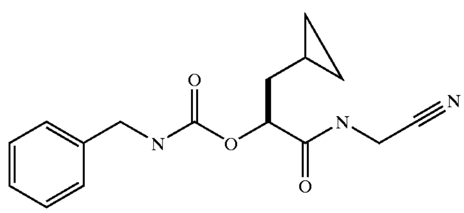 | Benzyl-carbamic acid 1-(cyanomethyl-carbamoyl)-2-cyclopropyl-ethyl ester |
| 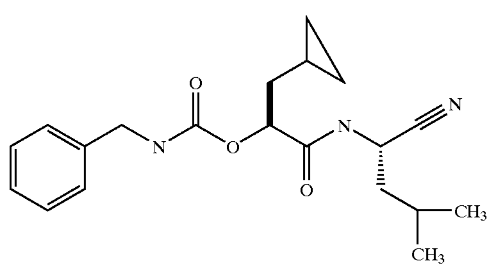 | Benzyl-carbamic acid 1-(1-cyano-3-methyl-butylcarbamoyl)-2-cyclopropyl-ethyl ester |
| 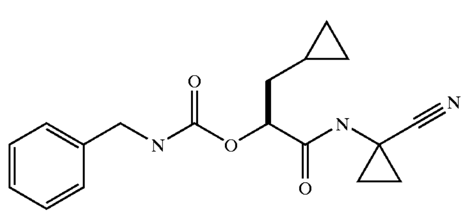 | Benzyl-carbamic acid 1-(1-cyano-cyclopropylcarbamoyl)-2-cyclopropyl-ethyl ester |
| 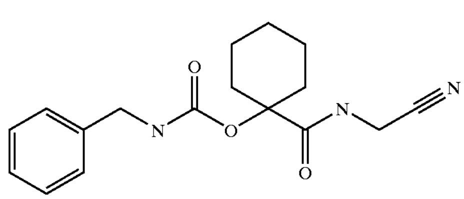 | Benzyl-carbamic acid 1-(cyanomethyl-carbamoyl)-cyclohexyl ester |

-continued

| Structure | Chemical Name* |
|---|---|
| 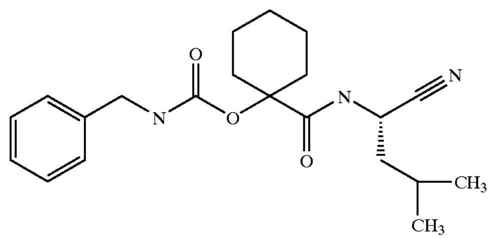 | Benzyl-carbamic acid 1-(1-cyano-3-methyl-butylcarbamoyl)-cyclohexyl ester |
| 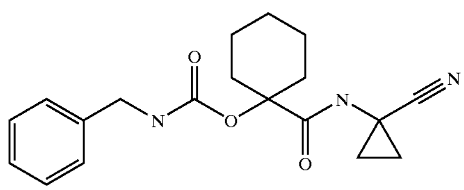 | Benzyl-carbamic acid 1-(1-cyano-cyclopropylcarbamoyl)-cyclohexyl ester |
| 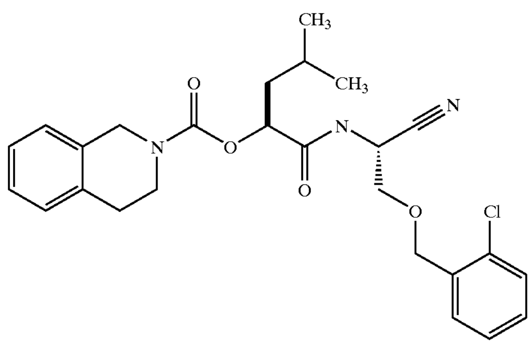 | 3,4-Dihydro-1H-isoquinoline-2-carboxylic acid 1-{[(2-chloro-benzyloxymethyl)-cyano-methyl]-carbamoyl}-3-methyl-butyl ester |
| 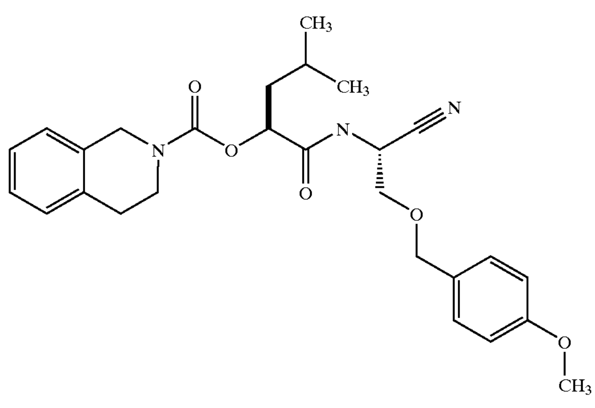 | 3,4-Dihydro-1H-isoquinoline-2-carboxylic acid 1-{[cyano-(4-methoxy-benzyloxymethyl)-methyl]-carbamoyl}-3-methyl-butyl ester |
| 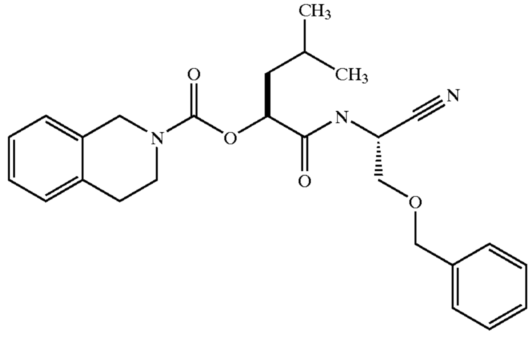 | 3,4-Dihydro-1H-isoquinoline-2-carboxylic acid 1-[(benzyloxymethyl-cyano-methyl)-carbamoyl]-3-methyl-butyl ester |

-continued

| Structure | Chemical Name* |
|---|---|
| 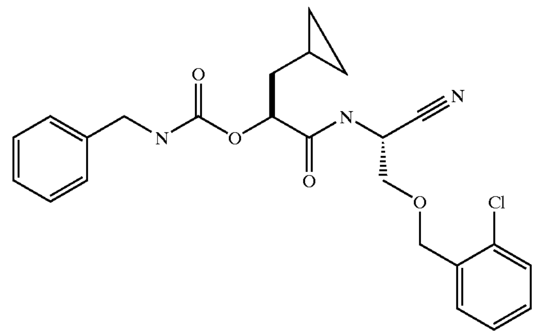 | Benzyl-carbamic acid 1-{[(2-chloro-benzyloxymethyl)-cyano-methyl]-carbamoyl}-2-cyclopropyl-ethyl ester |
| 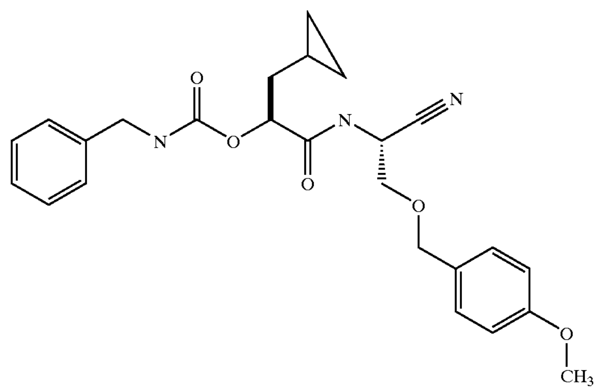 | Benzyl-carbamic acid 1-{[cyano-(4-methoxy-benzyloxymethyl)-methyl]-carbamoyl}-2-cyclopropyl-ethyl ester |
| 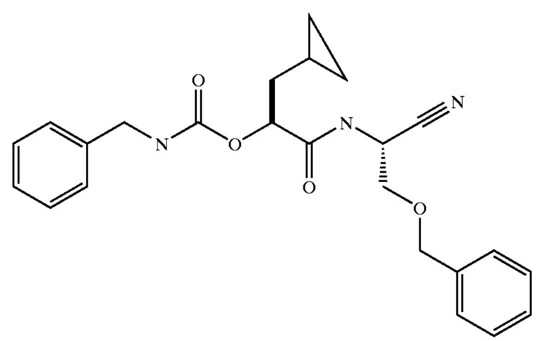 | Benzyl-carbamic acid 1-[(benzyloxymethyl-cyano-methyl)-carbamoyl]-2-cyclopropyl-ethyl ester |
| 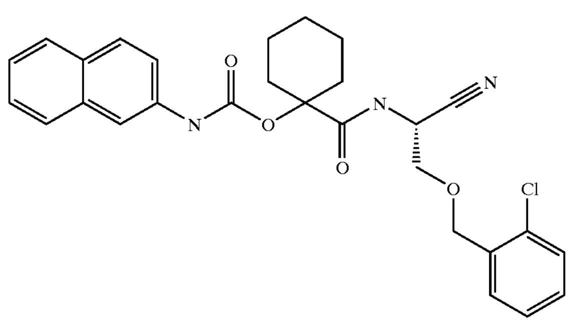 | Naphthalen-2-yl-carbamic acid 1-{[(2-chloro-benzyloxymethyl)-cyano-methyl]-carbamoyl}-cyclohexyl ester |

| Structure | Chemical Name* |
| --- | --- |
| 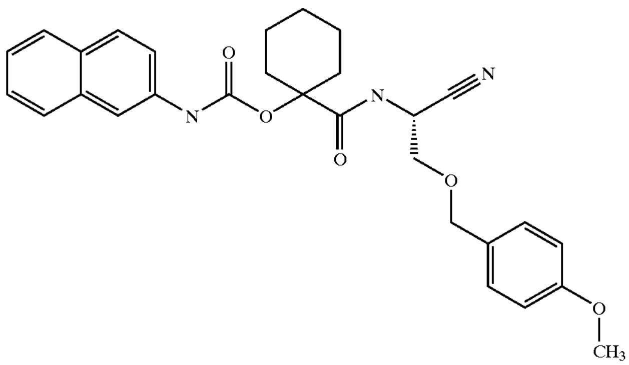 | Naphthalen-2-yl-carbamic acid 1-{[cyano-(4-methoxy-benzyloxymethyl)-methyl]-carbamoyl}-cyclohexyl ester |
| 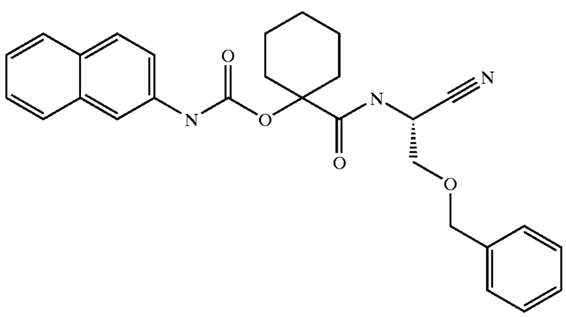 | Naphthalen-2-yl-carbamic acid 1-[(benzyloxymethyl-cyano-methyl)-carbamoyl]-cyclohexyl ester |
| 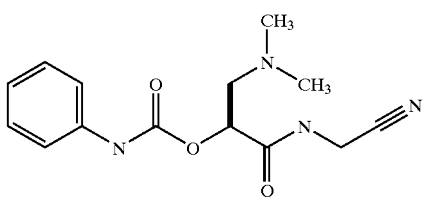 | Phenyl-carbamic acid 1-(cyanomethyl-carbamoyl)-2-dimethylamino-ethyl ester |
| 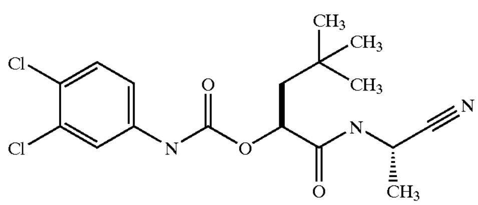 | (3,4-Dichloro-phenyl)-carbamic acid 1-[(cyano-methyl-methyl)-carbamoyl]-3,3-dimethyl-butyl ester |
| 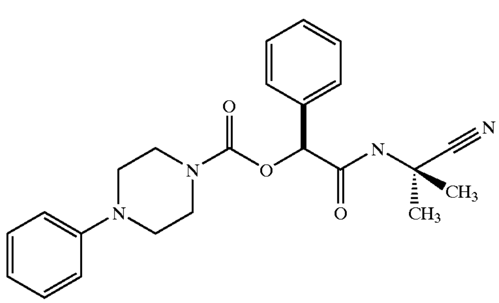 | 4-Phenyl-piperazine-1-carboxylic acid [(cyano-dimethyl-methyl)-carbamoyl]-phenyl-methyl ester |

-continued

| Structure | Chemical Name* |
|---|---|
| | 5-Pyridin-4-yl-thiophene-2-carboxylic acid (1-cyano-3-methanesulfonyl-propylcarbamoyl)-pyridin-3-yl-methyl ester |
| | 5-Pyridin-4-yl-thiophene-2-carboxylic acid (1-cyano-3-methanesulfonyl-propylcarbamoyl)-pyridin-3-yl-methyl ester |
| 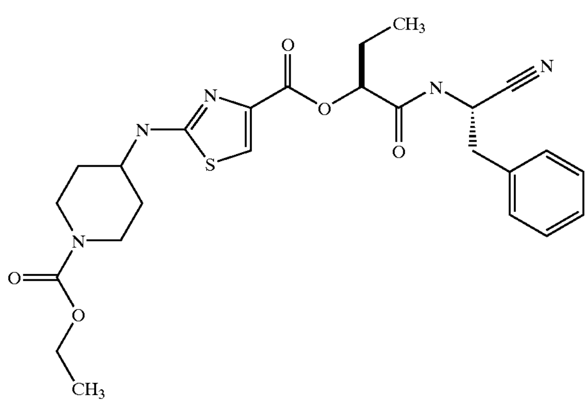 | 4-(4-{1-[(Benzyl-cyano-methyl)-carbamoyl]-propoxycarbonyl}-thiazol-2-ylamino)-piperidine-1-carboxylic acid ethyl ester |
| 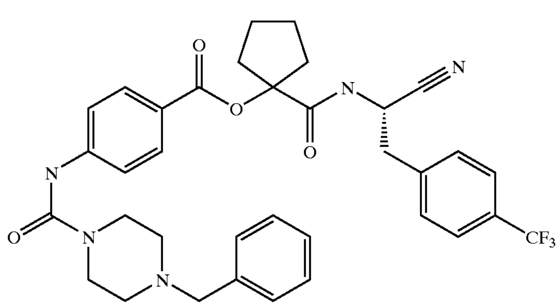 | 4-[(4-Benzyl-piperazine-1-carbonyl)-amino]-benzoic acid 1-{[cyano-(4-methyl-benzyl)-methyl]-carbamoyl}-cyclopentyl ester |

-continued

| Structure | Chemical Name* |
| --- | --- |
| 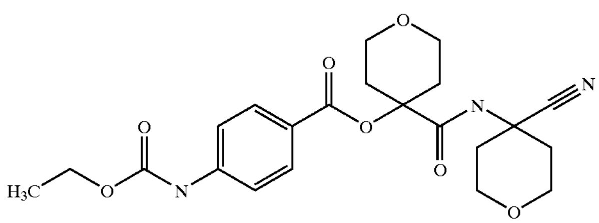 | 4-Ethoxycarbonylamino-benzoic acid 4-(4-cyano-tetrahydro-pyran-4-ylcarbamoyl)-tetrahydro-pyran-4-yl ester |
| 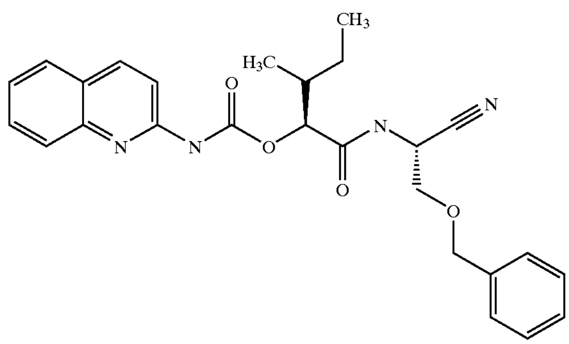 | Quinolin-2-yl-carbamic acid 1-[(benzyloxymethyl-cyano-methyl)-carbamoyl]-2-methyl-butyl ester |
| 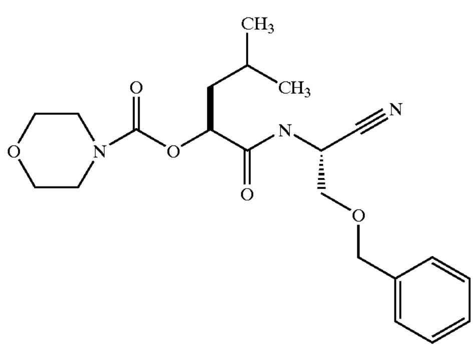 | Morpholine-4-carboxylic acid 1-[(benzyloxymethyl-cyano-methyl)-carbamoyl]-3-methyl-butyl ester |
| 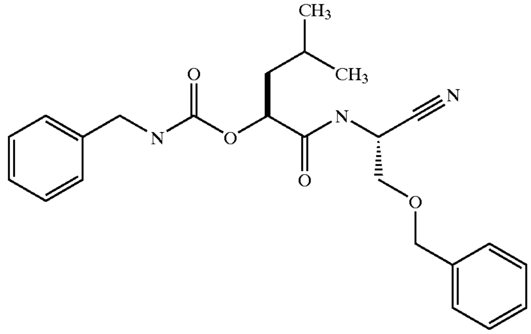 | Benzyl-carbamic acid 1-[(benzyloxymethyl-cyano-methyl)-carbamoyl]-3-methyl-butyl ester |

-continued

| Structure | Chemical Name* |
|---|---|
| 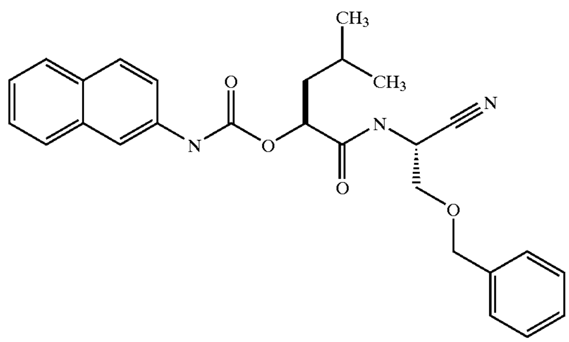 | Naphthalen-2-yl-carbamic acid 1-[(benzyloxymethyl-cyano-methyl)-carbamoyl]-3-methyl-butyl ester |
| 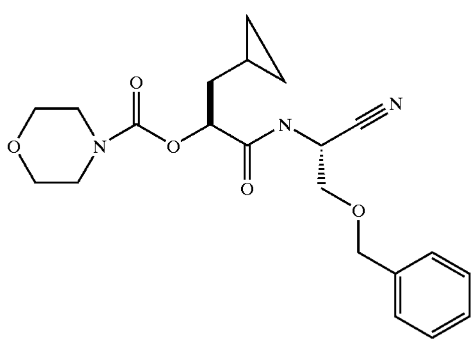 | Morpholine-4-carboxylic acid 1-[(benzyloxymethyl-cyano-methyl)-carbamoyl]-2-cyclopropyl-ethyl ester |
| 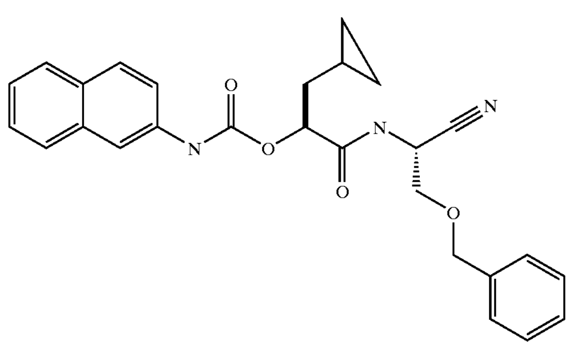 | Naphthalen-2-yl-carbamic acid 1-[(benzyloxymethyl-cyano-methyl)-carbamoyl]-2-cyclopropyl-ethyl ester |
| 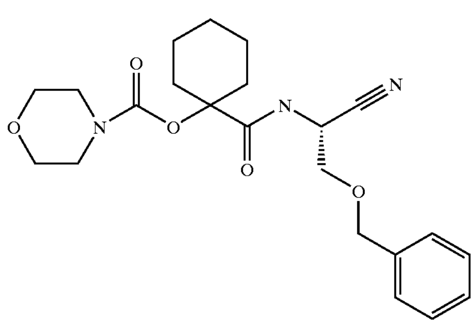 | Morpholine-4-carboxylic acid 1-[(benzyloxymethyl-cyano-methyl)-carbamoyl]-cyclohexyl ester |

| Structure | Chemical Name* |
|---|---|
| 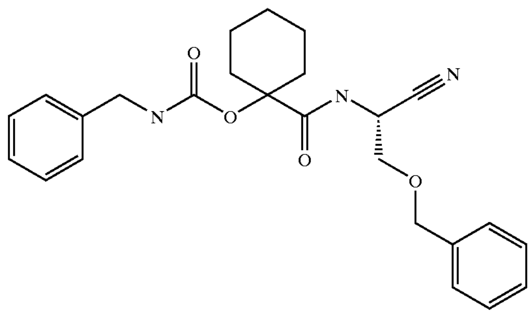 | Benzyl-carbamic acid 1-[(benzyloxymethyl-cyano-methyl)-carbamoyl]-cyclohexyl ester |
| 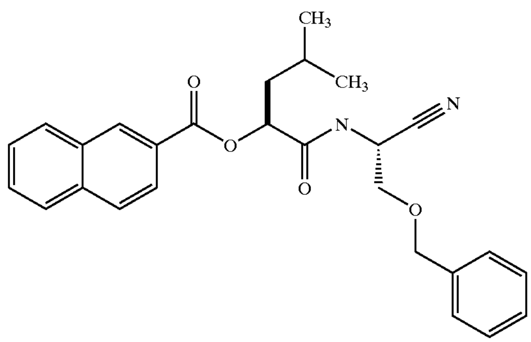 | Naphthalene-2-carboxylic acid 1-[(benzyloxymethyl-cyano-methyl)-carbamoyl]-3-methyl-butyl ester |
| 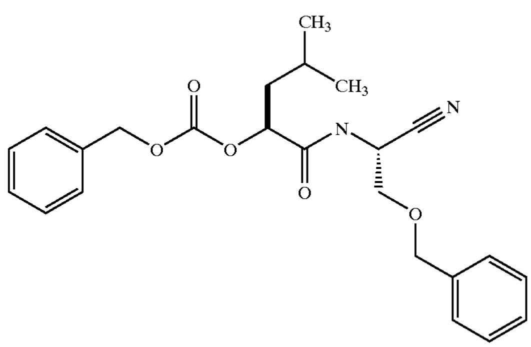 | Carbonic acid benzyl ester 1-[(benzyloxymethyl-cyano-methyl)-carbamoyl]-3-methyl-butyl ester |
| 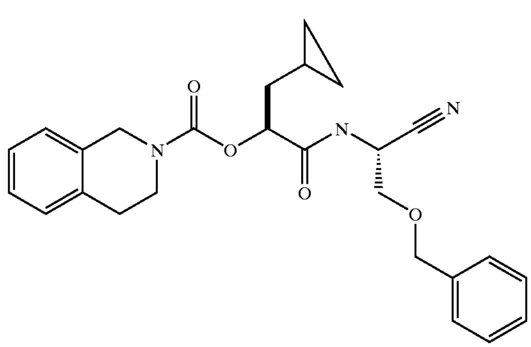 | 3,4-Dihydro-1H-isoquinoline-2-carboxylic acid 1-[(benzyloxymethyl-cyano-methyl)-carbamoyl]-2-cyclopropyl-ethyl ester |

-continued

| Structure | Chemical Name* |
|---|---|
| 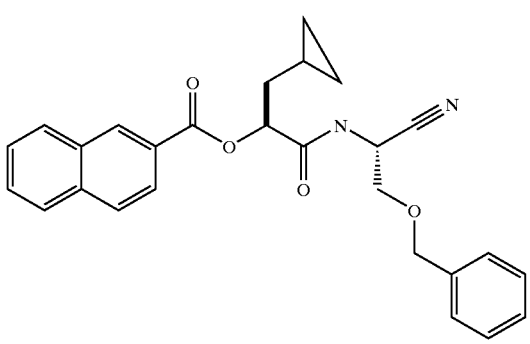 | Naphthalene-2-carboxylic acid 1-[(benzyloxymethyl-cyano-methyl)-carbamoyl]-2-cyclopropyl-ethyl ester |
| 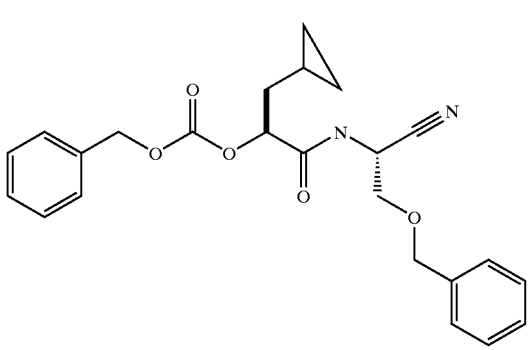 | Carbonic acid benzyl ester 1-[(benzyloxymethyl-cyano-methyl)-carbamoyl]-2-cyclopropyl-ethyl ester |
| 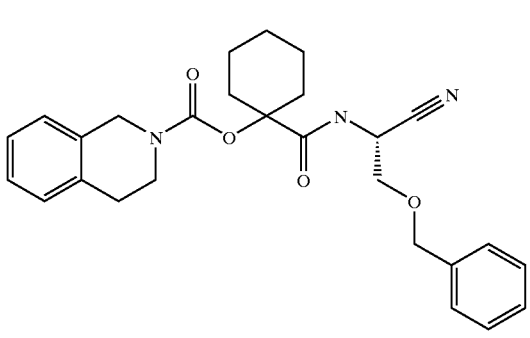 | 3,4-Dihydro-1H-isoquinoline-2-carboxylic acid 1-[(benzyloxymethyl-cyano-methyl)-carbamoyl]-cyclohexyl ester |
| 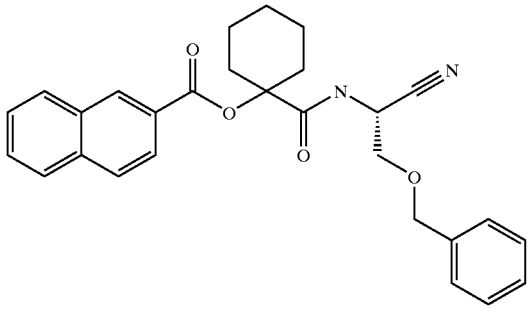 | Naphthalene-2-carboxylic acid 1-[(benzyloxymethyl-cyano-methyl)-carbamoyl]-cyclohexyl ester |

| Structure | Chemical Name* |
|---|---|
| 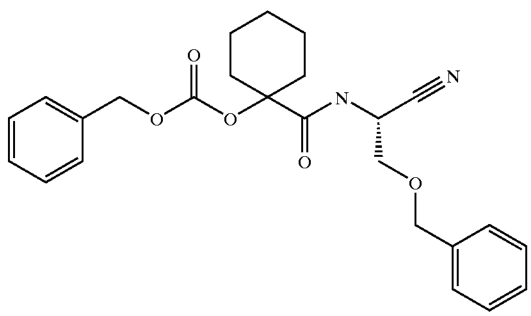 | Carbonic acid benzyl ester 1-[(benzyloxymethyl-cyano-methyl)-carbamoyl]-cyclohexyl ester |
| 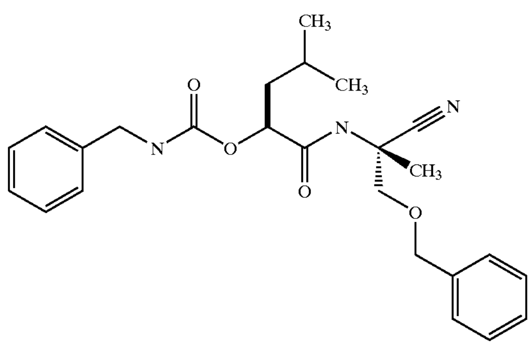 | Benzyl-carbamic acid 1-[(benzyloxymethyl-cyano-methyl-methyl)-carbamoyl]-3-methyl-butyl ester |
| 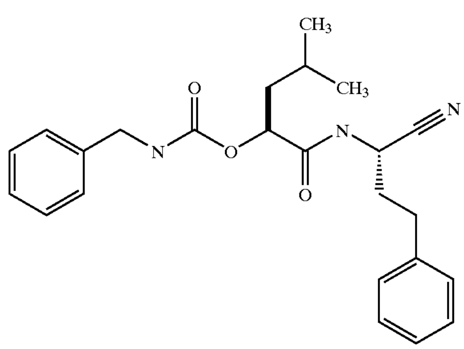 | Benzyl-carbamic acid 1-(1-cyano-3-phenyl-propylcarbamoyl)-3-methyl-butyl ester |
| 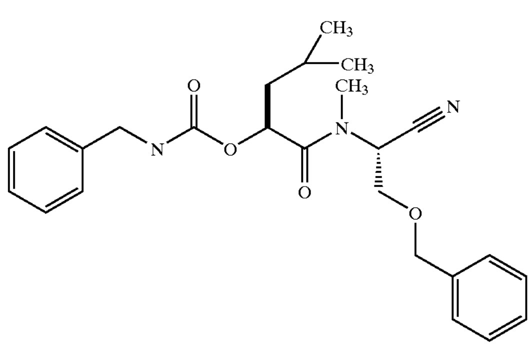 | Benzyl-carbamic acid 1-[(benzyloxymethyl-cyano-methyl)-methyl-carbamoyl]-3-methyl-butyl ester |

-continued

| Structure | Chemical Name* |
|---|---|
| 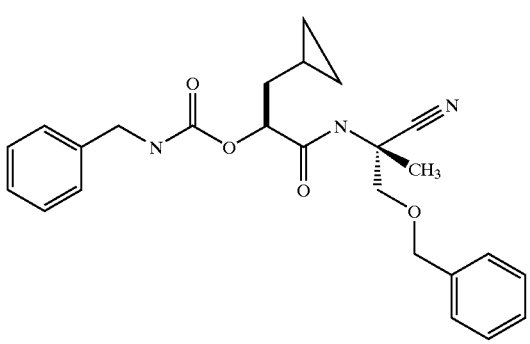 | Benzyl-carbamic acid 1-[(benzyloxymethyl-cyano-methyl-methyl)-carbamoyl]-2-cyclopropyl-ethyl ester |
| 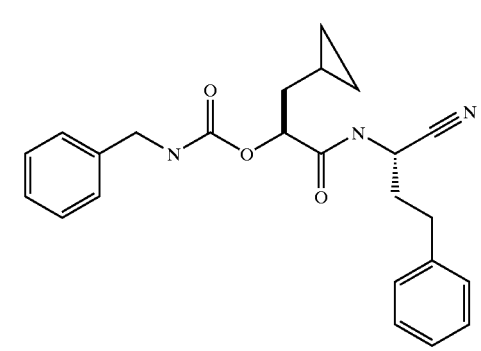 | Benzyl-carbamic acid 1-(1-cyano-3-phenyl-propylcarbamoyl)-2-cyclopropyl-ethyl ester |
| 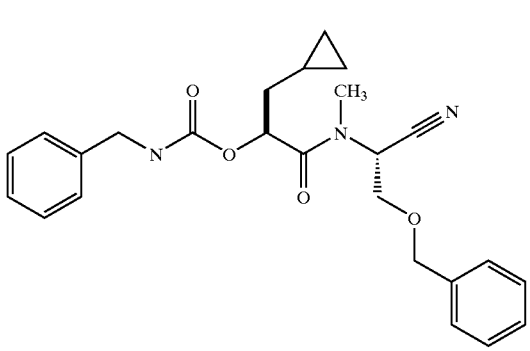 | Benzyl-carbamic acid 1-[(benzyloxymethyl-cyano-methyl)-methyl-carbamoyl]-2-cyclopropyl-ethyl ester |
| 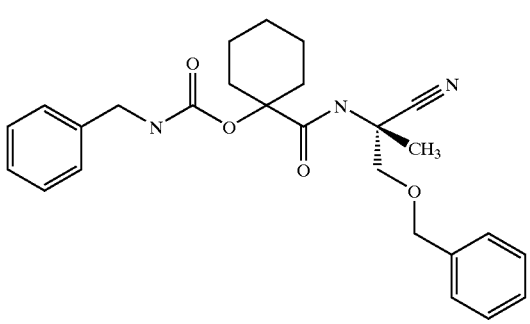 | Benzyl-carbamic acid 1-[(benzyloxymethyl-cyano-methyl-methyl)-carbamoyl]-cyclohexyl ester |

-continued

| Structure | Chemical Name* |
|---|---|
| 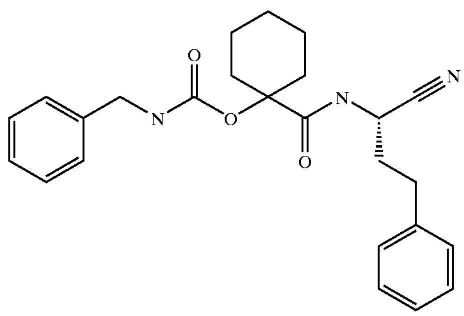 | Benzyl-carbamic acid 1-(1-cyano-3-phenyl-propylcarbamoyl)-cyclohexyl ester |
| 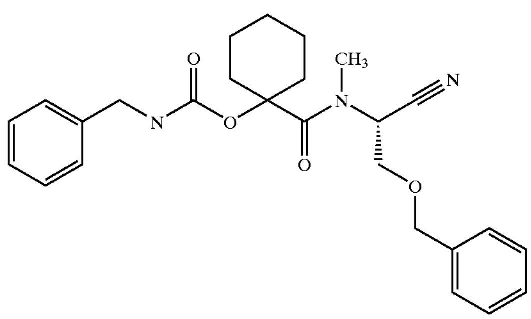 | Benzyl-carbamic acid 1-[(benzyloxymethyl-cyano-methyl)-methyl-carbamoyl]-cyclohexyl ester |
| 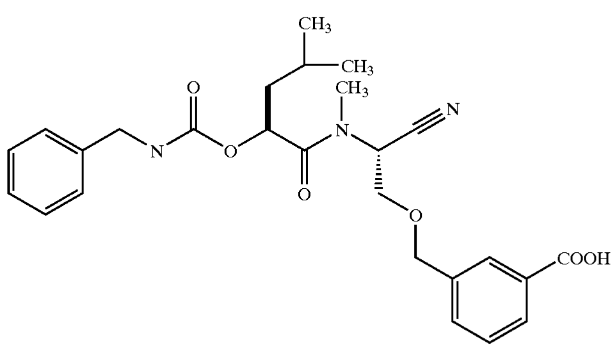 | 3-{2-[(2-Benzylcarbamoyloxy-4-methyl-pentanoyl)-methyl-amino]-2-cyano-ethoxymethyl}-benzoic acid |
| 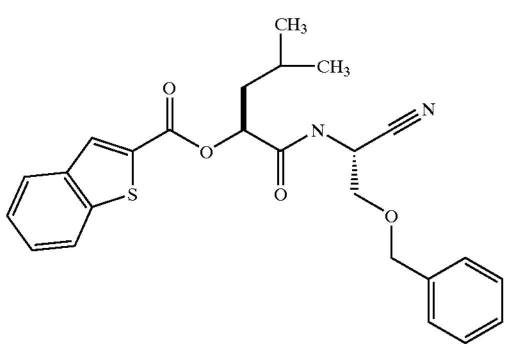 | Benzo[b]thiophene-2-carboxylic acid 1-[(benzyloxymethyl-cyano-methyl)-carbamoyl]-3-methyl-butyl ester |

-continued

| Structure | Chemical Name* |
|---|---|
| 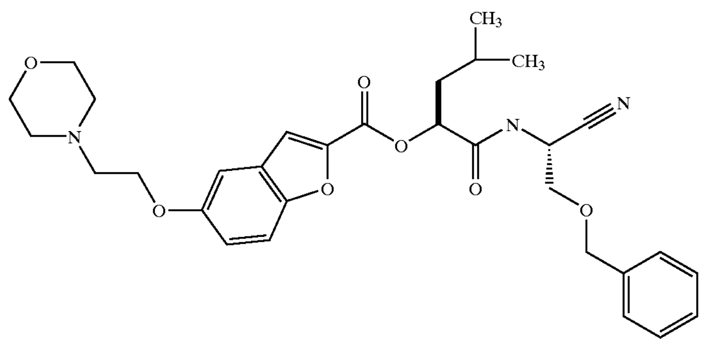 | 5-(2-Morpholin-4-yl-ethoxy)-benzofuran-2-carboxylic acid 1-[(benzyloxymethyl-cyano-methyl)-carbamoyl]-3-methyl-butyl ester |
| 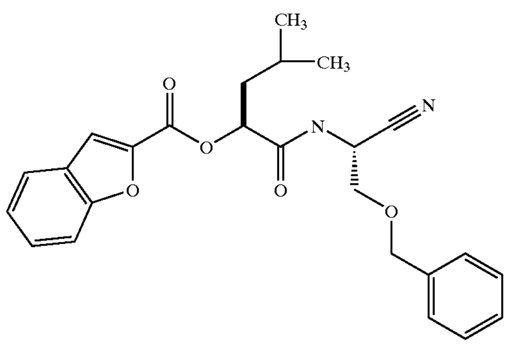 | Benzofuran-2-carboxylic acid 1-[(benzyloxymethyl-cyano-methyl)-carbamoyl]-3-methyl-butyl ester |
| 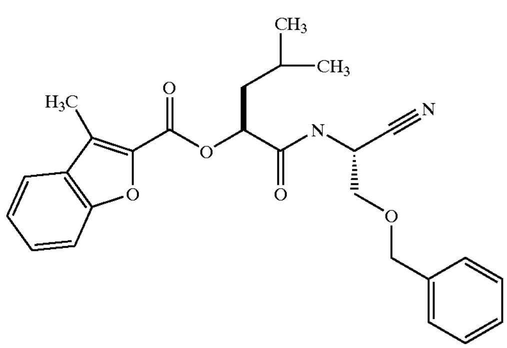 | 3-Methyl-benzofuran-2-carboxylic acid 1-[(benzyloxymethyl-cyano-methyl)-carbamoyl]-3-methyl-butyl ester |
| 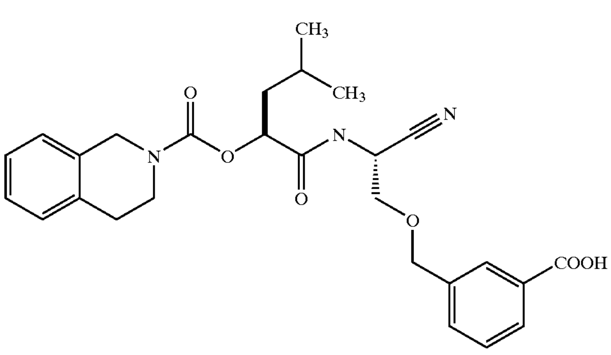 | 3,4-Dihydro-1H-isoquinoline-2-carboxylic acid 1-{[(3-carboxy-benzyloxymethyl)-cyano-methyl]-carbamoyl}-3-methyl-butyl ester |

| Structure | Chemical Name* |
|---|---|
| 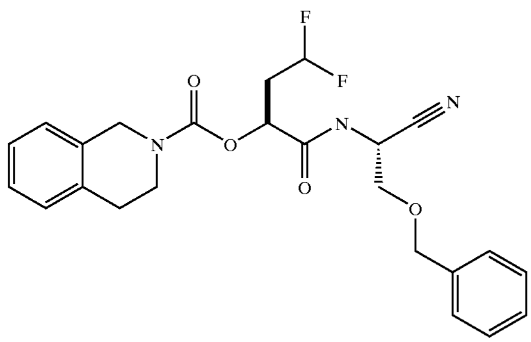 | 3,4-Dihydro-1H-isoquinoline-2-carboxylic acid 1-[(benzyloxymethyl-cyano-methyl)-carbamoyl]-3,3-difluoro-propyl ester |
| 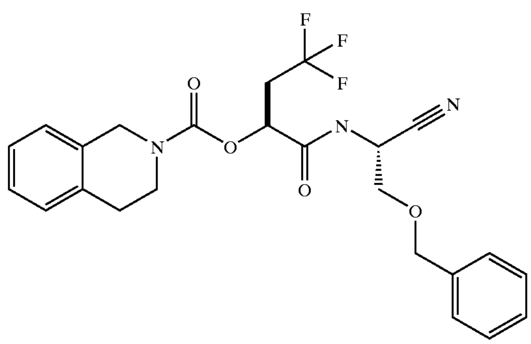 | 3,4-Dihydro-1H-isoquinoline-2-carboxylic acid 1-[(benzyloxymethyl-cyano-methyl)-carbamoyl]-3,3,3-trifluoro-propyl ester |
| 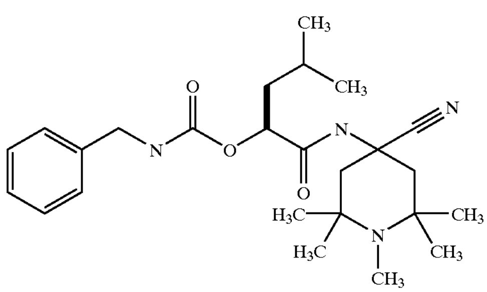 | Benzyl-carbamic acid 1-(4-cyano-1,2,2,6,6-pentamethyl-piperidin-4-ylcarbamoyl)-3-methyl-butyl ester |
| 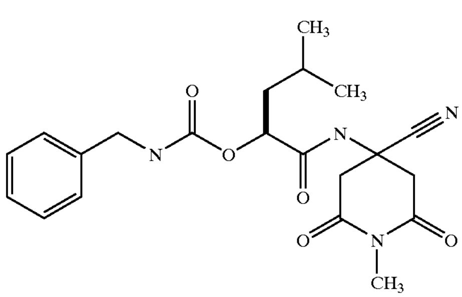 | Benzyl-carbamic acid 1-(4-cyano-1-methyl-2,6-dioxo-piperidin-4-ylcarbamoyl)-3-methyl-butyl ester |

| Structure | Chemical Name* |
|---|---|
| 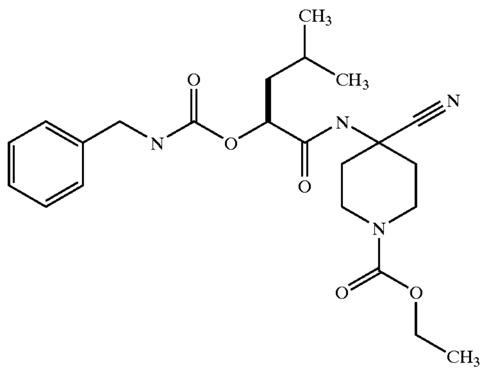 | 4-(2-Benzylcarbamoyloxy-4-methyl-pentanoylamino)-4-cyano-piperidine-1-carboxylic acid ethyl ester |
| 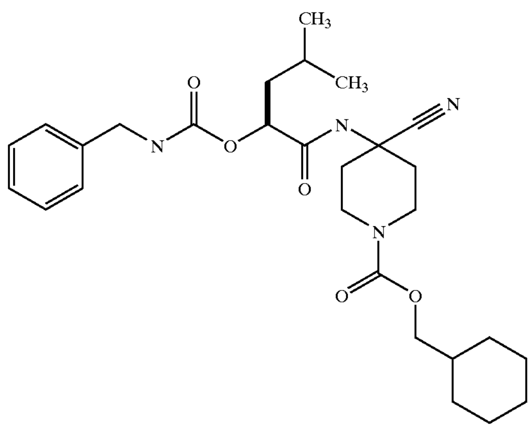 | 4-(2-Benzylcarbamoyloxy-4-methyl-pentanoylamino)-4-cyano-piperidine-1-carboxylic acid cyclohexylmethyl ester |
| 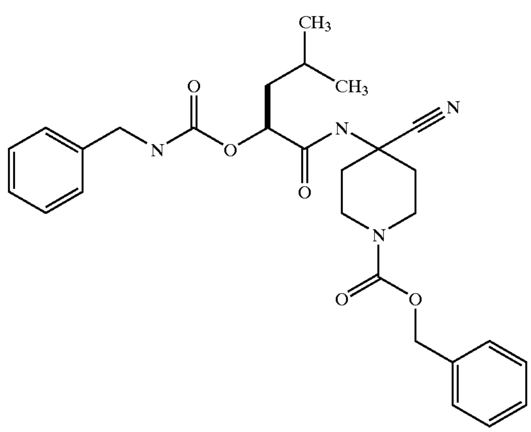 | 4-(2-Benzylcarbamoyloxy-4-methyl-pentanoylamino)-4-cyano-piperidine-1-carboxylic acid benzyl ester |
| 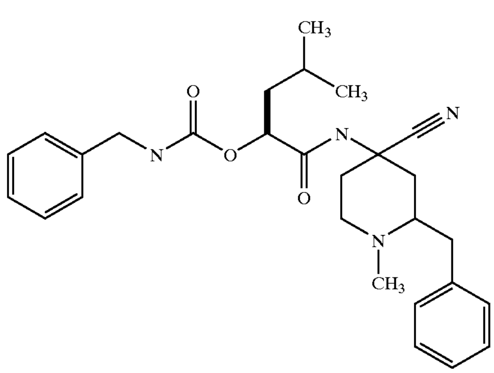 | Benzyl-carbamic acid 1-(2-benzyl-4-cyano-1-methyl-piperidin-4-ylcarbamoyl)-3-methyl-butyl ester |

-continued

| Structure | Chemical Name* |
|---|---|
| 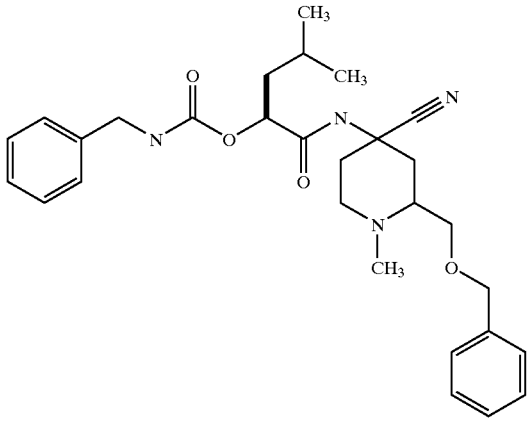 | Benzyl-carbamic acid 1-(2-benzyloxymethyl-4-cyano-1-methyl-piperidin-4-ylcarbamoyl)-3-methyl-butyl ester |
| 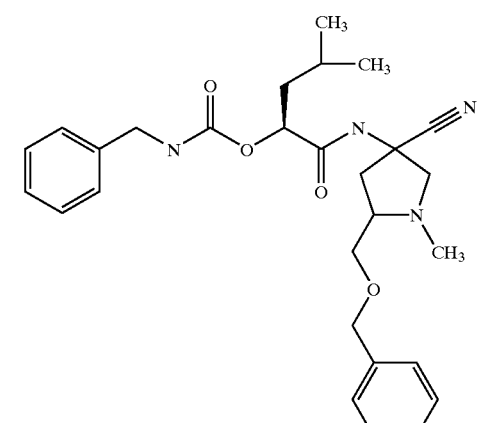 | Benzyl-carbamic acid 1-(5-benzyloxymethyl-3-cyano-1-methyl-pyrrolidin-3-ylcarbamoyl)-3-methyl-butyl ester |
| 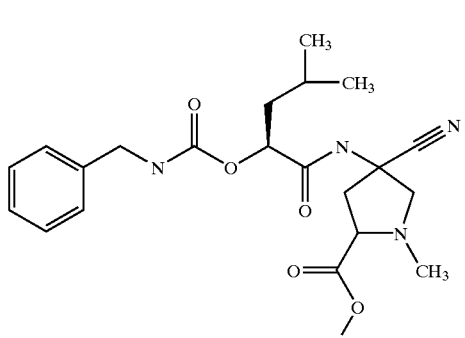 | 4-(2-Benzylcarbamoyloxy-4-methyl-pentanoylamino)-4-cyano-1-methyl-pyrrolidine-2-carboxylic acid methyl ester |
| 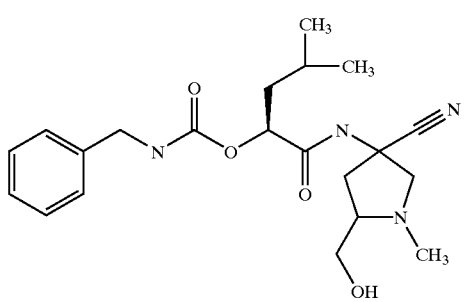 | Benzyl-carbamic acid 1-(3-cyano-5-hydroxymethyl-1-methyl-pyrrolidin-3-ylcarbamoyl)-3-methyl-butyl ester |

| Structure | Chemical Name* |
|---|---|
| 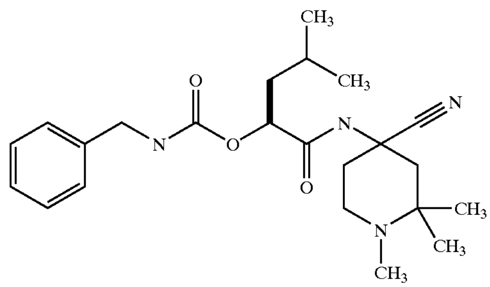 | Benzyl-carbamic acid 1-(4-cyano-1,2,2-trimethyl-piperidin-4-ylcarbamoyl)-3-methyl-butyl ester |
| 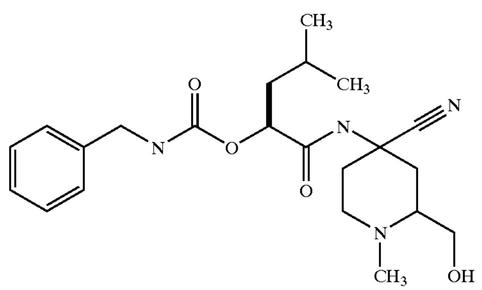 | Benzyl-carbamic acid 1-(4-cyano-2-hydroxymethyl-1-methyl-piperidin-4-ylcarbamoyl)-3-methyl-butyl ester |
| 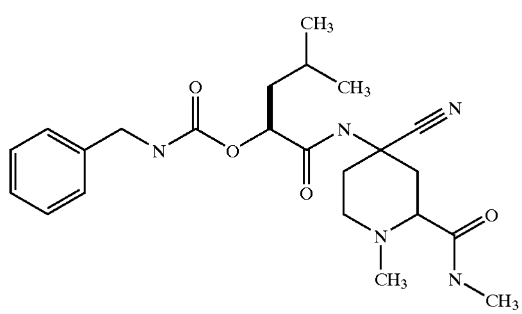 | Benzyl-carbamic acid 1-(4-cyano-1-methyl-2-methylcarbamoyl-piperidin-4-ylcarbamoyl)-3-methyl-butyl ester |
| 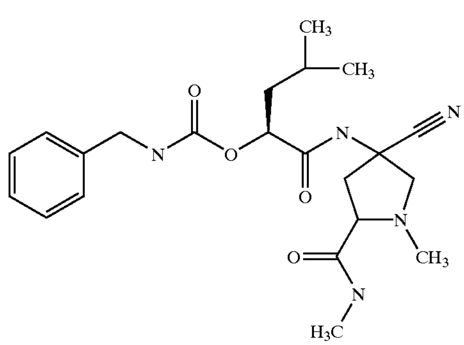 | Benzyl-carbamic acid 1-(3-cyano-1-methyl-5-methylcarbamoyl-pyrrolidin-3-ylcarbamoyl)-3-methyl-butyl ester |

| Structure | Chemical Name* |
|---|---|
| 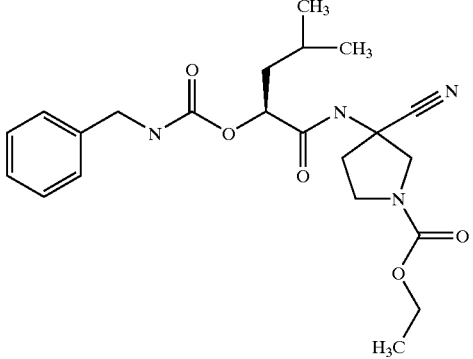 | 3-(2-Benzylcarbamoyloxy-4-methyl-pentanoylamino)-3-cyano-pyrrolidine-1-carboxylic acid ethyl ester |
| 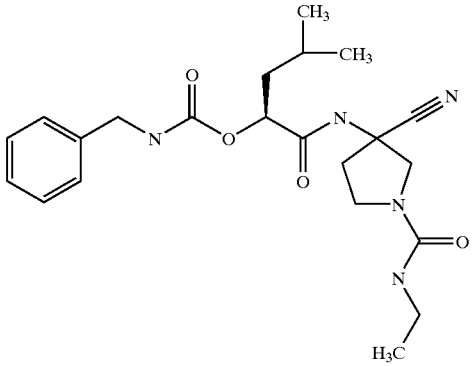 | Benzyl-carbamic acid 1-(3-cyano-1-ethylcarbamoyl-pyrrolidin-3-ylcarbamoyl)-3-methyl-butyl ester |
| 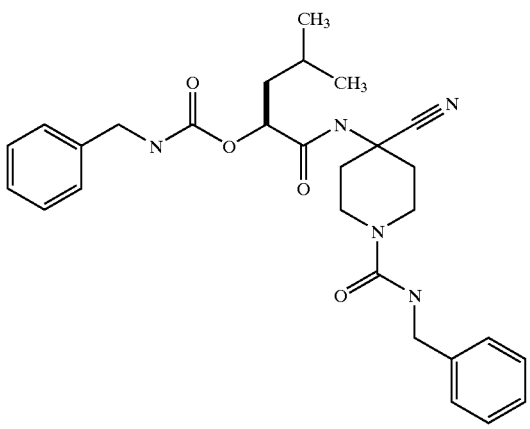 | Benzyl-carbamic acid 1-(1-benzylcarbamoyl-4-cyano-piperidin-4-ylcarbamoyl)-3-methyl-butyl ester |
| 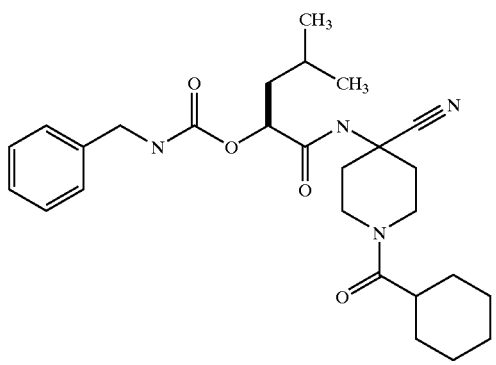 | Benzyl-carbamic acid 1-(4-cyano-1-cyclohexanecarbonyl-piperidin-4-ylcarbamoyl)-3-methyl-butyl ester |

-continued

| Structure | Chemical Name* |
|---|---|
| 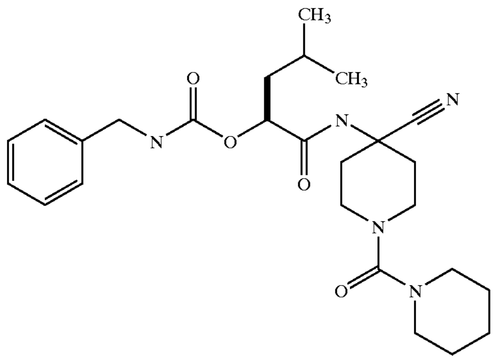 | Benzyl-carbamic acid 1-[4-cyano-1-(piperidine-1-carbonyl)-piperidin-4-ylcarbamoyl]-3-methyl-butyl ester |
| 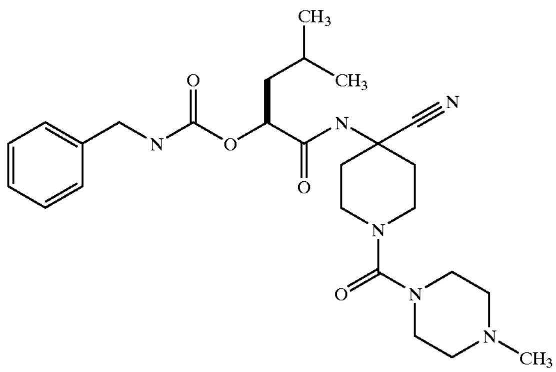 | Benzyl-carbamic acid 1-[4-cyano-1-(4-methyl-piperazine-1-carbonyl)-piperidin-4-ylcarbamoyl]-3-methyl-butyl ester |
| 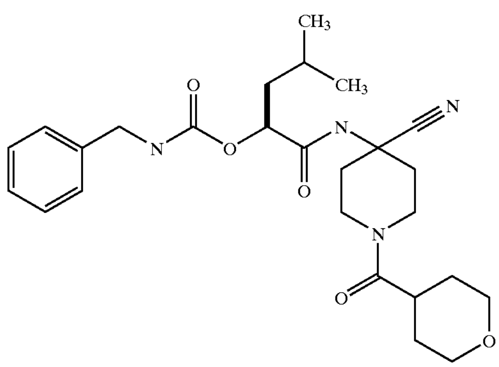 | Benzyl-carbamic acid 1-[4-cyano-1-(tetrahydro-pyran-4-carbonyl)-piperidin-4-ylcarbamoyl]-3-methyl-butyl ester |
| 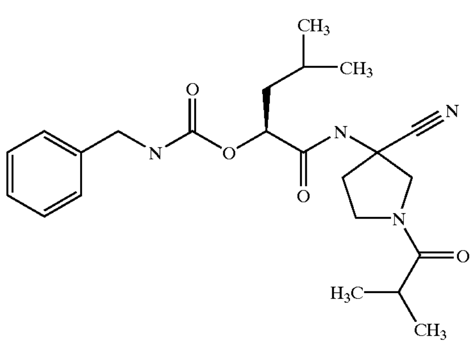 | Benzyl-carbamic acid 1-(3-cyano-1-isobutyryl-pyrrolidin-3-ylcarbamoyl)-3-methyl-butyl ester |

-continued
| Structure | Chemical Name* |
|---|---|
| 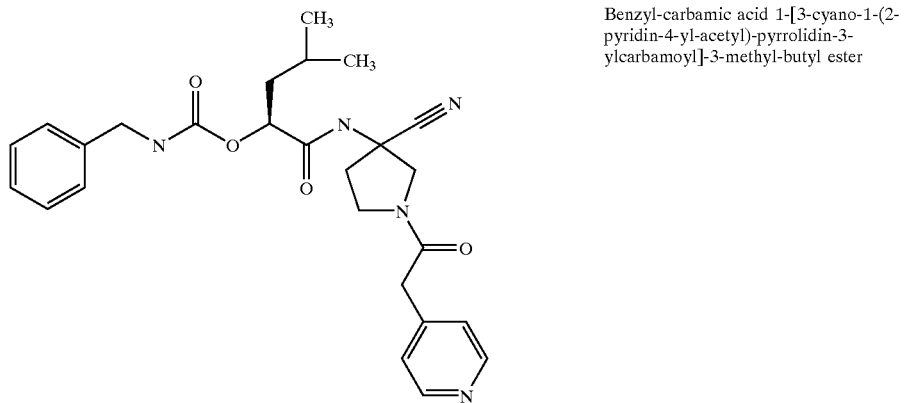 | Benzyl-carbamic acid 1-[3-cyano-1-(2-pyridin-4-yl-acetyl)-pyrrolidin-3-ylcarbamoyl]-3-methyl-butyl ester |
| 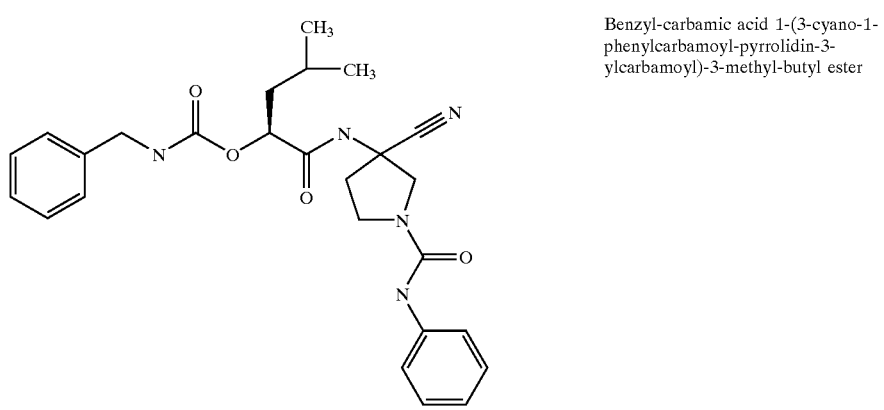 | Benzyl-carbamic acid 1-(3-cyano-1-phenylcarbamoyl-pyrrolidin-3-ylcarbamoyl)-3-methyl-butyl ester |
| 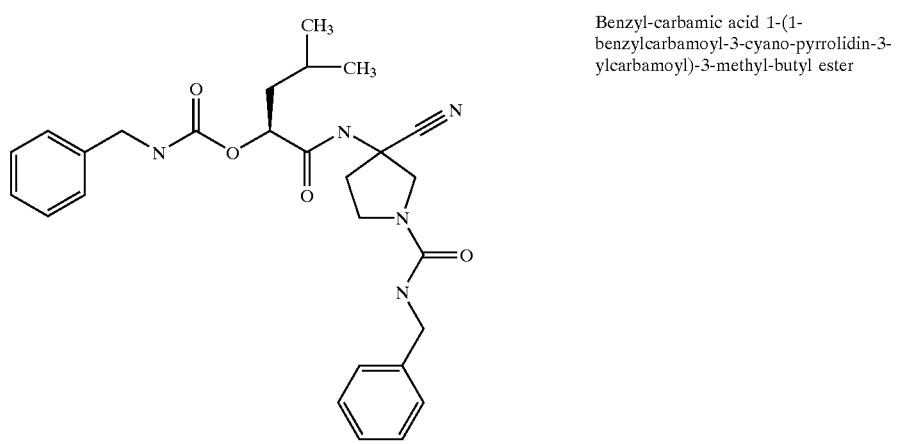 | Benzyl-carbamic acid 1-(1-benzylcarbamoyl-3-cyano-pyrrolidin-3-ylcarbamoyl)-3-methyl-butyl ester |

-continued

| Structure | Chemical Name* |
|---|---|
| 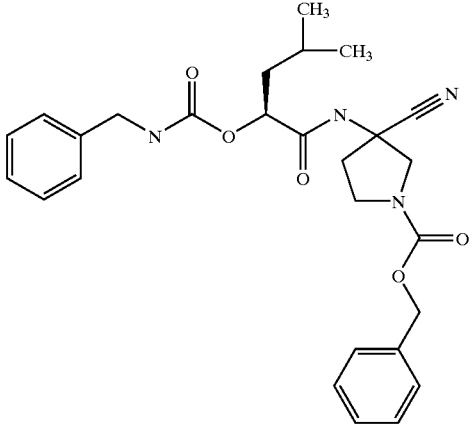 | 3-(2-Benzylcarbamoyloxy-4-methyl-pentanoylamino)-3-cyano-pyrrolidine-1-carboxylic acid benzyl ester |
| 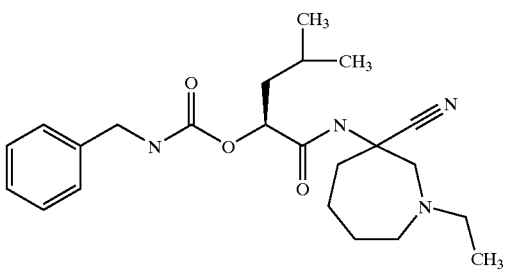 | Benzyl-carbamic acid 1-(3-cyano-1-ethyl-azepan-3-ylcarbamoyl)-3-methyl-butyl ester |
| 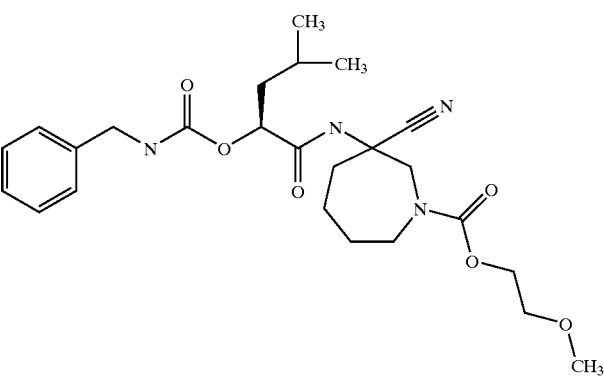 | 3-(2-Benzylcarbamoyloxy-4-methyl-pentanoylamino)-3-cyano-azepane-1-carboxylic acid 2-methoxy-ethyl ester |
| 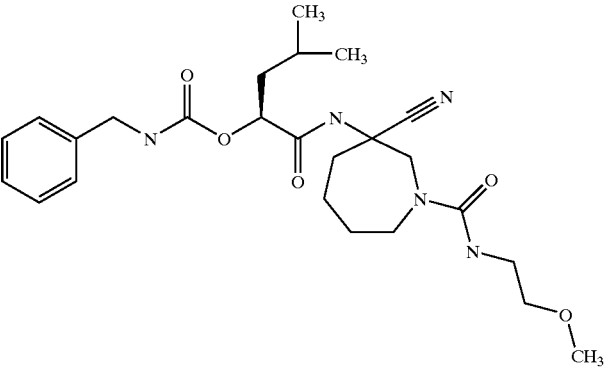 | Benzyl-carbamic acid 1-[3-cyano-1-(2-methoxy-ethylcarbamoyl)-azepan-3-ylcarbamoyl]-3-methyl-butyl ester |

-continued

| Structure | Chemical Name* |
|---|---|
| 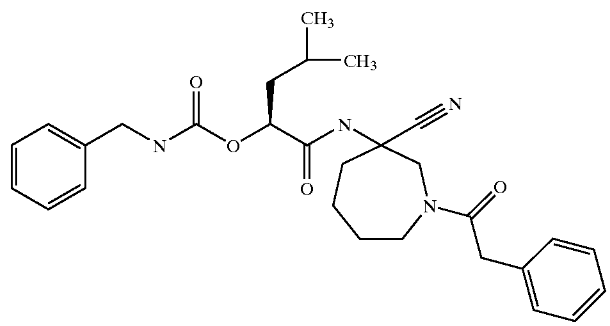 | Benzyl-carbamic acid 1-(3-cyano-1-phenylacetyl-azepan-3-ylcarbamoyl)-3-methyl-butyl ester |
| 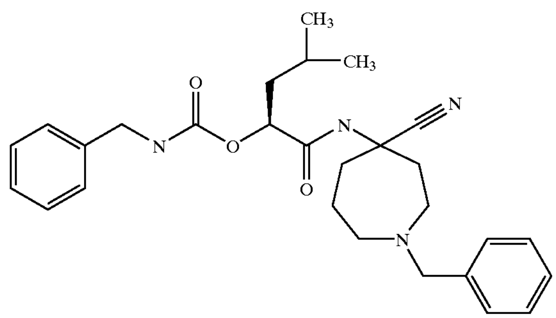 | Benzyl-carbamic acid 1-(1-benzyl-4-cyano-azepan-4-ylcarbamoyl)-3-methyl-butyl ester |
| 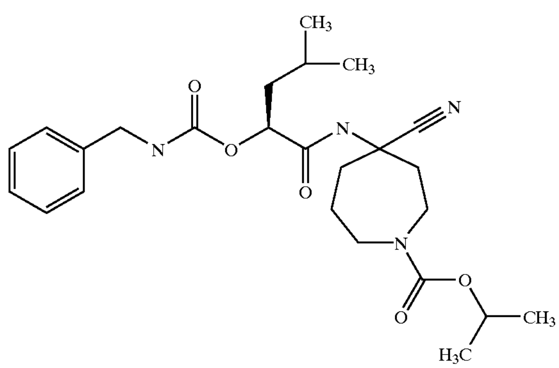 | 4-(2-Benzylcarbamoyloxy-4-methyl-pentanoylamino)-4-cyano-azepane-1-carboxylic acid isopropyl ester |
| 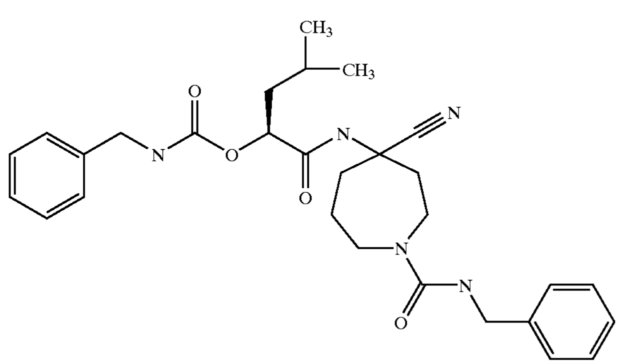 | Benzyl-carbamic acid 1-(1-benzylcarbamoyl-4-cyano-azepan-4-ylcarbamoyl)-3-methyl-butyl ester |

-continued

| Structure | Chemical Name* |
|---|---|
| 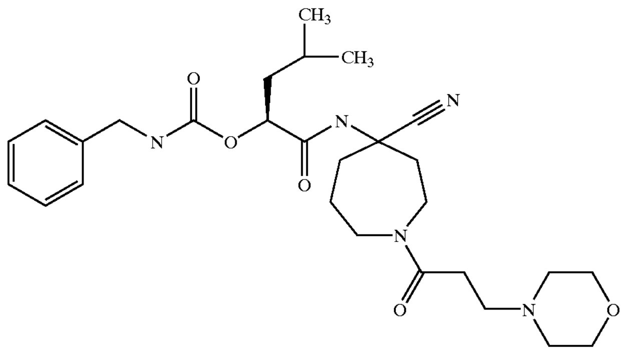 | Benzyl-carbamic acid 1-[4-cyano-1-(3-morpholin-4-yl-propionyl)-azepan-4-ylcarbamoyl]-3-methyl-butyl ester |
| 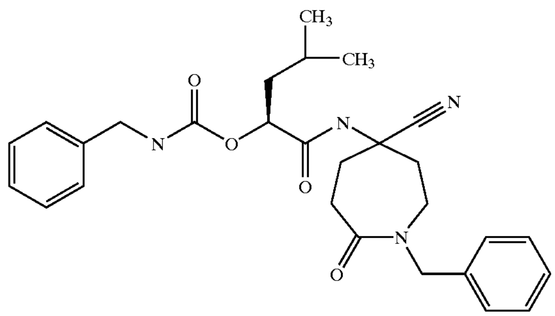 | Benzyl-carbamic acid 1-(1-benzyl-4-cyano-7-oxo-azepan-4-ylcarbamoyl)-3-methy-butyl ester |
| 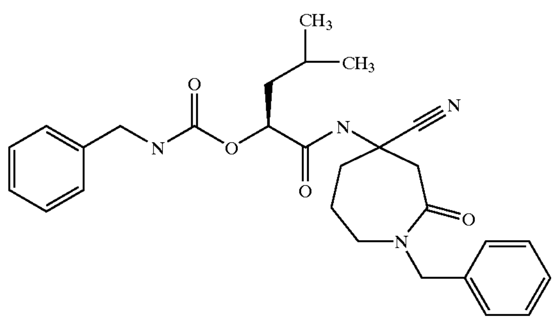 | Benzyl-carbamic acid 1-(1-benzyl-4-cyano-2-oxo-azepan-4-ylcarbamoyl)-3-methyl-butyl ester |
| 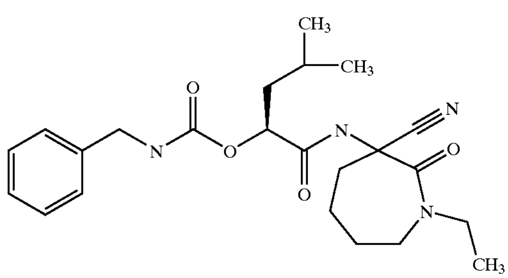 | Benzyl-carbamic acid 1-(3-cyano-1-ethyl-2-oxo-azepan-3-ylcarbamoyl)-3-methyl-butyl ester |
| 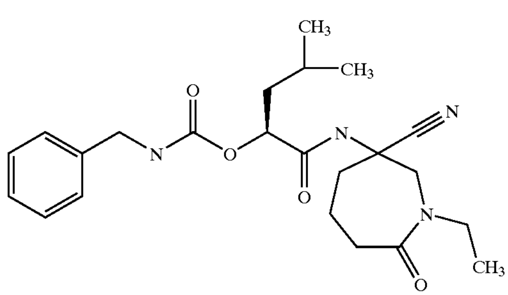 | Benzyl-carbamic acid 1-(3-cyano-1-ethyl-7-oxo-azepan-3-ylcarbamoyl)-3-methyl-butyl ester |

| Structure | Chemical Name* |
|---|---|
| 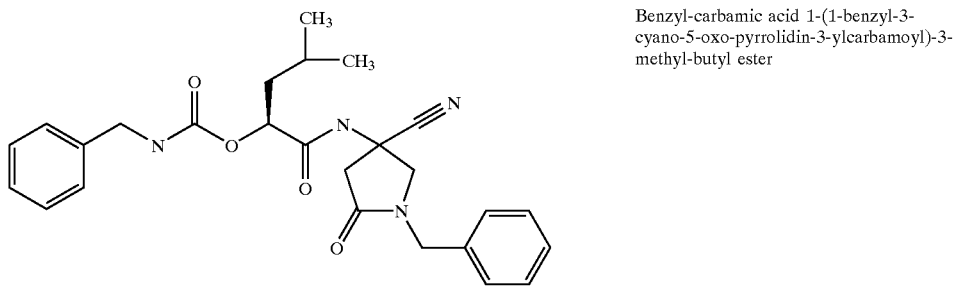 | Benzyl-carbamic acid 1-(1-benzyl-3-cyano-5-oxo-pyrrolidin-3-ylcarbamoyl)-3-methyl-butyl ester |
| 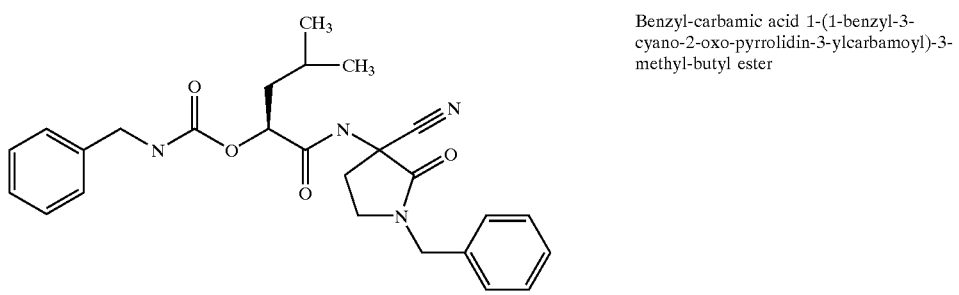 | Benzyl-carbamic acid 1-(1-benzyl-3-cyano-2-oxo-pyrrolidin-3-ylcarbamoyl)-3-methyl-butyl ester |
| 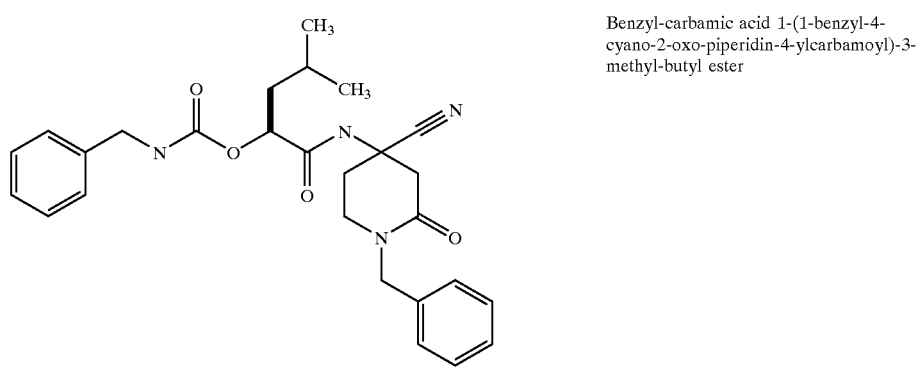 | Benzyl-carbamic acid 1-(1-benzyl-4-cyano-2-oxo-piperidin-4-ylcarbamoyl)-3-methyl-butyl ester |
| 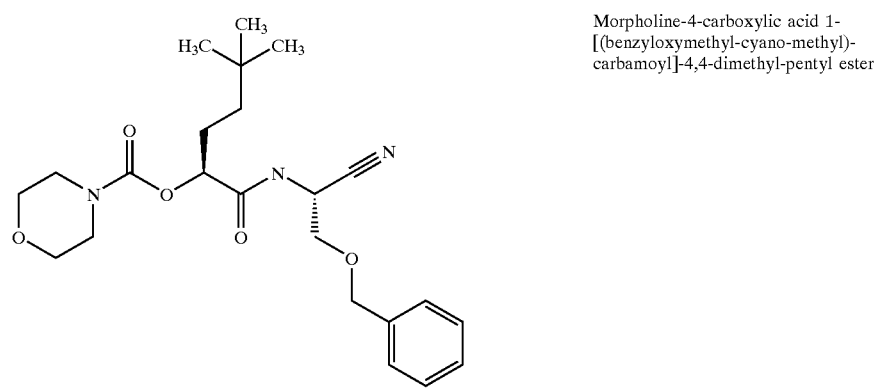 | Morpholine-4-carboxylic acid 1-[(benzyloxymethyl-cyano-methyl)-carbamoyl]-4,4-dimethyl-pentyl ester |

| Structure | Chemical Name* |
| --- | --- |
| 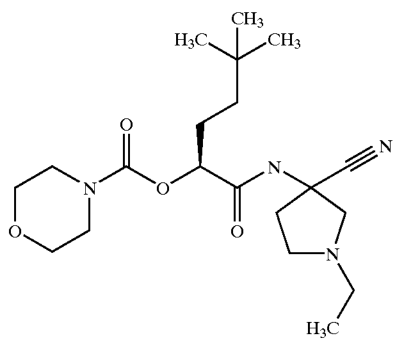 | Morpholine-4-carboxylic acid 1-(3-cyano-1-ethyl-pyrrolidin-3-ylcarbamoyl)-4,4-dimethyl-pentyl ester |
| 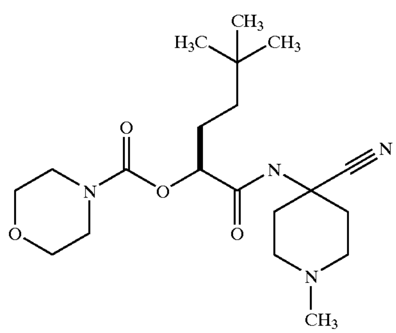 | Morpholine-4-carboxylic acid 1-(4-cyano-1-methyl-piperidin-4-ylcarbamoyl)-4,4-dimethyl-pentyl ester |
| 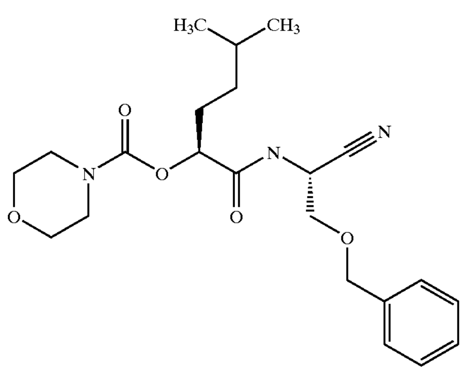 | Morpholine-4-carboxylic acid 1-[(benzyloxymethyl-cyano-methyl)-carbamoyl]-4-methyl-pentyl ester |
| 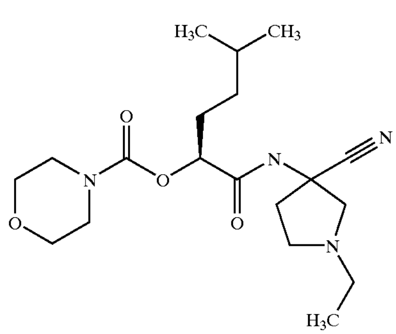 | Morpholine-4-carboxylic acid 1-(3-cyano-1-ethyl-pyrrolidin-3-ylcarbamoyl)-4-methyl-pentyl ester |

-continued

| Structure | Chemical Name* |
|---|---|
| 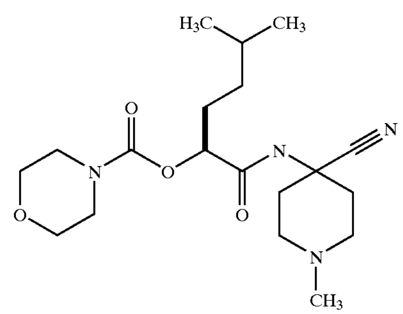 | Morpholine-4-carboxylic acid 1-(4-cyano-1-methyl-piperidin-4-ylcarbamoyl)-4-methyl-pentyl ester |
| 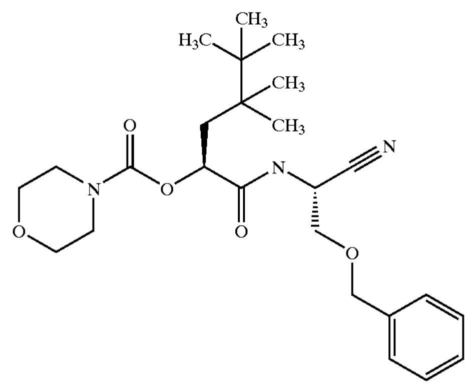 | Morpholine-4-carboxylic acid 1-[(benzyloxymethyl-cyano-methyl)-carbamoyl]-3,3,4,4-tetramethyl-pentyl ester |
| 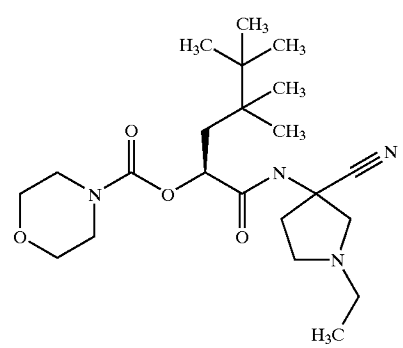 | Morpholine-4-carboxylic acid 1-(3-cyano-1-ethyl-pyrrolidin-3-ylcarbamoyl)-3,3,4,4-tetramethyl-pentyl ester |
| 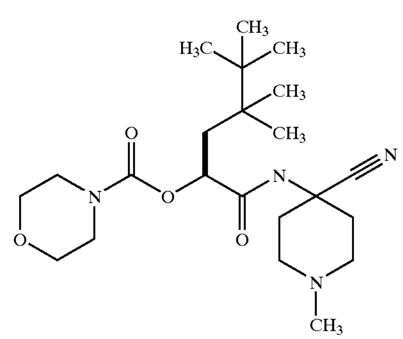 | Morpholine-4-carboxylic acid 1-(4-cyano-1-methyl-piperidin-4-ylcarbamoyl)-3,3,4,4-tetramethyl-pentyl ester |

| Structure | Chemical Name* |
|---|---|
| 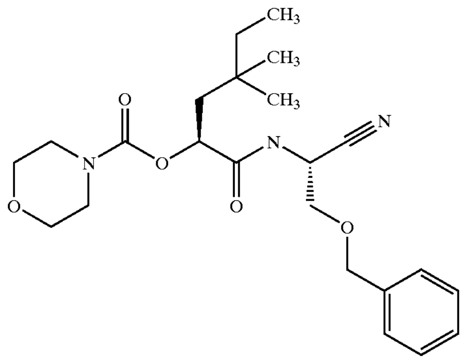 | Morpholine-4-carboxylic acid 1-[(benzyloxymethyl-cyano-methyl)-carbamoyl]-3,3-dimethyl-pentyl ester |
| 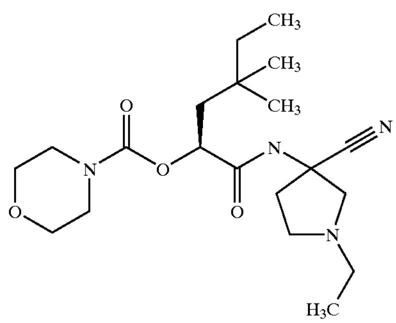 | Morpholine-4-carboxylic acid 1-(3-cyano-1-ethyl-pyrrolidin-3-ylcarbamoyl)-3,3-dimethyl-pentyl ester |
| 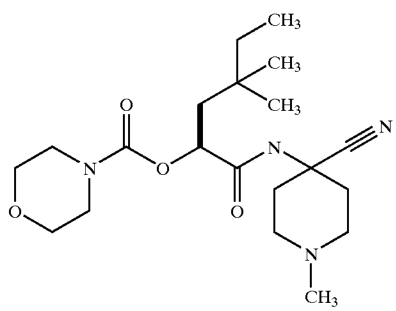 | Morpholine-4-carboxylic acid 1-(4-cyano-1-methyl-piperidin-4-ylcarbamoyl)-3,3-dimethyl-pentyl ester |
| 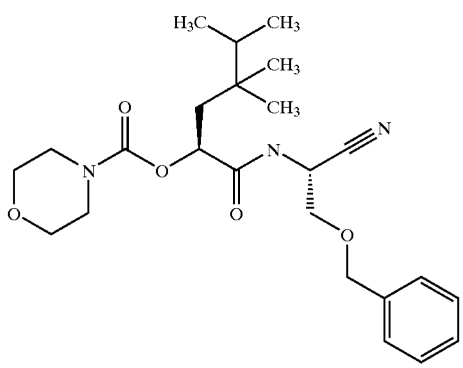 | Morpholine-4-carboxylic acid 1-[(benzyloxymethyl-cyano-methyl)-carbamoyl]-3,3,4-trimethyl-pentyl ester |

| Structure | Chemical Name* |
|---|---|
| 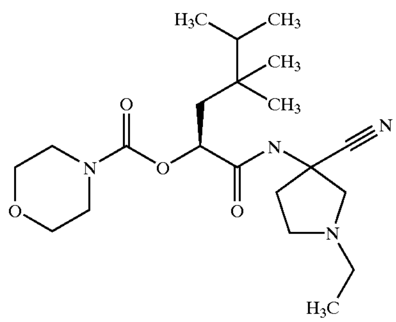 | Morpholine-4-carboxylic acid 1-(3-cyano-1-ethyl-pyrrolidin-3-ylcarbamoyl)-3,3,4-trimethyl-pentyl ester |
| 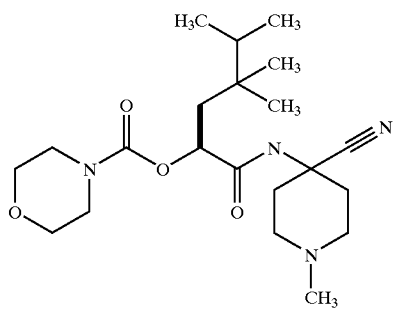 | Morpholine-4-carboxylic acid 1-(4-cyano-1-methyl-piperidin-4-ylcarbamoyl)-3,3,4-trimethyl-pentyl ester |
| 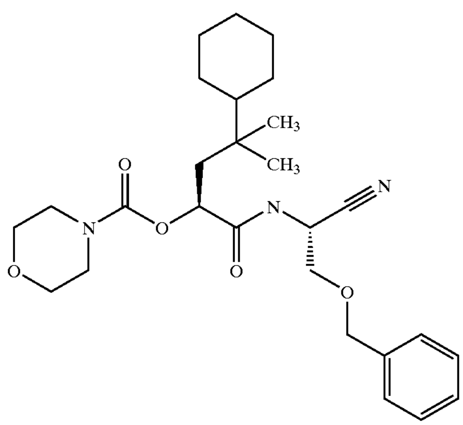 | Morpholine-4-carboxylic acid 1-[(benzyloxymethyl-cyano-methyl)-carbamoyl]-3-cyclohexyl-3-methyl-butyl ester |
| 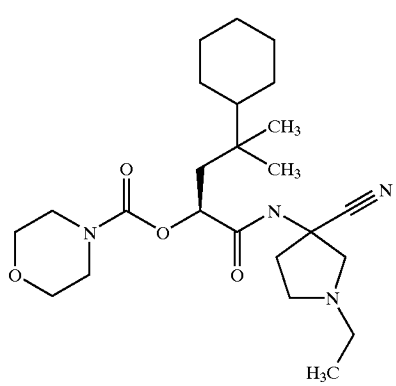 | Morpholine-4-carboxylic acid 1-(3-cyano-1-ethyl-pyrrolidin-3-ylcarbamoyl)-3-cyclohexyl-3-methyl-butyl ester |

-continued

| Structure | Chemical Name* |
|---|---|
| 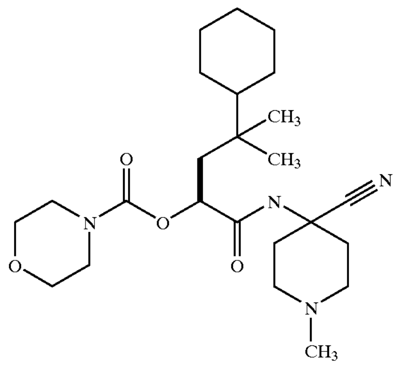 | Morpholine-4-carboxylic acid 1-(4-cyano-1-methyl-piperidin-4-ylcarbamoyl)-3-cyclohexyl-3-methyl-butyl ester |
| 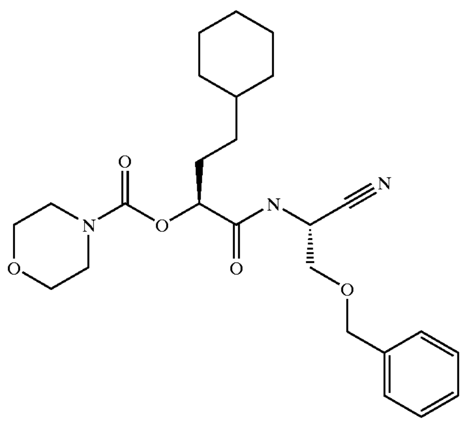 | Morpholine-4-carboxylic acid 1-[(benzyloxymethyl-cyano-methyl)-carbamoyl]-3-cyclohexyl-propyl ester |
| 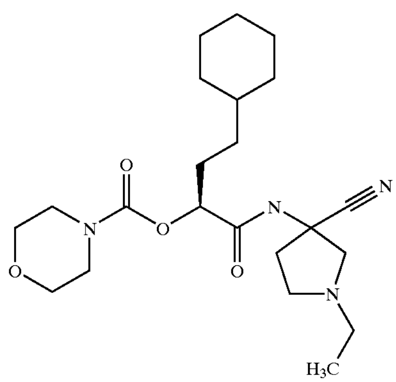 | Morpholine-4-carboxylic acid 1-(3-cyano-1-ethyl-pyrrolidin-3-ylcarbamoyl)-3-cyclohexyl-propyl ester |
| 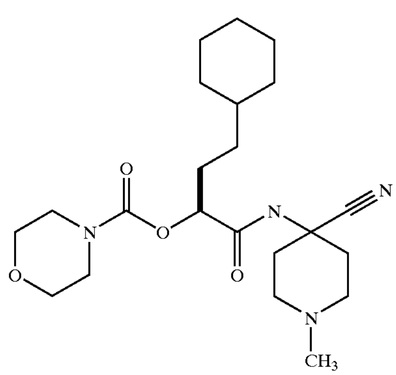 | Morpholine-4-carboxylic acid 1-(4-cyano-1-methyl-piperidin-4-ylcarbamoyl)-3-cyclohexyl-propyl ester |

-continued

| Structure | Chemical Name* |
|---|---|
| 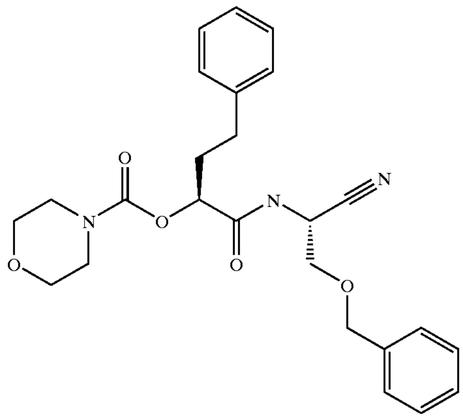 | Morpholine-4-carboxylic acid 1-[(benzyloxymethyl-cyano-methyl)-carbamoyl]-3-phenyl-propyl ester |
| 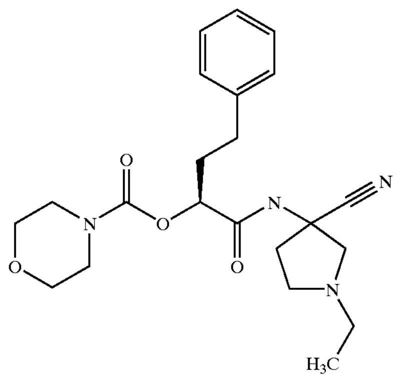 | Morpholine-4-carboxylic acid 1-(3-cyano-1-ethyl-pyrrolidin-3-ylcarbamoyl)-3-phenyl-propyl ester |
| 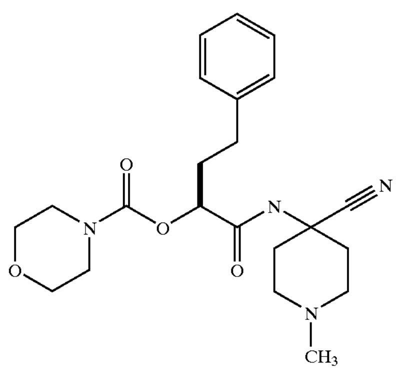 | Morpholine-4-carboxylic acid 1-(4-cyano-1-methyl-piperidin-4-ylcarbamoyl)-3-phenyl-propyl ester |
| 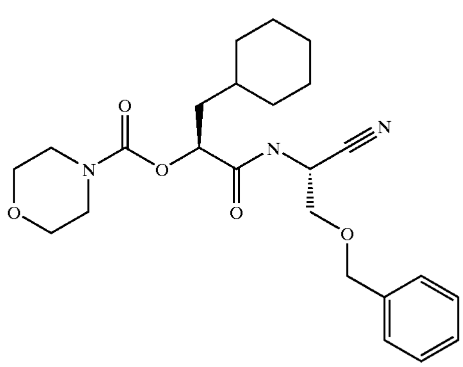 | Morpholine-4-carboxylic acid 1-[(benzyloxymethyl-cyano-methyl)-carbamoyl]-2-cyclohexyl-ethyl ester |

| Structure | Chemical Name* |
|---|---|
| 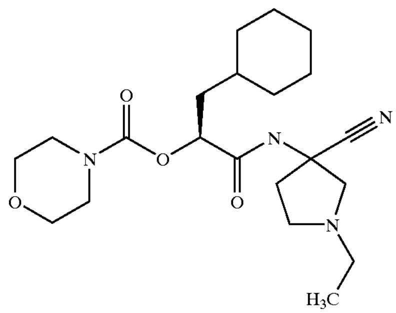 | Morpholine-4-carboxylic acid 1-(3-cyano-1-ethyl-pyrrolidin-3-ylcarbamoyl)-2-cyclohexyl-ethyl ester |
| 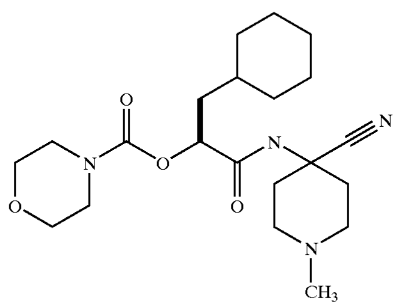 | Morpholine-4-carboxylic acid 1-(4-cyano-1-methyl-piperidin-4-ylcarbamoyl)-2-cyclohexyl-ethyl ester |
| 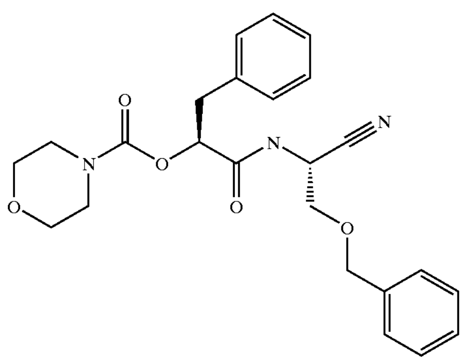 | Morpholine-4-carboxylic acid 1-[(benzyloxymethyl-cyano-methyl)-carbamoyl]-2-phenyl-ethyl ester |
| 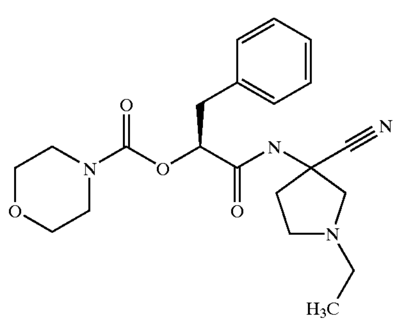 | Morpholine-4-carboxylic acid 1-(3-cyano-1-ethyl-pyrrolidin-3-ylcarbamoyl)-2-phenyl-ethyl ester |

-continued

| Structure | Chemical Name* |
|---|---|
| 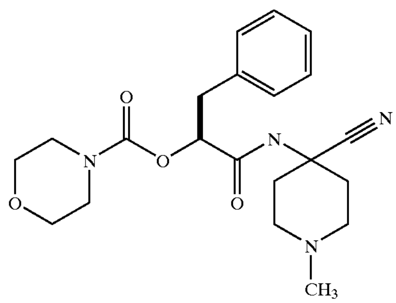 | Morpholine-4-carboxylic acid 1-(4-cyano-1-methyl-piperidin-4-ylcarbamoyl)-2-phenyl-ethyl ester |
| 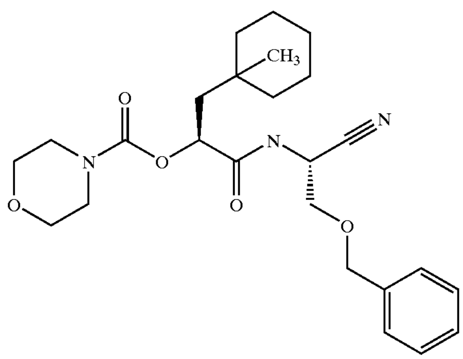 | Morpholine-4-carboxylic acid 1-[(benzyloxymethyl-cyano-methyl)-carbamoyl]-2-(1-methyl-cyclohexyl)-ethyl ester |
| 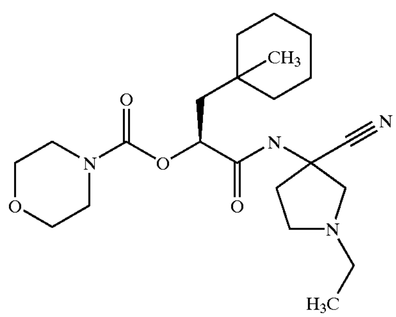 | Morpholine-4-carboxylic acid 1-(3-cyano-1-ethyl-pyrrolidin-3-ylcarbamoyl)-2-(1-methyl-cyclohexyl)-ethyl ester |
| 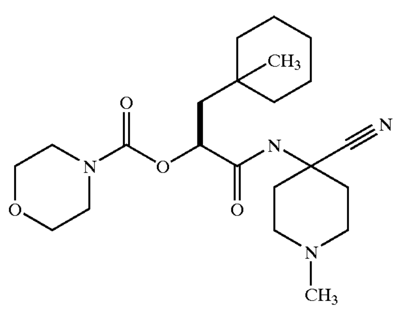 | Morpholine-4-carboxylic acid 1-(4-cyano-1-methyl-piperidin-4-ylcarbamoyl)-2-(1-methyl-cyclohexyl)-ethyl ester |

| Structure | Chemical Name* |
|---|---|
| 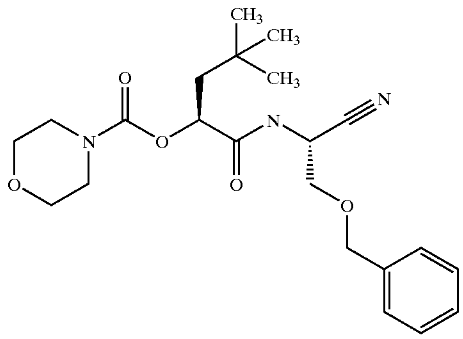 | Morpholine-4-carboxylic acid 1-[(benzyloxymethyl-cyano-methyl)-carbamoyl]-3,3-dimethyl-butyl ester |
| 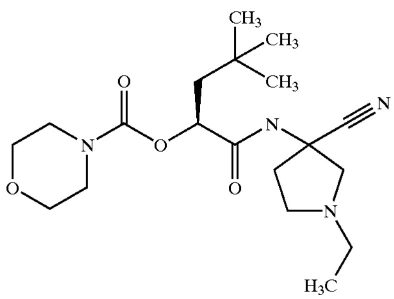 | Morpholine-4-carboxylic acid 1-(3-cyano-1-ethyl-pyrrolidin-3-ylcarbamoyl)-3,3-dimethyl-butyl ester |
| 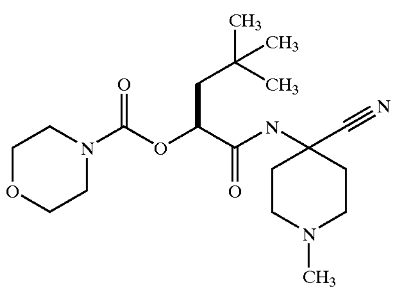 | Morpholine-4-carboxylic acid 1-(4-cyano-1-methyl-piperidin-4-ylcarbamoyl)-3,3-dimethyl-butyl ester |
| 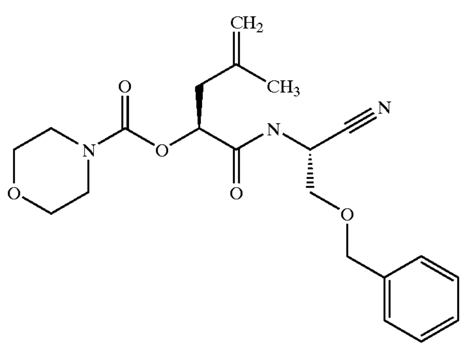 | Morpholine-4-carboxylic acid 1-[(benzyloxymethyl-cyano-methyl)-carbamoyl]-3-methyl-but-3-enyl ester |
| 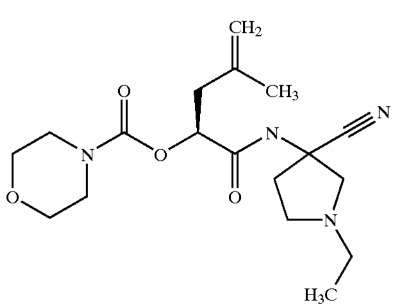 | Morpholine-4-carboxylic acid 1-(3-cyano-1-ethyl-pyrrolidin-3-ylcarbamoyl)-3-methyl-but-3-enyl ester |

| Structure | Chemical Name* |
|---|---|
| 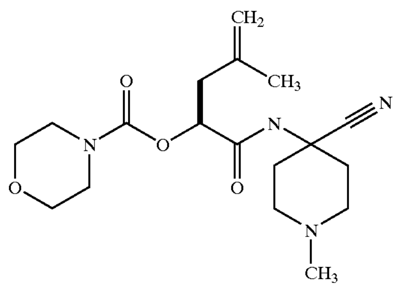 | Morpholine-4-carboxylic acid 1-(4-cyano-1-methyl-piperidin-4-ylcarbamoyl)-3-methyl-but-3-enyl ester |
| 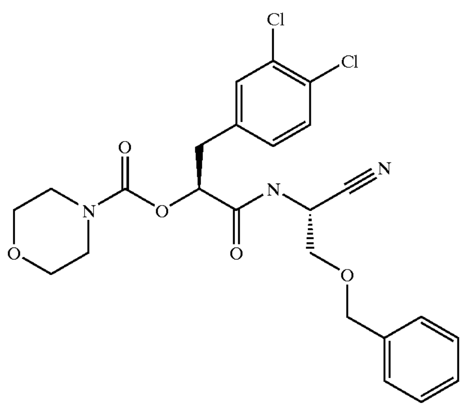 | Morpholine-4-carboxylic acid 1-[(benzyloxymethyl-cyano-methyl)-carbamoyl]-2-(3,4-dichloro-phenyl)-ethyl ester |
| 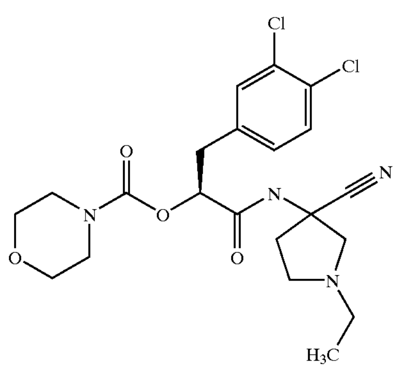 | Morpholine-4-carboxylic acid 1-(3-cyano-1-ethyl-pyrrolidin-3-ylcarbamoyl)-2-(3,4-dichloro-phenyl)-ethyl ester |
| 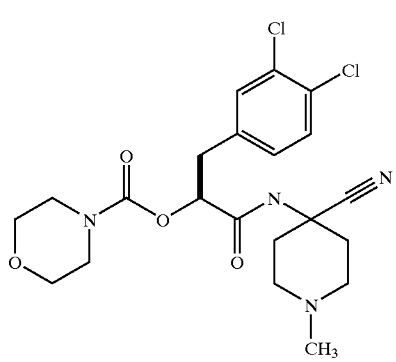 | Morpholine-4-carboxylic acid 1-(4-cyano-1-methyl-piperidin-4-ylcarbamoyl)-2-(3,4-dichloro-phenyl)-ethyl ester |

| Structure | Chemical Name* |
|---|---|
| 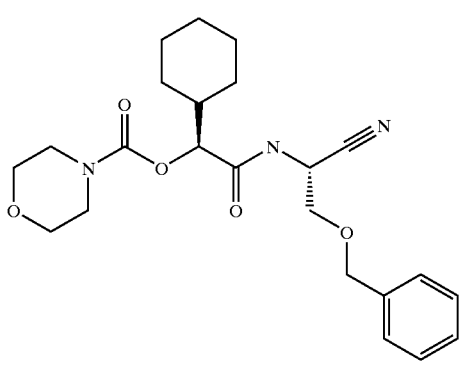 | Morpholine-4-carboxylic acid [(benzyloxymethyl-cyano-methyl)-carbamoyl]-cyclohexyl-methyl ester |
| 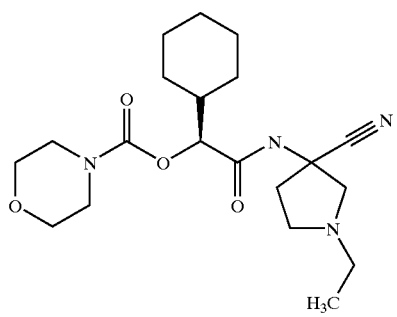 | Morpholine-4-carboxylic acid (3-cyano-1-ethyl-pyrrolidin-3-ylcarbamoyl)-cyclohexyl-methyl ester |
| 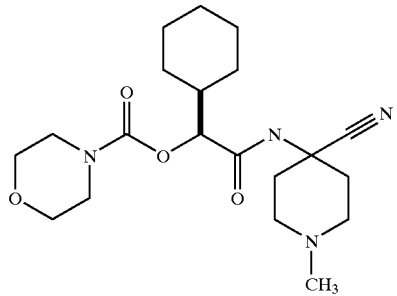 | Morpholine-4-carboxylic acid (4-cyano-1-methyl-piperidin-4-ylcarbamoyl)-cyclohexyl-methyl ester |
| 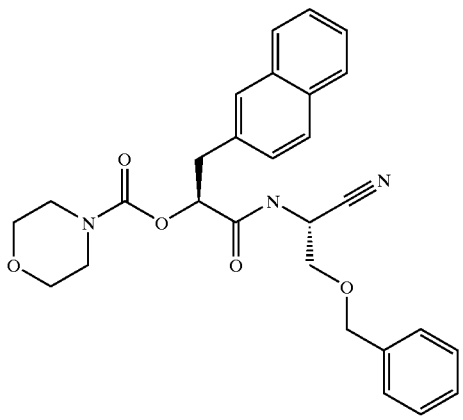 | Morpholine-4-carboxylic acid 1-[(benzyloxymethyl-cyano-methyl)-carbamoyl]-2-naphthalen-2-yl-ethyl ester |

-continued

| Structure | Chemical Name* |
|---|---|
| 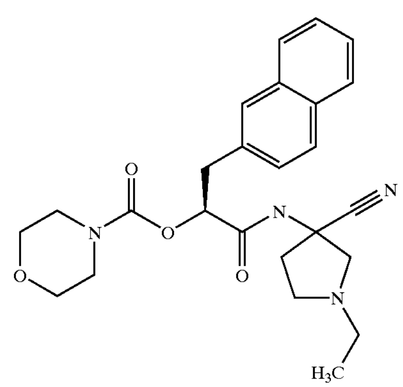 | Morpholine-4-carboxylic acid 1-(3-cyano-1-ethyl-pyrrolidin-3-ylcarbamoyl)-2-naphthalen-2-yl-ethyl ester |
| 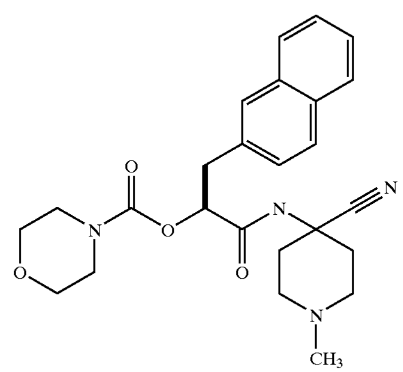 | Morpholine-4-carboxylic acid 1-(4-cyano-1-methyl-piperidin-4-ylcarbamoyl)-2-naphthalen-2-yl-ethyl ester |
| 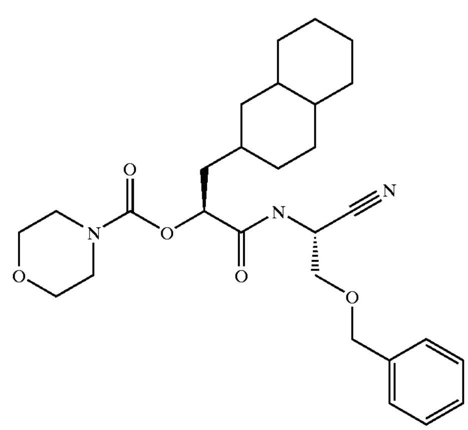 | Morpholine-4-carboxylic acid 1-[(benzyloxymethyl-cyano-methyl)-carbamoyl]-2-(decahydro-naphthalen-2-yl)-ethyl ester |
| 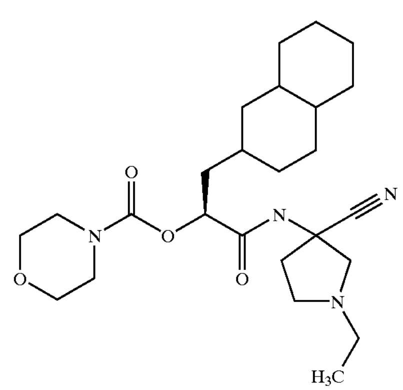 | Morpholine-4-carboxylic acid 1-(3-cyano-1-ethyl-pyrrolidin-3-ylcarbamoyl)-2-(decahydro-naphthalen-2-yl)-ethyl ester |

-continued

| Structure | Chemical Name* |
|---|---|
| 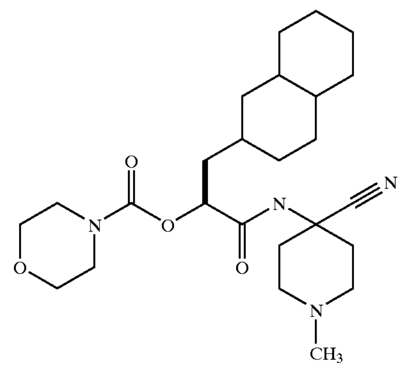 | Morpholine-4-carboxylic acid 1-(4-cyano-1-methyl-piperidin-4-ylcarbamoyl)-2-(decahydro-naphthalen-2-yl)-ethyl ester |
| 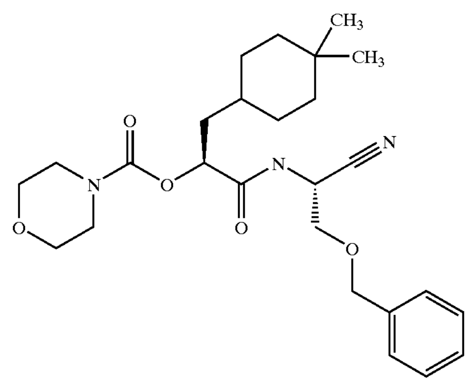 | Morpholine-4-carboxylic acid 1-[(benzyloxymethyl-cyano-methyl)-carbamoyl]-2-(4,4-dimethyl-cyclohexyl)-ethyl ester |
| 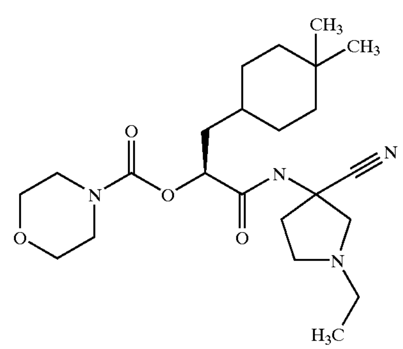 | Morpholine-4-carboxylic acid 1-(3-cyano-1-ethyl-pyrrolidin-3-ylcarbamoyl)-2-(4,4-dimethyl-cyclohexyl)-ethyl ester |
| 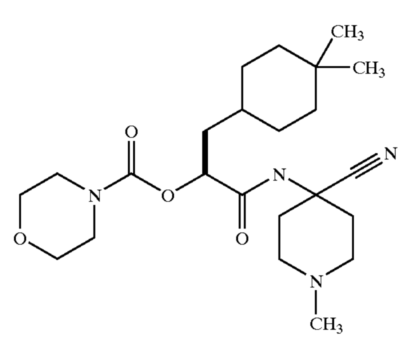 | Morpholine-4-carboxylic acid 1-(4-cyano-1-methyl-piperidin-4-ylcarbamoyl)-2-(4,4-dimethyl-cyclohexyl)-ethyl ester |

-continued

| Structure | Chemical Name* |
|---|---|
| 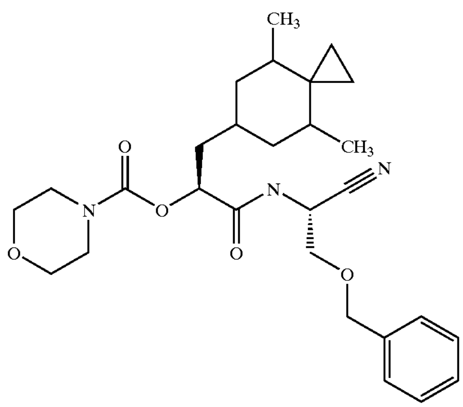 | Morpholine-4-carboxylic acid 1-[(benzyloxymethyl-cyano-methyl)-carbamoyl]-2-(4,8-dimethyl-spiro[2.5]oct-6-yl)-ethyl ester |
| 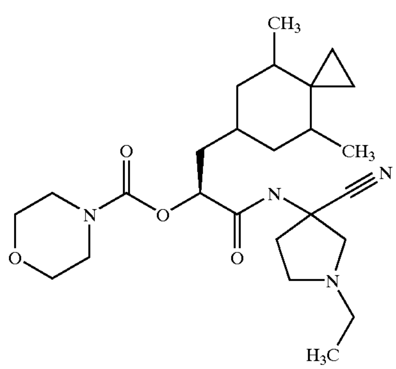 | Morpholine-4-carboxylic acid 1-(3-cyano-1-ethyl-pyrrolidin-3-ylcarbamoyl)-2-(4,8-dimethyl-spiro[2.5]oct-6-yl)-ethyl ester |
| 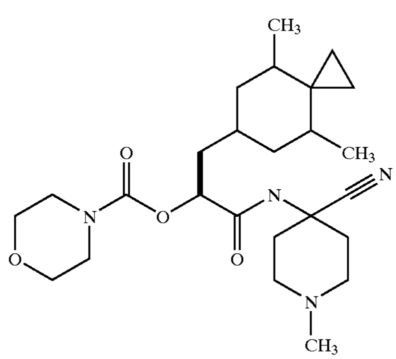 | Morpholine-4-carboxylic acid 1-(4-cyano-1-methyl-piperidin-4-ylcarbamoyl)-2-(4,8-dimethyl-spiro[2.5]oct-6-yl)-ethyl ester |
| 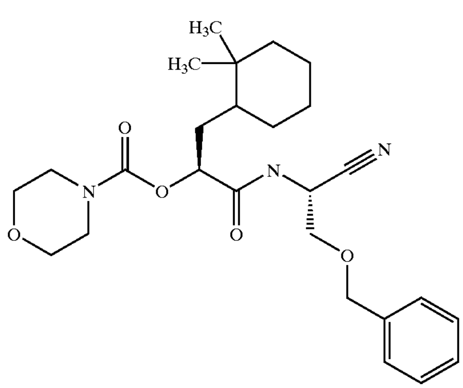 | Morpholine-4-carboxylic acid 1-[(benzyloxymethyl-cyano-methyl)-carbamoyl]-2-(2,2-dimethyl-cyclohexyl)-ethyl ester |

-continued

| Structure | Chemical Name* |
|---|---|
| 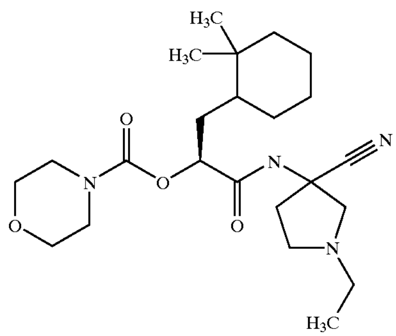 | Morpholine-4-carboxylic acid 1-(3-cyano-1-ethyl-pyrrolidin-3-ylcarbamoyl)-2-(2,2-dimethyl-cyclohexyl)-ethyl ester |
| 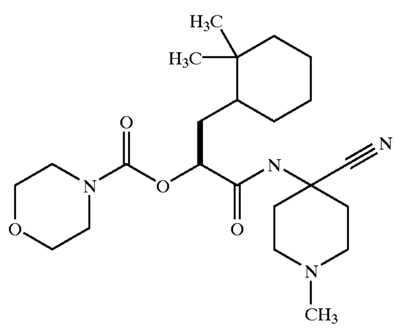 | Morpholine-4-carboxylic acid 1-(4-cyano-1-methyl-piperidin-4-ylcarbamoyl)-2-(2,2-dimethyl-cyclohexyl)-ethyl ester |
| 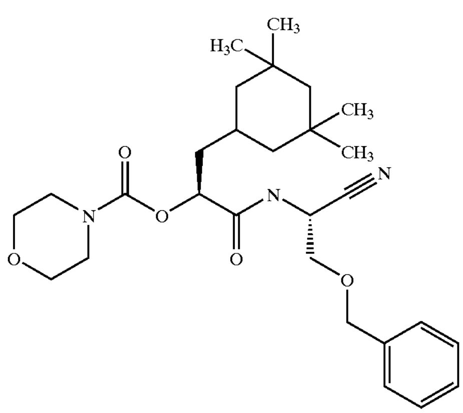 | Morpholine-4-carboxylic acid 1-[(benzyloxymethyl-cyano-methyl)-carbamoyl]-2-(3,3,5,5-tetramethyl-cyclohexyl)-ethyl ester |
| 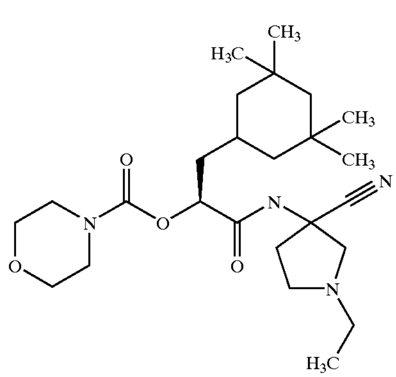 | Morpholine-4-carboxylic acid 1-(3-cyano-1-ethyl-pyrrolidin-3-ylcarbamoyl)-2-(3,3,5,5-tetramethyl-cyclohexyl)-ethyl ester |

| Structure | Chemical Name* |
|---|---|
| 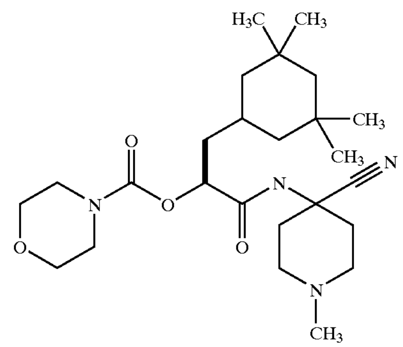 | Morpholine-4-carboxylic acid 1-(4-cyano-1-methyl-piperidin-4-ylcarbamoyl)-2-(3,3,5,5-tetramethyl-cyclohexyl)-ethyl ester |
| 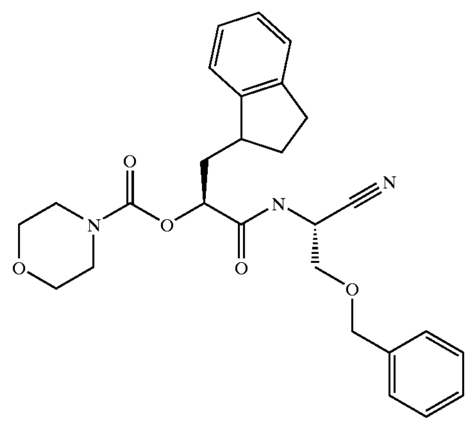 | Morpholine-4-carboxylic acid 1-[(benzyloxymethyl-cyano-methyl)-carbamoyl]-2-indan-1-yl-ethyl ester |
| 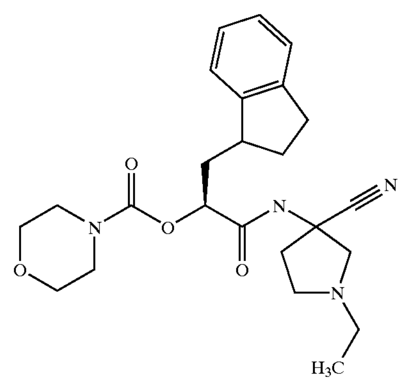 | Morpholine-4-carboxylic acid 1-(3-cyano-1-ethyl-pyrrolidin-3-ylcarbamoyl)-2-indan-1-yl-ethyl ester |
| 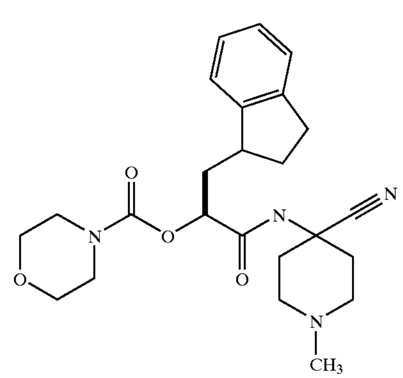 | Morpholine-4-carboxylic acid 1-(4-cyano-1-methyl-piperidin-4-ylcarbamoyl)-2-indan-1-yl-ethyl ester |

-continued

| Structure | Chemical Name* |
|---|---|
| 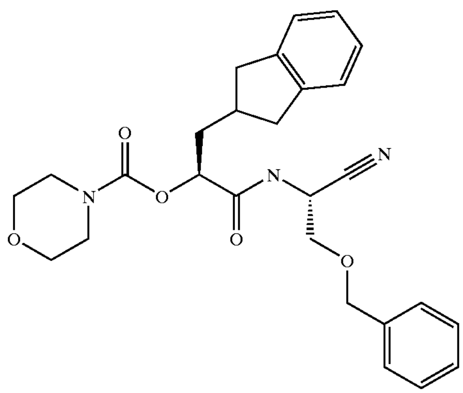 | Morpholine-4-carboxylic acid 1-[(benzyloxymethyl-cyano-methyl)-carbamoyl]-2-indan-2-yl-ethyl ester |
| 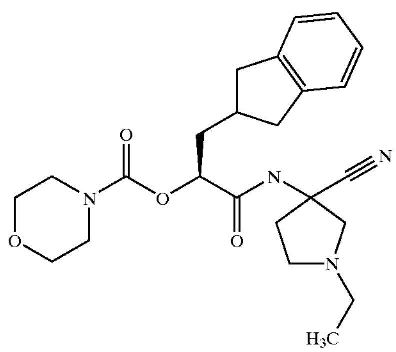 | Morpholine-4-carboxylic acid 1-(3-cyano-1-ethyl-pyrrolidin-3-ylcarbamoyl)-2-indan-2-yl-ethyl ester |
| 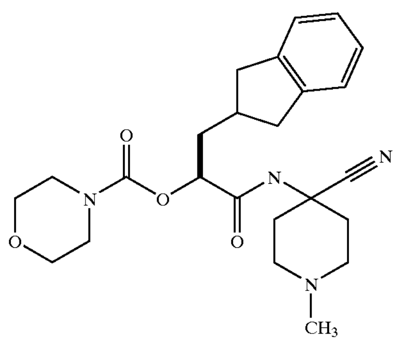 | Morpholine-4-carboxylic acid 1-(4-cyano-1-methyl-piperidin-4-ylcarbamoyl)-2-indan-2-yl-ethyl ester |
| 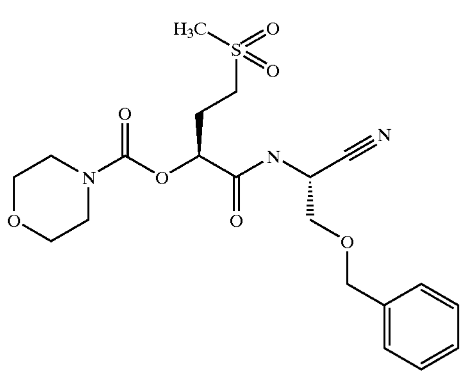 | Morpholine-4-carboxylic acid 1-[(benzyloxymethyl-cyano-methyl)-carbamoyl]-3-methanesulfonyl-propyl ester |

-continued

| Structure | Chemical Name* |
|---|---|
| 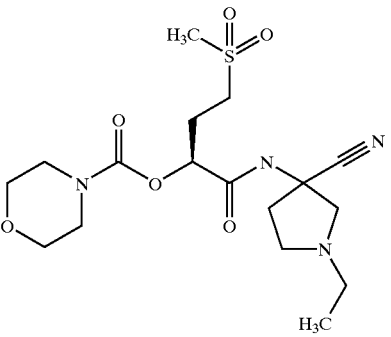 | Morpholine-4-carboxylic acid 1-(3-cyano-1-ethyl-pyrrolidin-3-ylcarbamoyl)-3-methanesulfonyl-propyl ester |
| 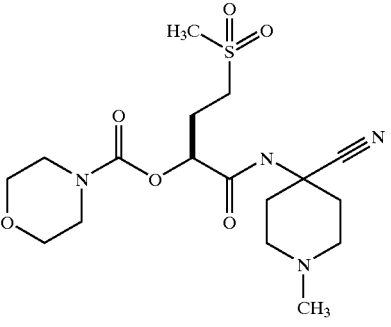 | Morpholine-4-carboxylic acid 1-(4-cyano-1-methyl-piperidin-4-ylcarbamoyl)-3-methanesulfonyl-propyl ester |
| 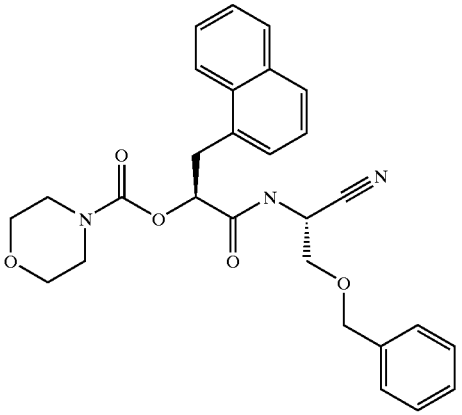 | Morpholine-4-carboxylic acid 1-[(benzyloxymethyl-cyano-methyl)-carbamoyl]-2-naphthalen-1-yl-ethyl ester |
| 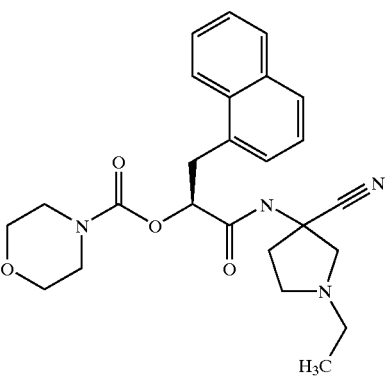 | Morpholine-4-carboxylic acid 1-(3-cyano-1-ethyl-pyrrolidin-3-ylcarbamoyl)-2-naphthalen-1-yl-ethyl ester |

-continued

| Structure | Chemical Name* |
|---|---|
| 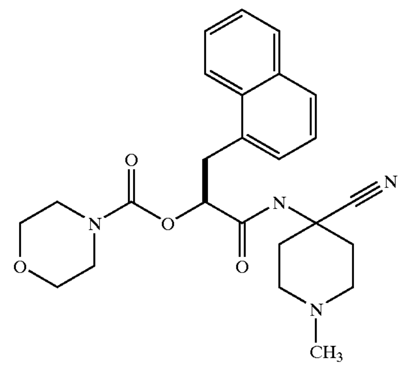 | Morpholine-4-carboxylic acid 1-(4-cyano-1-methyl-piperidin-4-ylcarbamoyl)-2-naphthalen-1-yl-ethyl ester |
| 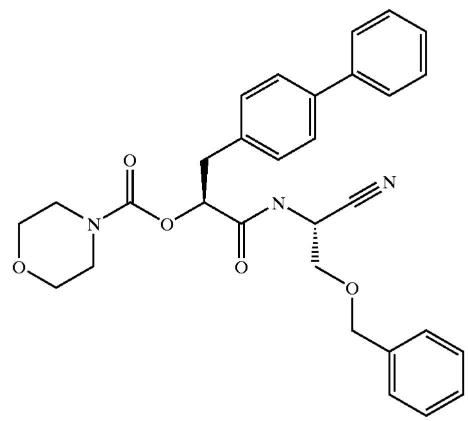 | Morpholine-4-carboxylic acid 1-[(benzyloxymethyl-cyano-methyl)-carbamoyl]-2-biphenyl-4-yl-ethyl ester |
| 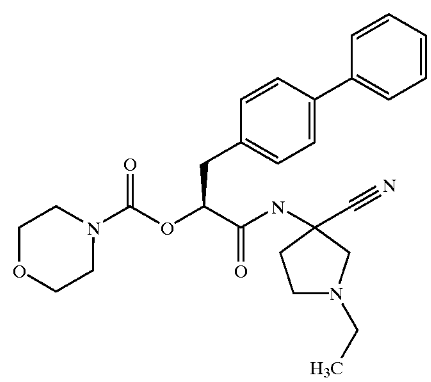 | Morpholine-4-carboxylic acid 2-biphenyl-4-yl-1-(3-cyano-1-ethyl-pyrrolidin-3-ylcarbamoyl)-ethyl ester |
| 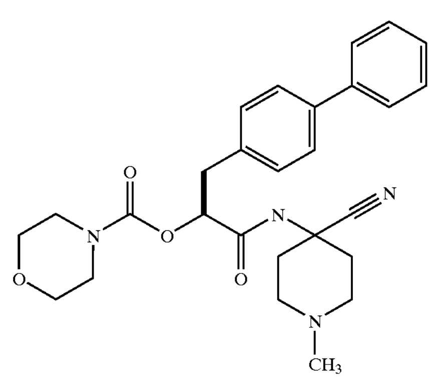 | Morpholine-4-carboxylic acid 2-biphenyl-4-yl-1-(4-cyano-1-methyl-piperidin-4-ylcarbamoyl)-ethyl ester |

| Structure | Chemical Name* |
|---|---|
| 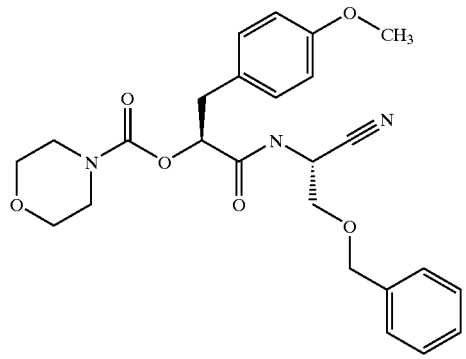 | Morpholine-4-carboxylic acid 1-[(benzyloxymethyl-cyano-methyl)-carbamoyl]-2-(4-methoxy-phenyl)-ethyl ester |
| 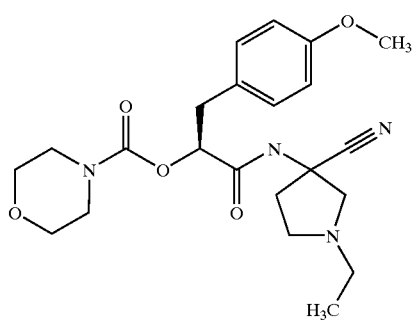 | Morpholine-4-carboxylic acid 1-(3-cyano-1-ethyl-pyrrolidin-3-ylcarbamoyl)-2-(4-methoxy-phenyl)-ethyl ester |
| 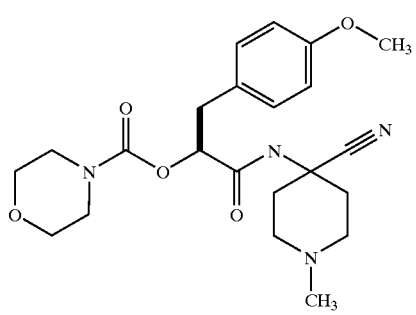 | Morpholine-4-carboxylic acid 1-(4-cyano-1-methyl-piperidin-4-ylcarbamoyl)-2-(4-methoxy-phenyl)-ethyl ester |
| 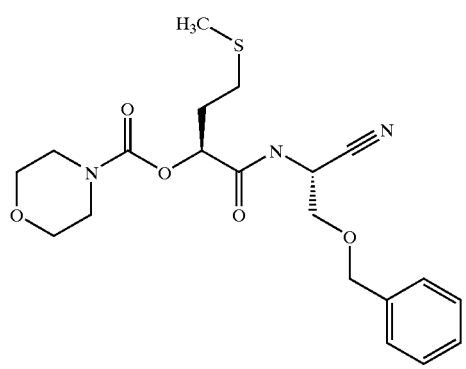 | Morpholine-4-carboxylic acid 1-[(benzyloxymethyl-cyano-methyl)-carbamoyl]-3-methylsulfanyl-propyl ester |

| Structure | Chemical Name* |
|---|---|
| 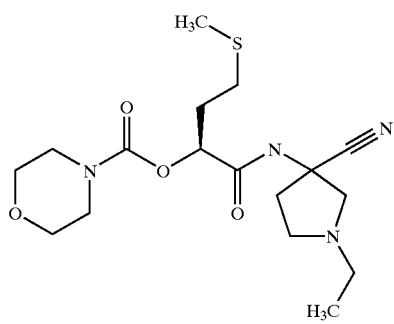 | Morpholine-4-carboxylic acid 1-(3-cyano-1-ethyl-pyrrolidin-3-ylcarbamoyl)-3-methylsulfanyl-propyl ester |
| 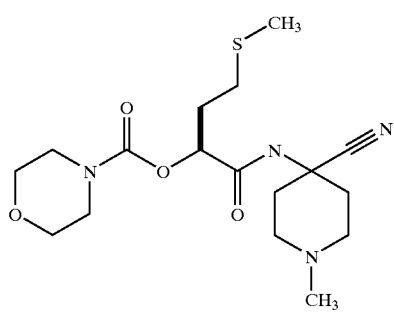 | Morpholine-4-carboxylic acid 1-(4-cyano-1-methyl-piperidin-4-ylcarbamoyl)-3-methylsulfanyl-propyl ester |
| 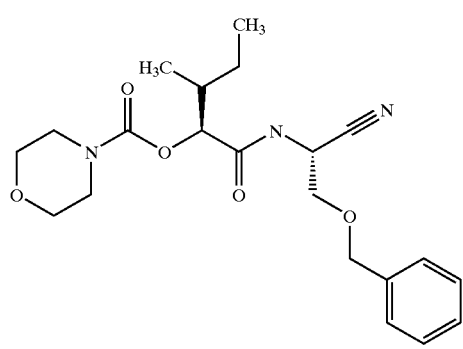 | Morpholine-4-carboxylic acid 1-[(benzyloxymethyl-cyano-methyl)-carbamoyl]-2-methyl-butyl ester |
| 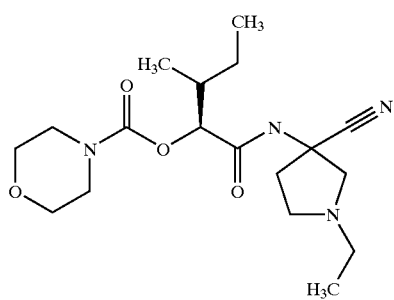 | Morpholine-4-carboxylic acid 1-(3-cyano-1-ethyl-pyrrolidin-3-ylcarbamoyl)-2-methyl-butyl ester |

-continued

| Structure | Chemical Name* |
|---|---|
| 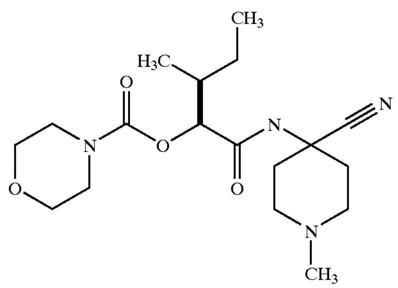 | Morpholine-4-carboxylic acid 1-(4-cyano-1-methyl-piperidin-4-ylcarbamoyl)-2-methyl-butyl ester |
| 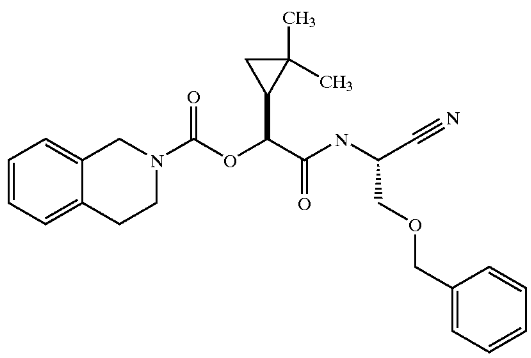 | 3,4-Dihydro-1H-isoquinoline-2-carboxylic acid [(benzyloxymethyl-cyano-methyl)-carbamoyl]-(2,2-dimethyl-cyclopropyl)-methyl ester |
| 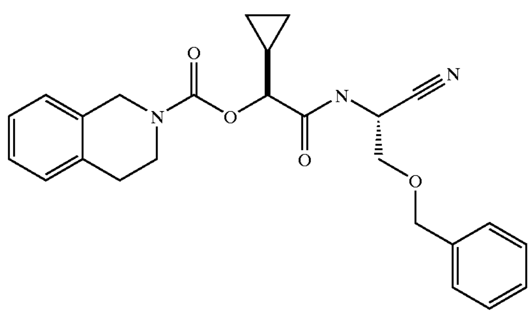 | 3,4-Dihydro-1H-isoquinoline-2-carboxylic acid [(benzyloxymethyl-cyano-methyl)-carbamoyl]-cyclopropyl-methyl ester |
| 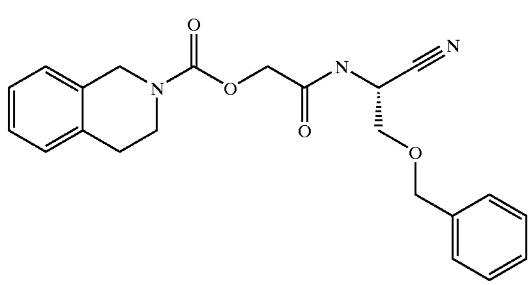 | 3,4-Dihydro-1H-isoquinoline-2-carboxylic acid [(benzyloxymethyl-cyano-methyl)-carbamoyl]-methyl ester |
| 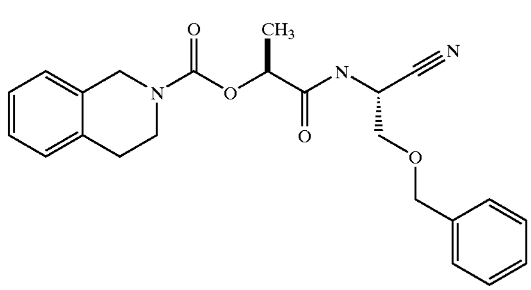 | 3,4-Dihydro-1H-isoquinoline-2-carboxylic acid 1-[(benzyloxymethyl-cyano-methyl)-carbamoyl]-ethyl ester |

-continued

| Structure | Chemical Name* |
|---|---|
| 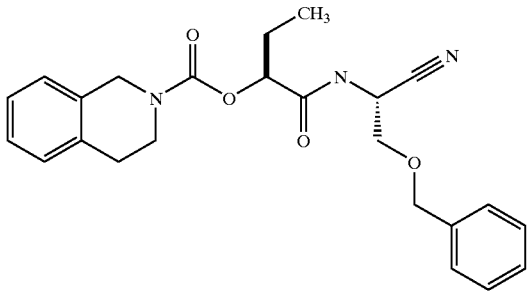 | 3,4-Dihydro-1H-isoquinoline-2-carboxylic acid 1-[(benzyloxymethyl-cyano-methyl)-carbamoyl]-propyl ester |
| 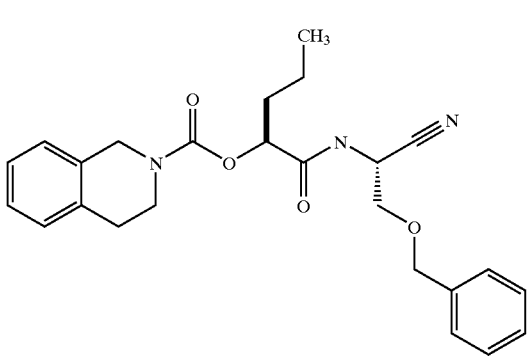 | 3,4-Dihydro-1H-isoquinoline-2-carboxylic acid 1-[(benzyloxymethyl-cyano-methyl)-carbamoyl]-butyl ester |
| 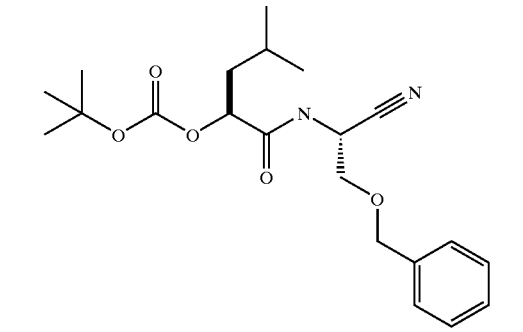 | Carbonic acid (S)-1-[((R)-benzyloxymethyl-cyano-methyl)-carbamoyl]-3-methyl-butyl ester tert-butyl ester |
| 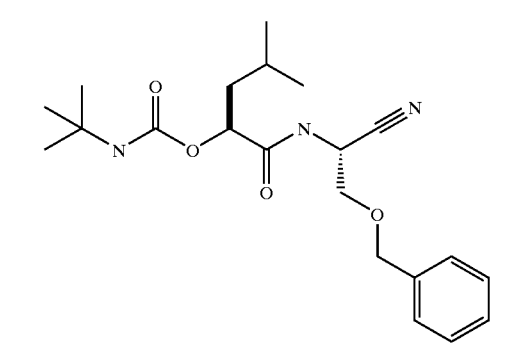 | tert-Butyl-carbamic acid (S)-1-[((R)-benzyloxymethyl-cyano-methyl)-carbamoyl]-3-methyl-butyl ester |

*No stereochemistry is designated in the chemical names.

Methods of Therapeutic Use

The compounds of the invention are useful in inhibiting the activity of cysteine proteases, such as cathepsins S, K, F, L and B. In doing so, these compounds are useful in blocking disease processes mediated by these cysteine proteases. Accordingly, the compounds of the present invention are useful in treating cysteine protease mediated disease states, i.e., those diseases in which cysteine protease activity contributes to the pathology and/or symptomatology of the disease. A variety of such cysteine protease mediated disease states are known in the art and are disclosed, for example, in the references cited in the "Background of the Invention" section above. Examples of such diseases include chronic inflammatory disorders, emphysema, malaria, Chagas' disease, a disease characterized by bone resorption, bone loss or excessive cartilage or bone matrix degradation, autoimmune diseases, Alzheimer's disease, atherosclerosis, endometriosis, asthma and airway inflammatory diseases.

Compounds of this invention effectively block degradation of the invariant chain to CLIP by cathepsin S, and thus inhibit antigen presentation and antigen-specific immune responses. Control of antigen specific immune responses is an attractive means for treating autoimmune diseases and other undesirable T-cell mediated immune responses. Thus, there is provided methods of treatment using the compounds of this invention for such conditions. These encompass autoimmune diseases and other diseases involving inappropriate antigen specific immune responses including, but not limited to, rheumatoid arthritis, systemic lupus erythematosus, Crohn's disease, ulcerative colitis, multiple sclerosis, Guillain-Barre syndrome, psoriasis, Grave's disease, myasthenia gravis, scleroderma, endometriosis, glomerulonephritis, atopic dermatitis, insulin-dependent diabetes mellitus and asthma. The compounds of the invention can also be used to treat other disorders associated with extracellular proteolysis such as Alzheimer's disease and atherosclerosis. The compounds of the invention can also be used to treat other disorders associated with inappropriate autoimmune responses, T-cell mediated immune responses, or extracellular proteolysis mediated by cathepsin S, unrelated to those listed above or discussed in the Background of the Invention. Therefore, the invention also provides methods of modulating an autoimmune disease comprising administering to a patient in need of such treatment a pharmaceutically effect amount of a compound according to the invention.

Compounds of the invention also inhibit cathepsin K. In doing so, they may block bone resorption, bone loss and inappropriate degradation of bone collagen and other bone matrix proteases. Thus, there is provided a method for treating diseases characterized by bone resporption, bone loss or excessive cartilage or bone matrix degradation such as osteoporosis, Paget's disease, Gaucher disease, gingivitis, periodontitis, osteoarthritis and rheumatoid arthritis, or diseases characterized by increases in bone resporption and demineralization of bone, such as those associated with many cancers and with bone metastases of breast and prostate tumors. In view of their Cathepsin K inhibitory activity, the compounds of the invention may also be useful for treating disorders associated with excessive elastin degradation such as lymphangiomyomatosis, vascular inflammation, and cardiovascular diseases such as atherosclerosis. Inhibition of cathepsins F, L, and B are also within the scope of the invention due to similarity of the active sites in cysteine proteases as described above.

In addition, the compounds according to the invention can be used for the treatment of any other specific disease-state or condition not specifically mentioned above which have been treated, are being treated or will in the future be treated with compounds that are inhibitors of cathepsins S, K, F, L or B.

The activity of particular compounds disclosed herein against the various cathepsins, for example, cathepsin S and K, may be determined without undue experimentation by one of ordinary skill in the art in view of the knowledge in the art, the guidance provided throughout this specification and by the screens described in the section below entitled "Assessment of Biological Properties."

Certain compounds of the invention have been tested for and have demonstrated cathepsin K inhibitory activity in one or more of the screens described below. Based on this testing, the following are compounds of the invention that would be expected to possess selective inhibitory activity against cathepsin K:

(3,4-Dichloro-phenyl)-carbamic acid 1-[(cyano-methyl-methyl)-carbamoyl]-3,3-dimethyl-butyl ester;

3-(2-Benzylcarbamoyloxy-4-methyl-pentanoylamino)-3-cyano-azepane-1-carboxylic acid 2-methoxy-ethyl ester;

3-(2-Benzylcarbamoyloxy-4-methyl-pentanoylamino)-3-cyano-pyrrolidine-1-carboxylic acid ethyl ester;

3-(2-Benzylcarbamoyloxy-4-methyl-pentanoylamino)-3-cyano-pyrrolidine-1-carboxylic acid benzyl ester;

3,4-Dihydro-1H-isoquinoline-2-carboxylic acid [(benzyloxymethyl-cyano-methyl)-carbamoyl]-(2,2-dimethyl-cyclopropyl)-methyl ester;

3,4-Dihydro-1H-isoquinoline-2-carboxylic acid [(benzyloxymethyl-cyano-methyl)-carbamoyl]-cyclopropyl-methyl ester;

3,4-Dihydro-1H-isoquinoline-2-carboxylic acid [(benzyloxymethyl-cyano-methyl)-carbamoyl]-methyl ester;

3,4-Dihydro-1H-isoquinoline-2-carboxylic acid 1-[(benzyloxymethyl-cyano-methyl)-carbamoyl]-3-methyl-butyl ester;

3,4-Dihydro-1H-isoquinoline-2-carboxylic acid 1-[(benzyloxymethyl-cyano-methyl)-carbamoyl]-2-cyclopropyl-ethyl ester;

3,4-Dihydro-1H-isoquinoline-2-carboxylic acid 1-[(benzyloxymethyl-cyano-methyl)-carbamoyl]-cyclohexyl ester 3,4-Dihydro-1H-isoquinoline-2-carboxylic acid 1-[(benzyloxymethyl-cyano-methyl)-carbamoyl]-3,3-difluoro-propyl ester 3,4-Dihydro-1H-isoquinoline-2-carboxylic acid 1-[(benzyloxymethyl-cyano-methyl)-carbamoyl]-3,3,3-trifluoro-propyl ester 3,4-Dihydro-1H-isoquinoline-2-carboxylic acid 1-[(benzyloxymethyl-cyano-methyl)-carbamoyl]-ethyl ester 3,4-Dihydro-1H-isoquinoline-2-carboxylic acid 1-[(benzyloxymethyl-cyano-methyl)-carbamoyl]-propyl ester 3,4-Dihydro-1H-isoquinoline-2-carboxylic acid 1-[(benzyloxymethyl-cyano-methyl)-carbamoyl]-butyl ester 3,4-Dihydro-1H-isoquinoline-2-carboxylic acid 1-{[(2-chloro-benzyloxymethyl)-cyano-methyl]-carbamoyl}-3-methyl-butyl ester 3,4-Dihydro-1H-isoquinoline-2-carboxylic acid 1-{[(3-carboxy-benzyloxymethyl)-cyano-methyl]-carbamoyl}-3-methyl-butyl ester 3,4-Dihydro-1H-isoquinoline-2-carboxylic acid 1-{[cyano-(4-methoxy-benzyloxymethyl)-methyl]-carbamoyl}-3-methyl-butyl ester 3-{2-[(2-Benzylcarbamoyloxy-4-methyl-pentanoyl)-methyl-amino]-2-cyano-ethoxymethyl}-benzoic acid 3-Methyl-benzofuran-2-carboxylic acid 1-[(benzyloxymethyl-cyano-methyl)-carbamoyl]-3-methyl-butyl ester 4-(2-Benzylcarbamoyloxy-4-methyl-pentanoylamino)-4-cyano-1-methyl-pyrrolidine-2-carboxylic acid methyl ester 4-(2-Benzylcarbamoyloxy-4-methyl-pentanoylamino)-4-cyano-azepane-1-carboxylic acid isopropyl ester 4-(2-Benzylcarbamoyloxy-4-methyl-pentanoylamino)-4-cyano-piperidine-1-carboxylic acid ethyl ester 4-(2-Benzylcarbamoyloxy-4-methyl-pentanoylamino)-4-cyano-piperidine-1-carboxylic acid cyclohexylmethyl ester 4-(2-Benzylcarbamoyloxy-4-methyl-pentanoylamino)-4-cyano-piperidine-1-carboxylic acid benzyl ester 4-(4-{1-[(Benzyl-cyano-methyl)-carbamoyl]-propoxycarbonyl}-thiazol-2-ylamino)-piperidine-1-carboxylic acid ethyl ester 4-[(4-Benzyl-piperazine-1-carbonyl)-amino]-benzoic acid 1-{[cyano-(4-methyl-benzyl)-methyl]-carbamoyl}-cyclopentyl ester 4-Ethoxycarbonylamino-benzoic acid 4-(4-cyano-tetrahydro-pyran-4-ylcarbamoyl)-tetrahydro-pyran-4-yl ester 4-Phenyl-piperazine-1-carboxylic acid [(cyano-dimethyl-methyl)-carbamoyl]-phenyl-methyl ester 5-(2-Morpholin-4-yl-ethoxy)-benzofuran-2-carboxylic acid 1-[(benzyloxymethyl-cyano-methyl)-carbamoyl]-3-methyl-butyl ester 5-Pyridin-4-yl-thiophene-2-carboxylic acid (1-cyano-3-methanesulfonyl-propylcarbamoyl)-pyridin-3-yl-methyl ester 5-Pyridin-4-yl-thiophene-2-carboxylic acid (1-cyano-3-methanesulfonyl-propylcarbamoyl)-pyridin-3-yl-methyl ester Benzo[b]thiophene-2-carboxylic acid 1-[(benzyloxymethyl-cyano-methyl)-carbamoyl]-3-methyl-butyl ester Benzofuran-2-carboxylic acid 1-[(benzyloxymethyl-cyano-methyl)-carbamoy]-3-methyl-butyl ester Benzyl-carbamic acid 1-(1-benzyl-3-cyano-2-oxo-pyrrolidin-3-ylcarbamoyl)-3-methyl-butyl ester Benzyl-carbamic acid 1-(1-benzyl-3-cyano-5-oxo-pyrrolidin-3-ylcarbamoyl)-3-methyl-butyl ester Benzyl-carbamic acid 1-(1-benzyl-4-cyano-2-oxo-azepan-4-ylcarbamoyl)-3-methyl-butyl ester Benzyl-carbamic acid 1-(1-benzyl-4-cyano-2-oxo-piperidin-4-ylcarbamoyl)-3-methyl-butyl ester Benzyl-carbamic acid 1-(1-benzyl-4-cyano-7-oxo-azepan-4-ylcarbamoyl)-3-methyl-butyl ester Benzyl-carbamic acid 1-(1-benzyl-4-cyano-azepan-4-ylcarbamoyl)-3-methyl-butyl ester Benzyl-carbamic acid 1-(1-benzylcarbamoyl-3-cyano-pyrrolidin-3-ylcarbamoyl)-3-methyl-butyl ester Benzyl-carbamic acid 1-(1-benzylcarbamoyl-4-cyano-azepan-4-ylcarbamoyl)-3-methyl-butyl ester Benzyl-carbamic acid 1-(1-benzylcarbamoyl-4-cyano-piperidin-4-ylcarbamoyl)-3-methyl-butyl ester Benzyl-carbamic acid 1-(1-cyano-3-methyl-butylcarbamoyl)-2-cyclopropyl-ethyl ester Benzyl-carbamic acid 1-(1-cyano-3-methyl-butylcarbamoyl)-3-methyl-butyl ester Benzyl-carbamic acid 1-(1-cyano-3-methyl-butylcarbamoyl)-cyclohexyl ester Benzyl-carbamic acid 1-(1-cyano-3-phenyl-propylcarbamoyl)-2-cyclopropyl-ethyl ester Benzyl-carbamic acid 1-(1-cyano-3-phenyl-propylcarbamoyl)-3-methyl-butyl ester Benzyl-carbamic acid 1-(1-cyano-3-phenyl-propylcarbamoyl)-cyclohexyl ester Benzyl-carbamic acid 1-(1-cyano-cyclopropylcarbamoyl)-2-cyclopropyl-ethyl ester Benzyl-carbamic acid 1-(1-cyano-cyclopropylcarbamoyl)-3-methyl-butyl ester Benzyl-carbamic acid 1-(1-cyano-cyclopropylcarbamoyl)-cyclohexyl ester Benzyl-carbamic acid 1-(2-benzyl-4-cyano-1-methyl-piperidin-4-ylcarbamoyl)-3-methyl-butyl ester Benzyl-carbamic acid 1-(2-benzyloxymethyl-4-cyano-1-methyl-piperidin-4-ylcarbamoyl)-3-methyl-butyl ester Benzyl-carbamic acid 1-(3-cyano-1-ethyl-2-oxo-azepan-3-ylcarbamoyl)-3-methyl-butyl ester Benzyl-carbamic acid 1-(3-cyano-1-ethyl-7-oxo-azepan-3-ylcarbamoyl)-3-methyl-butyl ester Benzyl-carbamic acid 1-(3-cyano-1-ethyl-azepan-3-ylcarbamoyl)-3-methyl-butyl ester Benzyl-carbamic acid 1-(3-cyano-1-ethylcarbamoyl-pyrrolidin-3-ylcarbamoyl)-3-methyl-butyl ester Benzyl-carbamic acid 1-(3-cyano-1-isobutyryl-pyrrolidin-3-ylcarbamoyl)-3-methyl-butyl ester Benzyl-carbamic acid 1-(3-cyano-1-methyl-5-methylcarbamoyl-pyrrolidin-3-ylcarbamoyl)-3-methyl-butyl ester Benzyl-carbamic acid 1-(3-cyano-1-phenylacetyl-azepan-3-ylcarbamoyl)-3-methyl-butyl ester Benzyl-carbamic acid 1-(3-cyano-1-phenylcarbamoyl-pyrrolidin-3-ylcarbamoyl)-3-methyl-butyl ester Benzyl-carbamic acid 1-(3-cyano-5-hydroxymethyl-1-methyl-pyrrolidin-3-ylcarbamoyl)-3-methyl-butyl ester Benzyl-carbamic acid 1-(4-cyano-1,2,2,6,6-pentamethyl-piperidin-4-ylcarbamoyl)-3-methyl-butyl ester Benzyl-carbamic acid 1-(4-cyano-1,2,2-trimethyl-piperidin-4-ylcarbamoyl)-3-methyl-butyl ester Benzyl-carbamic acid 1-(4-cyano-1-cyclohexanecarbonyl-piperidin-4-ylcarbamoyl)-3-methyl-butyl ester Benzyl-carbamic acid 1-(4-cyano-1-methyl-2,6-dioxo-piperidin-4-ylcarbamoyl)-3-methyl-butyl ester Benzyl-carbamic acid 1-(4-cyano-1-methyl-2-methylcarbamoyl-piperidin-4-ylcarbamoyl)-3-methyl-butyl ester Benzyl-carbamic acid 1-(4-cyano-2-hydroxymethyl-1-methyl-piperidin-4-ylcarbamoyl)-3-methyl-butyl ester Benzyl-carbamic acid 1-(5-benzyloxymethyl-3-cyano-1-methyl-pyrrolidin-3-ylcarbamoyl)-3-methyl-butyl ester Benzyl-carbamic acid 1-(cyanomethyl-carbamoyl)-2-cyclopropyl-ethyl ester Benzyl-carbamic acid 1-(cyanomethyl-carbamoyl)-3-methyl-butyl ester Benzyl-carbamic acid 1-(cyanomethyl-carbamoyl)-cyclohexyl ester Benzyl-carbamic acid 1-[(benzyloxymethyl-cyano-methyl)-carbamoyl]-2-cyclopropyl-ethyl ester Benzyl-carbamic acid 1-[(benzyloxymethyl-cyano-methyl)-carbamoyl]-3-methyl-butyl ester Benzyl-carbamic acid 1-[(benzyloxymethyl-cyano-methyl)-carbamoyl]-cyclohexyl ester Benzyl-carbamic acid 1-[(benzyloxymethyl-cyano-methyl)-methyl-carbamoyl]-3-methyl-butyl ester Benzyl-carbamic acid 1-[(benzyloxymethyl-cyano-methyl)-methyl-carbamoyl]-2-cyclopropyl-ethyl ester Benzyl-carbamic acid 1-[(benzyloxymethyl-cyano-methyl)-methyl-carbamoyl]-cyclohexyl ester Benzyl-carbamic acid 1-[(benzyloxymethyl-cyano-methyl-methyl)-carbamoyl]-3-methyl-butyl ester Benzyl-carbamic acid 1-[(benzyloxymethyl-cyano-methyl-methyl)-carbamoyl]-2-cyclopropyl-ethyl ester Benzyl-carbamic acid 1-[(benzyloxymethyl-cyano-methyl-methyl)-carbamoyl]-cyclohexyl ester Benzyl-carbamic acid 1-[3-cyano-1-(2-methoxy-ethylcarbamoyl)-azepan-3-ylcarbamoyl]-3-methyl-butyl ester Benzyl-carbamic acid 1-[3-cyano-1-(2-pyridin-4-yl-acetyl)-pyrrolidin-3-ylcarbamoyl]-3-methyl-butyl ester Benzyl-carbamic acid 1-[4-cyano-1-(3-morpholin-4-yl-propionyl)-azepan-4-ylcarbamoyl]-3-methyl-butyl ester Benzyl-carbamic acid 1-[4-cyano-1-(4-methyl-piperazine-1-carbonyl)-piperidin-4-ylcarbamoyl]-3-methyl-butyl ester Benzyl-carbamic acid 1-[4-cyano-1-(piperidine-1-carbonyl)-piperidin-4-ylcarbamoyl]-3-methyl-butyl ester Benzyl-carbamic acid 1-[4-cyano-1-(tetrahydro-pyran-4-carbonyl)-piperidin-4-ylcarbamoyl]-3-methyl-butyl ester
Benzyl-carbamic acid 1-{[(2-chloro-benzyloxymethyl)-cyano-methyl]-carbamoyl}-2-cyclopropyl-ethyl ester
Benzyl-carbamic acid 1-{[cyano-(4-methoxy-benzyloxymethyl)-methyl]-carbamoyl}-2-cyclopropyl-ethyl ester
Carbonic acid (S)-1-[((R)-benzyloxymethyl-cyano-methyl)-carbamoyl]-3-methyl-butyl ester tert-butyl ester
Carbonic acid benzyl ester 1-[(benzyloxymethyl-cyano-methyl)-carbamoyl]-3-methyl-butyl ester
Carbonic acid benzyl ester 1-[(benzyloxymethyl-cyano-methyl)-carbamoyl]-2-cyclopropyl-ethyl ester
Carbonic acid benzyl ester 1-[(benzyloxymethyl-cyano-methyl)-carbamoyl]-cyclohexyl ester
Naphthalen-2-yl-carbamic acid 1-[(benzyloxymethyl-cyano-methyl)-carbamoyl]-cyclohexyl ester
Naphthalen-2-yl-carbamic acid 1-[(benzyloxymethyl-cyano-methyl)-carbamoyl]-3-methyl-butyl ester
Naphthalen-2-yl-carbamic acid 1-[(benzyloxymethyl-cyano-methyl)-carbamoyl]-2-cyclopropyl-ethyl ester
Naphthalen-2-yl-carbamic acid 1-{[(2-chloro-benzyloxymethyl)-cyano-methyl]-carbamoyl}-cyclohexyl ester
Naphthalen-2-yl-carbamic acid 1-{[cyano-(4-methoxy-benzyloxymethyl)-methyl]-carbamoyl}-cyclohexyl ester
Naphthalene-2-carboxylic acid 1-[(benzyloxymethyl-cyano-methyl)-carbamoyl]-3-methyl-butyl ester
Naphthalene-2-carboxylic acid 1-[(benzyloxymethyl-cyano-methyl)-carbamoyl]-2-cyclopropyl-ethyl ester
Naphthalene-2-carboxylic acid 1-[(benzyloxymethyl-cyano-methyl)-carbamoyl]-cyclohexyl ester
Phenyl-carbamic acid 1-(cyanomethyl-carbamoyl)-2-dimethylamino-ethyl ester
Quinolin-2-yl-carbamic acid 1-[(benzyloxymethyl-cyano-methyl)-carbamoyl]-2-methyl-butyl ester; and
tert-Butyl-carbamic acid (S)-1-[((R)-benzyloxymethyl-cyano-methyl)-carbamoyl]-3-methyl-butyl ester Certain compounds of the invention have been tested for and have demonstrated cathepsin S inhibitory activity in one or more of the screens described below. Based on this testing, the following are compounds of the invention that would be expected to possess selective inhibitory activity against cathepsin S:

Morpholine-4-carboxylic acid (3-cyano-1-ethyl-pyrrolidin-3-ylcarbamoyl)-cyclohexyl-methyl ester
Morpholine-4-carboxylic acid (4-cyano-1-methyl-piperidin-4-ylcarbamoyl)-cyclohexyl-methyl ester
Morpholine-4-carboxylic acid [(benzyloxymethyl-cyano-methyl)-carbamoyl]-cyclohexyl-methyl ester
Morpholine-4-carboxylic acid 1-(3-cyano-1-ethyl-pyrrolidin-3-ylcarbamoyl)-4,4-dimethyl-pentyl ester
Morpholine-4-carboxylic acid 1-(3-cyano-1-ethyl-pyrrolidin-3-ylcarbamoyl)-4-methyl-pentyl ester
Morpholine-4-carboxylic acid 1-(3-cyano-1-ethyl-pyrrolidin-3-ylcarbamoyl)-3,3,4,4-tetramethyl-pentyl ester
Morpholine-4-carboxylic acid 1-(3-cyano-1-ethyl-pyrrolidin-3-ylcarbamoyl)-3,3-dimethyl-pentyl ester
Morpholine-4-carboxylic acid 1-(3-cyano-1-ethyl-pyrrolidin-3-ylcarbamoyl)-3,3,4-trimethyl-pentyl ester
Morpholine-4-carboxylic acid 1-(3-cyano-1-ethyl-pyrrolidin-3-ylcarbamoyl)-3-cyclohexyl-3-methyl-butyl ester
Morpholine-4-carboxylic acid 1-(3-cyano-1-ethyl-pyrrolidin-3-ylcarbamoyl)-3-cyclohexyl-propyl ester
Morpholine-4-carboxylic acid 1-(3-cyano-1-ethyl-pyrrolidin-3-ylcarbamoyl)-3-phenyl-propyl ester
Morpholine-4-carboxylic acid 1-(3-cyano-1-ethyl-pyrrolidin-3-ylcarbamoyl)-2-cyclohexyl-ethyl ester
Morpholine-4-carboxylic acid 1-(3-cyano-1-ethyl-pyrrolidin-3-ylcarbamoyl)-2-phenyl-ethyl ester
Morpholine-4-carboxylic acid 1-(3-cyano-1-ethyl-pyrrolidin-3-ylcarbamoyl)-2-(1-methyl-cyclohexyl)-ethyl ester
Morpholine-4-carboxylic acid 1-(3-cyano-1-ethyl-pyrrolidin-3-ylcarbamoyl)-3,3-dimethyl-butyl ester
Morpholine-4-carboxylic acid 1-(3-cyano-1-ethyl-pyrrolidin-3-ylcarbamoyl)-3-methyl-but-3-enyl ester
Morpholine-4-carboxylic acid 1-(3-cyano-1-ethyl-pyrrolidin-3-ylcarbamoyl)-2-(3,4-dichloro-phenyl)-ethyl ester
Morpholine-4-carboxylic acid 1-(3-cyano-1-ethyl-pyrrolidin-3-ylcarbamoyl)-2-naphthalen-2-yl-ethyl ester
Morpholine-4-carboxylic acid 1-(3-cyano-1-ethyl-pyrrolidin-3-ylcarbamoyl)-2-(decahydro-naphthalen-2-yl)-ethyl ester
Morpholine-4-carboxylic acid 1-(3-cyano-1-ethyl-pyrrolidin-3-ylcarbamoyl)-2-(4,4-dimethyl-cyclohexyl)-ethyl ester
Morpholine-4-carboxylic acid 1-(3-cyano-1-ethyl-pyrrolidin-3-ylcarbamoyl)-2-(4,8-dimethyl-spiro[2.5]oct-6-yl)-ethyl ester
Morpholine-4-carboxylic acid 1-(3-cyano-1-ethyl-pyrrolidin-3-ylcarbamoyl)-2-(2,2-dimethyl-cyclohexyl)-ethyl ester
Morpholine-4-carboxylic acid 1-(3-cyano-1-ethyl-pyrrolidin-3-ylcarbamoyl)-2-(3,3,5,5-tetramethyl-cyclohexyl)-ethyl ester
Morpholine-4-carboxylic acid 1-(3-cyano-1-ethyl-pyrrolidin-3-ylcarbamoyl)-2-indan-1-yl-ethyl ester
Morpholine-4-carboxylic acid 1-(3-cyano-1-ethyl-pyrrolidin-3-ylcarbamoyl)-2-indan-2-yl-ethyl ester
Morpholine-4-carboxylic acid 1-(3-cyano 1-ethyl-pyrrolidin-3-ylcarbamoyl)-3-methanesulfonyl-propyl ester
Morpholine-4-carboxylic acid 1-(3-cyano-1-ethyl-pyrrolidin-3-ylcarbamoyl)-2-naphthalen-1-yl-ethyl ester
Morpholine-4-carboxylic acid 1-(3-cyano-1-ethyl-pyrrolidin-3-ylcarbamoyl)-2-(4-methoxy-phenyl)-ethyl ester
Morpholine-4-carboxylic acid 1-(3-cyano-1-ethyl-pyrrolidin-3-ylcarbamoyl)-3-methylsulfanyl-propyl ester
Morpholine-4-carboxylic acid 1-(3-cyano-1-ethyl-pyrrolidin-3-ylcarbamoyl)-2-methyl-butyl ester
Morpholine-4-carboxylic acid 1-(4-cyano-1-methyl-piperidin-4-ylcarbamoyl)-4,4-dimethyl-pentyl ester
Morpholine-4-carboxylic acid 1-(4-cyano-1-methyl-piperidin-4-ylcarbamoyl)-4-methyl-pentyl ester
Morpholine-4-carboxylic acid 1-(4-cyano-1-methyl-piperidin-4-ylcarbamoyl)-3,3,4,4-tetramethyl-pentyl ester
Morpholine-4-carboxylic acid 1-(4-cyano-11-methyl-piperidin-4-ylcarbamoyl)-3,3-dimethyl-pentyl ester
Morpholine-4-carboxylic acid 1-(4-cyano-11-methyl-piperidin-4-ylcarbamoyl)-3,3,4-trimethyl-pentyl ester
Morpholine-4-carboxylic acid 1-(4-cyano-1-methyl-piperidin-4-ylcarbamoyl)-3-cyclohexyl-3-methyl-butyl ester
Morpholine-4-carboxylic acid 1-(4-cyano-1-methyl-piperidin-4-ylcarbamoyl)-3-cyclohexyl-propyl ester
Morpholine-4-carboxylic acid 1-(4-cyano-1-methyl-piperidin-4-ylcarbamoyl)-3-phenyl-propyl ester
Morpholine-4-carboxylic acid 1-(4-cyano-1-methyl-piperidin-4-ylcarbamoyl)-2-cyclohexyl-ethyl ester
Morpholine-4-carboxylic acid 1-(4-cyano-1-methyl-piperidin-4-ylcarbamoyl)-2phenyl-ethyl ester;

Morpholine-4-carboxylic acid 1-(4-cyano-1-methyl-piperidin-4-ylcarbamoyl)-2-(1-methyl-cyclohexyl)-ethyl ester;
Morpholine-4-carboxylic acid 1-(4-cyano-1-methyl-piperidin-4-ylcarbamoyl)-3,3-dimethyl-butyl ester;
Morpholine-4-carboxylic acid 1-(4-cyano-1-methyl-piperidin-4-ylcarbamoyl)-3-methyl-but-3-enyl ester;
Morpholine-4-carboxylic acid 1-(4-cyano-1-methyl-piperidin-4-ylcarbamoyl)-2-(3,4-dichloro-phenyl)-ethyl ester;
Morpholine-4-carboxylic acid 1-(4-cyano-1-methyl-piperidin-4-ylcarbamoyl)-2-naphthalen-2-yl-ethyl ester;
Morpholine-4-carboxylic acid 1-(4-cyano-1-methyl-piperidin-4-ylcarbamoyl)-2-(decahydro-naphthalen-2-yl)-ethyl ester;
Morpholine-4-carboxylic acid 1-(4-cyano-1-methyl-piperidin-4-ylcarbamoyl)-2-(4,4-dimethyl-cyclohexyl)-ethyl ester;
Morpholine-4-carboxylic acid 1-(4-cyano-1-methyl-piperidin-4-ylcarbamoyl)-2-(4,8-dimethyl-spiro[2.5]oct-6-yl)-ethyl ester;
Morpholine-4-carboxylic acid 1-(4-cyano-1-methyl-piperidin-4-ylcarbamoyl)-2-(2,2-dimethyl-cyclohexyl)-ethyl ester;
Morpholine-4-carboxylic acid 1-(4-cyano-1-methyl-piperidin-4-ylcarbamoyl)-2-(3,3,5,5-tetramethyl-cyclohexyl)-ethyl ester;
Morpholine-4-carboxylic acid 1-(4-cyano-1-methyl-piperidin-4-ylcarbamoyl)-2-indan-1-yl-ethyl ester;
Morpholine-4-carboxylic acid 1-(4-cyano-1-methyl-piperidin-4-ylcarbamoyl)-2-indan-2-yl-ethyl ester;
Morpholine-4-carboxylic acid 1-(4-cyano-1-methyl-piperidin-4-ylcarbamoyl)-3-methanesulfonyl-propyl ester;
Morpholine-4-carboxylic acid 1-(4-cyano-1-methyl-piperidin-4-ylcarbamoyl)-2-naphthalen-1-yl-ethyl ester;
Morpholine-4-carboxylic acid 1-(4-cyano-1-methyl-piperidin-4-ylcarbamoyl)-2-(4-methoxy-phenyl)-ethyl ester;
Morpholine-4-carboxylic acid 1-(4-cyano-1-methyl-piperidin-4-ylcarbamoyl)-3-methylsulfanyl-propyl ester;
Morpholine-4-carboxylic acid 1-(4-cyano-1-methyl-piperidin-4-ylcarbamoyl)-2-methyl-butyl ester;
Morpholine-4-carboxylic acid 1-[(benzyloxymethyl-cyano-methyl)-carbamoyl]-3-methyl-butyl ester;
Morpholine-4-carboxylic acid 1-[(benzyloxymethyl-cyano-methyl)-carbamoyl]-2-cyclopropyl-ethyl ester;
Morpholine-4-carboxylic acid 1-[(benzyloxymethyl-cyano-methyl)-carbamoyl]-cyclohexyl ester;
Morpholine-4-carboxylic acid 1-[(benzyloxymethyl-cyano-methyl)-carbamoyl]-4,4-dimethyl-pentyl ester;
Morpholine-4-carboxylic acid 1-[(benzyloxymethyl-cyano-methyl)-carbamoyl]-4-methyl-pentyl ester;
Morpholine-4-carboxylic acid 1-[(benzyloxymethyl-cyano-methyl)-carbamoyl]-3,3,4,4-tetramethyl-pentyl ester;
Morpholine-4-carboxylic acid 1-[(benzyloxymethyl-cyano-methyl)-carbamoyl]-3,3-dimethyl-pentyl ester;
Morpholine-4-carboxylic acid 1-[(benzyloxymethyl-cyano-methyl)-carbamoyl]-3,3,4-trimethyl-pentyl ester;
Morpholine-4-carboxylic acid 1-[(benzyloxymethyl-cyano-methyl)-carbamoyl]-3-cyclohexyl-3-methyl-butyl ester;
Morpholine-4-carboxylic acid 1-[(benzyloxymethyl-cyano-methyl)-carbamoyl]-3-cyclohexyl-propyl ester;
Morpholine-4-carboxylic acid 1-[(benzyloxymethyl-cyano-methyl)-carbamoyl]-3-phenyl-propyl ester;
Morpholine-4-carboxylic acid 1-[(benzyloxymethyl-cyano-methyl)-carbamoyl]-2-cyclohexyl-ethyl ester;
Morpholine-4-carboxylic acid 1-[(benzyloxymethyl-cyano-methyl)-carbamoyl]-2-phenyl-ethyl ester;
Morpholine-4-carboxylic acid 1-[(benzyloxymethyl-cyano-methyl)-carbamoyl]-2-(1-methyl-cyclohexyl)-ethyl ester;
Morpholine-4-carboxylic acid 1-[(benzyloxymethyl-cyano-methyl)-carbamoyl]-3,3-dimethyl-butyl ester;
Morpholine-4-carboxylic acid 1-[(benzyloxymethyl-cyano-methyl)-carbamoyl]-3-methyl-but-3-enyl ester;
Morpholine-4-carboxylic acid 1-[(benzyloxymethyl-cyano-methyl)-carbamoyl]-2-(3,4-dichloro-phenyl)-ethyl ester;
Morpholine-4-carboxylic acid 1-[(benzyloxymethyl-cyano-methyl)-carbamoyl]-2-naphthalen-2-yl-ethyl ester;
Morpholine-4-carboxylic acid 1-[(benzyloxymethyl-cyano-methyl)-carbamoyl]-2-(decahydro-naphthalen-2-yl)-ethyl ester;
Morpholine-4-carboxylic acid 1-[(benzyloxymethyl-cyano-methyl)-carbamoyl]-2-(4,4-dimethyl-cyclohexyl)-ethyl ester;
Morpholine-4-carboxylic acid 1-[(benzyloxymethyl-cyano-methyl)-carbamoyl]-2-(4,8-dimethyl-spiro[2.5]oct-6-yl)-ethyl ester;
Morpholine-4-carboxylic acid 1-[(benzyloxymethyl-cyano-methyl)-carbamoyl]-2-(2,2-dimethyl-cyclohexyl)-ethyl ester;
Morpholine-4-carboxylic acid 1-[(benzyloxymethyl-cyano-methyl)-carbamoyl]-2-(3,3,5,5-tetramethyl-cyclohexyl)-ethyl ester;
Morpholine-4-carboxylic acid 1-[(benzyloxymethyl-cyano-methyl)-carbamoyl]-2-indan-1-yl-ethyl ester;
Morpholine-4-carboxylic acid 1-[(benzyloxymethyl-cyano-methyl)-carbamoyl]-2-indan-2-yl-ethyl ester;
Morpholine-4-carboxylic acid 1-[(benzyloxymethyl-cyano-methyl)-carbamoyl]-3-methanesulfonyl-propyl ester;
Morpholine-4-carboxylic acid 1-[(benzyloxymethyl-cyano-methyl)-carbamoyl]-2-naphthalen-1-yl-ethyl ester;
Morpholine-4-carboxylic acid 1-[(benzyloxymethyl-cyano-methyl)-carbamoyl]-2-biphenyl-4-yl-ethyl ester
Morpholine-4-carboxylic acid 1-[(benzyloxymethyl-cyano-methyl)-carbamoyl]-2-(4-methoxy-phenyl)-ethyl ester;
Morpholine-4-carboxylic acid 1-[(benzyloxymethyl-cyano-methyl)-carbamoyl]-3-methylsulfanyl-propyl ester;
Morpholine-4-carboxylic acid 1-[(benzyloxymethyl-cyano-methyl)-carbamoyl]-2-methyl-butyl ester;
Morpholine-4-carboxylic acid 2-biphenyl-4-yl-1-(3-cyano-1-ethyl-pyrrolidin-3-ylcarbamoyl)-ethyl ester; and
Morpholine-4-carboxylic acid 2-biphenyl-4-yl-1-(4-cyano-1-methyl-piperidin-4-ylcarbamoyl)-ethyl ester.

For therapeutic use, the compounds of the invention may be administered in any conventional dosage form in any conventional manner to a patient, e.g. a mammal, in need of such treatment. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 15%, but more preferably at least about 20%, of a compound of the invention (w/w) or a combination thereof. Alternatively, the compounds may be administered separately (either serially or in parallel). Separate dosing allows for greater flexibility in the dosing regime.

As mentioned above, dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements are well-recognized in the art and may be selected by those of ordinary skill in the art from available methods and techniques suitable for a particular patient. In some embodiments, dosage levels range from about 10–1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

Assessment of Biological Properties
Expression and Purification of Recombinant Human Cathepsin S
Cloning of Human Cathepsin S:

U937 RNA was subjected to reverse transcriptase/polymerase chain reaction with primer A (5'cacaatgaaacggctggtttg 3') and primer B (5'ctagatttctgggtaagaggg 3') designed to specifically amplify the cathepsin S cDNA. The resulting 900 bp DNA fragment was subcloned into pGEM-T (Promega) and sequenced to confirm its identity. This construct was used for all subsequent manipulations. This procedure is typical for cloning of known genes and is established in its field.

Human Pre-Pro-Cat S was removed from pGem-T vector (Promega, 2800 Woods Hollow Rd, Madison, Wis. 53711) by digestion with restriction enzyme SacII, followed by treatment with T4 DNA polymerase to generate a blunt end, and a second restriction enzyme digest with SalI. It was subcloned into pFastBac1 donor plasmid (GibcoBRL, 8717 Grovemont Cr., Gaithersburg, Md. 20884) which had been cut with restriction enzyme BamHI and blunt-ended and then cut with restriction enzyme SalI. The ligation mixture was used to transform DH5a competent cells (GibcoBRL) and plated on LB plates containing 100 ug/ml ampicillin. Colonies were grown in overnight cultures of LB media containing 50 ug/ml Ampicillin, plasmid DNA isolated and correct insert confirmed by restriction enzyme digestion. Recombinant pFastBac donor plasmid was transformed into DH10Bac competent cells (GibcoBRL). Large white colonies were picked from LB plates containing 50 ug/ml kanamycin, 7 ug/ml gentamicin, 10 ug/ml tetracycline, 100 ug/ml Bluo-gal, and 40 ug/ml IPTG. DNA was isolated and used to transfect Sf9 insect cells using CellFECTIN reagent (GibcoBRL). Cells and supernatant were harvested after 72 hours. Viral supernatant was passaged twice and presence of Cat S confirmed by PCR of the supernatant.

SF9 cells were infected with recombinant baculovirus at a MOI of 5 for 48–72 hrs. Cell pellet was lysed and incubated in buffer at pH 4.5 at 37 for 2 hours to activate Cat S from pro-form to active mature form (Bromme, D & McGrath, M., *Protein Science*, 1996, 5:789–791.) Presence of Cat S was confirmed by SDS-PAGE and Western blot using rabbit anti-human proCat S.
Inhibition of Cathepsin S Human recombinant cathepsin S expressed in Baculovirus is used at a final concentration of 10 nM in buffer. Buffer is 50 mM Na Acetate, pH 6.5, 2.5 mM EDTA, 2.5 mM TCEP. Enzyme is incubated with either compound or DMSO for 10 min at 37° C. Substrate 7-amino-4-methylcoumarin, CBZ-L-valyl-L-valyl-L-arginineamide (custom synthesis by Molecular Probes) is diluted to 20 uM in water (final concentration of 5 uM), added to assay and incubated for additional 10 minutes at 37° C. Compound activity is measured by diminished fluorescence compared to DMSO control when read at 360 nm excitation and 460 nm emission.

Another assay for Cathepsin S inhibitory activity is the cell based assay described in Riese, R. J. et al., Immunity, 1996, 4, 357–366, incorporated herein by reference.

Preferred compounds for the inhibition of Cathepsin S are those that will exhibit an $IC_{50}$ of 10 micromolar or below in the above assays.
Inhibition of Cathepsin K, F, L and B:

Inhibition of these enzymes by particular compounds of the invention may be determined without undue experimentation by using art recognized methods as provided in the references cited hereinbelow each of which is incorporated herein by reference:

A Cathepsin K bone resorption cellular assay can be carried out as follows:

In vitro culturing of murine osteoclasts can be accomplished by a modification of previous published protocols (1–6). Briefly, tibiae and femur are removed from 6–10 week-old C57BL/6 male mice. Marrow is flushed from the bones and placed into MEM-alpha media (Gibco) supplemented with 10% FCS (Gibco). After washing, 100 mm tissue culture dishes is seeded at $1\times10^6$ cells/cm$^2$ (at $2\times10^6$ cells/mL) and supplemented with 10 nM 1,25-dihydroxyvitamin D3 (Sigma) and cultured at 37° C. and 5% $CO_2$.

Cultures are fed every 3 days by removing 80% of the media and replacement with fresh media and vitamin $D_3$. In vitro bone resorption assays can be carried out similar to those previously described (1, 7–9) with modifications: After 7 days in culture, osteoclasts are trypsinized and scraped off 100 mm dishes and split into 96 well plates containing bovine cortical bone slices. After 2 hours at 37° C., non-adherent cells are removed by washing and MEM-alpha media containing 0.7 g sodium bicarbonate/liter is added to the wells and media is supplemented with 100 ng/mL sRANKL (R&D Systems). After 3–4 days, supernatants are removed and analyzed for the presence of C-terminal peptides from type I collagen using a one-step ELISA (Osteometer Biotech) originally described by Foged et al. (10).

1. S. K. Lee, S. R. Goldring, and J. A. Lorenzo. (1995) *Endocrinology* 136: 4572.

2. N. Takahashi et al. (1988) *Endocrinology* 122: 1373.
3. N. Takahashi et al. (1988) *Endocrinology* 123: 1504.
4. T. Akatsu et al. (1992) *J. Bone Miner. Res.* 7: 1297.
5. T. Akatsu et al. (1989) *J. Bone Miner. Res.* 4: 29.
6. T. Shuto et al. (1994) *Endocrinology* 134: 1121.
7. A. Boyde, N. N. Ali, and S. J. Jones. (1984) *Br. Dent. J.* 156: 216.
8. D. W. Dempster et al. (1987) *J. Bone Miner. Res.* 2: 443.
9. R. J. Murrills et al. (1989) *J. Bone Miner. Res.* 4: 259.
10. N. T. Foged et al. (1996) *J. Bone Miner. Res.* 11: 226.

Preferred compounds for the inhibition of Cathepsin K are those that will exhibit an $IC_{50}$ of 50 micromolar or below in the above cellular assay.

A Cathepsin K enzymatic assay is disclosed in the following reference:

Bromme, D., Okamoto, K., Wang, B. B., and Biroc, S. (1996) *J. Biol. Chem.* 271, 2126–2132.

Preferred compounds for the inhibition of Cathepsin K are those that will exhibit an $IC_{50}$ of 10 micromolar or below in the above enzymatic assay.

Cathepsins B and L assays are to be found in the following reference:

Methods in Enzymology, Vol.244, Proteolytic Enzymes: Serine and Cysteine Peptidases, Alan J. Barrett, ed.

Cathepsin F assays are to be found in the following references:

Wang, B., Shi, G. P., Yao, P. M., Li, Z., Chapman, H. A., and Bromme, D. (1998) *J. Biol. Chem.* 273, 32000–32008.

Santamaria, I., Velasco, G., Pendas, A. M., Paz, A., and Lopez-Otin, C (1999) *J. Biol. Chem.* 274, 13800–13809.

Preferred compounds for the inhibition of Cathepsins B, L and F are those that will exhibit an $IC_{50}$ of 10 micromolar or below in the above assays.

What is claimed is:

1. A compound of the following formula (I):

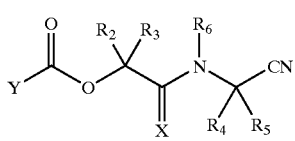

wherein:

Y is $R_1$, $R_1O—$, $R_1S—$, $(R_1)_2N—$;

Each $R_1$ is independently hydrogen, C3–10alkyl, C3–8 cycloalkyl, aryl, benzyl, tetrahydronaphthyl, indenyl, indanyl, C1–10alkylsulfonylC1–10alkyl, C3–8cycloalkylsulfonylC1–10alkyl, arylsulfonylC1–10alkyl, a heterocyclyl or heteroaryl selected from pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyrazinyl, tetrazolyl, pyrazolyl, indolyl, benzofuranyl, benzothienyl, dihydrobenzofuranyl, dihydrobenzothienyl, benzimidazolyl, benzothiazolyl, benzisoxazolyl, benzisothiazolyl, quinolinyl, tetrahydroquinolinyl, isoquinolinyl, tetrahydroisoquinolinyl, quinazolinyl, tetrahydroquinazolinyl, benzoxazolyl, 2H-benzo[e][1,3]oxazine and quinoxalinyl, wherein each $R_1$ is optionally substituted by one or more $R_a$; or $R_1$ is $R_a$ or $R_b$;

Each $R_a$ is independently hydrogen C3–10 alkyl, C3–8 cycloalkyl, aryl, tetrahydronaphthyl, indenyl, indanyl, a heterocycle or heteroaryl selected from the group consisting of pyrrolidinyl, piperidinyl, morpholinyl, thiomorpholinyl, piperazinyl, indolinyl, furanyl, thienyl, pyrrolyl, oxazolyl, dihydro-oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, benzoxazolyl, benzisoxazolyl, quinolinyl, isoquinolinyl, quinazolinyl, and quinoxalinyl, C1–10 alkoxy, C1–10alkanoyl, C1–10alkanoyloxy, aryloxy, benzyloxy, aroyl, C1–10 alkoxycarbonyl, aryloxycarbonyl, aroyloxy, heterocyclyloxy, heterocyclyl-C1–6alkoxy, heteroaryloxy or heteroaryl-C1–6alkoxy, wherein the heterocyclyl or heteroaryloxy moiety is selected from those described in this paragraph, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_a$ is C1–10 mono- or dialkyl amino, C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by one or more C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_a$ is C1–10 alkoxycarbonylamino, aryloxycarbonylamino, heterocyclylcarbonylamino, heteroarylcarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_a$ is halogen, hydroxy, oxo, carboxy, cyano, nitro, carboxamide, amidino or guanidino, wherein $R_a$ may be further optionally substituted by one or more $R_b$;

$R_b$ is a C3–6 saturated or unsaturated alkyl group wherein one or more carbon atoms are optionally replaced by O, N, S(O), S(O)$_2$ or S and wherein said alkyl group is optionally independently substituted with one or two oxo groups, and/or one or more: —NH$_2$, C1–4 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl;

or R$_b$ is C3–6 cycloalkyl, C1–6 alkoxy, aryl, aryloxy, benzyloxy, halogen, hydroxy, oxo, carboxy, cyano, nitro, mono-C1–5alkylamino, di-C1–5alkylamino, carboxamide, amidino or guanidino;

R$_2$ and R$_3$ are each independently a hydrogen, C3–8 cycloalkyl, arylC1–5alkyl, aryl, or a C1–10 saturated or unsaturated alkyl group wherein one or more C atoms are optionally replaced by O, NH, S(O), or S and wherein said alkyl group is optionally independently substituted with one or two oxo groups, and/or one or more: —NH$_2$, C$_{1-4}$ alkyl, aryl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl, benzoxazolyl or quinoxalinyl; wherein each R$_2$ and R$_3$ is independently optionally substituted by one or more R$_c$; or R$_2$ and R$_3$ are each independently R$_c$;

R$_c$ is C1–10 alkyl, C3–4 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiro[2.5]octanyl, cubanyl, tetrahydronaphthyl, decahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, tetrahydrothiopyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, dihydrobenzofuranyl, octohydrobenzofuranyl, benzofuranyl, benzothienyl, dihydrobenzofuranyl, dihydrobenzothienyl, benzimidazolyl, benzothiazolyl, tetrahydroquinolinyl, quinolinyl, tetrahydroisoquinolinyl, isoquinolinyl, quinazolinyl, quinoxalinyl, C1–10 alkoxy, aryloxy, C1–10 alkanoyl, aroyl, C1–10 alkoxycarbonyl, aryloxycarbonyl, C1–10 alkanoyloxy, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or R$_c$ is C1–10alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or R$_c$ is C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or R$_c$ is halogen, hydroxy, oxo, carboxy, cyano, nitro, amidino or guanidino;

Each R$_c$ may be further optionally substituted by one or more R$_d$;

R$_d$ is C1–5 alkyl, C3–4 cycloalkyl, aryl, arylC1–5alkyl, C1–5 alkoxy, aryloxy, arylC1–5alkoxy, aroyl, amino, halogen, hydroxy, oxo, carboxy, cyano, nitro, amidino or guanidino; or R$_2$ and R$_3$ together with the carbon they are attached optionally form a nonaromatic 3–10 membered mono- or bicyclic optionally partially unsaturated cycloalkyl or a 3–10 membered mono- or bicyclic heterocycle each in turn optionally substituted by one or more R$_c$ as described hereinabove;

R$_4$ and R$_5$ are each independently a hydrogen, or a C1–10 saturated or unsaturated alkyl group wherein one or more C atoms are optionally replaced by O, NH, S(O), S(O)$_2$ or S and wherein said alkyl group is optionally independently substituted with one or two oxo groups, and/or one or more: —NH$_2$, C$_{1-4}$ alkyl, aryl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl, benzoxazolyl or quinoxalinyl;

or R$_4$ and R$_5$ are each independently C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, aryl, tetrahydronaphthyl, indenyl, indanyl, C3–7cycloalkylsulfonylC1–5alkyl, arylsulfonylC1–5alkyl, heterocyclyl selected from pyrrolidinyl, piperidinyl, morpholinyl, thiomorpholinyl, piperazinyl, indolinyl, pyranyl, tetrahydropyranyl, thiopyranyl, tetrahydrothiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridizinyl, tetrazolyl, triazolyl, pyrazolyl, indolyl, benzofuranyl, benzothienyl, dihydrobenzofuranyl, dihydrobenzothienyl, benzimidazolyl, benzothiazolyl, quinolinyl, tetrahydroquinolinyl, isoquinolinyl, tetrahydroisoquinolinyl, quinazolinyl, tetrahydroquinazolinyl, benzoxazolyl and quinoxalinyl, C1–10alkanoyl, aroyl, C1–10alkoxycarbonyl, arylC1–5alkoxycarbonyl, aryloxycarbonyl, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_4$ and $R_5$ are each independently C1–10 alkanoylamino, aroylamino, C1–10 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_4$ and $R_5$ are each independently C1–10 alkoxycarbonylamino, aryloxycarbonylamino, C1–10 alkylcarbamoyloxy, arylcarbamoyloxy, C1–10 alkylsulfonylamino, arylsulfonylamino, C1–10 alkylaminosulfonyl, arylaminosulfonyl, amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_4$ and $R_5$ are each independently halogen, hydroxy, carboxy, cyano, nitro, carboxamide, amidino or guanidino;

wherein each $R_4$ and $R_5$ may be further optionally independently substituted by one or more $R_e$;

or $R_4$ and $R_5$ together with the carbon they are attached to optionally form a heterocyclic ring said heterocyclic ring being selected from: azepanyl, piperidinyl, pyrrolidinyl, azetidinyl, oxepanyl, tetrahydropyranyl, tetrahydrothiopyranyl, tetrahydrofuranyl, oxetanyl, azocanyl, oxocanyl, 1,3-diazocanyl, 1,4-diazocanyl, 1,5-diazocanyl, 1,3-dioxocanyl, 1,4-dioxocanyl, 1,5-dioxocanyl, 1,3-oxazocanyl, 1,4-oxazocanyl, 1,5-oxazocanyl, 1,3-diazepanyl, 1,4-diazepanyl, 1,3-dioxepanyl, 1,4-dioxepanyl, 1,3-oxazepanyl, 1,4-oxazepanyl, 1,2-thiazocanyl-1,1-dioxide, 1,2,8-thiadiazocanyl-1,1-dioxide, 1,2-thiazepanyl-1,1-dioxide, 1,2,7-thiadiazepanyl-1,1-dioxide, tetrahydrothiophenyl, hexahydropyrimidinyl, hexahydropyridazinyl, piperazinyl, 1,4,5,6-tetrahydropyrimidinyl, pyrazolidinyl, dihydrooxazolyl, dihydrothiazolyl, dihydroimidazolyl, isoxazolinyl, oxazolidinyl, 1,2-thiazinanyl-1,1-dioxide, 1,2,6-thiadiazinanyl-1,1-dioxide, isothiazolidinyl-1,1-dioxide, imidazolidinyl-2,4-dione, imidazolidinyl, morpholinyl, dioxanyl, tetrahydropyridinyl, thiomorpholinyl, thiazolidinyl, dihydropyranyl, dithianyl, decahydro-quinolinyl, decahydro-isoquinolinyl, 1,2,3,4-tetrahydro-quinolinyl, indolinyl, octahydro-quinolizinyl, dihydro-indolizinyl, octahydro-indolizinyl, octahydro-indolyl, decahydroquinazolinyl, decahydroquinoxalinyl, 1,2,3,4-tetrahydroquinazolinyl or 1,2,3,4-tetrahydroquinoxalinyl;

or $R_4$ and $R_5$ together with the carbon they are attached to optionally form a C6–C10 bridged bicyclic ring group wherein one or more carbon atoms are optionally replaced by a heteroatom chosen from N, O, S, S(O) or $S(O)_2$;

or $R_4$ and $R_5$ together with the carbon they are attached to optionally form a carbocyclic ring group, said carbocyclic ring group being selected from:

cyclopropanyl, cyclobutanyl, cyclopentanyl, cyclohexanyl, cycloheptanyl, cyclooctanyl, cyclononanyl, cyclodecanyl, cubanyl, bicyclo[1.1.0]propanyl, bicyclo[2.1.0]butanyl, bicyclo[3.1.0]hexanyl, bicyclo[4.1.0]heptanyl, bicyclo[5.1.0]octanyl, bicyclo[2.2.0]hexanyl, bicyclo[3.2.0]heptanyl, bicyclo[4.2.0]octanyl, bicyclo[5.2.0]nonanyl, bicyclo[3.3.0]octanyl, bicyclo[4.3.0]nonanyl, bicyclo[5.3.0]decanyl, bicyclo[4.4.0]decanyl, bicyclo[5.4.0]undecanyl, bicyclo[1.1.1]pentanyl, bicyclo[2.1.1]hexanyl, bicyclo[3.1.1]heptanyl, bicyclo[4.1.1]octanyl, bicyclo[5.1.1]nonanyl, bicyclo[2.2.1]heptanyl, bicyclo[3.2.1]octanyl, bicyclo[4.2.1]nonanyl, bicyclo[5.2.1]decanyl, bicyclo[2.2.2]octanyl, bicyclo[3.2.2]nonanyl, bicyclo[4.2.2]decanyl, bicyclo[5.2.2]undecanyl, bicyclo[3.3.2]decanyl, bicyclo[4.3.2]undecanyl, bicyclo[5.3.2]dodecanyl, bicyclo[3.3.3]undecanyl, bicyclo[4.3.3]dodecanyl, bicyclo[5.3.3]tridecanyl;

each of the above ring groups formed by the combination of $R_4$ and $R_5$ being optionally substituted with one or more $R_e$; or $R_4$ and $R_5$ are each independently $R_e$;

$R_e$ is a $C_{1-10}$ saturated or unsaturated alkyl group wherein one or more C atoms are optionally replaced by O, NH, S(O), $S(O)_2$ or S and wherein said alkyl group is optionally independently substituted with one or two oxo groups, and/or one or more: —$NH_2$, $C_{1-4}$ alkyl, aryl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl, benzoxazolyl or quinoxalinyl;

or $R_e$ is a C1–10alkoxy, C1–10alkoxyC1–10alkyl, C1–10alkylaminoC1–10alkyl, C1–10alkylthioC1–10alkyl wherein the sulfur atom may be oxidized to a sulfoxide or sulfone, C3–8 cycloalkyl, C3–8 cycloalkyloxy, aryl, tetrahydronaphthyl, indenyl, indanyl, pyrrolidinyl, piperidinyl, morpholinyl, thiomorpholinyl, piperazinyl, indolinyl, thiopyranyl, tetrahydrothiopyranyl, pyranyl, tetrahydropyranyl, tetrahydrofuranyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, benzoxazolyl, benzisoxazolyl, quinolinyl, isoquinolinyl, quinazolinyl, quinoxalinyl, C1–10alkanoyl, aroyl, C1–10alkanoyloxy, aryloxy, benzyloxy, C1–10 alkoxycarbonyl, arylC1–3alkoxycarbonyl, aryloxycarbonyl, aroyloxy, carbamoyl wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl, quinoxalinyl, or $R_e$ is ureido wherein either nitrogen atom may be independently substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_e$ is amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_e$ is halogen, hydroxy, oxo, carboxy, cyano, nitro, carboxamide, amidino or guanidino, wherein $R_e$ may be further optionally substituted by one or more $R_f$, $R_f$ is C1–5 alkyl, C3–6 cycloalkyl, tolylsulfonyl, C1–5 alkoxy, aryl, aryloxy, benzyloxy, halogen, hydroxy, oxo, carboxy, cyano, nitro, carboxamide, amidino or guanidino;

or $R_f$ is aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl, or $R_f$ is amino wherein the nitrogen atom may be independently mono or di-substituted by C1–10 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl or quinoxalinyl;

or $R_f$ is a C1–10 saturated or unsaturated alkyl group wherein one or more C atoms are optionally replaced by O, NH, S(O), S(O)$_2$ or S and wherein said alkyl group is optionally independently substituted with one or two oxo groups, and/or one or more: —NH$_2$, C$_{1-4}$ alkyl, aryl, pyrrolidinyl, piperidinyl, morpholinyl, thiomorpholinyl, piperazinyl, indolinyl, pyranyl, thiopyranyl, furanyl, thienyl, pyrrolyl, oxazolyl, isoxazolyl, thiazolyl, imidazolyl, pyridinyl, pyrimidinyl, pyrazinyl, indolyl, benzofuranyl, benzothienyl, dihydrobenzofuranyl, dihydrobenzothienyl, benzimidazolyl, benzothiazolyl, quinolinyl, isoquinolinyl, quinazolinyl, benzoxazolyl or quinoxalinyl;

$R_6$ is hydrogen, hydroxy, C1–3 alkyl, or C3–6 cycloalkyl;

X is O or S; or a pharmaceutically acceptable acid or salt thereof;

with the proviso that:

when $R_2$ is hydrogen or alkyl; and $R_3$ is hydrogen, alkyl or benzyl; and $R_4$ is hydrogen, alkyl or cycloalkyl; and $R_5$ is hydrogen, alkyl or cycloalkyl; or $R_4$ and $R_5$ together with the carbon atom they are attached to form cylopentanyl, cyclohexanyl or cycloheptanyl; and $R_6$ is hydrogen; then Y is not phenyl substituted by optionally substituted pyrimidinyl.

2. The compound according to claim 1, wherein:

Y is $R_1$, $R_1$O— or $(R_1)_2$N—;

Each $R_1$ is independently hydrogen, C3–7 alkyl, C3–7 cycloalkyl, phenyl, naphthyl, benzyl, tetrahydronaphthyl, C1–7alkylsulfonylC1–7alkyl, C3–7cycloalkylsulfonylC1–7alkyl, arylsulfonylC1–7alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, thiazolyl, imidazolyl, pyridinyl, isoxazolyl, pyrimidinyl, pyrazinyl, pyridazinyl, indolyl, quinolinyl, isoquinolyl, tetrahydroisoquinolyl, benzofuranyl, benzothienyl, beozimidazolyl, benzothiazolyl, benzoisoxazolyl, benzisothiazolyl, benzoxazolyl, or 2H-benzo[e][1,3]oxazine; wherein each $R_1$ is optionally substituted by one or more $R_a$; or $R_1$ is $R_a$ or $R_b$;

Each $R_a$ is independently hydrogen, C3–7 alkyl, C3–6 cycloalkyl, phenyl, naphthyl, pyrrolidinyl, piperidinyl, morpholinyl, thiomorpholinyl, piperazinyl, furanyl, thienyl, oxazolyl, dihydrooxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothiazolyl, benzoxazolyl, quinolinyl, isoquinolinyl, quinazolinyl, quinoxalinyl, C1–7 alkoxy, C1–7alkanoyl, C1–7alkanoyloxy, aryloxy, benzyloxy, aroyl, C1–7 alkoxycarbonyl, aryloxycarbonyl, aroyloxy, carbamoyl wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_3$ is C1–7 alkanoylamino, aroylamino, C1–7 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_a$ is C1–7 alkoxycarbonylamino, aryloxycarbonylamino, heterocyclylcarbonylamino, heteroarylcarbonylamino, C1–7 alkylcarbamoyloxy, arylcarbamoyloxy, C1–7 alkylsulfonylamino, arylsulfonylamino, C1–7 alkylaminosulfonyl, arylaminosulfonyl, amino wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_a$ is halogen, hydroxy, oxo, carboxy, cyano, nitro, carboxamide, amidino or guanidino, wherein $R_a$ may be further optionally substituted by one or more $R_b$;

$R_b$ is a C3–6 saturated alkyl group wherein one or two carbon atoms are optionally replaced by O or S and wherein said alkyl group is optionally independently substituted with one or two oxo groups and/or one or more: C1–4 alkyl, aryl, piperidinyl, morpholinyl, thiomorpholinyl or piperazine;

or $R_b$ is C3–6 cycloalkyl, aryl, C1–6 alkoxy, aryloxy, benzyloxy, halogen, hydroxy, oxo, carboxy, cyano, nitro, carboxamide, amidino or guanidino;

$R_2$ is hydrogen or methyl or ethyl;

$R_3$ is a hydrogen, C2–5alkylene, C3–7 cycloalkyl, arylC1–3alkyl, aryl or a C1–6 saturated alkyl group wherein one or two of the C atoms are optionally replaced by O, NH or S;

wherein $R_3$ is optionally substituted by one or more $R_c$; or $R_3$ is $R_c$;

$R_c$ is C1–5 alkyl, C3–4 cycloalkyl, aryl, indanyl, indenyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiro[2.5]octanyl, cubanyl, 1,2,3,4-tetrahydronaphthyl, pyrrolidinyl, piperidinyl, morpholinyl, thiomorpholinyl, piperazinyl, indolinyl, furanyl, tetrahydrofuranyl, pyranyl, tetrahydropyranyl, thienyl, pyrrolyl, oxazolyl, thiazolyl, imidazolyl, pyrazolyl, triazolyl, tetrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl, quinoxalinyl, C1–5 alkoxy, aryloxy, C1–5 alkanoyl, aroyl, C1–5 alkoxycarbonyl, aryloxycarbonyl, C1–5 alkanoyloxy, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_c$ is C1–5 alkanoylamino, aroylamino, C1–5 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_c$ is C1–5 alkoxycarbonylamino, aryloxycarbonylamino, C1–5 alkylcarbamoyloxy, arylcarbamoyloxy, C1–5 alkylsulfonylamino, arylsulfonylamino, C1–5 alkylaminosulfonyl, arylaminosulfonyl, amino wherein the nitrogen atom may be independently mono or di-substituted by C1–5 alkyl, aryl, pyrrolidinyl, piperidinyl, morpholinyl, thiomorpholinyl, piperazinyl, indolinyl, furanyl, thienyl, pyrrolyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_c$ is halogen, hydroxy, oxo, carboxy, cyano, nitro, amidino or guanidino;

Each $R_c$ may be further optionally substituted by one or more $R_d$;

$R_d$ is C1–5 alkyl, C3–4 cycloalkyl, aryl, arylC1–4-alkyl, C1–5 alkoxy, aryloxy, arylC1–5alkoxy, aroyl, halogen, hydroxy, oxo or cyano;

or $R_2$ and $R_3$ together with the carbon they are attached optionally form a nonaromatic 5–7 membered cycloalkyl or a 5–7 membered heterocycle, each optionally substituted by $R_c$ as described hereinabove;

$R_4$ and $R_5$ are each independently hydrogen, or a C1–8 saturated alkyl group wherein one or two C atoms are optionally replaced by O, S(O), S(O)$_2$ or S and wherein said alkyl group is optionally substituted with one or two oxo groups and/or one or more: aryl, indolyl or indolinyl;

or $R_4$ and $R_5$ are each independently C1–8alkoxyC1–8alkyl, C1–8alkylaminoC1–8alkyl, C1–8alkylthioC1–8alkyl wherein the sulfur atom may be oxidized to a sulfoxide or sulfone, C3–7 cycloalkyl, aryl, tetrahydronaphthyl, indanyl, heterocyclyl selected from pyrrolidinyl, piperidinyl, morpholinyl, thiomorpholinyl, piperazinyl, indolinyl, pyranyl, tetrahydropyranyl, thiopyranyl, tetrahydrothiopyranyl, furanyl, tetrahydrofuranyl, thienyl, oxazolyl, thiazolyl, imidazolyl, pyridinyl, pyrimidinyl, pyrazinyl, tetrazolyl, triazolyl, pyrazolyl, indolyl, benzofuranyl, benzothienyl, benzimidazolyl, benzothiazolyl, quinolinyl, isoquinolinyl, quinazolinyl, benzoxazolyl and quinoxalinyl, C1–7alkanoyl, aroyl, C1–7 alkoxycarbonyl, arylC1–4alkoxycarbonyl, aryloxycarbonyl, carbamoyl wherein the nitrogen atom may be independently mono or di-substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_4$ and $R_5$ are each independently C1–7 alkanoylamino, aroylamino, C1–7 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–7 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_4$ and $R_5$ are each independently C1–7 alkoxycarbonylamino, aryloxycarbonylamino, C1–7 alkylcarbamoyloxy, arylcarbamoyloxy, C1–7 alkylsulfonylamino, arylsulfonylamino, C1–7 alkylaminosulfonyl, arylaminosulfonyl, amino wherein the nitrogen atom may be independently mono or di-substituted by C1–7 alkyl, aryl, pyrrolidinyl, piperidinyl, morpholinyl, thiomorpholinyl, piperazinyl, furanyl, thienyl, pyrrolyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_4$ and $R_5$ are each independently halogen, hydroxy, carboxy, cyano, nitro or carboxamide, wherein each $R_4$ and $R_5$ may be further optionally independently substituted by one or more $R_e$;

or $R_4$ and $R_5$ together with the carbon they are attached optionally form a heterocyclic ring said heterocyclic ring being selected from:

piperidinyl, pyrrolidinyl, tetrahydropyranyl, tetrahydrothiopyranyl, azetidinyl, azepanyl, oxepanyl, tetrahydrofuranyl, oxetanyl, hexahydropyrimidinyl, hexahydropyridazinyl, piperazinyl, 1,4,5,6-tetrahydropyrimidinyl, octahydro-indolizinyl, octahydro-quinolizinyl, decahydro-quinolinyl, 1,2,3,4-tetrahydro-quinolinyl, dihydro-oxazolyl, 1,2-thiazinanyl-1,1-dioxide, 1,2,6-thiadiazinanyl-1,1-dioxide, isothiazolidinyl-1,1-dioxide, imidazolidinyl, pyrazolidinyl or $R_4$ and $R_5$ together with the carbon atom they are attached to form a cyclopropanyl, cyclobutanyl, cyclopentanyl, cyclohexanyl, cycloheptanyl, or a bridged bicyclo group chosen from aza-bicyclo[3.2.1]octane, aza-bicyclo[2.2.1]heptane, aza-bicyclo[2.2.2]octane, aza-bicyclo[3.2.2]nonane, aza-bicyclo[2.1.1]hexane, aza-bicyclo[3.1.1]heptane, aza-bicyclo[3.3.2]decane and 2-oxa or 2-thia-5-aza-bicyclo[2.2.1]heptane;

each ring being substituted with one or more $R_e$;

$R_e$ is C1–8 saturated alkyl group wherein one or two of the C atoms are optionally replaced by O, S(O), S(O)$_2$ or S, and wherein said alkl group is optionally independently substituted with one or two oxo groups and/or one or more: $C_{1-4}$alkyl or aryl;

or $R_e$ is C1–7alkoxy, C1–7alkoxyC1–7alkyl, C1–7alkylaminoC1–7alkyl, C1–7alkylthioC1–7alkyl wherein the sulfur atom may be oxidized to a sulfoxide or sulfone, C3–7 cycloalkyl, aryl, tetrahydronaphthyl, indanyl, pyrrolidinyl, piperidinyl, morpholinyl, thiomorpholinyl, piperazinyl, thiopyranyl, tetrahydrothiopyranyl, tetrahydropyranyl, tetrahydrofuranyl, furanyl, thienyl, oxazolyl, thiazolyl, imidazolyl, pyridinyl, pyrimidinyl, pyrazinyl, indolyl, benzofuranyl, benzothienyl, benzimidazolyl, benzothiazolyl, benzoxazolyl, quinolinyl, isoquinolinyl, quinazolinyl, quinoxalinyl, C1–5 alkanoyl, aroyl, C1–5alkanoyloxy, aryloxy, benzyloxy, C1–5 alkoxycarbonyl, aryloxycarbonyl, aroyloxy, carbamoyl wherein the nitrogen atom may be independently mono or di-substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_e$ is ureido wherein either nitrogen atom may be independently substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_e$ is amino wherein the nitrogen atom may be independently mono or di-substituted by C1–5 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl or quinoxalinyl, or $R_e$ is halogen, hydroxy, oxo, carboxy, cyano, nitro, carboxamide, amidino or guanidino, wherein $R_e$ may be further optionally substituted by one or more $R_f$;

$R_f$ is methyl, ethyl, t-butyl, tolylsulfonyl, C1–3 alkoxy, cyclopropyl, cyclobutyl, cyclopentyl, cyclohexyl, phenyl, naphthyl, phenoxy, benzyloxy, fluoro, chloro, bromo, hydroxy, oxo, carboxy, cyano, nitro amino or carboxamide;

$R_6$ is nyorogen or methyl;

and

X is O.

3. The compound according to claim 2, wherein:

Each $R_1$ is independently hydrogen, C3–5 alkyl, C3–6 cycloalkyl, phenyl, benzyl, naphthyl, C1–3alkylsulfonylC1–3alkyl, C3–6cycloalkylsulfonylC1–3alkyl, arylsulfonylC1–3alkyl, pyrrolidinyl, piperidinyl, morpholinyl, thiomorpholinyl, piperazinyl, furanyl, thienyl, oxazolyl, thiazolyl, imidazolyl, pyridinyl, isoxazolyl, pyrimidinyl, pyrazinyl, pyridazinyl, indolyl, quinolinyl, tetrahydroisoquinolyl, benzofuranyl, benzthienyl, benzimidazolyl, benzothiazolyl, benzoxazolyl, 2H-benzo[e][1,3] oxazine; wherein each $R_1$ is optionally substituted by one or more $R_a$; or $R_1$ is $R_a$ or $R_b$;

Each $R_a$ is independently hydrogen, C3 alkyl, cyclopropyl, cyclopentyl, cyclohexyl, phenyl, naphthyl, pyrrolidinyl, piperidinyl, morpholinyl, thiomorpholinyl, piperazinyl, furanyl, thienyl, oxazolyl, dihydro-oxazolyl, thiazolyl, imidazolyl, pyridinyl, pyrimidinyl, benzimidazolyl, benzothiazolyl, benzoxazolyl, C1–3 alkoxy, C1–3alkanoyl, C1–3alkanoyloxy, aryloxy, benzyloxy, aroyl, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl, piperazinyl, thienyl, oxazolyl, thiazolyl, imidazolyl, pyridinyl, pyrimidinyl, benzimidazolyl or benzothiazolyl, or $R_a$ is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or $R_a$ is C1–5 alkoxycarbonylamino, aryloxycarbonylamino, heterocyclylcarbonylamino, heteroarylcarbonylamino C1–5 alkylcarbamoyloxy, arylcarbamoyloxy, $C_{1-5}$alkylsulfonylamino, arylsulfonylamino, C1–5 alkylaminosulfonyl, arylaminosulfonyl, amino wherein the nitrogen atom may be independently mono or di-substituted by C1–6 alkyl, aryl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, wherein $R_a$ may be further optionally substituted by one or more $R_b$;

$R_b$ is a C3–6 saturated alkyl group wherein one or two carbon atoms are optionally replaced by O or S and wherein said alkyl group is optionally independently substituted with an oxo group and/or one or more: C1–4 alkyl, aryl, piperidinyl, morpholinyl, thiomorpholinyl or piperazine;

or $R_b$ is C3–6 cycloalkyl, aryl, C1–3 alkoxy, aryloxy, benzyloxy, halogen, hydroxy, oxo, carboxy, cyano, nitro, carboxamide, amidino or guanidino;

$R_2$ is hydrogen or methyl;

$R_3$ is hydrogen, C2–5alkylene, C3–6 cycloalkyl or arylC1–2alkyl, phenyl, naphthyl, or a C1–6 saturated alkyl group wherein one or two of the C atoms are optionally replaced by O, NH or S; wherein $R_3$ is optionally substituted by one or more $R_c$; or $R_3$ is $R_c$;

$R_c$ is C1–4 alkyl, phenyl, naphthyl, indanyl, bicyclo [2.2.1]heptanyl, bicyclo[2.2.2]octanyl, bicyclo [4.1.0]heptanyl, bicyclo[3.1.0]hexanyl, bicyclo [1.1.1]pentanyl, spiro[2.5]octanyl, cubanyl, 1,2,3,4-tetrahydronaphthyl pyrrolidinyl, piperidinyl, morpholinyl, thiomorpholinyl, indolinyl, furanyl, tetrahydrofuranyl, pyranyl, tetrahydropyranyl, thienyl, pyrrolyl, oxazolyl, thiazolyl, imidazolyl, pyrazolyl, pyridinyl, pyrimidinyl, pyrazinyl, indolyl, benzofuranyl, benzothienyl, benzimidazolyl, benzothiazolyl, quinolinyl, isoquinolinyl, quinazolinyl, quinoxalinyl, C1–4 alkoxy, phenoxy, naphthyloxy, C1–3 alkanoyl, benzoyl, C1–3 alkoxycarbonyl, phenoxycarbonyl, C1–3 alkanoyloxy, benzoyloxy, carbamoyl wherein the nitrogen atom may be independently mono or di-substituted by C1–5 alkyl or aryl, or $R_c$ is C1–3 alkanoylamino, benzoylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–5 alkyl or aryl, or $R_c$ is C1–3 alkoxycarbonylamino, aryloxycarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–5 alkyl or aryl, or $R_c$ is halogen, hydroxy, oxo, carboxy, cyano, nitro, amidino or guanidino, wherein each $R_c$ may be further optionally substituted by one or more $R_d$;

$R_d$ is C1–3 alkyl, C3–4 cycloalkyl, phenyl, benzyl, C1–3 alkoxy, phenoxy, phenylC1–3alkoxy, benzoyl, halogen, hydroxy, oxo or cyano;

$R_2$ and $R_3$ together with the carbon they are attached optionally form a nonaromatic 5–6 membered cycloalkyl or a 5–6 membered heterocycle, each optionally substituted by $R_c$ as described hereinabove;

$R_4$ and $R_5$ are each independently hydrogen, or a C1–5 saturated alkyl group wherein one or two C atoms are optionally replaced by O, S(O), S(O)$_2$ or S and wherein said alkyl group is optionally substituted with one oxo group and/or one or more: phenyl, naphthyl or indolyl;

or $R_4$ and $R_5$ are each independently C1–6alkoxyC1–6alkyl, C1–6alkylaminoC1–6alkyl, C1–6alkylthioC1–6alkyl wherein the sulfur atom may be oxidized to a sulfoxide or sulfone, C3–6 cycloalkyl, phenyl, naphthyl, , indanyl, heterocyclyl selected from pyrrolidinyl, piperidinyl, morpholinyl, thiomorpholinyl, piperazinyl, tetrahydropyranyl, tetrahydrothiopyranyl, furanyl, tetrahydrofuranyl, thienyl, oxazolyl, thiazolyl, imidazolyl, pyridinyl, pyrimidinyl, pyrazolyl, benzofuranyl, benzothienyl, benzimidazolyl, benzothiazolyl, quinolinyl, isoquinolinyl and benzoxazolyl, C1–3alkanoyl, benzoyl, naphthoyl, C1–4 alkoxycarbonyl, arylC1–2alkoxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl or pyrimidinyl, or $R_4$ and $R_5$ are each independently C1–4 alkanoylamino, aroylamino, C1–4 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, phenyl, naphthyl, pyrrolidinyl, piperidinyl, morpholinyl, piperazinyl, oxazolyl, thiazolyl, imidazolyl, pyridinyl, pyrimidinyl, pyrazinyl, indolyl, benzofuranyl, benzothienyl, benzimidazolyl or benzothiazolyl, or $R_4$ and $R_5$ are each independently C1–4 alkoxycarbonylamino, phenoxycarbonylamino, C1–4 alkylcarbamoyloxy, phenylcarbamoyloxy, C1–4 alkylsulfonylamino, phenylsulfonylamino, C1–3 alkylaminosulfonyl, phenylaminosulfonyl, amino wherein the nitrogen atom may be independently mono or di-substituted by C1–4 alkyl, aryl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzothiazolyl, or $R_4$ and $R_5$ are each independently halogen, hydroxy, carboxy, cyano, nitro or carboxamide, wherein each $R_4$ and $R_5$ may be further optionally indenpendtly substituted by one or more $R_e$; or $R_4$ and $R_5$ together with the carbon they are attached optionally form cyclopropanyl, cyclopentanyl, cyclohexanyl, or a heterocyclic ring said heterocyclic ring being selected from: piperidinyl, pyrrolidinyl, azetidinyl, tetrahydropyranyl, tetrahydrothiopyranyl, tetrahydrofuranyl, each ring being optionally substituted with one or more $R_e$;

$R_e$ is C1–5 saturated alkyl group wherein one or two of the C atoms are optionally replaced by O, S(O), S(O)$_2$ or S, and wherein said alkyl group is optionally independently substituted with one oxo group and/or one or more: $C_{1-4}$alkyl, phenyl or naphthyl;

or $R_e$ is C1–4 alkoxy, C3–7 cycloalkyl, phenyl, naphthyl, indanyl, pyrrolidinyl, piperidinyl, morpholinyl, thiomorpholinyl, piperazinyl, tetrahydrothiopyranyl, tetrahydropyranyl, tetrahydrofuranyl, thienyl, oxazolyl, thiazolyl, imidazolyl, pyridinyl, pyrimidinyl, pyrazinyl, indolyl, benzimidazolyl, benzothiazolyl, benzoxazolyl, quinolinyl, isoquinolinyl, quinazolinyl, quinoxalinyl, C1–4 alkanoyl, aroyl, C1–4alkanoyloxy, phenoxy, naphthyloxy, benzyloxy, C1–4 alkoxycarbonyl, phenoxycarbonyl, benzoyloxy, carbamoyl wherein the nitrogen atom may be independently mono or di-substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl, or benzothiazolyl, or $R_e$ is ureido wherein either nitrogen atom may be independently substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzothiazolyl, or $R_e$ is amino wherein the nitrogen atom may be independently mono or di-substituted by C1–3 alkyl, phenyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, benzimidazolyl or benzothiazolyl, or $R_e$ is halogen, hydroxy, oxo, carboxy, cyano, nitro or carboxamide, wherein $R_e$ may be further optionally substituted by one or more $R_f$;

$R_f$ is methyl, ethyl, t-butyl, tolylsulfonyl, methoxy, cyclopropyl, cyclopentyl, cyclohexyl, phenyl, phenoxy, benzyloxy, fluoro, chloro, bromo, hydroxy, oxo, carboxy or carboxamide;

and $R_6$ is hydrogen.

4. The compound according to claim 3, wherein:

Each $R_1$ is independently hydrogen, C3–5 alkyl, C3–6 cycloalkyl, phenyl, benzyl, naphthyl, pyrrolidinyl, piperidinyl, morpholinyl, thiomorpholinyl, piperazinyl, furanyl, thienyl, oxazolyl, thiazolyl, imidazolyl, pyridinyl, pyrimidinyl, pyrazinyl, pyridazinyl, indolyl, quinolinyl, tetrahydroisoquinolyl; benzofuranyl, benzthienyl, benzimidazolyl, benzothiazolyl, benzoxazolyl, 2-H-benzo[e][1,3]oxazine ; wherein each $R_1$ is optionally substituted by one or more $R_a$; or $R_1$ is $R_a$ or $R_b$;

Each $R_a$ is independently C3 alkyl, cyclopropyl, cyclohexyl, phenyl, pyrrolidinyl, piperidinyl, morpholinyl, thiomorpholinyl, piperazinyl, thienyl, oxazolyl, dihydro-oxazolyl, imidazolyl, pyridinyl, C1–3 alkoxy, C1–3alkanoyl, C1–3alkanoyloxy, aryloxy, benzyloxy, benzoyl, C1–3 alkoxycarbonyl, aryloxycarbonyl, aroyloxy, carbamoyl wherein the nitrogen atom may be independently mono or di-substituted by C1–3 alkyl, aryl, pyrrolidinyl, piperidinyl, morpholinyl, thiomorpholinyl or piperazinyl, or $R_a$ is C1–3 alkanoylamino, aroylamino, C1–3 alkylthio wherein the sulfur atom may be oxidized to a sulfoxide or sulfone, arylthio wherein the sulfur atom may be oxidized to a sulfoxide or sulfone, ureido wherein either nitrogen atom may be independently substituted by C1–3 alkyl, aryl, pyrrolidinyl, piperidinyl, morpholinyl, thiomorpholinyl or piperazinyl, or $R_a$ is C1–3 alkoxycarbonylamino, aryloxycarbonylamino, heterocyclylcarbonylamino, C1–3 alkylcarbamoyloxy, arylcarbamoyloxy, C1–3 alkylsulfonylamino, arylsulfonylamino, C1–3 alkylaminosulfonyl, arylaminosulfonyl, amino wherein the nitrogen atom may be independently mono or di-substituted by C1–3 alkyl, aryl, pyrrolidinyl, piperidinyl, morpholinyl, thiomorpholinyl or piperazinyl, or $R_a$ is halogen, hydroxy, oxo, carboxy, cyano, nitro, carboxamide, amidino or guanidino, wherein $R_a$ may be further optionally substituted by one or more $R_b$;

$R_b$ is C3–4 saturated alkyl wherein one carbon atom is optionally replaced by O and wherein said alkyl group is optionally independently substituted with an oxo group and/or one or two: C1–4 alkyl, phenyl, morpholinyl or thiomorpholinyl;

or $R_b$ is cyclopropyl, cyclopentyl, cyclohexyl, phenyl, methoxy, ethoxy, n-propoxy, i-propoxy, phenoxy, benzyloxy, fluoro, chloro, bromo, iodo, hydroxy, oxo, carboxy, cyano, nitro or carboxamide;

$R_2$ is hydrogen;

$R_3$ is a hydrogen, C2–4alkylene, C5–6 cycloalkyl, benzyl or naphthylmethyl, phenyl, or a C1–4 saturated alkyl group wherein one of the C atoms is optionally replaced by O, NH or S; wherein $R_3$ is optionally substituted by one or more $R_c$; or $R_3$ is $R_c$;

$R_c$ is C1–3 alkyl, C3–4 cycloalkyl, phenyl, naphthyl, indanyl, bicyclo[2.2.1]heptanyl, bicyclo[2.2.2] octanyl, bicyclo[4.1.0]heptanyl, bicyclo[3.1.0] hexanyl, bicyclo[1.1.1]pentanyl, spiro[2.5]octanyl, cubanyl, 1,2,3,4-tetrahydronaphthyl, furanyl, tetrahydropyranyl, thienyl, oxazolyl, thiazolyl, imidazolyl, pyridinyl, pyrimidinyl, indolyl, benzofuranyl, benzothienyl, benzothiazolyl, C1–3 alkoxy, phenoxy, naphthyloxy, C1–2 alkanoyl, benzoyl, C1–2 alkoxycarbonyl, phenoxycarbonyl, C1–2alkanoyloxy, benzoyloxy, carbamoyl wherein the nitrogen atom may be independently mono or di-substituted by C1–3 alkyl or aryl, or $R_c$ is C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl or aryl, or $R_c$ is C1–2 alkoxycarbonylamino, phenoxycarbonylamino, C1–2 alkylcarbamoyloxy, arylcarbamoyloxy, C1–2 alkylsulfonylamino, phenylsulfonylamino, C1–2alkylaminosulfonyl, phenylaminosulfonyl, amino wherein the nitrogen atom may be independently mono or di-substituted by C1–3 alkyl or phenyl, or $R_c$ is halogen, hydroxy, oxo, carboxy or cyano, wherein each $R_c$ may be further optionally substituted by one or more $R_d$;

$R_d$ is methyl, cyclopropyl, phenyl, benzyl, methoxy, phenoxy, benzyloxy, benzoyl, fluoro, chloro, oxo or cyano;

$R_2$ and $R_3$ together with the carbon they are attached optionally form cyclohexyl optionally substituted by $R_c$ as described hereinabove;

$R_4$ and $R_5$ are each independently hydrogen, or a C1–5 saturated alkyl group wherein one C atom is optionally replaced by O, S or $S(O)_2$ and wherein said alkyl group is optionally substituted with phenyl or indolyl;

or $R_4$ and $R_5$ are each independently C1–5alkoxyC1–5alkyl, C1–5alkylaminoC1–5alkyl, C1–5alkylthioC1–5alkyl wherein the sulfur atom may be oxidized to a sulfoxide or sulfone, C3–6 cycloalkyl, phenyl, naphthyl, indanyl, heterocyclyl selected from pyrrolidinyl, piperidinyl, morpholinyl, thiomorpholinyl, piperazinyl, tetrahydropyranyl, oxazolyl, thiazolyl, imidazolyl, pyridinyl, pyrimidinyl, benzimidazolyl and benzothiazolyl, C1–3alkanoyl, benzoyl, naphthoyl, C1–3 alkoxycarbonyl, benzyloxycarbonyl, phenoxycarbonyl, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl or pyrimidinyl, or $R_4$ and $R_5$ are each independently C1–3 alkanoylamino, aroylamino, C1–3 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzofuranyl, benzothienyl, benzimidazolyl or benzothiazolyl, or $R_4$ and $R_5$ are each independently is C1–3 alkoxycarbonylamino, phenoxycarbonylamino, C1–3 alkylcarbamoyloxy, phenylcarbamoyloxy, C1–3 alkylsulfonylamino, phenylsulfonylamino, C1–3 alkylaminosulfonyl, phenylaminosulfonyl, amino wherein the nitrogen atom may be independently mono or di-substituted by C1–3 alkyl, phenyl, pyrrolidinyl, piperidinyl, morpholinyl, thiomorpholinyl, piperazinyl, oxazolyl, thiazolyl, imidazolyl, pyridinyl, pyrimidinyl, benzimidazolyl or benzothiazolyl, or $R_4$ and $R_5$ are each independently halogen, hydroxy, oxo, carboxy, cyano or carboxamide, each $R_4$ and $R_5$ may be further optionally independently substituted by one or more $R_e$;

or $R_4$ and $R_5$ together with the carbon they are attached optionally form a cyclopropanyl or a heterocyclic ring said heterocyclic ring being selected from: piperidinyl, pyrrolidinyl and tetrahydropyranyl, each ring being optionally substituted with one or more $R_e$;

$R_e$ is C1–5 saturated alkyl group wherein one of the C atoms is optionally replaced by O, S(O), $S(O)_2$ or S, and wherein said alkyl group is optionally independently substituted with one oxo group and/or a $C_{1-4}$alkyl or phenyl;

or $R_e$ is C1–3 alkoxy, C3–7 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzothiazolyl, benzoxazolyl, C1–3 alkanoyl, aroyl, C1–3alkanoyloxy, phenoxy, benzyloxy, C1–3 alkoxycarbonyl, phenoxycarbonyl, benzoyloxy, carbamoyl wherein the nitrogen atom may be independently mono or di-substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzothiazolyl, or $R_e$ is ureido wherein either nitrogen atom may be independently substituted by C1–3 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzothiazolyl, or $R_e$ is amino wherein the nitrogen atom may be independently mono or di-substituted by C1–3 alkyl, phenyl, naphthyl, pyrrolidinyl, piperidinyl, morpholinyl, piperazinyl, oxazolyl, thiazolyl, imidazolyl, pyridinyl, pyrimidinyl, benzimidazolyl or benzothiazolyl, or $R_e$ is halogen, hydroxy, oxo, carboxy, cyano or carboxamide, wherein $R_e$ may be further optionally substituted by one or more $R_f$;

and $R_f$ is methyl, cyclopentyl, cyclohexyl, phenyl, tolylsulfonyl, methoxy, phenoxy, benzyloxy, fluoro, chloro, bromo, hydroxy, oxo, carboxy or carboxamide.

5. The compound according to claim 4, wherein:

Each $R_1$ is independently a hydrogen, i-propyl, cyclopropyl, cyclopentyl, cyclohexyl, phenyl, benzyl, naphthyl, pyrrolidinyl, piperidinyl, morpholinyl, thiomorpholinyl, piperazinyl, furanyl, thienyl, thiazolyl, quinolyl, tetrahydroisoquinolyl, imidazolyl, pyridinyl, pyrazinyl, or 2H-benzo[e][1,3]oxazine; wherein each $R_1$ is optionally substituted by one or more $R_a$; or $R_1$ is $R_a$ or $R_b$;

Each $R_a$ is independently cyclopropyl, phenyl, pyrrolidinyl, piperidinyl, morpholinyl, thiomorpholinyl, piperazinyl, thienyl, dihyrdooxazolyl, imidazolyl, pyridinyl, methoxy, acetyl, acetoxy, phenoxy, benzyloxy, benzoyl, methoxycarbonyl, phenoxycarbonyl, benzoyloxy, carbamoyl wherein the nitrogen atom may be independently mono or di-substituted by methyl, ethyl or phenyl, or $R_a$ is acetylamino, benzoylamino, methylthio, phenylthio wherein the sulfur atom may be oxidized to a sulfoxide or sulfone, ureido wherein either nitrogen atom may be independently substituted by methyl, ethyl or phenyl, or $R_a$ is C1–3alkoxycarbonylamino, phenoxycarbonylamino, piperazinylcarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, phenyl, or piperidinyl, or $R_a$ is fluoro, chloro, bromo, iodo, hydroxy, oxo, carboxy, cyano, nitro or carboxamide, wherein $R_a$ may be further optionally substituted by one or more $R_b$;

$R_b$ is C3–4 saturated alkyl group, wherein one carbon atom is optionally replaced by O and wherein said alkyl group is optionally independently substituted with an oxo group and/or a C1–4 alkyl, phenyl or morpholinyl;

or $R_b$ is cyclopropyl, phenyl, methoxy, phenoxy, benzyloxy, fluoro, chloro, hydroxy, oxo, carboxy or carboxamide;

$R_3$ is a hydrogen, C2–4alkylene, C5–6 cycloalkyl, phenyl, benzyl or naphthylmethyl or a C1–4 saturated alkyl group wherein one of the C atoms is optionally replaced by O or S; wherein $R_3$ is optionally substituted by one or more $R_c$; or $R_3$ is $R_c$;

$R_c$ is methyl, ethyl, n-propyl, i-propyl, C3 cycloalkyl, phenyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, spiro[2.5]octanyl, cubanyl, 1,2,3,4-tetrahydronaphthyl, thienyl, oxazolyl, thiazolyl, pyridinyl, indolyl, benzofuranyl, benzothienyl, benzothiazolyl, methoxy, ethoxy, phenoxy, acetyl, benzoyl, methoxycarbonyl, phenoxycarbonyl, acetoxy, benzoyloxy, carbamoyl wherein the nitrogen atom may be independently mono or di-substituted by methyl, ethyl or aryl, or $R_c$ is acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or aryl, or $R_c$ is methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_c$ is fluoro, chloro or oxo, wherein each $R_c$ may be further optionally substituted by one or more $R_d$;

$R_d$ is methyl, cyclopropyl, phenyl, methoxy, fluoro, chloro or oxo;

$R_4$ and $R_5$ are each independently hydrogen, C1–4 saturated alkyl, C1–4alkoxyC1–4alkyl, C1–4alkylaminoC1–4alkyl, C1–4alkylthioC1–4alkyl wherein the sulfur atom may be oxidized to a sulfoxide or sulfone, cyclopropyl, cyclopentyl, cyclohexyl, phenyl, naphthyl, benzyl, indanyl, heterocyclyl selected from pyrrolidinyl, piperidinyl, morpholinyl, piperazinyl, tetrahydropyranyl, oxazolyl, thiazolyl, imidazolyl, pyridinyl, pyrimidinyl, benzimidazolyl and benzothiazolyl, C1–2alkanoyl, benzoyl, naphthoyl, C1–2 alkoxycarbonyl, benzyloxycarbonyl, phenoxycarbonyl, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_4$ and $R_5$ are each independently C1–2 alkanoylamino, benzoylamino, C1–2 alkylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl, pyrimidinyl, benzimidazolyl or benzothiazolyl, or $R_4$ and $R_5$ are each independently C1–2 alkoxycarbonylamino, phenoxycarbonylamino, C1–2 alkylcarbamoyloxy, phenylcarbamoyloxy, C1–2 alkylsulfonylamino, phenylsulfonylamino, C1–2 alkylaminosulfonyl, phenylaminosulfonyl, amino wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_4$ and $R_5$ are each independently fluoro, chloro, bromo, hydroxy, oxo, carboxy or carboxamide, wherein each $R_4$ and $R_5$ may be further optionally indenpendtly substituted by one or more $R_e$;

$R_e$ is C1–3 saturated alkyl, C1–3 alkoxy, C3–6 cycloalkyl, phenyl, naphthyl, indanyl, pyrrolidinyl, piperidinyl, morpholinyl, piperazinyl, tetrahydropyranyl, indolyl, thienyl, oxazolyl, thiazolyl, imidazolyl, pyridinyl, pyrimidinyl, benzimidazolyl, benzothiazolyl, benzoxazolyl, C1–2 alkanoyl, aroyl, C1–2alkanoyloxy, phenoxy, benzyloxy, C1–2 alkoxycarbonyl, phenoxycarbonyl, benzoyloxy, carbamoyl wherein the nitrogen atom may be independently mono or di-substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is ureido wherein either nitrogen atom may be independently substituted by C1–2 alkyl, phenyl, pyrrolidinyl, piperidinyl, morpholinyl, piperazinyl, oxazolyl, thiazolyl, imidazolyl, pyridinyl or pyrimidinyl, or $R_e$ is amino wherein the nitrogen atom may be independently mono or di-substituted by C1–2 alkyl, phenyl, naphthyl, pyrrolidinyl, piperidinyl, morpholinyl, piperazinyl, oxazolyl, thiazolyl, imidazolyl, pyridinyl or pyrimidinyl, or $R_e$ is fluoro, chloro, bromo, hydroxy, oxo, carboxy or carboxamide, wherein $R_e$ may be further optionally substituted by one or more $R_f$;

and $R_f$ is methyl, cyclopentyl, cyclohexyl, phenyl, tolylsulfonyl, methoxy, phenoxy, benzyloxy, fluoro, chloro, hydroxy, oxo, carboxy or carboxamide.

6. The compound according to claim 5, wherein:

Each $R_1$ is independently hydrogen, i-propyl, cyclopropyl, cyclohexyl, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl, quinolyl, tetrahydroisoquinolyl, or 2H-benzo[e][1,3]oxazine; wherein each $R_1$ is optionally substituted by one or more $R_a$; or $R_1$ is $R_a$ or $R_b$;

Each $R_a$ is independently phenyl, thienyl, dihydrooxazolyl, pyridinyl, methoxy, acetyl, acetoxy, phenoxy, benzyloxy, benzoyl, methoxycarbonyl, benzoyloxy, carbamoyl wherein the nitrogen atom may be independently mono or di-substituted by methyl or phenyl, or $R_a$ is acetylamino, methylthio, phenylthio wherein the sulfur atom may be oxidized to a sulfoxide or sulfone, ureido wherein either nitrogen atom may be independently substituted by methyl or phenyl, or $R_a$ is methoxycarbonylamino, piperazinylcarbonylamino, methylcarbamoyloxy, phenylcarbamoyloxy, methylsulfonylamino, phenylsulfonylamino, amino wherein the nitrogen atom may be independently mono or di-substituted by methyl or phenyl, or $R_a$ is fluoro, chloro, hydroxy, oxo, carboxy, cyano or carboxamide;

wherein $R_a$ may be further optionally substituted by one or more $R_b$;

$R_3$ is an alkyl group selected from n-propyl or i-propyl, wherein one carbon atom is optionally replaced by O and wherein said alkyl group is optionally independently substituted with an oxo group and/or phenyl or morpholinyl;

or $R_b$ is phenyl, methoxy, phenoxy, fluoro, chloro or oxo;

$R_3$ is a hydrogen, methyl, ethyl, n-propyl, n-butyl, i-butyl, methoxymethyl, methylthiomethyl, propenyl, butenyl, i-butenyl, cyclohexyl, phenyl, benzyl or naphthylmethyl wherein $R_3$ is optionally substituted by one or more $R_c$;

$R_c$ is methyl, ethyl, n-propyl, i-propyl, cyclopropyl, phenyl, indanyl, bicyclo[2.2.1]heptanyl, bicyclo[2.2.2]octanyl, bicyclo[4.1.0]heptanyl, bicyclo[3.1.0]hexanyl, bicyclo[1.1.1]pentanyl, cubanyl, 1,2,3,4-tetrahydronaphthyl, pyridinyl, methoxy, phenoxy, acetyl, benzoyl, methoxycarbonyl, phenoxycarbonyl, acetoxy, benzoyloxy, methylthio wherein the sulfur atom may be oxidized to a sulfoxide or sulfone, phenylthio wherein the sulfur atom may be oxidized to a sulfoxide or sulfone, dimethylamino, diethylamino, fluoro, chloro or oxo;

$R_4$ and $R_5$ are each independently hydrogen, C1–4 saturated alkyl, C1–2alkoxyC1–2alkyl, C1–2alkylaminoC1–2alkyl, C1–2alkylthioC1–2alkyl wherein the sulfur atom may be oxidized to a sulfoxide or sulfone, , cyclopropyl, cyclopentyl, cyclohexyl, phenyl, benzyl, heterocyclyl selected from pyrrolidinyl, piperidinyl, morpholinyl, tetrahydropyranyl, pyridinyl, and pyrimidinyl, acetyl, benzoyl, methoxycarbonyl, ethoxycarbonyl, benzyloxycarbonyl, carbamoyl wherein the nitrogen atom may be independently mono or di-substituted by methyl, ethyl or phenyl, or $R_4$ and $R_5$ are each independently acetylamino, benzoylamino, methylthio wherein the sulfur atom may be oxidized to a sulfoxide or sulfone, phenylthio wherein the sulfur atom may be oxidized to a sulfoxide or sulfone, ureido wherein either nitrogen atom may be independently substituted by methyl, ethyl or phenyl, or $R_4$ and $R_5$ are each independently methoxycarbonylamino, ethoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom may be independently mono or di-substituted by methyl, ethyl or phenyl, or $R_4$ and $R_5$ are each independently fluoro, chloro, hydroxy, oxo, carboxy or carboxamide, wherein each $R_4$ and $R_5$ may be further optionally indenpendtly substituted by one or more $R_e$;

$R_e$ is methyl, methoxy, ethoxy, cyclopropyl, cyclopentyl, cyclohexyl, phenyl, naphthyl, indanyl, piperidinyl, morpholinyl, indolyl, thienyl, pyridinyl, acetyl, benzoyl, acetyloxy, phenoxy, benzyloxy, methoxycarbonyl, ethoxycarbonyl, carbamoyl wherein the nitrogen atom may be independently mono or di-substituted by methyl, ethyl or phenyl, or $R_e$ is ureido wherein either nitrogen atom may be independently substituted by methyl, ethyl or phenyl, or $R_e$ is amino wherein the nitrogen atom may be independently mono or di-substituted by methyl, ethyl or phenyl, or $R_e$ is fluoro, chloro, hydroxy, oxo, carboxy or carboxamide, wherein $R_e$ may be further optionally substituted by one or more $R_f$;

and $R_f$ is methyl, cyclopentyl, cyclohexyl, phenyl, tolylsulfonyl, methoxy, phenoxy, benzyloxy, carboxy, fluoro, chloro or oxo.

7. The compound according to claim 6, wherein:

Each $R_1$ is independently hydrogen, i-propyl, benzyloxy, cyclohexyl, benzyl, phenyl, carboxyphenyl, naphthyl, 4-(acetylamino)-phenyl, 4-(methanesulfonylamino)-phenyl, 4-methoxyphenyl, 3-phenoxyphenyl, 4-chlorophenyl, 3,4-dichlorophenyl, 4-fluorophenyl, 2-fluorophenyl, 2-fluoro-4-chlorophenyl, naphthyl, thienylmethyl, piperidinyl, morpholinyl, pyrrolidinyl, piperazinyl, furanyl, thienyl, thiazolyl, quinolyl, tetrathydroisoquinolyl, 5-chlorothienyl, pyridin-4-yl, pyrazinyl, 2H-benzo[e][1,3]oxazine, methylamino, ethylamino, dimethylamino or diethylamino;

$R_3$ is methyl, ethyl, n-propyl, i-propyl, n-butyl, i-butyl, methoxymethyl, methylthiomethyl, vinyl, propenyl, butenyl, i-butenyl, cyclohexyl, phenyl, benzyl or naphthylmethyl wherein $R_3$ is optionally substituted by one or more $R_c$;

$R_c$ is methyl, cyclopropyl, phenyl, indanyl, 1,2,3,4-tetrahydronaphthyl, methoxy, methylthio wherein the sulfur atom may be oxidized to a sulfoxide or sulfone, dimethylamino, fluoro or chloro;

$R_4$ and $R_5$ are each independently hydrogen, methyl, ethyl, n-propyl, n-butyl, t-butyl, i-propyl, i-butyl, methoxymethyl, methylthiomethyl or methylthioethyl wherein the sulfur atom may be oxidized to a sulfoxide or sulfone, cyclopropyl, cyclopentyl, cyclohexyl, phenyl, benzyl, piperidinyl, tetrahydropyranyl, pyrimidinyl, acetyl, benzoyl, ethoxycarbonyl, benzyloxycarbonyl, methylsulfonylamino, phenylsulfonylamino, methylamino, dimethylamino, fluoro, oxo or carboxy, wherein each $R_4$ and $R_5$ may each be further optionally independently substituted by one or more $R_e$;

$R_e$ is methyl, cyclopropyl, cyclopentyl, cyclohexyl, phenyl, carboxyphenyl, naphthyl, indanyl, thienyl, methylthienyl, methoxy, phenoxy, benzyloxy, piperidinyl, pyridinyl, indolyl, 1-(tolyl-sulfonyl)-indolyl, carbamoyl wherein the nitrogen atom may be independently mono or di-substituted by methyl, phenyl or benzyl, or $R_e$ is hydroxy, fluoro, chloro, oxo, dimethylamino or trifluoromethyl.

8. The compound according to claim 7, wherein:

Y is $R_1$, $R_1O$— or $R_1NH$—;

Each $R_1$ is independently hydrogen, phenyl, benzyl, naphthyl, 4-(acetylamino)phenyl, 4-(methanesulfonylamino)-phenyl, 3-phenoxyphenyl, 4-chlorophenyl, 3,4-dichlorophenyl, 4-fluorophenyl, thienylmethyl, morpholinyl, pyrrolidinyl, piperidinyl, piperazinyl, furanyl, thienyl, thiazolyl, quinolyl, tetrahydroisoquinolyl, 5-chlorothienyl, pyridin-4-yl, 2H-benzo[e][1,3]oxazine or pyrazinyl;

$R_3$ is ethyl, n-propyl, n-butyl, i-butyl, 2,2-dimethylpropyl, 3-methylbutyl, 3,3-dimethylbutyl, 2,2,3-trimethylbutyl, 2,2,3,3,-tetramethylbutyl, cyclopropylmethyl, methoxymethyl, methylthiomethyl, methylsulfonylmethyl, dimethylaminomethyl, propenyl, i-butenyl, cyclohexyl, phenyl, benzyl, 4-methoxybenzyl, 4-chlorobenzyl, 3,4-dichlorobenzyl, 3-chlorobenzyl, 2,4-dichlorobenzyl, 4-methylbenzyl, 3-methylbenzyl or naphth-2-ylmethyl;

and $R_4$ and $R_5$ are each independently hydrogen, methyl, ethyl, n-propyl, n-butyl, n-pentyl, 2-pentyl, 3-pentyl, phenylethyl, phenylpropyl, 2,2-dimethylpropyl, t-butyl, i-propyl, i-butyl, cyclopropyl, cyclopentyl, cyclohexyl, cyclopropylmethyl, cyclopentylmethyl, cyclohexylmethyl, phenyl, benzyl, naphthylmethyl, indanylmethyl, pyridinylmethyl, indolylmethyl, thienylmethyl, 5-methylthienylmethyl, piperidinyl, piperidinylcarbonyl, pyridinylcarbonyl, tetrahydropyranyl, pyrimidinyl, acetyl, benzoyl, ethoxycarbonyl, benzyloxycarbonyl, t-butoxycarbonyl, methylcarbamoyl, phenylcarbamoyl, benzylcarbamoyl, methylsulfonylamino, phenylsulfonylamino, methylamino, dimethylamino, methylcyclohexyl, methylbenzyl, trifluoromethylbenzyl, methoxybenzyl, 3-carboxyphenylmethoxymethyl, phenoxybenzyl, benzyloxybenzyl, benzyloxymethyl, N-[(4-methylphenyl)-sulfonyl]-indolylmethyl, fluorobenzyl, difluorobenzyl, chlorobenzyl, N,N-dimethylaminoacetyl, trifluoromethylbenzyl, fluoro, oxo or carboxy.

9. The compound according to claim 8, wherein:

Each $R_1$ is independently hydrogen, phenyl, benzyl, naphthyl, tetrahydroisoquinolin-2-yl or morpholin-4-yl, $R_3$ is ethyl, n-propyl, n-butyl, i-butyl, 2,2-dimethylpropyl, cyclopropylmethyl, dimethylaminomethyl, phenyl or benzyl;

and $R_4$ is hydrogen;

and $R_5$ is methyl, ethyl, n-propyl, n-butyl, n-pentyl, 2-pentyl, 3-pentyl, phenylethyl, phenylpropyl, 2,2-dimethylpropyl, t-butyl, i-propyl, i-butyl, cyclopropyl, cyclopentyl, cyclohexyl, cyclopropylmethyl, cyclopentylmethyl, cyclohexylmethyl, phenyl, benzyl, naphthylmethyl, indanylmethyl, pyridinylmethyl, indolylmethyl, thienylmethyl, methylthienylmethyl, methylbenzyl, methoxybenzyl, methoxybenzyl-m-carboxylic acid, phenoxybenzyl, benzyloxybenzyl, benzyloxymethyl, N-[(4-methylphenyl)-sulfonyl]-indolylmethyl, fluorobenzyl, difluorobenzyl, chlorobenzyl, N,N-dimethylaminoacetyl or trifluoromethylbenzyl.

10. The compound according to claim 9, wherein:

$R_5$ phenylethyl, phenylpropyl, 2,2-dimethylpropyl, cyclopropylmethyl, cyclopentylmethyl, cyclohexylmethyl, benzyl, naphthylmethyl, indanylmethyl, pyridinylmethyl, indolylmethyl, thienylmethyl, methylthienylmethyl, methylbenzyl, methoxybenzyl, phenoxybenzyl, benzyloxybenzyl, benzyloxymethyl.

11. A compound of formula (I):

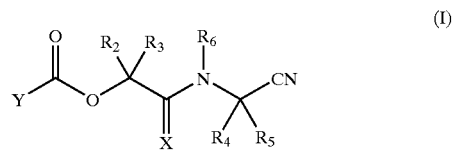

wherein:

Y is C1–6alkoxy, C1–6alkylamino, naphthyl, morpholinyl, tetrahydroisoquinolinyl, phenylamino, benzylamino, naphthylamino, benzyloxy, benzofuranyl, benzothienyl, phenylpiperazinyl, pyridinylthienyl, C1–3alkoxyphenylpiperidinylamino, C1–3alkoxycarbonylpiperidinylaminothiazolyl benzylpiperazinylcarbonylaminophenyl, morpholin-4-yl-C1–3alkoxybenzofuranyl, C1–3alkoxycarbonylamino-phenyl, quinolinylamino, wherein each is optionally substituted by one or more C1–3alkyl or halogen;

$R_2$ is hydrogen or methyl;

$R_3$ is hydrogen;
  C1–10 saturated alkyl group optionally substituted by one or more: halogen;
    C3–4 cycloalkyl optionally substituted by one or more C1–3alkyl; phenyl or naphthyl optionally substituted by one or more halogen, C1–3alkyl or C1–3alkoxy;
    decahydronaphthyl;
    spiro[2.5]octyl optionally substituted by one or more C1–3alkyl;
    indanyl;
    C1–3alkylthio wherein the sulfur atom may oxidized to a sulfoxide or a sulfone;
    or biphenylyl;

C2–6alkenyl;

C3–6cycloalkyl optionally substituted by one or more C1–3alkyl;

dialkylaminomethyl;

phenyl or pyridyl;

or $R_2$ and $R_3$ together with the carbon atom they are attached to form cyclopentyl, cyclohexyl, tetrahydropyranyl, pyrrolidinyl optionally substituted with C1–3alkyl, C3–6cycloalkyl, C3–6cycloalkyl-C1–3-alkyl or phenyl-C1–3alkyl, or piperidnyl optionally substituted with C1–3alkyl, C3–6cycloalkyl, C3–6cycloalkyl-C1–3-alkyl or phenyl-C1–3alkyl;

$R_4$ is hydrogen or C1–6 saturated alkyl group;

$R_5$ is hydrogen, C1–6 saturated alkyl group, C1–3alkyl-sulfonyl-C1–3alkyl, phenyl-C1–3alkyl, trifluoromethylbenzyl, phenylethylindolyl-C1–3-alkyl or benzyloxy-C1–3-alkyl, wherein each is optionally substituted by halo, carboxy, or C1–3alkoxy;

or $R_4$ and $R_5$ together with the carbon atom they are attached to form a cyclopropanyl, cyclobutanyl, cyclopentanyl, cyclohexanyl, cycloheptanyl, tetrahydropyranyl; or pyrrolidinyl, piperidinyl or azepanyl, each being optionally substituted with one or more: oxo, C1–3alkyl, hydroxyC1–3alkyl, benzyloxyC1–3alkyl, C3–6cycloalkyl, C3–6cycloalkyl-C1–3-alkyl, phenyl-C1–3alkyl, tosyl-indolylC1–3alkyl, C1–3alkanoyl, phenylC1–3alkanoyl, pyridinylC1–3alkanoyl, morpholinylC1–3alkanoyl, C1–3alkylcarbamoyl, C1–3alkoxy-C1–3alkylcarbamoyl, C1–3alkoxycarbamoyl, C1–3alkoxy-C1–3alkoxycarbamoyl, phenylcarbamoyl, phenylC1–3alkylcarbamoyl, benzyloxycarbamoyl, cyclohexanylcarbonyl, cyclohexylC1–3alkoxycarbonyl, phenylcarbonyl, phenylC1–3alkoxycarbonyl, piperidinylcarbonyl, piperazinylcarbonyl, or tetrahydropyranylcarbonyl, wherein each of the foregoing substituents on the pyrrolidinyl, piperidinyl or azepanyl can be further optionally substituted by one or more C1–3alkyl or halogen;

and $R_6$ is hydrogen or methyl.

12. The compound according to claim 11, wherein:

Y is naphthyl, morpholinyl, tetrahydroisoquinolinyl, benzylamino, naphthylamino, benzyloxy, 4-phenylpiperazin-1-yl, 5-(pyridin-4-yl)-2-thienyl, 1-(4-alkoxyphenyl)-piperidin-4-yl amino, 2-[1-(alkoxycarbonyl)piperidin-4-yl amino]thiazol-4-yl, 4-[4-(benzyl)-piperazin-1-yl carbonylamino]phenyl or 4-(alkoxycarbonylamino)phenyl, quinolin-2-yl amino, wherein each is optionally substituted by one or more halogen;

$R_2$ is hydrogen or methyl;

$R_3$ is ethyl, n-propyl, n-butyl, i-butyl, 2,2-dimethylpropyl, cyclopropyl, cyclopropylmethyl, cyclobutanylmethyl, dialkylaminomethyl, phenyl, benzyl, phenylethyl or pyridyl;

or $R_2$ and $R_3$ together with the carbon atom they are attached to form cyclopentyl or cyclohexyl;

$R_4$ is hydrogen, methyl or ethyl;

$R_5$ is hydrogen, methyl, ethyl, n-propyl, i-propyl, n-butyl, i-butyl, methylsulfonylethyl, benzyl, trifluoromethylbenzyl, phenylethyl, indolylmethyl, benzyloxymethyl, methoxy-benzyloxymethyl or halobenzyloxymethyl;

or $R_4$ and $R_5$ together with the carbon atom they are attached to form a cyclohexanyl;

and $R_6$ is hydrogen.

13. A compound according to claim 1, wherein when $R_2$ is hydrogen and $R_3$ is other than hydrogen, then the stereoconfiguration about the carbon atom to which $R_2$ and $R_3$ are attached is as shown below:

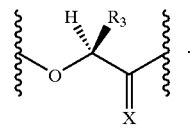

14. A compound according to claim 1 or 13, wherein when $R_4$ is hydrogen and $R_5$ is other than hydrogen, then the stereoconfiguration about the carbon atom to which $R_4$ and $R_5$ are attached is as shown below:

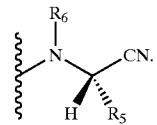

15. A compound selected from:

Morpholine-4-carboxylic acid 1-[(benzyloxymethyl-cyano-methyl)-carbamoyl]-3-methyl-butyl ester;

Benzyl-carbamic acid 1-(4-cyano-1-propyl-piperidin-4-ylcarbamoyl)-3methyl-butyl ester;

Benzyl-carbamic acid 1-(1-benzyl-3-cyano-pyrrolidin-3-ylcarbamoyl)-3-methyl-butyl ester;

Morpholine-4-carboxylic acid 1-(4-cyano-1-methyl-piperidin-4-ylcarbamoyl)-3-methyl-butyl ester;

Morpholine-4-carboxylic acid 1-(4-cyano-1-propyl-piperidin-4-ylcarbamoyl)-3-methyl-butyl ester;

Morpholine-4-carboxylic acid 1-(1-benzyl-4-cyano-piperidin-4-ylcarbamoyl)-3-methyl-butyl ester;

Morpholine-4-carboxylic acid 1-(1-benzyl-3-cyano-pyrrolidin-3-ylcarbamoyl)-3-methyl-butyl ester;

Morpholine-4-carboxylic acid 1-(3-cyano-1-cyclohexylmethyl-pyrrolidin-3-ylcarbamoyl)-3-methyl-butyl ester;

Morpholine-4-carboxylic acid 1-(3-cyano-1-cyclohexyl-pyrrolidin-3-ylcarbamoyl)-3-methyl-butyl ester;

Morpholine-4-carboxylic acid 1-(3-cyano-1-cyclohexyl-pyrrolidin-3-ylcarbamoyl)-cyclohexyl ester;

Morpholine-4-carboxylic acid 1-(3-cyano-1-cyclohexylmethyl-pyrrolidin-3-ylcarbamoyl)-cyclohexyl ester;

Morpholine-4-carboxylic acid 1-(1-benzyl-3-cyano-pyrrolidin-3-ylcarbamoyl)-cyclohexyl ester;

Morpholine-4-carboxylic acid 1-(1-benzyl-4-cyano-piperidin-4-ylcarbamoyl)-cyclohexyl ester;

Morpholine-4-carboxylic acid 1-(4-cyano-1-propyl-piperidin-4-ylcarbamoyl)-cyclohexyl ester;

Morpholine-4-carboxylic acid 1-(4-cyano-1-methyl-piperidin-4-ylcarbamoyl)-cyclohexyl ester;

Benzyl-carbamic acid 1-(4-cyano-1-methyl-piperidin-4-ylcarbamoyl)-3-methyl-butyl ester;

Benzyl-carbamic acid 1-(1-benzyl-4-cyano-piperidin-4-ylcarbamoyl)-3-methyl-butyl ester;

Benzyl-carbamic acid 1-(3-cyano-1-cyclohexylmethyl-pyrrolidin-3-ylcarbamoyl)-3-methyl-butyl ester;

Benzyl-carbamic acid 1-(3-cyano-1-cyclohexyl-pyrrolidin-3-ylcarbamoyl)-3-methyl-butyl ester;

Benzyl-carbamic acid 1-(4-cyano-1-methyl-piperidin-4-ylcarbamoyl)-cyclohexyl ester;

Benzyl-carbamic acid 1-(4-cyano-1-propyl-piperidin-4-ylcarbamoyl)-cyclohexyl ester;

Benzyl-carbamic acid 1-(1-benzyl-4-cyano-piperidin-4ylcarbamoyl)-cyclohexyl ester;

Benzyl-carbamic acid 1-(1-benzyl-3-cyano-pyrrolidin-3-ylcarbamoyl)-cyclohexyl ester;

Benzyl-carbamic acid 1-(3-cyano-1-cyclohexylmethyl-pyrrolidin-3-ylcarbamoyl)-cyclohexyl ester;

Benzyl-carbamic acid 1-(3-cyano-1-cyclohexyl-pyrrolidin-3-ylcarbamoyl)-cyclohexyl ester;

Naphthalen-2-yl-carbamic acid 1-(4-cyano-1-methyl-piperidin-4-ylcarbamoyl)-3-methyl-butyl ester;

Naphthalen-2-yl-carbamic acid 1-(4-cyano-1-propyl-piperidin-4-ylcarbamoyl)-3-methyl-butyl ester;
Naphthalen-2-yl-carbamic acid 1-(1-benzyl-4-cyano-piperidin-4-ylcarbamoyl)-3-methyl-butyl ester;
Naphthalen-2-yl-carbamic acid 1-(1-benzyl-3-cyano-pyrrolidin-3-ylcarbamoyl)-3-methyl-butyl ester;
Naphthalen-2-yl-carbamic acid 1-(3-cyano-1-cyclohexylmethyl-pyrrolidin-3-ylcarbamoyl)-3-methyl-butyl ester;
Naphthalen-2-yl-carbamic acid 1-(3-cyano-1-cyclohexyl-pyrrolidin-3-ylcarbamoyl)-3-methyl-butyl ester;
Naphthalen-2-yl-carbamic acid 1-(4-cyano-1-methyl-piperidin-4-ylcarbamoyl)-cyclohexyl ester;
Naphthalen-2-yl-carbamic acid 1-(4-cyano-1-propyl-piperidin-4-ylcarbamoyl)-cyclohexyl ester;
Naphthalen-2-yl-carbamic acid 1-(1-benzyl-4-cyano-piperidin-4-ylcarbamoyl)-cyclohexyl ester;
Naphthalen-2-yl-carbamic acid 1-(1-benzyl-3-cyano-pyrrolidin-3-ylcarbamoyl)-cyclohexyl ester;
Naphthalen-2-yl-carbamic acid 1-(3-cyano-1-cyclohexylmethyl-pyrrolidin-3-ylcarbamoyl)-cyclohexyl ester;
Naphthalen-2-yl-carbamic acid 1-(3-cyano-1-cyclohexyl-pyrrolidin-3-ylcarbamoyl)-cyclohexyl ester;
Morpholine-4-carboxylic acid 1-[3-cyano-1-(4-fluoro benzyl)-pyrrolidin-3-ylcarbamoyl]-cyclohexyl ester;
Morpholine-4-carboxylic acid 1-[3-cyano-1-(2,4-difluoro benzyl)-pyrrolidin-3-ylcarbamoyl]-cyclohexyl ester;
Morpholine-4-carboxylic acid 1-[3-cyano-1-(2,4,6-trifluoro-benzyl)-pyrrolidin-3-ylcarbamoyl]-3-methyl-butyl ester;
Benzyl-carbamic acid 1-[3-cyano-1-(2,3,4,5,6-pentafluoro-benzyl)-pyrrolidin-3-ylcarbamoyl]-cyclohexyl ester;
Morpholine-4-carboxylic acid 1-[4-cyano-1-(2,4-difluoro benzyl)-piperidin-4-ylcarbamoyl]-3-methyl-butyl ester;
Morpholine-4-carboxylic acid 1-[4-cyano-1-(2,6-difluoro benzyl)-piperidin-4-ylcarbamoyl]-3-methyl-butyl ester;
Morpholine-4-carboxylic acid 1-[4-cyano-1-(3,5-difluoro benzyl)-piperidin-4-ylcarbamoyl]-3-methyl-butyl ester;
Benzyl-carbamic acid 1-[4-cyano-1-(2,4,6-trifluoro benzyl)-piperidin-4-ylcarbamoyl]-3-methyl-butyl ester;
Morpholine-4-carboxylic acid 1-{3-cyano-1-[1-(toluene-4-sulfonyl)-1H-indol-3-ylmethyl]pyrrolidin-3ylcarbamoyl}-3-methyl-butyl ester;
Benzyl-carbamic acid 1-{4-cyano-1-[1-(toluene-4-sulfonyl)-1H-indol-3-ylmethyl]-piperidin-4-ylcarbamoyl}-3-methyl-butyl ester;
Benzyl-carbamic acid 1-(cyanomethyl-carbamoyl)-3-methyl-butyl ester;
Benzyl-carbamic acid 1-(1-cyano-3-methyl-butylcarbamoyl)-3-methyl-butyl ester;
Benzyl-carbamic acid 1-(1-cyano-cyclopropylcarbamoyl)-3-methyl-butyl ester;
Benzyl-carbamic acid 1-(cyanomethyl-carbamoyl)-2-cyclopropyl-ethyl ester;
Benzyl-carbamic acid 1-(1-cyano-3-methyl-butylcarbamoyl)-2-cyclopropyl-ethyl ester;
Benzyl-carbamic acid 1-(1-cyano-cyclopropylcarbamoyl)-2-cyclopropyl-ethyl ester;
Benzyl-carbamic acid 1-(cyanomethyl-carbamoyl)-cyclohexyl ester;
Benzyl-carbamic acid 1-(1-cyano-3-methyl-butylcarbamoyl)-cyclohexyl ester;
Benzyl-carbamic acid 1-(1-cyano-cyclopropylcarbamoyl)-cyclohexyl ester;
3,4-Dihydro-1H-isoquinoline-2-carboxylic acid 1-{[(2-chloro-benzyloxymethyl)-cyano-methyl]-carbamoyl}-3-methyl-butyl ester;
3,4-Dihydro-1H-isoquinoline-2-carboxylic acid 1-{[cyano-(4-methoxy-benzyloxymethyl)-methyl]-carbamoyl}-3-methyl-butyl ester;
3,4-Dihydro-1H-isoquinoline-2-carboxylic acid 1-[(benzyloxymethyl-cyano-methyl)-carbamoyl]-3-methyl-butyl ester;
Benzyl-carbamic acid 1-{[(2-chloro-benzyloxymethyl)-cyano-methyl]-carbamoyl}-2-cyclopropyl-ethyl ester;
Benzyl-carbamic acid 1-{[cyano-(4-methoxy-benzyloxymethyl)-methyl]-carbamoyl}-2-cyclopropyl-ethyl ester;
Benzyl-carbamic acid 1-[(benzyloxymethyl-cyano-methyl)-carbamoyl]-2-cylopropyl-ethyl ester;
Naphthalen-2-yl-carbamic acid 1-{[(2-chloro-benzyloxymethyl)-cyano-methyl]-carbamoyl}-cyclohexyl ester;
Naphthalen-2-yl-carbamic acid 1-{[cyano-(4-methoxy-benzyloxymethyl)-methyl]-carbamoyl}-cyclohexyl ester;
Naphthalen-2-yl-carbamic acid 1-[(benzyloxymethyl-cyano-methyl)-carbamoyl]-cyclohexyl ester;
Phenyl-carbamic acid 1-(cyanomethyl-carbamoyl)-2-dimethylamino-ethyl ester;
(3,4-Dichloro-phenyl)-carbamic acid 1-[(cyano-methyl-methyl)-carbamoyl]-3,3-dimethyl-butyl ester;
4-Phenyl-piperazine-1-carboxylic acid [(cyano-dimethyl-methyl)-carbamoyl]-phenyl-methyl ester;
5-Pyridin-4-yl-thiophene-2-carboxylic acid (1-cyano-3-methanesulfonyl-propylcarbamoyl)-pyridin-3-yl-methyl ester;
5-Pyridin-4-yl-thiophene-2-carboxylic acid (1-cyano-3-methanesulfonyl-propylcarbamoyl)-pyridin-3-ylmethyl ester;
4-(4-{1-[(Benzyl-cyano-methyl)-carbamoyl]-propoxycarbonyl}-thiazol-2-ylamino)-piperidine-1-carboxylic acid ethyl ester;
4-[(4-Benzyl-piperazine-1-carbonyl)-amino]-benzoic acid 1-{[cyano-(4-methyl-benzyl)-methyl]-carbamoyl}-cyclopentyl ester;
4-Ethoxycarbonylamino-benzoic acid 4-(4-cyano-tetrahydro-pyran-4-ylcarbamoyl)-tetrahydro-pyran-4-yl ester;
Quinolin-2-yl-carbamic acid 1-[(benzyloxymethyl-cyano-methyl)-carbamoyl]-2-methyl-butyl ester;
Morpholine-4-carboxylic acid 1-[(benzyloxymethyl-cyano-methyl)-carbamoyl]-3-methyl-butyl ester;
Benzyl-carbamic acid 1-[(benzyoxymethyl-cyano-methyl)-carbamoyl]-3-methyl-butyl ester;
Morpholine-4-carboxylic acid 1-[(benzyloxymethyl-cyano-methyl)-carbamoyl]-2-cyclopropyl-ethyl ester;
Naphthalen-2-yl-carbamic acid 1-[(benzyloxymethyl-cyano-methyl)-carbamoyl]-2-cyclopropyl-ethyl ester;

Morpholine-4-carboxylic acid 1-[(benzyloxymethyl-cyano-methyl)-carbamoyl]-cyclohexyl ester;
Benzyl-carbamic acid 1-[(benzyloxymethyl-cyano-methyl)-carbamoyl]-cyclohexyl ester;
Naphthalene-2-carboxylic acid 1-[(benzyloxymethyl-cyano-methyl)-carbamoyl]-3-methyl-butyl ester;
Carbonic acid benzyl ester 1-[(benzyloxymethyl-cyano-methyl)-carbamoyl]-3-methyl-butyl ester;
3,4-Dihydro-1H-isoquinoline-2-carboxylic acid 1-[(benzyloxymethyl-cyano-methyl)-carbamoyl]-2-cyclopropyl-ethyl ester;
Naphthalene-2-carboxylic acid 1-[(benzyloxymethyl-cyano-methyl)-carbamoyl]-2-cyclopropyl-ethyl ester;
Carbonic acid benzyl ester 1-[(benzyloxymethyl-cyano-methyl)-carbamoyl]-2-cyclopropyl-ethyl ester;
3,4-Dihydro-1H-isoquinoline-2-carboxylic acid 1-[(benzyloxymethyl-cyano-methyl)-carbamoyl]-cyclohexyl ester;
Naphthalene-2-carboxylic acid 1-[(benzyloxymethyl-cyano-methyl)-carbamoyl]-cyclohexyl ester;
Carbonic acid benzyl ester 1-[(benzyloxymethyl-cyano-methyl)-carbamoyl]-cyclohexyl ester;
Benzyl-carbamic acid 1-[(benzyloxymethyl-cyano-methyl-methyl)-carbamoyl]-3-methyl-butyl ester;
Benzyl-carbamic acid 1-(1-cyano-3-phenyl-propylcarbamoyl)-3-methyl-butyl ester;
Benzyl-carbamic acid 1-[(benzyloxymethyl-cyano-methyl)-methyl-carbamoyl]-3-methyl-butyl ester;
Benzyl-carbamic acid 1-[(benzyloxymethyl-cyano-methyl-methyl)-carbamoyl]-2-cyclopropyl-ethyl ester;
Benzyl-carbamic acid 1-(1-cyano-3-phenyl-propylcarbamoyl)-2-cyclopropyl-ethyl ester;
Benzyl-carbamic acid 1-[(benzyloxymethyl-cyano-methyl)-methyl-carbamoyl]-2-cyclopropyl-ethyl ester;
Benzyl-carbamic acid 1-[(benzyloxymethyl-cyano-methyl-methyl)-carbamoyl]-cyclohexyl ester;
Benzyl-carbamic acid 1-(1-cyano-3-phenyl-propylcarbamoyl)-cyclohexyl ester;
Benzyl-carbamic acid 1-[(benzyloxymethyl-cyano-methyl)-methyl-carbamoyl]-cyclohexyl ester;
3-{2-[(2-Benzylcarbamoyloxy-4-methyl-pentanoyl)-methyl-amino]-2-cyano-ethoxymethyl}-benzoic acid;
Benzo[b]thiophene-2-carboxylic acid 1-[(benzyloxymethyl-cyano-methyl)-carbamoyl]-3-methyl-butyl ester;
5-(2-Morpholin-4-yl-ethoxy)-benzofuran-2-carboxylic acid 1-[(benzyloxymethyl-cyano-methyl)-carbamoyl]-3-methyl-butyl ester;
Benzofuran-2-carboxylic acid 1-[(benzyloxymethyl-cyano-methyl)-carbamoyl]-3-methyl-butyl ester;
3-Methyl-benzofuran-2-carboxylic acid 1-[(benzyloxymethyl-cyano-methyl)-carbamoyl]-3-methyl-butyl ester;
3,4-Dihydro-1H-isoquinoline-2-carboxylic acid 1-{[(3-carboxy-benzyloxymethyl)-cyano-methyl]-carbamoyl}-3-methyl-butyl ester;
3,4-Dihydro-1H-isoquinoline-2-carboxylic acid 1-[(benzyloxymethyl-cyano-methyl)-carbamoyl]-3,3-difluoro-propyl ester;
3,4-Dihydro-1H-isoquinoline-2-carboxylic acid 1-[(benzyloxymethyl-cyano-methyl)-carbamoyl]-3,3,3-trifluoropropyl ester;
Benzyl-carbamic acid 1-(4-cyano-1,2,2,6,6-pentamethyl-piperidin-4-ylcarbamoyl)-3-methyl-butyl ester;
Benzyl-carbamic acid 1-(4-cyano-1-methyl-2,6-dioxo-piperidin-4-ylcarbamoyl)-3-methyl-butyl ester;
4-(2-Benzylcarbamoyloxy-4-methyl-pentanoylamino)-4-cyano-piperidine-1-carboxylic acid ethyl ester;
4-(2-Benzylcarbamoyloxy-4-methyl-pentanoylamino)-4-cyano-piperidine-1-carboxylic acid cyclohexylmethyl ester;
4-(2-Benzylcarbamoyloxy-4-methyl-pentanoylamino)-4-cyano-piperidine-1-carboxylic acid benzyl ester;
Benzyl-carbamic acid 1-(2-benzyl-4-cyano-1-methyl-piperidin-4-ylcarbamoyl)-3-methyl-butyl ester;
Benzyl-carbamic acid 1-(2-benzyloxymethyl-cyano-1-methyl-piperidin-4-ylcarbamoyl)-3-methyl-butyl ester;
Benzyl-carbamic acid 1-(5-benzyloxymethyl-3-cyano-1-methyl-pyrrolidin-3-ylcarbamoyl)-3-methyl-butyl ester;
4-(2-Benzylcarbamoyloxy-4-methyl-pentanoylamino)-4-cyano-1-methyl-pyrrolidine-2-carboxylic acid methyl ester;
Benzyl-carbamic acid 1-(3-cyano-5-hydroxymethyl-1-methyl-pyrrolidin-3-ylcarbamoyl)-3-methyl-butyl ester;
Benzyl-carbamic acid 1-(4-cyano-1,2,2-trimethyl-piperidin-4-ylcarbamoyl)-3-methyl-butyl ester;
Benzyl-carbamic acid 1-(4-cyano-2-hydroxymethyl-1-methyl-piperidin-4-yl carbamoyl)-3-methyl-butyl ester;
Benzyl-carbamic acid 1-(4-cyano-1-methyl-2-methylcarbamoyl-piperidin4-ylcarbamoyl)-3-methyl-butyl ester;
Benzyl-carbamic acid 1-(3-cyano-1-methyl-5-methylcarbamoyl-pyrrolidin-3-ylcarbamoyl)-3-methyl-butyl ester;
3(2-Benzylcarbamoyloxy-4-methyl-pentanoylamino)-3-cyano-pyrrolidine-1-carboxylic acid ethyl ester;
Benzyl-carbamic acid 1-(3-cyano-1-ethylcarbamoyl-pyrrolidin-3-ylcarbamoyl)-3-methyl-butyl ester;
Benzyl-carbamic acid 1-(1-benzylcarbamoyl-4-cyano-piperidin-4-ylcarbamoyl)-3-methyl-butyl ester;
Benzyl-carbamic acid 1-(4-cyano-1-cyclohexanecarbonyl-piperidin-4-ylcarbamoyl)-3-methyl-butyl ester;
Benzyl-carbamic acid 1-[4-cyano-1-(piperidine-1-carbonyl)-piperidin-4-ylcarbamoyl]-3-methyl-butyl ester;
Benzyl-carbamic acid 1-[4-cyano-1-(4-methyl-piperazine-1-carbonyl)-piperidin-4-ylcarbamoyl]-3-methyl-butyl ester;
Benzyl-carbamic acid 1-[4-cyano-1-(tetrahydro-pyran-4-carbonyl)-piperidin-4-ylcarbamoyl]-3-methyl butyl ester;
Benzyl-carbamic acid 1-(3-cyano-1-isobutyryl-pyrrolidin-3-ylcarbamoyl)-3-methyl-butyl ester;
Benzyl-carbamic acid 1-[3-cyano-1-(2-pyridin-4-yl-acetyl)-pyrrolidin-3-ylcarbamoyl]-3-methyl-butyl ester;
Benzyl-carbamic acid 1-(3-cyano-1-phenylcarbamoyl-pyrrolidin-3-ylcarbamoyl)-3-methyl-butyl ester;
Benzyl-carbamic acid 1-(1-benzylcarbamoyl-3-cyano-pyrrolidin-3-ylcarbamoyl)-3-methyl-butyl ester;
3-(2Benzylcarbamoyloxy-4-methyl-pentanoylamino)-3-cyano-pyrrolidine-1-carboxylic acid benzyl ester;

Benzyl-carbamic acid 1-(3-cyano-1-ethyl-azepan-3-ylcarbamoyl)-3-methyl-butyl ester;
3-(2-Benzylcarbamoyloxy-4-methyl-pentanoylamino)-3-cyano-pyrrolidine-1-carboxylic acid 2-methoxy-ethyl ester;
Benzyl-carbamic acid 1-(3-cyano-1-(2-methoxy-ethylcarbamoyl)-azepan-3-ylcarbamoyl]-3-methyl-butyl ester;
Benzyl-carbamic acid 1-(3-cyano-1-phenylacetyl-azepan-3-ylcarbamoyl)-3-methyl-butyl ester;
Benzyl-carbamic acid 1-(1-benzyl-4-cyano-azepan-4-ylcarbamoyl)-3-methyl-butyl ester;
4-(2-Benzylcarbamoyloxy-4-methyl-pentanoylamino)-4-cyano-azepane-1-carboxylic acid isopropyl ester;
Benzyl-carbamic acid 1-(1-benzylcarbamoyl-4-cyano-azepan-4-ylcarbamoyl)-3-methyl-butyl ester;
Benzyl-carbamic acid 1-[4-cyano-1-(3-morpholin-4-yl-propionyl)-azepan-4-ylcarbamoyl]-3-methyl-butyl ester;
Benzyl-carbamic acid 1-(1-benzyl-4-cyano-7-oxo-azepan-4-ylcarbamoyl)-3-methyl-butyl ester;
Benzyl-carbamic acid 1-(1-benzyl-4-cyano-2-oxo-azepan-4-ylcarbamoyl)-3-methyl-butyl ester;
Benzyl-carbamic acid 1-(3-cyano-1-ethyl-2-oxo-azepan-3-ylcarbamoyl)-3-methyl-butyl ester;
Benzyl-carbamic acid 1-(3-cyano-1-ethyl-7-oxo-azepan-3-ylcarbamoyl)-3-methyl-butyl ester;
Benzyl-carbamic acid 1-(1-benzyl-3-cyano-5-oxo-pyrrolidin-3-ylcarbamoyl)-3-methyl-butyl ester;
Benzyl-carbamic acid 1-(1-benzyl-3-cyano-2-oxo-pyrrolidin-3-ylcarbamoyl)-3-methyl-butyl ester;
Benzyl-carbamic acid 1-(1-benzyl-4-cyano-2-oxo-piperidin-4-ylcarbamoyl)-3-methyl-butyl ester;
Morpholine-4-carboxylic acid 1-[(benzyloxymethyl-cyano-methyl)-carbamoyl]-4,4-dimethyl-pentyl ester;
Morpholine-4-carboxylic acid 1-(3-cyano-1-ethyl-pyrrolidin-3-ylcarbamoyl)-4,4-dimethyl-pentyl ester;
Morpholine-4-carboxylic acid 1-(4-cyano-1-methyl-piperidin-4-ylcarbamoyl)-4,4-dimethyl-pentyl ester;
Morpholine-4-carboxylic acid 1-[(benzyloxymethyl-cyano-methyl)-carbamoyl]-4-methyl-pentyl ester;
Morpholine-4-carboxylic acid 1-(3-cyano-1-ethyl-pyrrolidin-3-ylcarbamoyl)-4-methyl-pentyl ester;
Morpholine-4-carboxylic acid 1-(4-cyano-1-methyl-piperidin-4-ylcarbamoyl)-4-methyl-pentyl ester;
Morpholine-4-carboxylic acid 1-[(benzyloxymethyl-cyano-methyl)-carbamoyl]-3,3,4,4-tetramethyl-pentyl ester;
Morpholine-4-carboxylic acid 1-(3-cyano-1-ethyl-pyrrolidin-3-ylcarbamoyl)-3,3,4,4-tetramethyl-pentyl ester;
Morpholine-4-carboxylic acid 1-(4-cyano-1-methyl-piperidin-4-ylcarbamoyl)-3,3,4,4-tetramethyl-pentyl ester;
Morpholine-4-carboxylic acid 1-[(benzyloxymethyl-cyano-methyl)-carbamoyl]-3,3-dimethyl-pentyl ester;
Morpholine-4-carboxylic acid 1-(3-cyano-1-ethyl-pyrrolidin-3-ylcarbamoyl)-3,3-dimethyl-pentyl ester;
Morpholine-4-carboxylic acid 1-(4-cyano-1-methyl-piperidin-4-ylcarbamoyl)-3,3-dimethyl-pentyl ester;
Morpholine-4-carboxylic acid 1-[(benzyloxymethyl-cyano-methyl)-carbamoyl]-3,3,4-trimethyl-pentyl ester;
Morpholine-4-carboxylic acid 1-(3-cyano-1-ethyl-pyrrolidin-3-ylcarbamoyl)-3,3,4-trimethyl-pentyl ester;
Morpholine-4-carboxylic acid 1-(4-cyano-1-methyl-piperidin-4-ylcarbamoyl)-3,3,4-trimethyl-pentyl ester;
Morpholine-4-carboxylic acid 1-[(benzyloxymethyl-cyano-methyl)-carbamoyly]-3-cyclohexyl-3-methyl-butyl ester;
Morpholine-4-carboxylic acid 1-(3-cyano-1-ethyl-pyrrolidin-3-ylcarbamoyl)-3-cyclohexyl-3-methyl-butyl ester;
Morpholine-4-carboxylic acid 1-(4-cyano-1-methyl-piperidin-4-ylcarbamoyl)-3-cyclohexyl-3-methyl-butyl ester;
Morpholine-4-carboxylic acid 1-[(benzyloxymethyl-cyano-methyl)-carbamoyl]-3-cyclohexyl-propyl ester;
Morpholine-4-carboxylic acid 1-(3-cyano-1-ethyl-pyrrolidin-3-ylcarbamoyl)-3-cyclohexyl-propyl ester;
Morpholine-4-carboxylic acid 1-(4-cyano-1-methyl-piperidin-4-ylcarbamoyl)-3-cyclohexyl-propyl ester;
Morpholine-4-carboxylic acid 1-[(benzyloxymethyl-cyano-methyl)-carbamoyl]-3-phenyl-propyl ester;
Morpholine-4-carboxylic acid 1-(3-cyano-1-ethyl-pyrrolidin-3-ylcarbamoyl)-3-phenyl-propyl ester;
Morpholine-4-carboxylic acid 1-(4-cyano-1-methyl-piperidin-4-ylcarbamoyl)-3-phenyl-propyl ester;
Morpholine-4-carboxylic acid 1-[(benzyloxymethyl-cyano-methyl)-carbamoyl]-2-cyclohexyl-ethyl ester;
Morpholine-4-carboxylic acid 1-(3-cyano-1-ethyl-pyrrolidin-3-ylcarbamoyl)-2-cyclohexyl-ethyl ester;
Morpholine-4-carboxylic acid 1-(4-cyano-1-methyl-piperidin-4-ylcarbamoyl)-2-cyclohexyl-ethyl ester;
Morpholine-4-carboxylic acid 1-[(benzyloxymethyl-cyano-methyl)-carbamoyl]-2-phenyl-ethyl ester;
Morpholine-4-carboxylic acid 1-(3-cyano-1-ethyl-pyrrolidin-3-ylcarbamoyl)-2-phenyl-ethyl ester;
Morpholine-4-carboxylic acid 1-(4-cyano-1-methyl-piperidin-4-ylcarbamoyl)-2-phenyl-ethyl ester;
Morpholine-4-carboxylic acid 1-[(benzyloxymethyl-cyano-methyl)-carbamoyl]-2-(1-methyl-cyclohexyl)-ethyl ester;
Morpholine-4-carboxylic acid 1-(3-cyano-1-ethyl-pyrrolidin-3-ylcarbamoyl)-2-(1-methyl-cyclohexyl)-ethyl ester;
Morpholine-4-carboxylic acid 1-(4-cyano-1-methyl-piperidin-4-ylcarbamoyl)-2-(1-methyl-cyclohexyl)-ethyl ester;
Morpholine-4-carboxylic acid 1-[(benzyloxymethyl-cyano-methyl)-carbamoyl]-3,3-dimethyl-butyl ester;
Morpholine-4-carboxylic acid 1-(3-cyano-1-ethyl-pyrrolidin-3-ylcarbamoyl)-3,3-dimethyl-butyl ester;
Morpholine-4-carboxylic acid 1-(4-cyano-1-methyl-piperidin-4-ylcarbamoyl)-3,3-dimethyl-butyl ester;
Morpholine-4-carboxylic acid 1-[(benzyloxymethyl-cyano-methyl)-carbamoyl]-3-methyl-but-3-enyl ester;
Morpholine-4-carboxylic acid 1-(3-cyano-1-ethyl-pyrrolidin-3-ylcarbamoyl)-3-methyl-but-3-enyl ester;
Morpholine-4-carboxylic acid 1-(4-cyano-1-methyl-piperidin-4-ylcarbamoyl)-3-methyl-but-3-enyl ester;
Morpholine-4-carboxylic acid 1-[(benzyloxymethyl-cyano-methyl)-carbamoyl]-2-(3,4-dichloro-phenyl)-ethyl ester;

Morpholine-4-carboxylic acid 1-(3-cyano-1-ethyl-pyrrolidin-3-ylcarbamoyl)-2-(3,4-dichloro-phenyl)-ethyl ester;

Morpholine-4-carboxylic acid 1-(4-cyano-1-methyl-piperidin-4-ylcarbamoyl)-2-(3,4-dichloro-phenyl)-ethyl ester;

Morpholine-4-carboxylic acid [(benzyloxymethyl-cyano-methyl)-carbamoyl]-cyclohexyl-methyl ester;

Morpholine-4-carboxylic acid (3-cyano-1-ethyl-pyrrolidin-3-ylcarbamoyl)-cyclohexyl-methyl ester;

Morpholine-4-carboxylic acid (4-cyano-1-methyl-piperidin-4-ylcarbamoyl)-cyclohexyl-methyl ester;

Morpholine-4-carboxylic acid 1-[(benzyloxymethyl-cyano-methyl)-carbamoyl]-2-Naphthalen-2-yl-ethyl ester;

Morpholine-4-carboxylic acid 1-(3-cyano-1-ethyl-pyrrolidin-3-ylcarbamoyl)-2-naphthalen-2-yl-ethyl ester;

Morpholine-4-carboxylic acid 1-(4-cyano-1-methyl-piperidin-4-ylcarbamoyl)-2-naphthalen-2-yl-ethyl ester;

Morpholine-4-carboxylic acid 1-[(benzyloxymethyl-cyano-methyl)-carbamoyl]-2-(decahydro-naphthalen-2yl)ethyl ester;

Morpholine-4-carboxylic acid 1-(3-cyano-1-ethyl-pyrrolidin-3-ylcarbamoyl)-2-(decahydro-naphthalen-2-yl)ethyl ester;

Morpholine-4-carboxylic acid 1-(4-cyano-1-methyl-piperidin-4-ylcarbamoyl)-2-(decahydro-naphthten-2yl)-ethyl ester;

Morpholine-4-carboxylic acid 1-[(benzyloxymethyl-cyano-methyl)-carbamoyl]-2-(4,4-dimethyl-cyclohexyl)-ethyl ester;

Morpholine-4-carboxylic acid 1-(3-cyano-1-ethyl-pyrrolidin-3-ylcarbamoyl)-2-(4,4-dimethyl-cyclohexyl)-ethyl ester;

Morpholine-4-carboxylic acid 1-(4-cyano-1-methyl-piperidin-4-ylcarbamoyl)-2(4,4-dimethyl-cyclohexyl)-ethyl ester;

Morpholine-4-carboxylic acid 1-[(benzyloxymethyl-cyano-methyl)-carbamoyl]-2-(4,8-dimethyl-spiro[2.5]oct-6-yl)ethyl ester;

Morpholine-4-carboxylic acid 1-(3-cyano-1-ethyl-pyrrolidin-3-ylcarbamoyl)-2-(4,8-dimethyl-spiro[2.5]oct-6-yl)ethyl ester;

Morpholine-4-carboxylic acid 1-(4-cyano-1-methyl-piperidin-4-ylcarbamoyl)-2-(4,8-dimethyl-spiro[2.5]oct-6-yl)-ethyl ester;

Morpholine-4-carboxylic acid 1-[(benyloxymethyl-cyano-methyl)-carbamoyl]-2-(2,2-dimethyl-cyclohexyl)-ethyl ester;

Morpholine-4-carboxylic acid 1-(3-cyano-1-ethyl-pyrrolidin-3-ylcarbamoyl)-2-(2,2-dimethyl-cyclohexyl)-ethyl ester;

Morpholine-4-carboxylic acid 1-(4-cyano-1-methyl-piperidin-4-ylcarbamoyl)-2-(2,2-dimethyl-cyclohexyl) ethyl ester;

Morpholine-4-carboxylic acid 1-[(benzyloxymethyl-cyano-methyl)-carbamoyl]-2-(3,3,5,5-tetramethyl-cyclohexyl)-ethyl ester;

Morpholine-4-carboxylic acid 1-(3-cyano-1-ethyl-pyrrolidin-3-ylcarbamoyl)-2-(3,3,5,5-tetramethyl-cyclohexyl)-ethyl ester;

Morpholine-4-carboxylic acid 1-(4-cyano-1-methyl-piperidin-4-ylcarbamoyl)-2-(3,3,5,5-tetramethyl-cyclohexyl)-ethyl ester;

Morpholine-4-carboxylic acid 1-[(benzyloxymethyl-cyano-methyl)-carbamoyl]-2-indan-1-yl-ethyl ester;

Morpholine-4-carboxylic acid 1-(3-cyano-1-ethyl-pyrrolidin-3-ylcarbamoyl)-2-indan-1-yl-ethyl ester;

Morpholine-4-carboxylic acid 1-(4-cyano-1-methyl-piperidin-4-ylcarbamoyl)-2-indan-1-yl-ethyl ester;

Morpholine-4-carboxylic acid 1-[(benzyloxymethyl-cyano-methyl)-carbamoyl]-2-indan-2-yl-ethyl ester;

Morpholine-4-carboxylic acid 1-(3-cyano-1-ethyl-pyrrolidin-3-ylcarbamoyl)-2-indan-2-yl-ethyl ester;

Morpholine-4-carboxylic acid 1-(4-cyano-1-methyl-piperidin-4-ylcarbamoyl)-2-indan-2-yl-ethyl ester;

Morpholine-4-carboxylic acid 1-[(benzyloxymethyl-cyano-methyl)-carbamoyl]-3-methanesulfonyl-propyl ester;

Morpholine-4-carboxylic acid 1-(3-cyano-1-ethyl-pyrrolidin-3-ylcarbamoyl)-3-methanesulfonyl-propyl ester;

Morpholine-4-carboxylic acid 1-(4-cyano-1-methyl-piperidin-4-ylcarbamoyl)-3-methanesulfonyl-propyl ester;

Morpholine-4-carboxylic acid 1-[(benzyloxymethyl-cyano-methyl)-carbamoyl]-2-naphthalen-1-yl-ethyl ester;

Morpholine-4-carboxylic acid 1-(3-cyano-1-ethyl-pyrrolidin-3-ylcarbamoyl)-2-naphthalen-1-yl-ethyl ester;

Morpholine-4-carboxylic acid 1-(4-cyano-1-methyl-piperidin-4-ylcarbamoyl)-2-naphthalen-1-yl-ethyl ester;

Morpholine-4-carboxylic acid 1-[(benzyloxymethyl-cyano-methyl)-carbamoyl]-2-biphenyl-4-yl-ethyl ester;

Morpholine-4-carboxylic acid 2-biphenyl-4-yl-1-(3-cyano-1-ethyl-pyrrolidin-3-ylcarbamoyl)-ethyl ester;

Morpholine-4-carboxylic acid 2-biphenyl-4-yl-1-(4-cyano-1-methyl-piperidin-4-ylcarbamoyl)-ethyl ester;

Morpholine-4-carboxylic acid 1-[(benzyloxymethyl-cyano-methyl)-carbamoyl]-2-(4-methoxy-phenyl)-ethyl ester;

Morpholine-4-carboxylic acid 1-(3-cyano-1-ethyl-pyrrolidin-3-ylcarbamoyl)-2-(4-methoxy-phenyl)-ethyl ester;

Morpholine-4-carboxylic acid 1-(4-cyano-1-methyl-piperidin-4-ylcarbamoyl)-2-(4-methoxy-phenyl)-ethyl ester;

Morpholine-4-carboxylic acid 1-[(benzyloxymethyl-cyano-methyl)-carbamoyl]-3-methylsulfanyl-propyl ester;

Morpholine-4-carboxylic acid 1-(3-cyano-1-ethyl-pyrrolidin-3-ylcarbamoyl)-3-methylsulfanyl-propyl ester;

Morpholine-4-carboxylic acid 1-(4-cyano-1-methyl-piperidin-4-ylcarbamoyl)-3-methylsulfanyl-propyl ester;

Morpholine-4-carboxylic acid 1-[(benzyloxymethyl-cyano-methyl)-carbamoyl]-2-methyl-butyl ester;

Morpholine-4-carboxylic acid 1-(3-cyano-1-ethyl-pyrrolidin-3-ylcarbamoyl)-2-methyl-butyl ester;

Morpholine-4-carboxylic acid 1-(4-cyano-1-methyl-piperidin-4-ylcarbamoyl)-2-methyl-butyl ester;

3,4-Dihydro-1H-isoquinoline-2-carboxylic acid [(benzyloxymethyl-cyano-methyl)-carbamoyl]-(2,2-dimethyl-cyclopropyl)-methyl ester;
3,4-Dihydro-1H-isoquinoline-2-carboxylic acid [(benzyloxymethyl-cyano-methyl)-carbamoyl]-cyclopropyl-methyl ester;
3,4-Dihydro-1H-isoquinoline-2-carboxylic acid [(benzyloxymethyl-cyano-methyl)-carbamoyl]-methyl ester;
3,4-Dihydro-1H-isoquinoline-2-carboxylic acid 1-[(benzyloxymethyl-cyano-methyl)-carbamoyl]-ethyl ester;
3,4-Dihydro-1H-isoquinoline-2-carboxylic acid 1-[(benzyloxymethyl-cyano-methyl)-carbamoyl]-propyl ester;
3,4-Dihydro-1H-isoquinoline-2-carboxylic acid 1-[(benzyloxymethyl-cyano-methyl)-carbamoyl]-butyl ester;
Carbonic acid (S)-1-[((R)-benzyloxymethyl-cyano-methyl)-carbamoyl]-3-methyl-butyl ester tert-butyl ester; and
tert-Butyl-carbamic acid (S)-1-[((R)-benzyloxymethyl-cyano-methyl)-carbamoyl]-3-methyl-butyl ester;
and the pharmaceutically acceptable derivatives thereof.
16. A compound according to claim 15, selected from:
(3,4-Dichloro-phenyl)-carbamic acid 1-[(cyano-methyl-methyl)-carbamoyl]-3,3-dimethyl-butyl ester;
3-(2-Benzylcarbamoyloxy-4-methyl-pentanoylamino)-3-cyano-azepane-1-carboxylic acid 2-methoxy-ethyl ester;
3-(2-Benzylcarbamoyloxy-4-methyl-pentanoylamino)-3-cyano-pyrrolidine-1-carboxylic acid ethyl ester;
3-(2-Benzylcarbamoyloxy-4-methyl-pentanoylamino)-3-cyano-pyrrolidine-1-carboxylic acid benzyl ester;
3,4-Dihydro-1H-isoquinoline-2-carboxylic acid [(benzyloxymethyl-cyano-methyl)-carbamoyl]-(2,2-dimethyl-cyclopropyl)-methyl ester;
3,4-Dihydro-1H-isoquinoline-2-carboxylic acid [(benzyloxymethyl-cyano-methyl)-carbamoyl]-cyclopropyl-methyl ester;
3,4-Dihydro-1H-isoquinoline-2-carboxylic acid [(benzyloxymethyl-cyano-methyl)-carbamoyl]-methyl ester;
3,4-Dihydro-1H-isoquinoline-2-carboxylic acid 1-[(benzyloxymethyl-cyano-methyl)-carbamoyl]-3-methyl-butyl ester;
3,4-Dihydro-1H-isoquinoline-2-carboxylic acid 1-[(benzyloxymethyl-cyano-methyl)-carbamoyl]-2-cyclopropyl-ethyl ester;
3,4-Dihydro-1H-isoquinoline-2-carboxylic acid 1-[(benzyloxymethyl-cyano-methyl)-carbamoyl]-cyclohexyl ester;
3,4-Dihydro-1H-isoquinoline-2-carboxylic acid 1-[(benzyloxymethyl-cyano-methyl)-carbamoyl]-3,3-difluoro-propyl ester;
3,4-Dihydro-1H-isoquinoline-2-carboxylic acid 1-[(benzyloxymethyl-cyano-methyl)-carbamoyl]-3,3,3-trifluoro-propyl ester;
3,4-Dihydro-1H-isoquinoline-2-carboxylic acid 1-[(benzyloxymethyl-cyano-methyl)-carbamoyl]-ethyl ester;
3,4-Dihydro-1H-isoquinoline-2-carboxylic acid 1-[(benzyloxymethyl-cyano-methyl)-carbamoyl]-propyl ester;
3,4-Dihydro-1H-isoquinoline-2-carboxylic acid 1-[(benzyloxymethyl-cyano-methyl)-carbamoyl]-butyl ester;
3,4-Dihydro-1H-isoquinoline-2-carboxylic acid 1-{[(2-chloro-benzyloxymethyl)-cyano-methyl]-carbamoyl}-3-methyl-butyl ester;
3,4-Dihydro-1H-isoquinoline-2-carboxylic acid 1-{[(3-carboxy-benzyloxymethyl)-cyano-methyl]-carbamoyl}-3-methyl-butyl ester;
3,4-Dihydro-1H-isoquinoline-2-carboxylic acid 1-{[cyano-(4-methoxy-benzyloxymethyl)-methyl]-carbamoyl}-3-methyl-butyl ester;
3-{2-[(2-Benzylcarbamoyloxy-4-methyl-pentanoyl)-methyl-amino]-2-cyano-ethoxymethyl}-benzoic acid;
3-Methyl-benzofuran-2-carboxylic acid 1-(benzyloxymethyl-cyano-methyl)-carbamoyl]-3-methyl-butyl ester;
4-(2-Benzylcarbamoyloxy-4-methyl-pentanoylamino)-4-cyano-1-methyl-pyrrolidine-2-carboxylic acid methyl ester;
4-(2-Benzylcarbamoyloxy-4-methyl-pentanoylamino)-4-cyano-azepane-1-carboxylic acid isopropyl ester;
4-(2-Benzylcarbamoyloxy-4-methyl-pentanoylamino)-4-cyano-piperidine-1-carboxylic acid ethyl ester;
4-(2-Benzylcarbamoyloxy-4-methyl-pentanoylamino)-4-cyano-piperidine-1-carboxylic acid cyclohexylmethyl ester;
4-(2-Benzylcarbamoyloxy-4-methyl-pentanoylamino)-4-cyano-piperidine-1-carboxylic acid benzyl ester;
4-(4-{1-[(Benzyl-cyano-methyl)-carbamoyl]-propoxycarbonyl}-thiazol-2-ylamino)-piperidine-1-carboxylic acid ethyl ester;
4-[(4-Benzyl-piperazine-1-carbonyl)-amino]-benzoic acid 1-{[cyano-(4-methyl-benzyl)-methyl]-carbamoyl}-cyclopentyl ester;
4-Ethoxycarbonylamino-benzoic acid 4-(4-cyano-tetrahydro-pyran-4-ylcarbamoyl)-tetrahydro-pyran-4-yl ester;
4-Phenyl-piperazine-1-carboxylic acid [(cyano-dimethyl-methyl)-carbamoyl]-phenyl-methyl ester;
5-(2-Morpholin-4-yl-ethoxy)-benzofuran-2-carboxylic acid 1-[(benzyloxymethyl-cyano-methyl)-carbamoyl]-3-methyl-butyl ester;
5-Pyridin-4-yl-thiophene-2-carboxylic acid (1-cyano-3-methanesulfonyl-propylcarbamoyl)-pyridin-3-yl-methyl ester;
5-Pyridin-4-yl-thiophene-2-carboxylic acid (1-cyano-3-methanesulfonyl-propylcarbamoyl)-pyridin-3-yl-methyl ester;
Benzo[b]thiophene-2-carboxylic acid 1-[(benzyloxymethyl-cyano-methyl)-carbamoyl]-3-methyl-butyl ester;
Benzofuran-2-carboxylic acid 1-[(benzyloxymethyl-cyano-methyl)-carbamoyl]-3-methyl-butyl ester;
Benzyl-carbamic acid 1-(1-benzyl-3-cyano-2-oxo-pyrrolidin-3-ylcarbamoyl)-3-methyl-butyl ester;
Benzyl-carbamic acid 1-(1-benzyl-3-cyano-5-oxo-pyrrolidin-3-ylcarbamoyl)-3-methyl-butyl ester;
Benzyl-carbamic acid 1-(1-benzyl-4-cyano-2-oxo-azepan-4-ylcarbamoyl)-3-methyl-butyl ester;
Benzyl-carbamic acid 1-(1-benzyl-4-cyano-2-oxo-piperidin-4-ylcarbamoyl)-3-methyl-butyl ester;
Benzyl-carbamic acid 1-(1-benzyl-4-cyano-7-oxo-azepan-4-ylcarbamoyl)-3-methyl-butyl ester;

Benzyl-carbamic acid 1-(1-benzyl-4-cyano-azepan-4-ylcarbamoyl)-3-methyl-butyl ester;
Benzyl-carbamic acid 1-(1-benzylcarbamoyl-3-cyano-pyrrolidin-3-ylcarbamoyl)-3-methyl-butyl ester;
Benzyl-carbamic acid 1-(1-benzylcarbamoyl-4-cyano-azepan-4-ylcarbamoyl)-3-methyl-butyl ester;
Benzyl-carbamic acid 1-(1-benzylcarbamoyl-4-cyano-piperidin-4-ylcarbamoyl)-3-methyl-butyl ester;
Benzyl-carbamic acid 1-(1-cyano-3-methyl-butylcarbamoyl)-2-cyclopropyl-ethyl ester;
Benzyl-carbamic acid 1-(1-cyano-3-methyl-butylcarbamoyl)-3-methyl-butyl ester;
Benzyl-carbamic acid 1-(1-cyano-3-methyl-butylcarbamoyl)-cyclohexyl ester;
Benzyl-carbamic acid 1-(1-cyano-3-phenyl-propylcarbamoyl)-2-cyclopropyl-ethyl ester;
Benzyl-carbamic acid 1-(1-cyano-3-phenyl-propylcarbamoyl)-3-methyl-butyl ester;
Benzyl-carbamic acid 1-(1-cyano-3-phenyl-propylcarbamoyl)-cyclohexyl ester;
Benzyl-carbamic acid 1-(1-cyano-cyclopropylcarbamoyl)-2-cyclopropyl-ethyl ester;
Benzyl-carbamic acid 1-(1-cyano-cyclopropylcarbamoyl)-3-methyl-butyl ester;
Benzyl-carbamic acid 1-(1-cyano-cyclopropylcarbamoyl)-cyclohexyl ester;
Benzyl-carbamic acid 1-(2-benzyl-4-cyano-1-methyl-piperidin-4-ylcarbamoyl)-3-methyl-butyl ester;
Benzyl-carbamic acid 1-(2-benzyloxymethyl-4-cyano-1-methyl-piperidin-4-ylcarbamoyl)-3-methyl-butyl ester;
Benzyl-carbamic acid 1-(3-cyano-1-ethyl-2-oxo-azepan-3-ylcarbamoyl)-3-methyl-butyl ester;
Benzyl-carbamic acid 1-(3-cyano-1-ethyl-7-oxo-azepan-3-ylcarbamoyl)-3-methyl-butyl ester;
Benzyl-carbamic acid 1-(3-cyano-1-ethyl-azepan-3-ylcarbamoyl)-3-methyl-butyl ester;
Benzyl-carbamic acid 1-(3-cyano-1-ethylcarbamoyl-pyrrolidin-3-ylcarbamoyl)-3-methyl-butyl ester;
Benzyl-carbamic acid 1-(3-cyano-1-isobutryl-pyrrolidin-3-ylcarbamoyl)-3-methyl-butyl ester;
Benzyl-carbamic acid 1-(3-cyano-1-methyl-5-methylcarbamoyl-pyrrolidin-3-ylcarbamoyl)-3-methyl-butyl ester;
Benzyl-carbamic acid 1-(3-cyano-1-phenylacetyl-azepan-3-ylcarbamoyl)-3-methyl-butyl ester;
Benzyl-carbamic acid 1-(3-cyano-1-phenylcarbamoyl-pyrrolidin-3-ylcarbamoyl)-3-methyl-butyl ester;
Benzyl-carbamic acid 1-(3-cyano-5-hydroxymethyl-1-methyl-pyrrolidin-3-ylcarbamoyl)-3-methyl-butyl ester;
Benzyl-carbamic acid 1-(4-cyano-1,2,2,6,6-pentamethyl-piperidin-4-ylcarbamoyl)-3-methyl-butyl ester;
Benzyl-carbamic acid 1-(4-cyano-1,2-trimethyl-piperidin-4-ylcarbamoyl)-3-methyl-butyl ester;
Benzyl-carbamic acid 1-(4-cyano-1-cyclohexanecarbonyl-piperidin-4-ylcarbamoyl)-3-methyl-butyl ester;
Benzyl-carbamic acid 1-(4-cyano-1-methyl-2,6-dioxo-piperidin-4-ylcarbamoyl)-3-methyl-butyl ester;
Benzyl-carbamic acid 1-(4-cyano-1-methyl-2-methylcarbamoyl-piperidin-4-ylcarbamoyl)-3-methyl-butyl ester;
Benzyl-carbamic acid 1-(4-cyano-2-hydroxymethyl-1-methyl-piperidin-4-ylcarbamoyl)-3-methyl-butyl ester;
Benzyl-carbamic acid 1-(5-benzyloxymethyl-3-cyano-1-methyl-pyrrolidin-3-ylcarbamoyl)-3-methyl-butyl ester;
Benzyl-carbamic acid 1-(cyanomethyl-carbamoyl)-2-cyclopropyl-ethyl ester;
Benzyl-carbamic acid 1-(cyanomethyl-carbamoyl)-3-methyl-butyl ester;
Benzyl-carbamic acid 1-(cyanomethyl-carbamoyl)-cyclohexyl ester;
Benzyl-carbamic acid 1-[(benzyloxymethyl-cyano-methyl)-carbamoyl]-2-cyclopropyl-ethyl ester;
Benzyl-carbamic acid 1-[(benzyloxymethyl-cyano-methyl)-carbamoyl]-3-methyl-butyl ester;
Benzyl-carbamic acid 1-[(benzyloxymethyl-cyano-methyl)-carbamoyl]-cyclohexyl ester;
Benzyl-carbamic acid 1-[(benzyloxymethyl-cyano-methyl)-methyl-carbamoyl]-3-methyl-butyl ester;
Benzyl-carbamic acid 1-[(benzyloxymethyl-cyano-methyl)-methyl-carbamoyl]-2-cyclopropyl-ethyl ester;
Benzyl-carbamic acid 1-[(benzyloxymethyl-cyano-methyl)-methyl-carbamoyl]-cyclohexyl ester;
Benzyl-carbamic acid 1-[(benzyloxymethyl-cyano-methyl-methyl)-carbamoyl]-3-methyl-butyl ester;
Benzyl-carbamic acid 1-[(benzyloxymethyl-cyano-methyl-methyl)-carbamoyl]-2-cyclopropyl-ethyl ester;
Benzyl-carbamic acid 1-[(benzyloxymethyl-cyano-methyl-methyl)-carbamoyl]-cyclohexyl ester;
Benzyl-carbamic acid 1-[3-cyano-1-(2-methoxy-ethylcarbamoyl)-azepan-3-ylcarbamoyl]-3-methyl-butyl ester;
Benzyl-carbamic acid 1-[3-cyano-1-(2-pyridin-4-yl-acetyl)-pyrrolidin-3-ylcarbamoyl]-3-methyl-butyl ester;
Benzyl-carbamic acid 1-[4-cyano-1-(3-morpholin-4-yl-propionyl)-azepan-4-ylcarbamoyl]-3-methyl-butyl ester;
Benzyl-carbamic acid 1-[4-cyano-1-(4-methyl-piperazine-1-carbonyl)-piperidin-4-ylcarbamoyl]-3-methyl-butyl ester;
Benzyl-carbamic acid 1-[4-cyano-1-(piperidine-1-carbonyl)-piperidin-4-ylcarbamoyl]-3-methyl-butyl ester;
Benzyl-carbamic acid 1-[4-cyano-1-(tetrahydro-pyran-4-carbonyl)-piperidin-4-ylcarbamoyl]-3-methyl-butyl ester;
Benzyl-carbamic acid 1-{[(2-chloro-benzyloxymethyl)-cyano-methyl]-carbamoyl}-2-cyclopropyl-ethyl ester;
Benzyl-carbamic acid 1-{[cyano-(4-methoxy-benzyloxymethyl)-methyl]-carbamoyl}-2-cyclopropyl-ethyl ester;
Carbonic acid (S)-1-[((R)-benzyloxymethyl-cyano-methyl)-carbamoyl]-3-methyl-butyl ester tert-butyl ester;
Carbonic acid benzyl ester 1-[(benzyloxymethyl-cyano-methyl)-carbamoyl]-3-methyl-butyl ester;
Carbonic acid benzyl ester 1-[(benzyloxymethyl-cyano-methyl)-carbamoyl]-2-cyclopropyl-ethyl ester;
Carbonic acid benzyl ester 1-[(benzyloxymethyl-cyano-methyl)-carbamoyl]-cyclohexyl ester;
Naphthalen-2-yl-carbamic acid 1-[(benzyloxymethyl-cyano-methyl)-carbamoyl]-cyclohexyl ester;

Naphthalen-2-yl-carbamic acid 1-[(benzyloxymethyl-cyano-methyl)-carbamoyl]-3-methyl-butyl ester;
Naphthalen-2-yl-carbamic acid 1-[(benzyloxymethyl-cyano-methyl)-carbamoyl]-2-cyclopropyl-ethyl ester;
Naphthalen-2-yl-carbamic acid 1-{[(2-chloro-benzyloxymethyl)-cyano-methyl]-carbamoyl}-cyclohexyl ester;
Naphthalen-2-yl-carbamic acid 1-{[cyano-(4-methoxy-benzyloxymethyl)-methyl]-carbamoyl}-cyclohexyl ester;
Naphthalene-2-carboxylic acid 1-[(benzyloxymethyl-cyano-methyl)-carbamoyl]-3-methyl-butyl ester;
Naphthalene-2-carboxylic acid 1-[(benzyloxymethyl-cyano-methyl)-carbamoyl]-2-cyclopropyl-ethyl ester;
Naphthalene-2-carboxylic acid 1-[(benzyloxymethyl-cyano-methyl)-carbamoyl]-cyclohexyl ester;
Phenyl-carbamic acid 1-(cyanomethyl-carbamoyl)-2-dimethylamino-ethyl ester;
Quinolin-2-yl-carbamic acid 1-[(benzyloxymethyl-cyano-methyl)-carbamoyl]-2-methyl-butyl ester; and
tert-Butyl-carbamic acid (S)-1-[((R)-benzyloxymethyl-cyano-methyl)-carbamoyl]-3-methyl-butyl ester;
or a pharmaceutically acceptable derivative thereof.

17. A compound according to claim 15 selected from:
Morpholine-4-carboxylic acid (3-cyano-1-ethyl-pyrrolidin-3-ylcarbamoyl)-cyclohexyl-methyl ester;
Morpholine-4-carboxylic acid (4-cyano-1-methyl-piperidin-4-ylcarbamoyl)-cyclohexyl-methyl ester;
Morpholine-4-carboxylic acid [(benzyloxymethyl-cyano-methyl)-carbamoyl]-cyclohexyl-methyl ester;
Morpholine-4-carboxylic acid 1-(3-cyano-1-ethyl-pyrrolidin-3-ylcarbamoyl)-4,4-dimethyl-pentyl ester;
Morpholine-4-carboxylic acid 1-(3-cyano-1-ethyl-pyrrolidin-3-ylcarbamoyl)-4-methyl-pentyl ester;
Morpholine-4-carboxylic acid 1-(3-cyano-1-ethyl-pyrrolidin-3-ylcarbamoyl)-3,3,4,4-tetramethyl-pentyl ester;
Morpholine-4-carboxylic acid 1-(3-cyano-1-ethyl-pyrrolidin-3-ylcarbamoyl)-3,3-dimethyl-pentyl ester;
Morpholine-4-carboxylic acid 1-(3-cyano-1-ethyl-pyrrolidin-3-ylcarbamoyl)-3,3,4-trimethyl-pentyl ester;
Morpholine-4-carboxylic acid 1-(3-cyano-1-ethyl-pyrrolidin-3-ylcarbamoyl)-3-cyclohexyl-3-methyl-butyl ester;
Morpholine-4-carboxylic acid 1-(3-cyano-1-ethyl-pyrrolidin-3-ylcarbamoyl)-3-cyclohexyl-propyl ester;
Morpholine-4-carboxylic acid 1-(3-cyano-1-ethyl-pyrrolidin-3-ylcarbamoyl)-3-phenyl-propyl ester;
Morpholine-4-carboxylic acid 1-(3-cyano-1-ethyl-pyrrolidin-3-ylcarbamoyl)-2-cyclohexyl-ethyl ester;
Morpholine-4-carboxylic acid 1-(3-cyano-1-ethyl-pyrrolidin-3-ylcarbamoyl)-2-phenyl-ethyl ester;
Morpholine-4-carboxylic acid 1-(3-cyano-1-ethyl-pyrrolidin-3-ylcarbamoyl)-2-(methyl-cyclohexyl)-ethyl ester;
Morpholine-4-carboxylic acid 1-(3-cyano-1-ethyl-pyrrolidin-3-ylcarbamoyl)-3,3-dimethyl-butyl-ethyl ester;
Morpholine-4-carboxylic acid 1-(3-cyano-1-ethyl-pyrrolidin-3-ylcarbamoyl)-3-methyl-but-3-enyl ester;
Morpholine-4-carboxylic acid 1-(3-cyano-1-ethyl-pyrrolidin-3-ylcarbamoyl)-2-(3,4-dichloro-phenyl)-ethyl ester;
Morpholine-4-carboxylic acid 1-(3-cyano-1-ethyl-pyrrolidin-3-ylcarbamoyl)-2-naphthalen-2-yl-ethyl ester;
Morpholine-4-carboxylic acid 1-(3-cyano-1-ethyl-pyrrolidin-3-ylcarbamoyl)-2-(decahydro-naphthalen-2-yl)-ethyl ester;
Morpholine-4-carboxylic acid 1-(3-cyano-1-ethyl-pyrrolidin-3-ylcarbamoyl)-2-(4,4-dimethyl-cyclohexyl)-ethyl ester;
Morpholine-4-carboxylic acid 1-(3-cyano-1-ethyl-pyrrolidin-3-ylcarbamoyl)-2-(4,8-dimethyl-spiro[2.5]oct-6-yl)ethyl ester;
Morpholine-4-carboxylic acid 1-(3-cyano-1-ethyl-pyrrolidin-3-ylcarbamoyl)-2-(2,2-dimethyl-cyclohexyl)-ethyl ester;
Morpholine-4-carboxylic acid 1-(3-cyano-1-ethyl-pyrrolidin-3-ylcarbamoyl)-2-(3,3,5,5-tetramethyl-cyclohexyl)-ethyl ester;
Morpholine-4-carboxylic acid 1-(3-cyano-1-ethyl-pyrrolidin-3-ylcarbamoyl)-2-indan-1-yl-ethyl ester;
Morpholine-4-carboxylic acid 1-(3-cyano-1-ethyl-pyrrolidin-3-ylcarbamoyl)-2-indan-2-yl-ethyl ester;
Morpholine-4-carboxylic acid 1-(3-cyano-1-ethyl-pyrrolidin-3-ylcarbamoyl)-3-methanesulfonyl-propyl ester;
Morpholine-4-carboxylic acid 1-(3-cyano-1-ethyl-pyrrolidin-3-ylcarbamoyl)-2-naphthalen-1-yl-ethyl ester;
Morpholine-4-carboxylic acid 1-(3-cyano-1-ethyl-pyrrolidin-3-ylcarbamoyl)-2-(4-methoxy-phenyl)-ethyl ester;
Morpholine-4-carboxylic acid 1-(3-cyano-1-ethyl-pyrrolidin-3-ylcarbamoyl)-3-methylsulfanyl-propyl ester;
Morpholine-4-carboxylic acid 1-(3-cyano-1-ethyl-pyrrolidin-3-ylcarbamoyl)-2-methyl-butyl ester;
Morpholine-4-carboxylic acid 1-(4-cyano-1-methyl-piperidin-4-ylcarbamoyl)-4,4-dimethyl-pentyl ester;
Morpholine-4-carboxylic acid 1-(4-cyano-1-methyl-piperidin-4-ylcarbamoyl)-4-methyl-pentyl ester;
Morpholine-4-carboxylic acid 1-(4-cyano-1-methyl-piperidin-4-ylcarbamoyl)-3,3,4,4-tetramethyl-pentyl ester;
Morpholine-4-carboxylic acid 1-(4-cyano-1-methyl-piperidin-4-ylcarbamoyl)-3,3-dimethyl-pentyl ester;
Morpholine-4-carboxylic acid 1-(4-cyano-1-methyl-piperidin-4-ylcarbamoyl)-3,3,4-trimethyl-pentyl ester;
Morpholine-4-carboxylic acid 1-(4-cyano-1-methyl-piperidin-4-ylcarbamoyl)-4-cyclohexyl-3-methyl-butyl ester;
Morpholine-4-carboxylic acid 1-(4-cyano-1-methyl-piperidin-4-ylcarbamoyl)-3-cyclohexyl-propyl ester;
Morpholine-4-carboxylic acid 1-(4-cyano-1-methyl-piperidin-4-ylcarbamoyl)-3-phenyl-propyl ester;
Morpholine-4-carboxylic acid 1-(4-cyano-1-methyl-piperidin-4-ylcarbamoyl)-2-cyclohexyl-1-ethyl ester;
Morpholine-4-carboxylic acid 1-(4-cyano-1-methyl-piperidin-4-ylcarbamoyl)-2-phenyl-ethyl ester;
Morpholine-4-carboxylic acid 1-(4-cyano-1-methyl-piperidin-4-ylcarbamoyl)-2-(1-methyl-cyclohexyl)-ethyl ester;
Morpholine-4-carboxylic acid 1-(4-cyano-1-methyl-piperidin-4-ylcarbamoyl)-3,3-dimethyl-butyl ester;

Morpholine-4-carboxylic acid 1-(4-cyano-1-methyl-piperidin-4-ylcarbamoyl)-3-methyl-but-3-enyl ester;
Morpholine-4-carboxylic acid 1-(4-cyano-1-methyl-piperidin-4-ylcarbamoyl)-2-(3,4-dichloro-phenyl)-ethyl ester;
Morpholine-4-carboxylic acid 1-(4-cyano-1-methyl-piperidin-4-ylcarbamoyl)-2-naphthalen-2-yl-ethyl ester;
Morpholine-4-carboxylic acid 1-(4-cyano-1-methyl-piperidin-4-ylcarbamoyl)-2-(decahydro-naphthalen-2-yl)-ethyl ester;
Morpholine-4-carboxylic acid 1-(4-cyano-1-methyl-piperidin-4-ylcarbamoyl)-2-(4,4-dimethyl-cyclohexyl)-ethyl ester;
Morpholine-4-carboxylic acid 1-(4-cyano-1-methyl-piperidin-4-ylcarbamoyl)-2-(4,8-dimethyl-spiro[2.5]oct-6-yl)ethyl ester;
Morpholine-4-carboxylic acid 1-(4-cyano-1-methyl-piperidin-4-ylcarbamoyl)-2-(2,2-dimethyl-cyclohexyl)-ethyl ester;
Morpholine-4-carboxylic acid 1-(4-cyano-1-methyl-piperidin-4-ylcarbamoyl)-2-(3,3,5,5-tetramethyl-cyclohexyl)-ethyl ester;
Morpholine-4-carboxylic acid 1-(4-cyano-1-methyl-piperidin-4-ylcarbamoyl)-2-indan-1-yl-ethyl ester;
Morpholine-4-carboxylic acid 1-(4-cyano-1-methyl-piperidin-4-ylcarbamoyl)-2-indan-2-yl-ethyl ester;
Morpholine-4-carboxylic acid 1-(4-cyano-1-methyl-piperidin-4-ylcarbamoyl)-3-methanesulfonyl-propyl ester;
Morpholine-4-carboxylic acid 1-(4-cyano-1-methyl-piperidin-4-ylcarbamoyl)-2-naphthalen-1-yl-ethyl ester;
Morpholine-4-carboxylic acid 1-(4-cyano-1-methyl-piperidin-4-ylcarbamoyl)-2-(4-methoxy-phenyl)-ethyl ester;
Morpholine-4-carboxylic acid 1-(4-cyano-1-methyl-piperidin-4-ylcarbamoyl)-3-methylsulfanyl-propyl ester;
Morpholine-4-carboxylic acid 1-(4-cyano-1-methyl-piperidin-4-ylcarbamoyl)-2-methyl-butyl ester;
Morpholine-4-carboxylic acid 1-[(benzyloxymethyl-cyano-methyl)-carbamoyl]-3-methyl-butyl ester;
Morpholine-4-carboxylic acid 1-[(benzyloxymethyl-cyano-methyl)-carbamoyl]-2-cyclopropyl-ethyl ester;
Morpholine-4-carboxylic acid 1-[(benzyloxymethyl-cyano-methyl)-carbamoyl]-cyclohexyl ester;
Morpholine-4-carboxylic acid 1-[(benzyloxymethyl-cyano-methyl)-carbamoyl]-4,4-dimethyl-pentyl ester;
Morpholine-4-carboxylic acid 1-[(benzyloxymethyl-cyano-methyl)-carbamoyl]-4-methyl-pentyl ester;
Morpholine-4-carboxylic acid 1-[(benzyloxymethyl-cyano-methyl)-carbamoyl]-3,3,4,4-tetramethyl-pentyl ester;
Morpholine-4-carboxylic acid 1-[(benzyloxymethyl-cyano-methyl)-carbamoyl]-3,3-dimethyl-pentyl ester;
Morpholine-4-carboxylic acid 1-[(benzyloxymethyl-cyano-methyl)-carbamoyl]-3,3,4-trimethyl-pentyl ester;
Morpholine-4-carboxylic acid 1-[(benzyloxymethyl-cyano-methyl)-carbamoyl]-3-cyclohexyl-3-methyl-butyl ester;
Morpholine-4-carboxylic acid 1-[(benzyloxymethyl-cyano-methyl)-carbamoyl]-3-cyclohexyl-propyl ester;
Morpholine-4-carboxylic acid 1-[(benzyloxymethyl-cyano-methyl)-carbamoyl]-3-phenyl-propyl ester;
Morpholine-4-carboxylic acid 1-[(benzyloxymethyl-cyano-methyl)-carbamoyl]-2-cyclohexyl-ethyl ester;
Morpholine-4-carboxylic acid 1-[(benzyloxymethyl-cyano-methyl)-carbamoyl]-2-phenyl-ethyl ester;
Morpholine-4-carboxylic acid 1-[(benzyloxymethyl-cyano-methyl)-carbamoyl]-2-(1-methyl-cyclohexyl)-ethyl ester;
Morpholine-4-carboxylic acid 1-[(benzyloxymethyl-cyano-methyl)-carbamoyl]-3,3-dimethyl-butyl ester;
Morpholine-4-carboxylic acid 1-[(benzyloxymethyl-cyano-methyl)-carbamoyl]-3-methyl-but-3-enyl ester;
Morpholine-4-carboxylic acid 1-[(benzyloxymethyl-cyano-methyl)-carbamoyl]-2-(3,4-dichloro-phenyl)-ethyl ester;
Morpholine-4-carboxylic acid 1-[(benzyloxymethyl-cyano-methyl)-carbamoyl]-2-naphthalen-2-yl-ethyl ester;
Morpholine-4-carboxylic acid 1-[(benzyloxymethyl-cyano-methyl)-carbamoyl]-2-(decahydro-naphthalen-2-yl)-ethyl ester;
Morpholine-4-carboxylic acid 1-[(benzyloxymethyl-cyano-methyl)-carbamoyl]-2-(4,4-dimethyl-cyclohexyl)-ethyl ester;
Morpholine-4-carboxylic acid 1-[(benzyloxymethyl-cyano-methyl)-carbamoyl]-2-(4,8-dimethyl-spiro[2.5]oct-6-yl)-ethyl ester;
Morpholine-4-carboxylic acid 1-[(benzyloxymethyl-cyano-methyl)-carbamoyl]-2-(2,2-dimethyl-cyclohexyl)-ethyl ester;
Morpholine-4-carboxylic acid 1-[(benzyloxymethyl-cyano-methyl)-carbamoyl]-2-(3,3,5,5-tetramethyl-cyclohexyl)-ethyl ester;
Morpholine-4-carboxylic acid 1-[(benzyloxymethyl-cyano-methyl)-carbamoyl]-2-indan-1-yl-ethyl ester;
Morpholine-4-carboxylic acid 1-[(benzyloxymethyl-cyano-methyl)-carbamoyl]-2-indan-2-yl-ethyl ester;
Morpholine-4-carboxylic acid 1-[(benzyloxymethyl-cyano-methyl)-carbamoyl]-3-methanesulfonyl-propyl ester;
Morpholine-4-carboxylic acid 1-[(benzyloxymethyl-cyano-methyl)-carbamoyl]-2-naphthalen-1-yl-ethyl ester;
Morpholine-4-carboxylic acid 1-[(benzyloxymethyl-cyano-methyl)-carbamoyl]-2-biphenyl-4-yl-ethyl ester;
Morpholine-4-carboxylic acid 1-[(benzyloxymethyl-cyano-methyl)-carbamoyl]-2-(4-methoxy-phenyl)-ethyl ester;
Morpholine-4-carboxylic acid 1-[(benzyloxymethyl-cyano-methyl)-carbamoyl]-3-methylsulfanyl-propyl ester;
Morpholine-4-carboxylic acid 1-[(benzyloxymethyl-cyano-methyl)-carbamoyl]-2-methyl-butyl ester;
Morpholine-4-carboxylic acid 2-biphenyl-4-yl-1-(3-cyano-1-ethyl-pyrrolidin-3-ylcarbamoyl)-ethyl ester; and
Morpholine-4-carboxylic acid 2-biphenyl-4-yl-1-(4-cyano-1-methyl-piperidin-4-ylcarbamoyl)-ethyl ester;
or the pharmaceutically acceptable derivatives thereof.

18. A pharmaceutical composition comprising a therapeutically effective amount of a compound according to claim 1, 11 or 15.

19. A method of making a compound of formula (I):

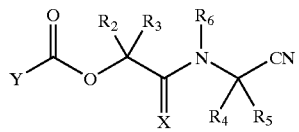

wherein X is oxygen, and $R_2$, $R_3$, $R_4$, $R_5$, $R_6$ and Y are as defined in claim 1, said method comprising steps (a), (b1) and (c), or comprising steps (a), (b2) and (c):

a) reacting a protected amino acid compound of formula (II), wherein R" is a protecting group, with ammonia under coupling conditions to provide an amide compound of formula (III), followed by deprotection to provide the amino acid amide compound of formula (IV):

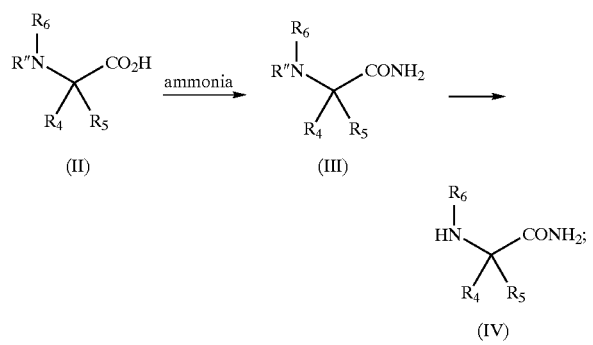

b1) reacting a hydroxy ester (V), wherein R' is a protecting group, with an activated acid compound YC(O)L wherein Y is $R_1$, $R_1O$—, $R_1S(O)_m$— or $(R_1)_3C$—, wherein $R_1$ is as defined in claim 1 and L is a leaving group, in the presence of a suitable base to provide the compound of formula (VI), followed by hydrolysis to provide a carboxylic acid of formula (VII):

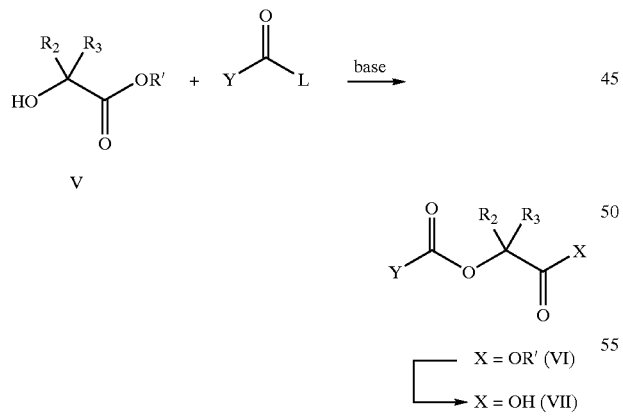

or b2) reacting the hydroxy ester (V) above with a chloroformate to provide a mixed anhydride, followed by reacting the mixed anhydride with an amine compound $(R_1)_2NH$ to provide a compound of formula (VI) wherein Y is $(R_1)_2N$—, followed by hydrolysis of the compound of formula (VI) to provide a carboxylic acid of formula (VII):

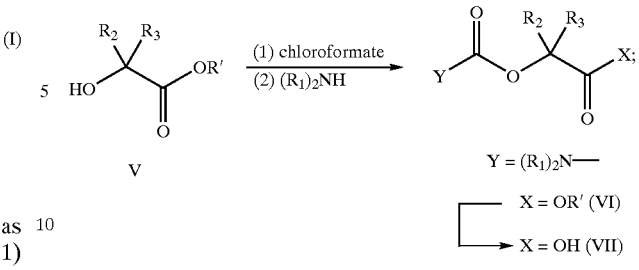

and c) reacting a compound of formula (IV) with a compound of formula (VII) under suitable coupling conditions, followed by dehydrating the resulting amide compound where X=CONH$_2$ to provide a nitrile of formula (I):

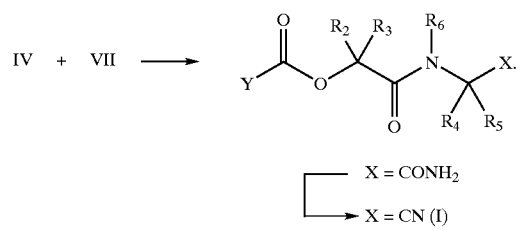

20. A method of making a compound of formula (I):

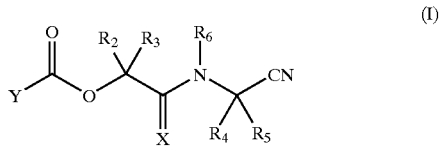

wherein X is oxygen and $R_2$, $R_3$, $R_4$, $R_5$, $R_6$ and Y are as defined in claim 1, said method comprising steps (a) and (b1) or steps (a) and (b2):

a) reacting a hydroxy acid (VIII) with an amino acid amide (IV) under suitable coupling conditions:

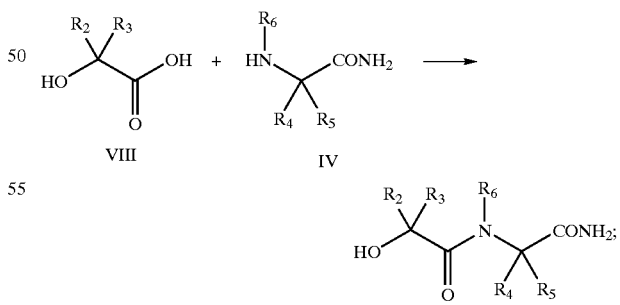

b1) reacting the product of step (a) with an activated acid compound YC(O)L wherein Y is $R_1$, $R_1O$—, $R_1S(O)_m$— or $(R_1)_3C$—, wherein $R_1$ is as defined in claim 1 and L is a leaving group, in the presence of a suitable base, followed by dehydrating the resulting amide compound to provide a nitrile of formula (I):

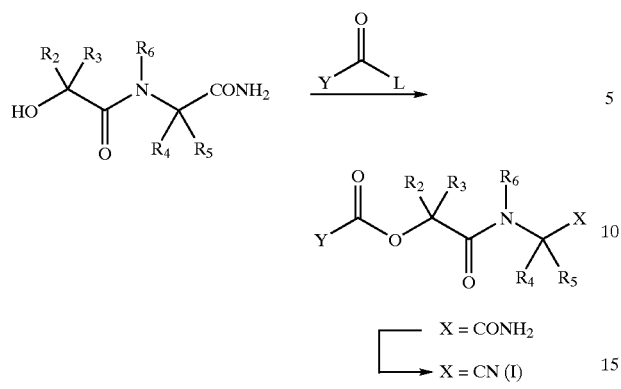

or b2) reacting the product of step (a) with a chloroformate to provide a mixed anhydride, followed by reacting the mixed anhydride with an amine compound $(R_1)_2NH$, followed by dehydrating the resulting amide compound to provide a nitrile of formula (I):

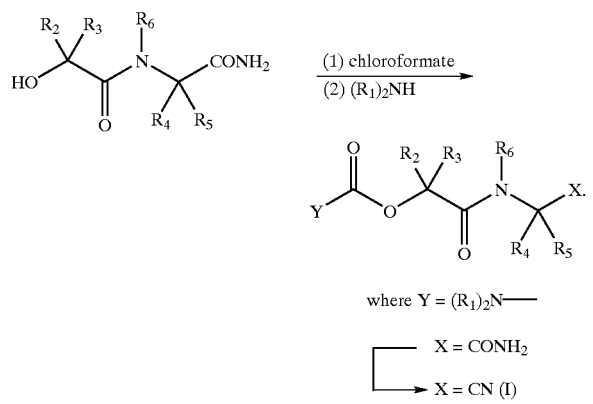

21. A method of making a compound of formula (I):

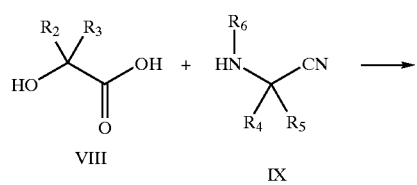

(I)

wherein X is oxygen and $R_2$, $R_3$, $R_4$, $R_5$, $R_6$ and Y are as defined in claim 1, said method comprising steps (a) and (b1) or steps (a) and (b2):

a) reacting a hydroxy acid (VIII) with an amino nitrile (IX) under coupling conditions:

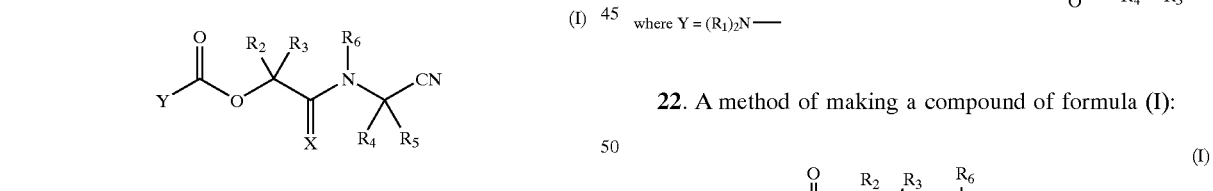

b1) reacting the product of step (a) with an activated acid compound YC(O)L wherein Y is $R_1$, $R_1O—$, $R_1S(O)_m—$ or $(R_1)_3C—$, wherein $R_1$ is as defined in claim 1 and L is a leaving group, in the presence of a suitable base, to provide a nitrile of formula (I):

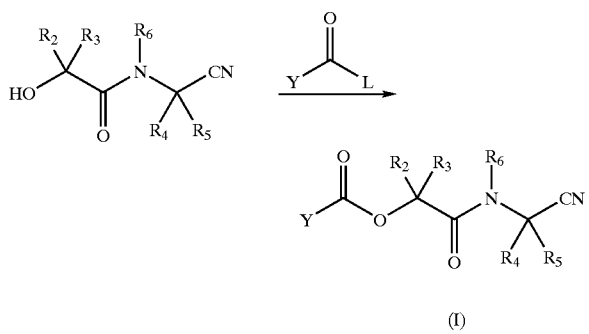

(I)

or (b2) reacting the product of step (a) with a chloroformate to provide a mixed anhydride, followed by reacting the mixed anhydride with an amine compound $(R_1)_2NH$, to provide a nitrile of formula (I):

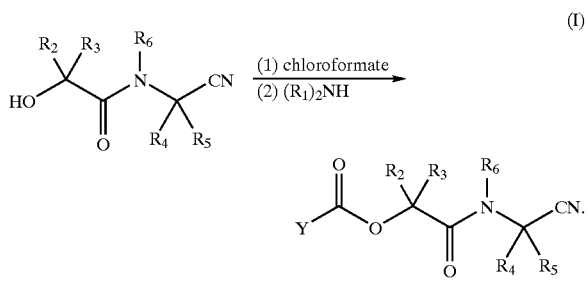

where Y = $(R_1)_2N—$

22. A method of making a compound of formula (I):

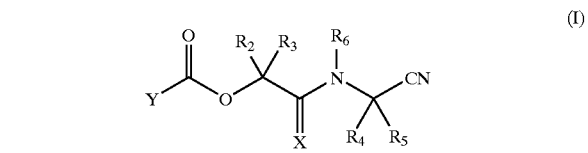

(I)

wherein X is oxygen, and $R_2$, $R_3$, $R_4$, $R_5$, $R_6$ and Y are as defined in claim 1, said method comprising steps (a1) and (b), or comprising steps (a2) and (b):

a1) reacting a hydroxy ester (V), wherein R' is a protecting group, with an activated acid compound YC(O)L wherein Y is $R_1$, $R_1O—$, $R_1S(O)_m—$ or $(R_1)_3C—$, wherein $R_1$ is as defined in claim 1 and L is a leaving group, in the presence of a suitable base to provide the compound of formula (VI), followed by hydrolysis to provide a carboxylic acid of formula (VII):

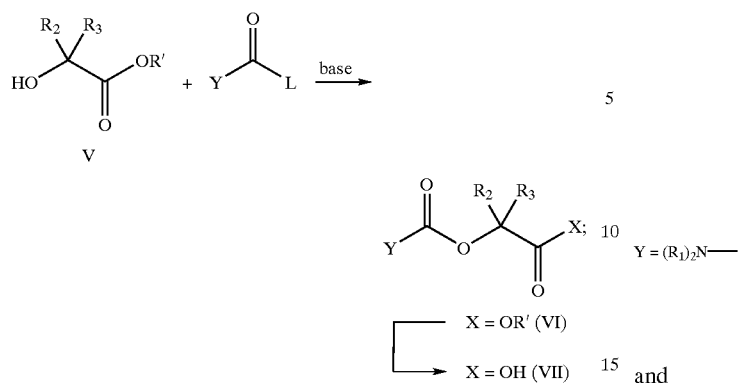

or a2) reacting the hydroxy ester (V) with a chloroformate to provide a mixed anhydride, followed by reacting the mixed anhydride with an amine compound $(R_1)_2NH$ to provide a compound of formula (VI) wherein Y is $(R_1)_2N—$, followed by hydrolysis of the compound of formula (VI) to provide a carboxylic acid of formula (VII):

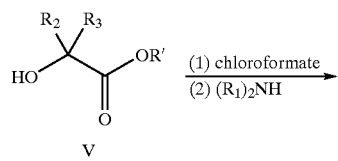

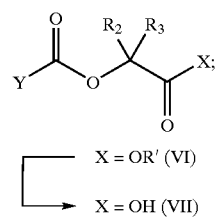

and (b) reacting an amino nitrile (IX) with compound (VII) under suitable coupling conditions to provide a nitrile of formula (I):

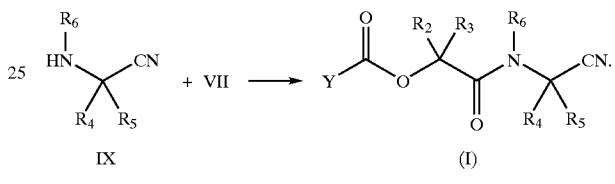

* * * * *